US009017984B2

(12) United States Patent
Hu et al.

(10) Patent No.: US 9,017,984 B2
(45) Date of Patent: *Apr. 28, 2015

(54) ENHANCED PRODUCTION OF FATTY ACID DERIVATIVES

(75) Inventors: Zhihao Hu, South San Francisco, CA (US); Fernando Valle, South San Francisco, CA (US)

(73) Assignee: REG Life Sciences, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/529,990

(22) Filed: Jun. 21, 2012

(65) Prior Publication Data

US 2012/0264983 A1    Oct. 18, 2012

Related U.S. Application Data

(63) Continuation of application No. 13/099,986, filed on May 3, 2011, now Pat. No. 8,283,143, which is a continuation of application No. 12/278,960, filed as application No. PCT/US2008/058788 on Mar. 28, 2008, now Pat. No. 8,110,670, said application No. 12/278,960 is a continuation-in-part of application No. PCT/US2007/011923, filed on May 18, 2007.

(60) Provisional application No. 60/908,547, filed on Mar. 28, 2007, provisional application No. 60/989,798, filed on Nov. 21, 2007, provisional application No. 60/802,016, filed on May 19, 2006, provisional application No. 60/801,995, filed on May 19, 2006.

(51) Int. Cl.
| | |
|---|---|
| *C12N 1/00* | (2006.01) |
| *C12N 1/20* | (2006.01) |
| *C12N 1/12* | (2006.01) |
| *C12P 7/64* | (2006.01) |
| *C12N 1/16* | (2006.01) |
| *C12N 1/14* | (2006.01) |
| *C10L 1/02* | (2006.01) |
| *C10L 1/19* | (2006.01) |
| *C11C 3/00* | (2006.01) |

(52) U.S. Cl.
CPC . *C12P 7/649* (2013.01); *C12N 1/20* (2013.01); *C12N 1/16* (2013.01); *C12N 1/14* (2013.01); *C12N 1/12* (2013.01); *C10L 1/02* (2013.01); *C10L 1/026* (2013.01); *C10L 1/19* (2013.01); *C11C 3/003* (2013.01); *C12P 7/6409* (2013.01); *C12P 7/6436* (2013.01); *C12P 7/6463* (2013.01); *Y02E 50/13* (2013.01); *Y02E 50/343* (2013.01)

(58) Field of Classification Search
USPC ............. 435/243, 157, 254.2, 252.3; 568/840
See application file for complete search history.

(56) References Cited

U.S. PATENT DOCUMENTS

| | | | |
|---|---|---|---|
| 6,750,048 | B2 | 6/2004 | Ruecker et al. |
| 6,982,155 | B1 | 1/2006 | Fukuda et al. |
| 7,056,714 | B2 | 6/2006 | Rosazza et al. |
| 7,118,896 | B2 | 10/2006 | Kalscheuer et al. |
| 7,314,974 | B2 | 1/2008 | Cao et al. |
| 7,425,433 | B2 | 9/2008 | Rosazza et al. |
| 8,110,670 | B2 * | 2/2012 | Hu et al. ................... 536/23.2 |
| 8,268,599 | B2 * | 9/2012 | Schirmer et al. ............ 435/147 |
| 2003/0040474 | A1 | 2/2003 | Kapeller-Libermann et al. |
| 2003/0097686 | A1 | 5/2003 | Knauf et al. |
| 2003/0233675 | A1 | 12/2003 | Cao et al. |
| 2004/0009576 | A1 | 1/2004 | Kalscheuer et al. |
| 2004/0180400 | A1 | 9/2004 | Rosazza et al. |
| 2005/0130126 | A1 | 6/2005 | Durmaz et al. |
| 2005/0250135 | A1 | 11/2005 | Klaenhammer et al. |
| 2006/0014977 | A1 | 1/2006 | Miller et al. |
| 2007/0251141 | A1 | 11/2007 | Bist et al. |
| 2007/0261138 | A1 | 11/2007 | Graham et al. |
| 2007/0270319 | A1 | 11/2007 | Seggelkow et al. |
| 2008/0161595 | A1 | 7/2008 | Huang et al. |
| 2008/0295388 | A1 | 12/2008 | Bazzani et al. |
| 2009/0038211 | A1 | 2/2009 | Sarin et al. |
| 2009/0047721 | A1 | 2/2009 | Trimbur et al. |
| 2009/0075333 | A1 | 3/2009 | Campbell et al. |
| 2009/0084025 | A1 | 4/2009 | Bhatia et al. |
| 2009/0117629 | A1 | 5/2009 | Schmidt-Dannert et al. |
| 2010/0242345 | A1 | 9/2010 | Keasling et al. |
| 2010/0251601 | A1 | 10/2010 | Hu et al. |
| 2010/0257777 | A1 | 10/2010 | Sanchez-Riera et al. |
| 2010/0257778 | A1 | 10/2010 | Gaertner et al. |
| 2010/0274033 | A1 | 10/2010 | Sanchez-Riera et al. |
| 2011/0072714 | A1 | 3/2011 | Gaertner et al. |

(Continued)

FOREIGN PATENT DOCUMENTS

| | | |
|---|---|---|
| DE | 10-2004-052115 A1 | 4/2006 |
| KR | 10-2007-17428 | 2/2007 |

(Continued)

OTHER PUBLICATIONS

Jahreis et al., "Adaptation of Sucrose Metabolism in the *Escherichia coli* Wild-Type Strain EC3132", *J.Bacteriol.*184(19): 5307-5316 (2002).

Kazan et al., "Effect of Glucose Concentration on the Growth Rate and some Intracellular Components of a Recombinant *E. coli* Culture", Process Biochemistry 30(3): 269-273 (1995).

Kornberg et al., "Routes for Fructose Utilization by *Escherichia coli*", J. Mol. Microbiol. Biotechnol. 3(3): 355-359 (2001).

Abbadi et al., "Knockout of the regulatory site of 3-ketoacyl-ACP synthase III enhances short-and medium-chain acyl-ACP synthesis", *Plant Journal*, 24(1): 1-9 (2000).

Abdel-Hamid et al., "Pyruvate oxidase contributes to the aerobic growth efficiency of *Escherichia coli*," Microbiology, 147(6): 1483-98 (2001).

Abdel-Hamid et al., "Coordinate Expression of the Acetyl Coenzyme A Carboxylase Genes, accB and accC, Is Necessary for Normal Regulation of Biotin Synthesis in *Escherichia coli*", *J. Bacteriol.*, 189:369-376 (2007).

Alper, et al., "Engineering for biofuels: exploiting innate microbial capacity or importing biosynthetic potential?", NRM 7: 715-723 (2009).

(Continued)

*Primary Examiner* — Suzanne M Noakes
*Assistant Examiner* — Jae W Lee
(74) *Attorney, Agent, or Firm* — Brigitte Hajos; REG Life Sciences, LLC

(57) ABSTRACT

Genetically engineered microorganisms that produce fatty alcohols from a sugar source by way of the fatty acid biosynthetic pathway, as well as methods of their use are provided.

22 Claims, 52 Drawing Sheets

(56) References Cited

U.S. PATENT DOCUMENTS

2011/0146142 A1  6/2011  Lee et al.
2011/0162259 A1  7/2011  Gaertner et al.

FOREIGN PATENT DOCUMENTS

| WO | WO 2007/136762 A2 | 11/2007 |
| WO | WO 2008/119082 A2 | 10/2008 |
| WO | WO 2009/042950 A1 | 4/2009 |
| WO | WO 2010/118409 A1 | 10/2010 |
| WO | WO 2010/118410 A1 | 10/2010 |
| WO | WO 2010/126891 A1 | 11/2010 |
| WO | WO 2011/038132 A1 | 3/2011 |
| WO | WO 2011/038134 A1 | 3/2011 |

OTHER PUBLICATIONS

Alvarez, et al., "Triacylglycerols in prokaryotic microorganisms", *Appl.Microbiol.Biotechnol.*, 60: 367-376 (2002).
Antoni, et al., "Biofuels from microbes", *Appl. Microbiol. Biotechnol.*, 77: 23-35 (2007).
Atsumi et al., "Metabolic engineering for advanced biofuels production from *Escherichia coli*", *Current Opin.Biotech*, 19:414-419 (2008).
Atsumi et al., "Metabolic engineering of *Escherichia coli* for 1-butanol production", *Metabolic Enginering 10*:305-311 (2008).
Atsumi et al., "Non-fermentative pathways for synthesis of branched-chain higher alcohols as biofuels", *Nature*, 451: 86-89 (2008).
Barnes, Jr. et al., "Studies on the Mechanism of Fatty Acid Synthesis. XIX. Preparation and General Properties of Palmityl Thioesterase", *J. Biol. Chem.*, 243(11):2955-2962 (1968).
Beekwilder et al., "Functional Characterization of Enzymes Forming Volatile Esters from Strawberry and Banana", *Plant Physiology*, 135: 1865-1878 (2004).
Beinert, H., "Recent developments in the field of iron-sulfur proteins", *FASEB J. 4*: 2483-2491 (1990).
Bergler et al., "Protein EnvM is the NADH-dependent Enoyl-ACP Reductase (FabI) of *Escherichia coli*," *J. Biol. Chem.*, 269(8): 5943-5946 (1994).
Bergler et al., "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", *Eur. J. Biochem. 242*: 689-694 (1996).
Berrios-Rivera et al., "The Effect of Increasing NADH Availability on the Redistribution of Metabolic Fluxes in *Escherichia coli* Chemostat Cultures", *Metabolic Engineering 4*: 230-237 (2002).
Birge et al., "Acyl Carrier Protein. XVI.Intermediate Reactions of Unsaturated Fatty Acid Synthesis in *Escerichia coli* and Studies of fab B Mutants", J.Biol.Chem. 247(16): 4921-4929 (1972).
Black et al., "Cloning, Sequencing, and Expression of the fadD Gene of *Escherichia coli* Encoding Acyl Coenzyme A Synthetase," *J. Biol. Chem. 267*(35): 25513-25520 (1992).
Black, P., "Primary Sequence of the *Escherichia coli fadL* Gene Encoding an Outer Membrane Protein Required for Long-Chain Fatty Acid Transport", *J. Bacteriololgy 173*(2): 435-442 (1991).
Black et al., "Mutational Analysis of a Fatty Acyl-Coenzyme A Synthetase Signature Motif Identifies Seven Amino Acid Residues That Modulate Fatty Acid Substrate Specificity", *J. Biol. Chem. 272*(8) 4896-4903 (1997).
Black et al., "Long-Chain Acyl-CoA—Dependent Regulation of Gene Expression in Bacteria, Yeast and Mammals", *J. Nutrition*, 305S-309S (2000).
Blanchard et al., "Overexpression and Kinetic Characterization of the Carboxyltransferase Component of Acetyl-CoA Carboxylase", *J.Biol.Chem. 273*(30): 19140-19145 (1998).
Bonamore et al., "The desaturase from *Bacillus subtilis*, a promising tool for the selective olefination of phospholipids", *J.Biotechnology 121*: 49-53 (2006).
Bonner et a.1, "Purification and Properties of Fatty Acyl Thioesterase I from *Escherichia coli*", *J. Biol.Chem. 247*(10): 3123-3133 (1972).

Boonstra et al., "The *udhA* Gene of *Escherichia coli* Encodes a Soluble Pyridine Nucleotide Transhydrogenase", *J.Bacteriol. 181*(3): 1030-1034 (1999).
Boulanger et al., "Purification and Structrual and Functional Characterization of FhuA, a Transporter of the *Escherichia coli* Outer Membrane," *Biochemistry*, 35(45): 14216-14224 (1996).
Bredwell et al., "Reactor Design Issues for Synthesis-Gas Fermentations", *Biotechnol. Prog. 15*: 834-844 (1999).
Broun et al., "Catalytic Plasticity of Fatty Acid Modification Enzymes Underlying Chemical Diversity of Plant Llipids", *Science* 282: 1315-1317 (1998).
Bunch et al., "The *IdhA* gene encoding the fermentative lactate dehydrogenase of *Escherichia coli*," *Microbiology*, 143(1): 187-95 (1997).
Cahoon et al., "Modification of the Fatty Acid Composition of *Escherichia coli* by Coexpression of a Plant Acyl-Acyl Carrier Protein Desaturase and Ferredoxin", *J.Bacteriol. 178*(3): 936-936 (1996).
Cahoon et al., "Redesign of soluble fatty acid desaturases from plants for altered substrate specificity and double bond position", *Proc. Natl. Acad. Sci.94*: 4872-4877 (1997).
Cahoon et al., "A Determinant of Substrate Specificity Predicted from the Acyl-Acyl Carrier Protein Desaturase of Developing Cat's Claw Seed", *Plant Physiol 117*: 593-598 (1998).
Campbell et al., "The Enigmatic *Escherichia coli fadE* Gene is *yafH*" *J. Bacteriol.*, 184(13): 3759-3764 (2002).
Campbell et al., "A New *Escherichia coli* metabolic competency: growth on fatty acids by a novel anaerobic β-oxidation pathway," *Mol. Microbiol.*, 47(3): 793-805 (2003).
Campbell et al., "*Escherichia coli* FadR Positively Regulates Transcription of the fabB Fatty Acid Biosynthetic Gene", *J.Bacteriol. 183*(20): 5982-5990 (2001).
Cann et al., "Production of 2-methyl-1-butanol in engineered *Escherichia coli*", *Appl Microbiol Biotechnol. 81*: 89-98 (2008).
Canoira et al., "Biodiesel from Jojoba oil-wax: Transesterification with methanol and properties as a fuel", *Biomass and Bioenergy 30*:76-81 ((2006).
Caviglia et al., "Rat Long Chain Acyl-CoA Synthetase 5, but Not 1, 2, 3, or 4, Complements *Escherichia coli fadD*," *J. Biol. Chem.*, 279(12): 11163-11169 (2004).
Chang et al., "Genetic and Biochemical Analyses of *Escherichia coli* Strains Having a Mutation in the Structural Gene (*poxB*) for Pyruvate Oxidase," *J. Bacteriol.*, 154(2): 756-62 (1983).
Chassagnole et al., "Dynamic Modeling of the Central Carbon Metabolism of *Escherichia coli*", *Biotech & Engineering 79*(1): 59-73 (2002).
Chen, "Permeability issues in whole-cell bioprocesses and cellular membrane engineering", *Appl Microbiol Biotechnol 74*: 730-738 (2007).
Cheng et al., "Mammalian Wax Biosynthesis, II. Expression Cloning of Wax Synthase cDNAs Encoding a Member of the Acyltransferase Enzyme Family*," *J. Biol. Chem.*, 279(36): 37798-37807 (2004).
Cho et al., "Defective Export of a Periplasmic Enzyme Disrupts Regulation of Fatty Acid Synthesis," *J. Biol. Chem.*, 270: 4216-4219 (1995).
Cho et al., "*Escherichia coli* Thioesterase I, Molecular Cloning and Sequencing of the Structural Gene and Identification as a Periplasmic Enzyme", *J.Biol.Chem 268*(13:5): 9238-9245 (1993).
Cho et al., "Transcriptional regulation of the *fad* regulon genes of *Escherichia coli* by ArcA", *Microbiology 152*: 2207-2219 (2006).
Choi et al., "β-Ketoacyl-acyl Carrier Protein Synthase III (FabH) Is a Determining Factor in Branched-Chain Fatty Acid Biosynthesis" *J. of Bacteriology* 182(2): 365-370 (2000).
Coleman et al., "Enzymes of triacylglycerol synthesis and their regulation" *Progress in Lipid Research 43*:134-176 (2004).
Collister et al., "Modification of the petroleum system concept: Origins of alkanes and isoprenoids in crude oils" *AAPG Bulletin* 88(5):587-611 (2004).
Conway et al., "Cloning and Sequencing of the Alcohol Dehydrogenase II Gene from *Zymomonas mobilis*" *J. Bacteriol.* 169(6): 2591-2597 (1987).

(56) References Cited

OTHER PUBLICATIONS da Silva et al., "Comparison of the Genomes of Two *Xanthomonas* Pathogens with Differing Host Specificities" *Nature*, 417: 459-463 (2002).
Database EMBL (online): "*Synechococcus*, PCC7942 Ribosomal Protein S1 of 30S Ribosome (rpls): ORF271, ORF231, ORF341, Carboxyltransferase alpha subunit (accA) ORF245, ORF227, and GTP cyclohydrolase I (folE) genes, complete cds, and ORF205 gene, partial cds," XP002564232 (1996).
Davis, J.B., "Microbial Incorporation of Fatty Acids Derived From n-Alkanes Into Glycerides and Waxes" *Applied Microbiology* 12(3): 210-214 (1964).
Davis et al., "Inhibition of *Escherichia coli* Acetyl Coenzyme A Carboxylase by Acyl-Acyl Carrier Protein" *J.Bacteriol.* 183(4): 1499-1503 (2001).
Davis et al., "Overproduction of Acetyl-CoA Carboxylase Activity Increases the Rate of Fatty Acid Biosynthesis in *Escherichia coli*" *J.Biol.Chem* 275(37:15) 28593-28598 (2000).
Dehesh et al., "KAS IV: A 3-ketoacyl-ACP synthase from *Cuphea* sp. Is a medium chain specific condensing enzyme", *The Plant Journal* 15(3):383-390 (1998).
Dehesh et al., "Production of high levels of 8:0 and 10:0 fatty acids in transgenic canola by overexpression of *Ch FatB2*, a thioesterase cDNA from *Cuphea hookeriana*" *The Plant Journal* 9(2): 167-172 (1996).
Delay et al., "In Vivo Functional Analyses of the Type II Acyl Carrier Proteins of Fatty Acid Biosynthesis", *J.Biol.Chem.* 282: 20319-20328 (2007).
Demendoza et al., "Thermal Regulation of Membrane Fluidity in *Escherichia coli*. Effects of Overproduction of P-Ketoacylacyl Carrier Protein Synthase 1", *J.Biol.Chem.* 258(4):2098-2101 (1983).
Demirbas, A., "Relationships derived from physical properties of vegetable oil and biodiesel fuels", *Fuel* 87: 1743-1748 (2008).
Demirbas, A., "Progress and recent trends in biofuels", *Progress in Energy and Combustion Science* 33: 1-18 (2007).
Denoya et al., "A Second Branched-Chain α-Keto Acid Dehydrogenase Gene Cluster (bkdFGH) from *Streptomyces avermitiffis*: Its Relationship to Avermectin Biosynthesis and the Construction of a *bkdF* Mutant Suitable for the Production of Novel Antiparasitic Avermectins," *J. Bacteriol.* 177(12): 3504-3511 (1995).
Deveaux et al., "Genetic and Biochemical Characterization of a Mutation (*fatA*) That Allows *trans* Unsaturated Fatty Acids to Replace the Essential *cis* Unsaturated Fatty Acids of *Escherichia coli*" *J.Bacteriol.* 171(3):1562-1568 (1989).
Domergue et al., "Acyl Carriers Used as Substrates by the Desaturases and Elongases Involved in Very Long-chain Polyunsaturated Fatty Acids Biosynthesis Reconstituted in Yeast" *J.Biol.Chem* 278(37):35115-35126 (2003).
Domka et al., "YliH (BssR) and YceP (BssS) Regulate *Escherichia coli* K-12 Biofilm Bormation by Influencing Cell Signaling" *Appl. and Environ. Microbiol.* 72(4):2449-2459 (2006).
Dormann et al., "Specificities of the Acyl-Acyl Carrier Protein (ACP) Thioesterase and Glycerol-3-Phosphate Acyltransferase for Octadecenoyl-ACP Isomers (Identification of a Petroselinoyl-ACP Thioesterase in Umbelliferae)", *Plant Physiol.104*: 839-844 (1994).
Doss, R.P., "Composition and Enzymatic Activity of the Extracellular Matrix Secreted by Germlings of *Botrytis cinerea*," *Appl. And Environ. Microbiol.*, 65(2): 404-408 (1999).
Durre, P., "Fermentative Butanol Production: Bulk Chemical and Biofuel" *Ann. N.Y. Acad. Sci. 1125*: 353-362 (2008).
Dworkin et al., "The PspA Protein of *Escherichia coli* is a Negative Regulator of sigma54-Dependent Transcirption", *J. Bacteriol.* 182(2): 311-319 (2000).
Edwards et al., "The *Escherichia coli* MG1655 in silico metabolic genotype: Its definition, characteristics, and capabilities", *PNAS* 97(10): 5528-5533 (2000).
Farewell et al., "Role of the *Escherichia coli* FadR Regulator in Stasis Survival and Growth Phase-Dependent Expression of the *uspA*, *fad*, and *fab* Genes", *J. Bacteriol.* 178(22): 6443-6450 (1996).

Fehler et al., "Biosynthesis of Hydrocarbons in *Anabaena variabilis*. Incorporation of [methyl-$^{14}$C]- and [methyl-$^{2}$H$_3$] Methionine into 7- and 8-Methylheptadecances", *Biochemistry* 9(2): 418-422 (1970).
Feng et al., "A New Member of the *Escherichia coli* fad Regulon: Transcriptional Regulation of *fadM* (*ybaW*)", *J. Bacteriol.* 191(20): 6320-6328 (2009).
Fischer et al., "Selection and optimization of microbial hosts for biofuels production" *Metabolic Engineering* 10:295-304 (2008).
Flaman et al., "Site-directed Mutagenesis of Acyl Carrier Protein (ACP) Reveals Amino Acid Residues Involved in ACP Structure and Acyl-ACP Synthetase Activity", *J.Biol.Chem.* 276(38): 35934-35939 (2001).
Fleischman et al., Accession No. YP_889972/GI:11849671 (2006).
Fozo et al., "The fabM Gene Product of *Streptococcus mutans* Is Responsible for the Synthesis of Monounsaturated Fatty Acids and Is Necessary for Survival at Low pH", *J. Bacteriol.* 186(13): 4152-4158 (2004).
Fujita et al., "Regulation of fatty acid metabolism in bacteria", *Mol. Microbiology* 66(4): 829-839 (2007).
Ghisla et al., Acyl-CoA dehydrogenases—A mechanistic overview, *Eur. J. Biochem.* 271: 494-508 (2004).
Hamilton-Kemp et al., "Production of the Long-Chain Alcohols Octanol, Decanol, and Dodecanol by *Escherichia coli*", *Current Microbiology* 51: 82-86 (2005).
Han et al., "A Novel Alternate Anaplerotic Pathway to the Glyoxylate Cycle in Streptomycetes," *J. Bacteriol.*, 179(16): 5157-5164 (1997).
Hantke, K., "Ferrous iron transport mutants in *Escherichia coli* K12", *FEMS Microbiology Letters* 44: 53-57 (1987).
He et al., "*Nocardia* sp. Carboxylic Acid Reductase: Cloning, Expression and Characterization of a New Aldehyde Oxidoreductase Family," Appl. And Environ. Microbiol., 70(3): 1874-1881 (2004).
Heath et al., "Regulation of Malonyl-CoA Metabolism by Acyl-Acyl Carrier Protein and β-Ketoacyl-Acyl Carrier Protein Synthases in *Escherichia coli*", *J.Biol.Chem.* 270(26):15531-15538 (1995).
Heath et al., "Regulation of Fatty Acid Elongation and Initiation by Acyl-Acyl Carrier Protein in *Escherichia coli*", *J.Biol.Chem.* vol. 271(4): 1833-1836 (1996).
Heath et al., "Inhibition of β-Ketoacyl-Acyl Carrier Protein Synthase III (FabH) by Acyl-Acyl Carrier Protein in *Escherichia coil*", *J.Biol. Chem.271*(18):10996-11000 (1996).
Heath et al., "Roles of the FabA and FabZ β-Hydroxyacyl-Acyl Carrier Protein Dehydratases in *Escherichia coli* Fatty Acid Biosynthesis", *J.Biol.Chem.* 271(44): 27795-27801 (1996).
Henry et al., "*Escherichia coli* Transcription Factor That Both Activates Fatty Acid Synthesis and Represses Fatty Acid Degradation", *J. Mol. Biol.* 222: 843-849 (1991).
Howell et al., "(*R*)-Citramalate Synthase in Methanogenic Archaea", *J. Bacteriol.* 181(1): 331-333 (1999).
Hu et al., Microalgal triacylglycerols as feedstocks for biofuel production: perspectives and advances, *The Plant Journal* 54: 621-639 (2008).
Huber et al., "Branched-Chain Fatty Acids Produced by Mutants of *Streptomyces fradiae*, Putative Precursors of the Lactone Ring of Tylosin", *Antimicrob.Agents.Chemother.* 34(8):1535-1541 (1990).
Hunt et al., "Characterization of an Acyl-CoA Thioesterase That Functions as a Major Regulator of Peroxisomal Lipid Metabolism" *J.Biol.Chem.* 277(2):1128-1138 (2002).
Imahara et al., "Thermodynamic study on cloud point of biodiesel with its fatty acid composition", *Fuel* 85: 1666-1670 (2006).
Ishige et al., "Long-Chain Aldehyde Dehydrogenase That Participates in *n*-Alkane Utilization and Wax Ester Synthesis in *Acinetobacter* sp. Strain M-1", *Appl. Environ. Microbiol.* 66(8): 3481-3486 (2000).
Ishige et al., "Wax Ester Production from n-Alkanes by *Acinetobacter* sp. Strain M-1: Ultrastructure of Cellular Inclusions and Role of Acyl Coenzyme A Reductase", *Appl. Environ. Microbiol.* 68(3): 1192-1195 (2002).
Jayakumar et al., "Cloning and expression of the multifunctional human fatty acid synthase and its subdomains in *Escherichia coli*", *PNAS* 93: 14509-14514 (1996).
Jiang, et al., "Inhibition of Fatty Acid Synthesis in *Escherichia coli* in the Absence of Phospholipid Synthesis and Release of Inhibition by Thioesterase Action" *J. Bacteriol.* 176(10): 2814-2821 (1994).

(56) References Cited

OTHER PUBLICATIONS

Jones et al., "Palmitoyl-Acyl Carrier Protein (ACP) Thioesterase and the Evolutionary-Origin of Plant Acyl-ACP Thioesterases", *Plant Cell*, vol. 7:359-371 (1995).

Joshi et al., "Flow properties of biodiesel fuel blends at low temperatures", *Fuel 86*: 143-151 (2007).

Juttner et al., "The reducing capacities of cyanobacteria for aldehydes and ketones," *Appl. Microbiol. and Biotechnol.*, 25: 52-54 (1986).

Juttner et al. "Environmental Factors Affecting the Formation of Mesityloxide Dimethylallyic Alcohol and Other Volatile Compounds Excreted by *Anabaena cylindrica*," *J. Gen. Microbiol.*, 129: 407-412 (1983).

Kalscheuer et al., "Synthesis of Novel Lipids in *Saccharomyces cerevisiae* by Heterologous Expression of an Unspecific Bacterial Acyltransferase" *Appl. Environ. Microbiol.*, 70(12):7119-7125 (2004).

Kalscheuer et al., "Analysis of Storage Lipid Accumulation in *Alcanivorax borkumensis*:Evidence for Alternative Triacylglycerol Biosynthesis Routes in Bacteria," *J.Bacteriol. 189*(3): 918-923 (2007).

Kameda et al., "Further purification, characterization and salt activation of acyl-CoA synthetase from *Escherichia coli*", *Biochimica et Biophysica Acta 840*: 29-36(1985).

Kameda et al., "Purification and Characterization of Acyl Coenzyme A Synthetase from *Escherichia coli*", *J.Biol.Chem. 256*(11): 5702-5707 (1981).

Kaneda, T., "Is0-and Anteiso-Fatty Acids in Bacteria: Biosynthesis, Function and Taxonomic Significance", *Microbiological Reviews, Am. Society for Microbiol.* 55(2): 288-302 (1991).

Keasling et al., "Metabolic engineering delivers next-generation biofuels", *Nature Biotechnology 26*(3):298-299 (2008).

Knoll et al., "Biochemical Studies of Three *Saccharomyces cerevisiae* Acyl-CoA Synthetases, Faalp, Faa2p, and Faa3p," *J. Biol. Chem.*, 269(23): 16348-16356 (1994).

Knothe et al., "Kinematic viscosity of biodiesel components (fatty acid alkyl esters) and related compounds at low temperatures", *Fuel 86*: 2560-2567 (2007).

Knothe, "Designer Biodiesel: Optimizing Fatty Ester Composition to Improve Fuel Properties," *Energy & Fuels 22*: 1358-1364 (2008).

Knothe, G., "Dependence of Biodiesel Fuel Properties on the Structure of Fatty Acid Alkyl Esters," *Fuel Process. Technol. 86*: 1059-1070 (2005).

Knothe et al., "Kinematic viscosity of biodiesel fuel components and related compounds. Influence of compound structure and comparison to petrodiesel fuel components", *Fuel 84*: 1059-1065 (2005).

Knudsen et al,. "Transacylation as a chain-termination mechanism in fatty acid synthesis by mammalian fatty acid synthetase. Synthesis of medium-chain-length (C8-C12) acyl-CoA esters by goat mammary-gland fatty acid synthetase", *Biochem. J. 202*: 139-143 (1982).

Kroumova et al., "A pathway for the biosynthesis of straight and branched, odd- and even-length, medium-chain fatty acids in plants", *PNAS 91*: 11437-11441 (1994).

Kumari et al., "Regulation of Acetyl Coenzyme A Synthetase in *Escherichia coli*", *J. Bacteriol.* 182(15): 4173-4179 (2000).

Lang et al., "Preparation and characterization of bio-diesels from various bio-oils", *Bioresource Tech. 80*: 53-62 (2001).

Lee et al., "Enhanced preference for π-bond containing substrates is correlated to Pro110 in the substrate-binding tunnel of *Escherichia coli* thioesterase I/protease I/lysophospholipase $L_1$" *Biochim. et Biophys. Acta*, 1774: 959-967 (2007).

Lee et al., "Metabolic engineering of microorganisms for biofuels production: from bugs to synthetic biology to fuels", *Current Opinion in Biotechnology 19*: 556-563 (2008).

Leonard et al., "A *Cuphea* β-ketoacyl-ACP synthase shifts the synthesis of fatty acids towards shorter chains in *Arabidopsis* seeds expressing *Cuphea* FatB thioesterases", *Plant Journal 13*(5): 621-628 (1998).

Li et al., "The Gene Encoding the Biotin Carboxylase Subunit of *Escherichia coli* Acetyl-CoA carboxylase", *J.Biol.Chem. 267*(2): 855-863 (1992).

Li et al., "Alteration of the Fatty Acid Profile of *Streptomyces coelicolor* by Replacement of the Initiation Enzyme 3-Ketoacyl Acyl Carrier Protein Synthase III (FabH)," *J. Bacteriol.*, 187(11): 3795-3799 (2005).

Li et al., "Purification, Characterization, and Properties of an Aryl Aldehyde Oxidoreductase from *Nocardia* Sp. Strain NRRL 5646," *J. Bacteriol. 179*(11): 3482-3487 (1997).

Li et al., "The carboxylic acid reduction pathway in *Nocardia*. Purification and characterization of the aldehyde reductase", *J. of Industrial Microbiology & Biotechnology 25*: 328-332 (2000).

Li et al., "Growth Rate Regulation of *Escherichia coli* Acetyl Coenzyme A Carboxylase, Which Catalyzes the First Committed Step of Lipid Biosynthesis", *J. Bacteriol.* 175(2): 332-340 (1993).

Lin et al., "Fed-Batch Culture of a Metabolically Engineered *Escherichia coli* Strain Designed for High-Level Succinate Production and Yield Under Aerobic Conditions", *Biotech.Engineering 90*: 1-5 (2005).

Link et al., "Methods for Generating Precise Deletions and Insertions in the Genome of Wild-Type *Escherichia coli*: Application to Open Reading Frame Characterization", *J.Bacteriol. 179*(20): 6228-6237 (1997).

Lu et al., "Overproduction of free fatty acids in *E. coli*: Implications for biodiesel production", *Metabolic Engineering 10*: 333-339 (2008).

Lynd et al., "Microbial Cellulose Utilization: Fundamentals and Biotechnology" *Microbiol.Mol.Biol.Rev. 66*(3): 506-577 (2002).

Lytle et al., "Involvement of Both Dockerin Subdomains in Assembly of the *Clostridium thermocellum* Cellulosome," *J. Bacteriol.*, 180(24): 6581-6585 (1998).

Magnuson et al., "Regulation of Fatty Acid Biosynthesis in *Escherichia coli*" *Microbiol.Reviews 57*(3): 522-542 (1993).

Marr, et al., "Effect of Temperature on the Composition of Fatty Acids in *Escherichia coli*", *J.Bacteriol. 84*: 1260-1267 (1962).

Massengo-Tiasse et al., "*Vibrio cholerae* FabV Defines a New Class of Enoyl-Acyl Carrier Protein Reductase", *J.Biol.Chem. 283*(3): 1308-1316 (2008).

Matsumoto et al., "Yeast whole-cell biocatalyst contructed by intracellular overproduction of *Rhizopus oryzae* lipase is applicable to biodiesel fuel production," *Appl Microbiol Biotechnol*, 57(4): 515-520 (2001).

Mayer et al., "Identification of amino acid residues involved in substrate specificity of plant acyl-ACP thioesterases using a bioinformatics-guided approach" *BMC Plant Biology 7*(1) (2007).

Metz et al., "Purification of a Jojoba Embryo Fatty Acyl-Coenzyme A Reductase and Expression of Its cDNA in High Erucic Acid Rapeseed", *Plant Physiol. 122*: 635-644 (2000).

Metzgar et al., "*Acinetobacter* sp. ADP1: an ideal model organism for genetic analysis and genome engineering", *Nucleic Acid Res. 32*(19):5780-5790 (2004).

Miller et al., "A Highly Catalytic and Selective Conversion of Carboxylic Acids to 1-Alkenes of One Less Carbon Atom," *J. Org. Chem*, 58(1): 18-20 (1993).

Mohan et al., "An *Escherichia coli* Gene (*FabZ*) Encoding (3R)-Hydroxymyristoyl Acyl Carrier Protein Dehydrase. Relation to fubA and Suppression of Mutations in Lipid A Biosynthesis", *J.Biol.Chem 269*(52): 32896-32903 (1994).

Morgan-Kiss et al, "The *Escherichia coli fadK* (*ydiD*) Gene Encodes an Anerobically Regulated Short Chain Acyl-CoA Synthetase," *J. Biol. Chem.*, 279(36): 37324-37333 (2004).

Morgan-Kiss et al., "The *Lactococcus lactis* FabF Fatty Acid Synthetic Enzyme can Functionally Replace both the FabB and FabF Proteins of *Escherichia coli* and the FabH Protein of *Lactococcus lactis*," *Arch. Microbiol.* 190: 427-437 (2008).

Naccarato et al., "In Vivo and In Vitro Biosynthesis of Free Fatty Alcohols in *Escherichia coli* K-12," *Lipids*, 9(6): 419-428 (1973).

NCBI Reference Sequence GI:49532534, Putative Alcohol Dehydrogenase [*Acinetobacter* sp. ADP1] (2004).

Nunn et al., "Transport of long-chain fatty acids by *Escherichia coli*: Mapping and characterization of mutants in the *fadL* gene" *PNAS 75*(7): 3377-3381 (1978).

Nunn et al., "Role for fadR in Unsaturated Fatty Acid Biosynthesis in *Escherichia coli*", *J.Bacteriol.* 154(2):554-560 (1983).

(56) References Cited

OTHER PUBLICATIONS

Nunn, W., "A Molecular View of Fatty Acid Catabolism in *Escherichia coli*", *Microbiol.Rev.50*(2): 179-192 (1986).
Pages et al, "Interaction between the Endoglucanase CelA and the Scaffolding Protein CipC of the *Clostridium cellulolyticum* Cellulosome," *J.Bacteriol. 178*(8): 2279-2286 (1996).
Peng et al., "Effect of *fadR* gene knockout on the metabolism of *Escherichia coli* based on analyses of protein expressions, enzyme activities and intracellular metabolite concentrations" *Enzyme and Microbial Tech. 38*: 512-520 (2006).
Perez et al., "*Escherichia coli* YqhD Exhibits Aldehyde Reductase Activity and Protects from the Harmful Effect of Lipid Peroxidation-derived Aldehydes" *J.Biol.Chem. 283*(12): 7346-7353 (2008).
Phung et al., "Genes for Fatty Acid Biosynthesis in the *Cyanobacterium synechococcus* sp. Strain PCC 7942," Abstracts of the General Meeting of the American Society of Microbiology, 524 (1995).
Pillai et al., "Functional characterization of β-ketoacyl-ACP reductase (FabG) from *Plasmodium falciparum*" *Biochem. and Biophysical Research Comm. 303*: 387-392 (2003).
Qiu et al., "Crystal structure and substrate specificity of the β-ketoacyl-acyl carrier protein synthase III (FabH) from *Staphylococcus aureus*", *Protein Science 14*: 2087-2094 (2005).
Rafi et al., "Structure of Acyl Carrier Protein Bound to FabI, the FASII Enoyl Reductase from *Escherichia coli*" *J.Biol.Chem. 281*(51): 39285-39293 (2006).
Rawlings et al., "The Gene Encoding *Escherichia coli* Acyl Carrier Protein Lies within a Cluster of Fatty Acid Biosynthetic Genes", *J.Biol.Chem. 267*(9):5751-5754 (1992).
Rawlings et al., "Biosynthesis of fatty acids and related metabolites", *Natural Product Reports 15*: 275-308 (1998).
Ray et al., "Activation of long chain fatty acids with acyl carrier protein: Demonstration of a new enzyme, acyl-acyl carrier protein synthetase, in *Escherichia coli*" *PNAS 73*(12):4374-4378 (1976).
Rehm et al., "Heterologous expression of the acyl-acyl carrier protein thioesterase gene from the plant *Umbellularia californica* mediates polyhydroxyalkanoate biosynthesis in recombinant *Escherichia coli*", *Appl. Microbiol. and Biotech. 55*: 205-209 (2001).
Reiser et al., "Isolation of Mutants of *Acinetobacter calcoaceticus* Deficient in Wax Ester Synthesis of Complementation of One Mutation with a Gene Encoding a Fatty Acyl Coenzyme A Reductase", *J. Bacteriol.*, 179(9): 2969-2975 (1997).
Ren et al., "FabG, an NADPH-Dependent 3-Ketoacyl Reductase of *Pseudomonas aeruginosa*, Provides Precursors for Medium-Chain-Length Poly-3-Hydroxyalkanoate Biosynthesis in *Escherichia coli*", *J. Bacteriol.182*(10):2978-2981 (2000).
Rock et al., "Acyl-Acyl Carrier Protein Synthetase from *Escherichia coli*", *Meth.Enzymol. 71*: 163-168 (1981).
Rock et al., "Increased Unsaturated Fatty Acid Production Associated with a Surpressor of the *fabA6*(Ts) Mutation in *Escherichia coli*," *J. Bacteriol.*, 178(18): 5382-5387 (1996).
Romero et al., "Metabolic Engineering of *Bacillus subtilis* for Ethanol Production: Lactate Dehydrogenase Plays a Key Role in Fermentative Metabolism", *Applied & Environmental Microbiology*, 73(16): 5190-5198 (2007).
Sabirova et al., "Mutation in a "*tesB*-Like" Hydroxyacyl-Coenzyme A-Specific Thioesterase Gene Causes Hyperproduction of Extracellular Polyhydroxyalkanoates by *Alcanivorax borkumensis* SK2", *J. Bacteriol. 188*(23): 8452-8459 (2006).
Saito et al., "Crystal structure of enoyl-acyl carrier protein reductase (FabK) from *Streptococcus pneumoniae* reveals the binding mode of an inhibitor", *Protein Science 17*: 691-699 ((2008).
Salas et al., "Characterization of substrate specificity of plant FatA and FatB acyl-ACP thioesterases", *Archives of Biochem. and Biophysics 403*: 25-34 (2002).
Sanchez et al., "Effect of Overexpression of a Soluble Pyridine Nucleotide Transhydrogenase (UdhA) on the Production of Poly(3-hydroxybutyrate) in *Escherichia coli*", *Biotechnol.Prog. 22*: 420-425 (2006).

Schneider-Belhaddad et al., "Solubilization, Partial Purification, and Characterization of a Fatty Aldehyde Decarbonylase from a Higher Plant, *Pisum sativum*", *Archives of Biochem. And Biophysics 377*(2): 341-349 (2000).
Schujman et al., "A malonyl-CoA-dependent switch in the bacterial response to a dysfunction of lipid metabolism", *Molecular Microbiology*, 68(4): 987-996 (2008).
Schweizer et al., "Microbial Type I Fatty Acid Synthases (FAS): Major Players in a Network of Cellular FAS Systems", *Microbiol. Mol.Biol.Rev. 68*(3): 501-517 (2004).
Shahid et al., "A review of biodiesel as vehicular fuel", *Renew. Sustain.Ener.Reviews 12*: 2484-2494 (2008).
Shockey et al., "*Arabidopsis* Contains Nine Long-Chain Acyl-Coenzyme A Synthetase Genes that Particpate in Fatty Acid and Glycerolipid Metabolism," *Plant Physiol.*, 129: 1710-1722 (2002).
Spencer et al., "Thioesterases I and II of *Escherichia coli*. Hydrolysis of Native Acyl-Acyl Carrier Protein Thioesters," *J. Biol.Chem.*, 253(17): 5922-5926 (1978).
Stöveken et al., "The Wax Ester Synthase/Acyl Coenzyme A:Diacylglycerol Acyltransferase from *Acinetobacter* sp. Strain ADP1: Characterization of a Novel Type of Acyltransferase", *J. Bacteriol. 187*(4):1369-1376 (2005).
Subrahmanyam et al., "Overproduction of a Functional Fatty Acid Biosynthetic Enzyme Blocks Fatty Acid Synthesis in *Escherichia coli*" *J.Bacteriol. 180*(17):4596-4602 (1998).
Sulzenbacher et al., "Crystal Structure of *E. coli* Alcohol Dehydrogenase YqhD: Evidence of a Covalently Modified NADP Coenzyme" *J.Mol.Biol. 342*: 489-502 (2004).
Ta et al., "Cloning, Sequencing, and Overexpression oaf [2Fe—2S] Ferredoxin Gene from *Escherichia coli*", *J.Biol.Chem. 267*(16):11120-11125 (1992).
Thomason et al., "Identification of the *Escherichia coli* K-12 ybhE Gene as pgl, Encoding 6-Phosphogluconolactonase" *J.Bacteriol. 186*(24): 8248-8253 (2004).
Thorpe et al., "Structure and mechanism of action of the Acyl-CoA dehydrogenases1", *FASEB J. 9*: 718-725 (1995).
Tong et al., "Acetyl-Coenzyme A Carboxylases: Versatile Targets for Drug Discovery", *J. Cellular Biochem. 99*: 1476-1488 (2006).
Toomey et al., "Studies on the Mechanism of Fatty Acid Synthesis XVI. Preparation and General Properties of Acyl-Malonyl Acyl Carrier Proteincondensing Enzyme From *Escherichia coli*", *J.Biol. Chem. 241*(5):1159-1165 (1996).
Tsay et al., "Isolation and Characterization of the β-Ketoacyl-acyl Carrier Protein Synthase I11 Gene (*fabH*) from *Escherichia coli* K-12", *J.Biol.Chem. 267*(10): 6807-6814 (1992).
UniProt accession No. Q325A2 "Subname: Full=Acyl-CoA thioesterase I" (2005).
Vadali et al., "Cofactor engineering of intracellular CoA/acetyl-CoA and its effect on metabolic flux redistribution in *Escherichia coli*" *Metabolic Engineering 6*: 133-139 (2004).
Van Den Berg et al., "The FadL family: unusual transporters for unusual substrates", *Curr.Opin.Struct.Biol. 15*: 401-407 (2005).
Vanderhoeven et al., "Biosynthesis and Elongation of Short- and Medium-Chain-Length Fatty Acids", *Plant Physiology 122*: 275-282 (2000).
Voelker et al. "Alteration of the Specificity and Regulation of Fatty Acid Synthesis of *Escherichia coli* by Expression of a Plant Medium-Chain Acyl-Acyl Carrier Protein Thioesterase," *J. Bacteriol.*, 176(23): 7320-7327 (1994).
Wang et al., "Functional Replacement of the FabA and FabB Proteins of *Escherichia coli* Fatty Acid Synthesis by *Enterococcus faecalis*FabZ and FabF Homologues", *J.Biol.Chem.279*(33): 34489-34495 (2004).
White et al., "Carboxylic acid reductase: a new tungsten enzyme catalyzes the reduction of non-activated carboxylic acids to aldehydes", *Eur. J. Biochem. 184*: 89-96 (1989).
Xu et al., "The FadRzDNA Complex. Transcriptional Control of Fatty Acid Metabolism in *Escherichia coli*", *J.Biol.Chem.276*(20): 17373-17379, 2001.
Yoo et al., "Determination of the native form of FadD, the *Escherichia coli* fatty acyl-CoA synthetase, and characterization of limited proteolysis by outer membrane protease OmpT", *Biochem. J. 360*: 699-706 (2001).

(56) References Cited

OTHER PUBLICATIONS

Zhang, et al. "The FabR (YijC) Transcription Factor Regulates Unsaturated Fatty Acid Biosynthesis in *Escherichia coli*," *J. Biol. Chem.*, 277(18): 15558-15565 (2002).
Zhang et al., "Inhibiting Bacterial Fatty Acid Synthesis", *J.Biol. Chem.* 281(26): 17541-17544 (2006).
Zhang et al., "Structural Basis for Catalytic and Inhibitory Mechanisms of β-Hydroxyacyl-acyl Carrier Protein Dehydratase (FabZ)", *J.Biol.Chem.* 283(9):5370-5379 (2008).
Zhang, et al. "Molecular effect of FadD on the regulation and metabolism of fatty acid in *Escherichia coli*," *FEMS Microbiol. Lett.*, 259(2): 249-253 (2006).
Zhu et al., "Functions of the *Clostridium acetobutylicium* FabF and FabZ proteins in unsaturated fatty acid biosynthesis", *BMC Microbiology* 9:119 (2009).
Zimhony et al., "Characterization of *Mycobacterium smegmatis* Expressing the *Mycobacterium tuberculosis* Fatty Acid Synthase I *(fas1)* Gene", *J.Bacteriol.* 186(13): 4051-4055 (2004).
International Search Report and Written Opinion from PCT/US2007/003736, mailed Aug. 24, 2007.
International Search Report and Written Opinion from PCT/US2008/058788, mailed Jan. 27, 2009.
International Search Report and Written Opinion from PCT/US2009/004734, mailed Nov. 17, 2009.
International Search Report and Written Opinion from PCT/US2009/054213, mailed Oct. 6, 2009.
International Search Report and Written Opinion from PCT/US2009/059903, mailed Jun. 2, 2010.
International Search Report and Written Opinion from PCT/US2009/059904, mailed Apr. 5, 2010.
International Search Report and Written Opinion from PCT/US2010/050024, mailed Jan. 27, 2011.
International Search Report and Written Opinion from PCT/US2010/050026, mailed Jan. 6, 2011.
Partial International Search Report from the International Search Authority of the European Patent Office, for PCT/US2008/058788, mailed May 11, 2009.
James et al., "Expression of Two *Escherichia coli* Acetyl-CoA Carboxylase Subunits is Autoregulated," *J. Biol. Chem.*, 279(4): 2520-2527 (2004).
Jiang et al., "Inhibition of Fatty Acid Synthesis in *Escherichia coli* in the Absence of Phospholipid Synthesis and Release of Inhibition by Thioesterase Action," *J. Bacteriology*, 176(10): 2814-2821 (1994).
Kalscheuer et al., "A Novel Bifunctional Wax Ester Synthase/Acyl-CoA: Diacylglycerol Acyltransferase Mediates Wax Ester & Triacylglycerol Biosynthesis in *Acinetobacter calcoaceticus* ADP1," *J. Biol. Chem.*, 278(10): 8075-8082 (2003).
Kalscheuer et al., "Neutral Lipid Biosynthesis in Engineered *Escherichia coli*: Jojoba Oil-Like Wax Esters and Fatty Acid Butyl Esters," *Applied and Environmental Microbiology*, 72(2): 1373-1379 (2006).
Kalscheuer et al., "Microdiesel: *Escherichia coli* Engineered for Fuel Production," *Microbiology*, 152(9): 2529-2536 (2006).
Lardizabal et al., "Purification of a Jojoba Embryo Wax Synthase, Cloning of its cDNA, & Production of High Levels of Wax in Seeds of Transgenic *Arabidopsis*," *Plant Physiology*, 122(3): 645-655 (2000).
Lykidis et al., "Genomic Prospecting for Microbial Biodiesel Production," *LBLN-301E*, No. 10: 1-39 (2008).
Morgan-Kiss et al., "The *Escherichia coli* fadK (ydiD) Gene Encodes an Anerobically Regulated Short Chain Acyl-CoA Synthetase," *J. Biol. Chem.*, 279(36): 37324-37333 (2004).
Qiu et al., "Metabolic Engineering of *Aeromonas hydrophila* for the Enhanced Production of Poly(3-hydroxybutyrate-co-3-hydroxyhexanoate)," *Applied Microbiology & Biotechnology*, 69(5): 537-542 (2006).
Voelker et al., "Alteration of the Specificity and Regulation of Fatty Acid Synthesis of *Escherichia coli* by Expression of a Plant Medium-Chain Acyl-Acyl Carrier Protein Thioesterase," *J. Bacteriology, Am. Soc. for Microbiology*, 176(23): 7320-7327 (1994).
Wu et al., "Studies of Biosynthesis of Waxes by Developing Jojoba Seed: III. Biosynthesis of Wax Esters from Acyl CoA and Long Chain Alcohols," *Lipids*, 16(12): 897-902 (1981).
Zhang et al., "Molecular Effect of FadD on the Regulation and Metabolism of Fatty Acid in *Escherichia coli*," *FEMS Microbiology Letters*, 259(2): 249-253 (2006).
European Patent Office, International Search Report and Written Opinion with respect to PCT/US2007/011923 (Feb. 22, 2008).
European Patent Office, International Search Report and Written Opinion with respect to PCT/US2008/058788 (Jan. 27, 2009).

\* cited by examiner

Fig. 1

*Accession Numbers are from NCBI, GenBank, Release 159.0 as of April 15, 2007*
*EC Numbers are from KEGG, Release 42.0 as of April 2007 (plus daily updates up to and including the date for this patent)*

| CATEGORY | GENE | NAME | ACCESSION | EC NUMBER | MODIFICATION | USE | ORGANISM |
|---|---|---|---|---|---|---|---|
| 1. Fatty Acid Production Increase / Product Production Increase | | | | | | | |
| *increase acyl-CoA* | | | | | | | |
| *reduce catabolism of derivatives and intermediates* | | | | | | | |
| *reduce feedback inhibition* | | | | | | | |
| *attenuate other pathways that consume fatty acids* | | | | | | | |
| | accA | Acetyl-CoA carboxylase, subunit A (carboxyltransferase alpha) | AAC73296, NP 414727 | 6.4.1.2 | Over-express | increase Malonyl-CoA production | *Escherichia coli, Lactococci* |
| | accB | Acetyl-CoA carboxylase, subunit B (BCCP: biotin carboxyl carrier protein) | NP 417721 | 6.4.1.2 | Over-express | increase Malonyl-CoA production | *Escherichia coli, Lactococci* |
| | accC | Acetyl-CoA carboxylase, subunit C (biotin carboxylase) | NP 417722 | 6.4.1.2, 6.3.4.14 | Over-express | increase Malonyl-CoA production | *Escherichia coli, Lactococci* |
| | accD | Acetyl-CoA carboxylase, subunit D (carboxyltransferase beta) | NP 416819 | 6.4.1.2 | Over-express | increase Malonyl-CoA production | *Escherichia coli, Lactococci* |
| | aceE | pyruvate dehydrogenase, subunit E1 | NP 414656, AAC73226 | 1.2.4.1 | Over-express | increase Acetyl-CoA production | *Escherichia coli* |
| | aceF | pyruvate dehydrogenase, subunit E2 | NP 414657 | 2.3.1.12 | Over-express | increase Acetyl-CoA production | *Escherichia coli* |
| | ackA | acetate kinase | AAC75356, NP 416799 | 2.7.2.1 | Delete or reduce | increase Acetyl-CoA production | *Escherichia coli* |
| | ackB | acetate kinase AckB | BAB81430 | 2.7.2.1 | Delete or reduce | increase Acetyl-CoA production | *Escherichia coli* |

Fig. 1 (cont.)

Accession Numbers are from NCBI, GenBank, Release 159.0 as of April 15, 2007
EC Numbers are from KEGG, Release 42.0 as of April 2007 (plus daily updates up to and including the date for this patent)

| | | | | | |
|---|---|---|---|---|---|
| acpP | acyl carrier protein | AAC74178 | NONE | Over-express | increase Acetyl-CoA production | Escherichia coli |
| fadD | acyl-CoA synthase | AP_002424 | 2.3.1.86, 6.2.1.3 | Over-express | increase Fatty acid production | Escherichia coli W3110 |
| adhE | alcohol dehydrogenase | CAA47743 | 1.1.1.1, 1.2.1.10 | Delete or reduce | increase Acetyl-CoA production | Escherichia coli W3111 |
| cer1 | Aldehyde decarbonylase | BAA11024 | 4.1.99.5 | Over-express | increase Acetyl-CoA production | Arabidopsis thaliana |
| fabA | beta-hydroxydecanoyl thioester dehydrase | NP_415474 | 4.2.1.60 | express | fatty acyl-CoA production | E. coli K12 |
| fabD | [acyl-carrier-protein] S-malonyltransferase | AAC74176 | 2.3.1.39 | Over-express | increase Acetyl-CoA production | E. coli K12 |
| fabF | 3-oxoacyl-[acyl-carrier-protein] synthase II | AAC74179 | 2.3.1.179 | Delete or OverExpress | increase Acetyl-CoA production | E. coli K12 |
| fabG | 3-oxoacyl-[acyl-carrier protein] reductase | AAC74177 | 1.1.1.100 | Over-express | increase Acetyl-CoA production | E. coli K12 |
| fabH | 3-oxoacyl-[acyl-carrier-protein] synthase III | AAC74175 | 2.3.1.180 | Over-express | increase Acetyl-CoA production | E. coli K12, lactococci |
| fabI | enoyl-[acyl-carrier-protein] reductase, NADH-dependent | NP_415804 | 1.3.1.9 | express | fatty acyl-CoA production | E. coli K12, lactococci |
| fabR | Transcriptional Repressor | NP_418398 | NONE | Delete or reduce | modulate unsaturated fatty acid production | E. coli K12 |
| fabZ | (3R)-hydroxymyristol acyl carrier protein dehydratase | NP_414722 | 4.2.1.- | | | |
| fadE | acyl-CoA dehydrogenase | AAC73325 | 1.3.99.3, 1.3.99.- | Delete or reduce | increase Acetyl-CoA production | E. coli K12 |
| acr1 | Fatty Acyl-CoA reductase | YP_047869, AAC45217 | 1.2.1.42 | Over-express | for fatty alcohol production | Acinetobacter sp, i.e. calcoaceticus |
| GST, gshB | Glutathione synthase | P04425 | 6.3.2.3 | Delete or reduce | increase Acyl-CoA | E. coli K12 |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | |
|---|---|---|---|---|---|
| gpsA | biosynthetic sn-glycerol 3-phosphate dehydrogenase | AAC76632, NP_418065 | EC: 1.1.1.94 | Delete or reduce | increase Acetyl-CoA production | E. coli K12 |
| ldhA | lactate dehydrogenase | AAC74462, NP_415898 | EC: 1.1.1.27, 1.1.1.28 | Delete or reduce | increase Acetyl-CoA production | E. coli K12 |
| Lipase | Triglyceride Lipase | CAA89087, CAA98876 | 3.1.1.3 | express | increase Fatty acid production | Saccharomyces cerevisiae |
| | Malonyl-CoA decarboxylase | AAA26500 | 4.1.1.9, 4.1.1.41 | Over-express | | Saccharopolyspora erythraea |
| panD | aspartate 1-decarboxylase | BAB96708 | 4.1.1.11 | Over-express | increase Acyl-CoA | Escherichia coli W3110 |
| panK a.k.a. coaA | pantothenate kinase | AAC76952 | 2.7.1.33 | Over-express | increase Acetyl-CoA production | E. coli |
| panK a.k.a. coaA, R106K | pantothenate kinase | AAC76952 | 2.7.1.33 | Express, Over-express, R106K mutation | increase Acetyl-CoA production | E. coli |
| pdh | Pyruvate dehydrogenase | BAB34380, AAC73226, NP_415392 | 1.2.4.1 | Over-express | increase Acetyl-CoA production | |
| pflB | formate acetyltransferase (pyruvate formate lyase) | AAC73989, P09373 | EC: 2.3.1.54 | Delete or reduce | increase Acetyl-CoA production | |
| plsB | acyltransferase | AAC77011 | 2.3.1.15 | D311E mutation | reduce limits on Acyl-CoA pool | E. coli K12 |
| poxB | pyruvate oxidase | AAC73958, NP_415392 | 1.2.2.2 | Delete or reduce | increase Acetyl-CoA production | |
| pta | phosphotransacetylase | AAC75357, NP_416800 | 2.3.1.8 | Delete or reduce | increase Acetyl-CoA production | |
| udhA | pyridine nucleotide transhydrogenase | CAA46822 | 1.6.1.1 | Over-express | conversion NADH to NADPH or vice versa | |

Fig. 1 (cont.)

Accession Numbers are from NCBI, GenBank, Release 159.0 as of April 15, 2007
EC Numbers are from KEGG, Release 42.0 as of April 2007 (plus daily updates up to and including the date for this patent)

| | | | | | | | |
|---|---|---|---|---|---|---|---|
| | | fadB | fused 3-hydroxybutyryl-CoA epimerase/delta(3)-cis-delta(2)-trans-enoyl-CoA isomerase/enoyl-CoA hydratase and 3-hydroxyacyl-CoA dehydrogenase | AP 003956 | 4.2.1.17, 5.1.2.3, 5.3.3.8, 1.1.1.35 | Delete or reduce | Block fatty acid degradation | E. coli |
| | | fadJ | 3-hydroxyacyl-CoA dehydrogenase; K01692 enoyl-CoA hydratase; K01782 3-hydroxybutyryl-CoA epimerase | AAC75401 | 1.1.1.35, 4.2.1.17, 5.1.2.3 | Delete or reduce | Block fatty acid degradation | E. coli |
| | | fadA | 3-ketoacyl-CoA thiolase | BAE77458 | 2.3.1.16 | Delete or reduce | Block fatty acid degradation | E. coli |
| | | fadI | beta-ketoacyl-CoA thiolase | AAC75402 | 2.3.1.16 | Delete or reduce | Block fatty acid degradation | E. coli |
| | | YdiO | acyl-coA dehydrogenase | YP 852786 | 1.3.99.- | Delete or reduce | Block fatty acid degradation | E. coli |
| 2. Structure Control | | | | | | | | |
| 2A. Chain Length Control | | | | | | | | |
| | 2 | tesA | thioesterase | P0ADA1 | 3.1.2.-, 3.1.1.5 | Delete and/or express | C18 Chain Length | |
| | | tesA without leader sequence | thioesterase | AAC73596, NP 415027 | | express or overexpress | C18:1 | E. coli |
| | | tesA without leader sequence: L109P | thioesterase | P0ADA1 | 3.1.2.-, 3.1.1.5 | Express and/or overexpress mutation L109P | <C18 Chain Length | E. coli |
| | | fatB1 (umbellularia) | thioesterase | Q41635 | 3.1.2.14 | express or overexpress | C12:0 | Umbellularia californica |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | |
|---|---|---|---|---|---|
| fatB2 (umbellul aria)DEL ETE umbelluri a) | thioesterase | AAC49269 | 3.1.2.14 | express or overexpress | C8:0 - C10:0 | *Cuphea hookeriana* |
| fatB3 | thioesterase | AAC72881 | 3.1.2.14 | express or overexpress | C14:0 - C16:0 | *Cuphea hookeriana* |
| fatB (cinnamon um) | thioesterase | Q39473 | 3.1.2.14 | express or overexpress | C14:0 | *Cinnamomum camphora* |
| fatB[M14 1T]* | thioesterase | CAA85388 | 3.1.2.14 | express or overexpress | C16:1 | *Arabidopsis thaliana* |
| fatA1 (Helianthu s) | thioesterase | AAL79361 | 3.1.2.14 | express or overexpress | C18:1 | *Helianthus annuus* |
| atfata (ARABID OPSIS FATA ACYL- ACP THIOEST ERASE) | thioesterase | NP_189147, NP_193041 | | express or overexpress | C18:1 | *Arabidopsis thaliana* |
| fatA | thioesterase | CAC39106 | 3.1.2.14 | express or overexpress | C18:1 | *Brassica juncea* |
| fatA (cuphea) | thioesterase | AAC72883 | 3.1.2.14 | express or overexpress | C18:1 | *Cuphea hookeriana* |

2B. Branching Control

| | |
|---|---|
| attenuate FabH | |

Fig. 1 (cont.)

Accession Numbers are from NCBI, GenBank, Release 159.0 as of April 15, 2007
EC Numbers are from KEGG, Release 42.0 as of April 2007 (plus daily updates up to and including the date for this patent)

| | | | | | | |
|---|---|---|---|---|---|---|
| express FabH from S. glaucescens or S. coelicolor and knock out endogenous use FabH | | | | | increase branched chain fatty acid derivatives | |
| express FabH from B. subtilis and knock out endogenous use FabH | | | | | | |
| bdk - E3 - dihydrolipoyl dehydrogenase subunit | | | EC 1.2.4.4 | | | |
| | bkd - E1 - alpha/beta subunit | decarboxylase subunits of branched-chain a-ketoacid dehydrogenase complex | | EC 1.2.4.4 | | |
| | bkd - E2 - dihydrolipoyl transacylase subunit | | | EC 1.2.4.4 | | |
| bkdA1 | | branched-chain a-ketoacid dehydrogenase a-subunit (E1a) | NP_628006 | EC 1.2.4.4 | express or Over-Express | make branched-chain acyl-CoA precursors | Streptomyces coelicolor |
| bkdB1 | | branched-chain a-ketoacid dehydrogenase a-subunit | NP_628005 | EC 1.2.4.4 | express or Over-Express | make branched-chain acyl-CoA | Streptomyces coelicolor |

Fig. 1 (cont.)

Accession Numbers are from NCBI, GenBank, Release 159.0 as of April 15, 2007
EC Numbers are from KEGG, Release 42.0 as of April 2007 (plus daily updates up to and including the date for this patent)

| | (E1b) | | | | precursors | |
|---|---|---|---|---|---|---|
| bkdC1 | dihydrolipoyl transacetylase (E2) | NP_628004 | EC 2.3.1.168 | express or Over-Express | make branched-chain acyl-CoA precursors | Streptomyces coelicolor |
| bkdA2 | branched-chain a-ketoacid dehydrogenase a-subunit (E1a) | NP_733618 | EC 1.2.4.4 | express or Over-Express | make branched-chain acyl-CoA precursors | Streptomyces coelicolor |
| bkdB2 | branched-chain a-ketoacid dehydrogenase b-subunit (E1b) | NP_628019 | EC 1.2.4.4 | express or Over-Express | make branched-chain acyl-CoA precursors | Streptomyces coelicolor |
| bkdC2 | dihydrolipoyl transacetylase (E2) | NP_628018 | EC 2.3.1.168 | express or Over-Express | make branched-chain acyl-CoA precursors | Streptomyces coelicolor |
| bkdA | branched-chain a-ketoacid dehydrogenase a-subunit (E1a) | BAC72074 | EC 1.2.4.4 | express or Over-Express | make branched-chain acyl-CoA precursors | Streptomyces avermitilis |
| bkdB | branched-chain a-ketoacid dehydrogenase b-subunit (E1b) | BAC72075 | EC 1.2.4.4 | express or Over-Express | make branched-chain acyl-CoA precursors | Streptomyces avermitilis |
| bkdC | dihydrolipoyl transacetylase (E2) | BAC72076 | EC 2.3.1.168 | express or Over-Express | make branched-chain acyl-CoA precursors | Streptomyces avermitilis |
| bkdF | branched-chain a-ketoacid dehydrogenase a-subunit (E1a) | BAC72088 | EC 1.2.4.4 | express or Over-Express | make branched-chain acyl-CoA precursors | Streptomyces avermitilis |
| bkdG | branched-chain a-ketoacid dehydrogenase b-subunit (E1b) | BAC72089 | EC 1.2.4.4 | express or Over-Express | make branched-chain acyl-CoA precursors | Streptomyces avermitilis |
| bkdH | dihydrolipoyl transacetylase (E2) | BAC72090 | EC 2.3.1.168 | express or Over-Express | make branched-chain acyl-CoA precursors | Streptomyces avermitilis |
| bkdAA | branched-chain a-ketoacid dehydrogenase a-subunit (E1a) | NP_390285 | EC 1.2.4.4 | express or Over-Express | make branched-chain acyl-CoA precursors | Bacillus subtilis |
| bkdAB | branched-chain a-ketoacid dehydrogenase b-subunit (E1b) | NP_390284 | EC 1.2.4.4 | express or Over-Express | make branched-chain acyl-CoA precursors | Bacillus subtilis |

Fig. 1 (cont.)
*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | precursors | |
|---|---|---|---|---|---|---|
| | bkdB | dihydrolipoyl transacetylase (E2) | NP_390283 | EC 2.3.1.168 | express or Over-Express | make branched-chain acyl-CoA precursors | *Bacillus subtilis* |
| | bkdA1 | branched-chain a-ketoacid dehydrogenase a-subunit (E1a) | AAA65614 | EC 1.2.4.4 | express or Over-Express | make branched-chain acyl-CoA precursors | *Pseudomonas putida* |
| | bkdA2 | branched-chain a-ketoacid dehydrogenase b-subunit (E1b) | AAA65615 | EC 1.2.4.4 | express or Over-Express | make branched-chain acyl-CoA precursors | *Pseudomonas putida* |
| | bkdC | dihydrolipoyl transacetylase (E2) | AAA65617 | EC 2.3.1.168 | express or Over-Express | make branched-chain acyl-CoA precursors | *Pseudomonas putida* |
| | lpd | dihydrolipoamide dehydrogenase (E3) | NP_414658 | 1.8.1.4 | express or Over-Express | make branched-chain acyl-CoA precursors | *Escherichia coli* |
| | IlvE | branched-chain amino acid aminotransferase | YP_026247 | 2.6.1.42 | express or Over-Express | make branched a-ketoacids | *Escherichia coli* |
| | IlvE | branched-chain amino acid aminotransferase | AAF34406 | 2.6.1.42 | express or Over-Express | make branched a-ketoacids | *Lactococcus lactis* |
| | IlvE | branched-chain amino acid aminotransferase | NP_745648 | 2.6.1.42 | express or Over-Express | make branched a-ketoacids | *Pseudomonas putida* |
| | IlvE | branched-chain amino acid aminotransferase | NP_629657 | 2.6.1.42 | express or Over-Express | make branched a-ketoacids | *Streptomyces coelicolor* |
| | ccr | crotonyl-CoA reductase | NP_630556 | 1.6.5.5.1.1.1.1 | express or Over-Express | Converting crotonyl-CoA to butyryl-CoA | *Streptomyces coelicolor* |
| | ccr | crotonyl-CoA reductase | AAD53915 | 1.6.5.5.1.1.1.1 | express or Over-Express | Converting crotonyl-CoA to butyryl-CoA | *Streptomyces cinnamonensis* |
| | IcmA, isobutyryl-CoA mutase | isobutyryl-CoA mutase, subunit A | NP_629554 | 5.4.99.2 | express or Over-Express | converting butyryl-CoA to isobutyryl-CoA | *Streptomyces coelicolor* |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | |
|---|---|---|---|---|---|
| IcmA, isobutyryl-CoA mutase | isobutyryl-CoA mutase, subunit A | AAC08713 | 5.4.99.2 | express or Over-Express | converting butyryl-CoA to isobutyryl-CoA | *Streptomyces cinnamonensis* |
| IcmB, isobutyryl-CoA mutase | isobutyryl-CoA mutase, subunit B | NP 630904 | 5.4.99.2 | express or Over-Express | converting butyryl-CoA to isobutyryl-CoA | *Streptomyces coelicolor* |
| IcmB, isobutyryl-CoA mutase | isobutyryl-CoA mutase, subunit B | CAB59633 | 5.4.99.2 | express or Over-Express | converting butyryl-CoA to isobutyryl-CoA | *Streptomyces cinnamonensis* |
| FabH, ACPs and fabF genes with specificity for branched chain acyl-CoAs | | | | | | |
| IlvE | branched-chain amino acid aminotransferase | CAC12788 | EC2.6.1.42 | over express | branched chain amino acid amino transferase | *Staphylococcus carnosus* |
| FabH1 | beta-ketoacyl-ACP synthase III | NP 626634 | 2.3.1.180 | express or Over-Express | initiation of branched-chain fatty acid biosynthesis | *Streptomyces coelicolor* |
| ACP | acyl-carrier protein | NP 626635 | NONE | | initiation and elongation of branched-chain fatty acid biosynthesis | *Streptomyces coelicolor* |
| FabF | beta-ketoacyl-ACP synthase II | NP 626636 | 2.3.1.179 | express or Over-Express | elongation of branched-chain fatty acid biosynthesis | *Streptomyces coelicolor* |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | |
|---|---|---|---|---|---|
| FabH3 | beta-ketoacyl-ACP synthase III | NP_823466 | 2.3.1.180 | express or Over-Express | initiation of branched-chain fatty acid biosynthesis | *Streptomyces avermitilis* |
| FabC3 (ACP) | acyl-carrier protein | NP_823467 | NONE | express or Over-Express | initiation and elongation of branched-chain fatty acid biosynthesis | *Streptomyces avermitilis* |
| FabF | beta-ketoacyl-ACP synthase II | NP_823468 | 2.3.1.179 | express or Over-Express | elongation of branched-chain fatty acid biosynthesis | *Streptomyces avermitilis* |
| FabH_A | beta-ketoacyl-ACP synthase III | NP_389015 | 2.3.1.180 | express or Over-Express | initiation of branched-chain fatty acid biosynthesis | *Bacillus subtilis* |
| FabH_B | beta-ketoacyl-ACP synthase III | NP_388898 | 2.3.1.180 | express or Over-Express | initiation of branched-chain fatty acid biosynthesis | *Bacillus subtilis* |
| ACP | acyl-carrier protein | NP_389474 | NONE | express or Over-Express | initiation and elongation of branched-chain fatty acid biosynthesis | *Bacillus subtilis* |
| FabF | beta-ketoacyl-ACP synthase II | NP_389016 | 2.3.1.179 | express or Over-Express | elongation of branched-chain fatty acid biosynthesis | *Bacillus subtilis* |
| SmalDRA FT_0818 | beta-ketoacyl-ACP synthase III | ZP_01643059 | 2.3.1.180 | express or Over-Express | initiation of branched-chain fatty acid biosynthesis | *Stenotrophomonas maltophilia* |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | | | |
|---|---|---|---|---|---|---|---|
| | SmaIDRA FT_0821 | acyl-carrier protein | ZP_01643063 | NONE | express or Over-Express | initiation and elongation of branched-chain fatty acid biosynthesis | *Stenotrophomonas maltophilia* |
| | SmaIDRA FT_0822 | beta-ketoacyl-ACP synthase II | ZP_01643064 | 2.3.1.179 | express or Over-Express | elongation of branched-chain fatty acid biosynthesis | *Stenotrophomonas maltophilia* |
| | FabH | beta-ketoacyl-ACP synthase III | YP_123672 | 2.3.1.180 | express or Over-Express | initiation of branched-chain fatty acid biosynthesis | *Legionella pneumophila* |
| | ACP | acyl-carrier protein | YP_123675 | NONE | express or Over-Express | initiation and elongation of branched-chain fatty acid biosynthesis | *Legionella pneumophila* |
| | FabF | beta-ketoacyl-ACP synthase II | YP_123676 | 2.3.1.179 | express or Over-Express | elongation of branched-chain fatty acid biosynthesis | *Legionella pneumophila* |
| | FabH | beta-ketoacyl-ACP synthase III | NP_415609 | 2.3.1.180 | delete or reduce | initiation of branched-chain fatty acid biosynthesis | *Escherichia coli* |
| | FabF | beta-ketoacyl-ACP synthase II | NP_415613 | 2.3.1.179 | delete or reduce | elongation of branched-chain fatty acid biosynthesis | *Escherichia coli* |
| *To Produce Cyclic Fatty Acids* | | | | | | | |
| | AnsJ | dehydratase (putative) | not available | not available | express or Over-Express | cyclohexylcarbonyl-CoA boiosynthesis | *Streptomyces collinus* |
| | AnsK | CoA ligase (putative) | not available | not available | express or Over-Express | cyclohexylcarbonyl-CoA boiosynthesis | *Streptomyces collinus* |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | |
|---|---|---|---|---|---|
| AnsL | dehydrogenase (putative) | not available | not available | express or Over-Express | cyclohexylcarbonyl-CoA boiosynthesis | *Streptomyces collinus* |
| ChcA | enoyl-CoA reductase | U72144 | EC 1.3.1.34 | express or Over-Express | cyclohexylcarbonyl-CoA boiosynthesis | *Streptomyces collinus* |
| AnsM | oxidorecutase (putative) | not available | not available | express or Over-Express | cyclohexylcarbonyl-CoA boiosynthesis | *Streptomyces collinus* |
| PlmJ | dehydratase (putative) | AAQ84158 | not available | express or Over-Express | cyclohexylcarbonyl-CoA boiosynthesis | *Streptomyces sp. HK803* |
| PlmK | CoA ligase (putative) | AAQ84158 | not available | express or Over-Express | cyclohexylcarbonyl-CoA boiosynthesis | *Streptomyces sp. HK803* |
| PlmL | dehydrogenase (putative) | AAQ84159 | not available | express or Over-Express | cyclohexylcarbonyl-CoA boiosynthesis | *Streptomyces sp. HK803* |
| ChcA | enoyl-CoA reductase | AAQ84160 | EC 1.3.1.34 | express or Over-Express | cyclohexylcarbonyl-CoA boiosynthesis | *Streptomyces sp. HK803* |
| PlmM | oxidorecutase (putative) | AAQ84161 | not available | express or Over-Express | cyclohexylcarbonyl-CoA boiosynthesis | *Streptomyces sp. HK803* |
| ChcB | enoyl-CoA isomerase | AF268489 | not available | express or Over-Express | cyclohexylcarbonyl-CoA boiosynthesis | *Streptomyces collinus* |
| ChcB/CaiD | enoyl-CoA isomerase | NP 629292 | 4.2.1.- | express or Over-Express | cyclohexylcarbonyl-CoA boiosynthesis | *Streptomyces coelicolor* |
| ChcB/CaiD | enoyl-CoA isomerase | NP 824296 | 4.2.1.- | express or Over-Express | cyclohexylcarbonyl-CoA boiosynthesis | *Streptomyces avermitilis* |

2C. Saturation Level Control

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | |
|---|---|---|---|---|---|
| Sfa | Suppressor of FabA | AAN79592, AAC44390 | NONE | Over-express | increase monounsaturated fatty acids | E.coli |
| also see FabA in sec. 1 | | | | express | produce unsaturated fatty acids | |
| GnsA | suppressors of the secG null mutation | ABD18647.1 | NONE | Over-express | increase unsaturated fatty acid esters | E.coli |
| GnsB | suppressors of the secG null mutation | AAC74076.1 | NONE | Over-express | increase unsaturated fatty acid esters | E.coli |
| also see section 2A - items with :0 are unsaturated (no double bonds) and with :1 are saturated (1 double bond) | | | | | | |
| fabB | 3-oxoacyl-[acyl-carrier-protein] synthase I | BAA16180 | EC:2.3.1.41 | overexpress | modulate unsaturated fatty acid production | Escherichia coli |
| fabK | trans-2-enoyl-ACP reductase II | AAF98273 | 1.3.1.9 | express | modulate unsaturated fatty acid production | Streptococcus pneumoniae |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | | |
|---|---|---|---|---|---|---|
| | fabI | enoyl-(acyl carrier protein) reductase | AAU39821 | 1.3.1.9 | express | modulate unsaturated fatty acid production | *Bacillus licheniformis* DSM 13 |
| | fabM | trans-2, cis-3-decenoyl-ACP isomerase | DAA05501 | 4.2.1.17 | Over-express | modulate unsaturated fatty acid production | *Streptococcus mutans* |
| 3. Final Product Output | | | | | | | |
| 3A. Wax Output | | | | | | | |
| | AT3G51970 | long-chain-alcohol O-fatty-acyltransferase | NP_190765 | 2.3.1.26 | express | wax production | *Arabidopsis thaliana* |
| | | thioesterase (see chain length control section) | | | express | increase fatty acid production | |
| | | fatty alcohol forming acyl-CoA reductase | | 1.1.1.* | express | convert acyl-coa to fatty alcohol | |
| | acr1 | acyl-CoA reductase (ACR1) | YP_047869 | 1.2.1.42 | express | convert acyl-coa to fatty alcohol | *Acinetobacter sp.* ADP1 |
| | yqhD | alcohol dehydrogenase | AP_003562 | 1.1.-.- | express | increase | *E. coli* W3110 |
| | ELO1 | Fatty acid elongase | BAD98251 | 2.3.1.- | express | produce very long chain length fatty acids | *Pichia angusta* |
| | plsC | acyltransferase | AAA16514 | 2.3.1.51 | express | | *Saccharomyces cerevisiae* |
| | DAGAT/DGAT | diacylglycerol acyltransferase | AAF19262 | 2.3.1.20 | express | wax production | *Arabidopsis thaliana* |
| | hWS | acyl-CoA wax alcohol acyltransferase | AAX48018 | 2.3.1.20 | express | wax production | *Homo sapiens* |
| | aft1 | bifunctional wax ester synthase/acyl-CoA:diacylglycerol acyltransferase | AAO17391 | 2.3.1.20, 2.3.1.75 | express | wax production | *Acinetobacter sp.* ADP1 |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | mWS | wax ester synthase (simmondsia) | AAD38041 | 2.3.1.-, 2.3.1.75 | express | | Simmondsia chinensis |
|---|---|---|---|---|---|---|---|
| 3B. Fatty Alcohol Output | | | | | | | |
| | | various thioesterases (refer to Sec. 2A) | | | | | |
| | acr1 | acyl-CoA reductase | YP_047869 | 1.2.1.42 | express | produce | Acinetobacter sp. ADP1 |
| | yqhD | alcohol dehydrogenase | AP_003562 | 1.1.-.- | express | produce | Escherichia coli W3110 |
| | BmFAR | FAR (fatty alcohol forming acyl-CoA reductase) | BAC79425 | 1.1.1.* | express | reduce fatty acyl-CoA to fatty alcohol | Bombyx mori |
| | Akr1a4 | Mammalian microsomal aldehyde reductase | NP_067448 | 1.1.12 | express | produce | Mus musculus |
| | GTNG_1865 | Long-chain aldehyde dehydrogenase | YP_001125970 | 1.2.1.3 | express | produce | Geobacillus thermodenitrificans NG80-2 |
| | FadD | acyl-CoA synthase | NP_416319 | EC 6.2.1.3 | express | produce more | E. Coli K12 |
| To make Butanol | | | | | | | |
| | atoB | acetyl-CoA acetyltransferase | YP_049388 | 2.3.1.9 | express | produce | Erwinia carotovora |
| | hbd | Beta-hydroxybutyryl-CoA dehydrogenase | BAD51424 | 1.1.1.157 | express | produce | Butyrivibrio fibrisolvens |
| | CPE0095 | crotonase | BAB79801 | 4.2.1.55 | express | produce | Clostridium perfringens |
| | bcd | butyryl-CoA dehydrogenase | AAM14583 | 1.3.99.2 | express | produce | Clostridium beijerinckii |
| | ALDH | coenzyme A-acylating aldehyde dehydrogenase | AAT66436 | 1.2.1.3 | express | produce | Clostridium beijerinckii |
| | AdhE | aldehyde-alcohol dehydrogenase | AAN80172 | 1.1.1.1 1.2.1.10 | express | produce | Escherichia coli CFT073 |

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| 3C. Fatty Acid Ester Output | | | | | | |
|---|---|---|---|---|---|---|
| | thioestera se | see chain length control section | | | | |
| | acr1 | acyl-CoA reductase | YP_047869 | 1.2.1.42 | express | produce | Acinetobacter sp. ADP1 |
| | yqhD | alcohol dehydrogenase | AP_003562 | 1.1.-.- | express | produce | E. Coli K12 |
| | AAT | alcohol O-acetyltransferase | AAG13130 | 2.3.1.84 | express | produce | Fragaria x ananassa |
| 4. Export | | | | | | |
| | Wax ester exporter (FATP family, Fatty Acid (long chain) Transport Protein) | | NP_524723 | NONE | express | export wax | Drosophila melanogaster |
| | ABC transport protein | putative alkane transporter | AAN73268 | NONE | express | export products | Rhodococcus erythropolis |
| | CER5 | wax transporter | At1g51500, AY734542, At3g21090, At1g51460 | NONE | express | export products | Arabidopsis thaliana |
| | AtMRP5 | Arabidopsis thaliana multidrug resistance-associated | NP_171908 | NONE | express | export products | Arabidopsis thaliana |
| | AmiS2 | ABC transporter AmiS2 | JC5491 | NONE | express | export products | Rhodococcus sp. |
| | AtPGP1 | ARABIDOPSIS THALIANA P GLYCOPROTEIN1 | NP_181228 | NONE | express | export products | Arabidopsis thaliana |

Fig. 1 (cont.)

Accession Numbers are from NCBI, GenBank, Release 159.0 as of April 15, 2007
EC Numbers are from KEGG, Release 42.0 as of April 2007 (plus daily updates up to and including the date for this patent)

| | | | | | |
|---|---|---|---|---|---|
| | AcrA | putative multidrug-efflux transport protein acrA | CAF23274 | NONE | express | export products | Candidatus Protochlamydia amoebophila UWE25 |
| | AcrB | probable multidrug-efflux transport protein, acrB | CAF23275 | NONE | express | export products | Candidatus Protochlamydia amoebophila UWE25 |
| | TolC | Outer membrane protein [Cell envelope biogenesis, transmembrane protein affects septum formation and cell membrane permeability | ABD59001 | NONE | express | export products | Francisella tularensis subsp. novicida |
| | AcrE | Acriflavine resistance protein | YP_312213 | NONE | express | export products | Shigella sonnei Ss046 |
| | AcrF | | P24181 | NONE | express | export products | Escherichia coli |
| | tll1618 | multidrug efflux transporter | NP_682408.1 | NONE | express

Fig. 1 (cont.)

*Accession Numbers are from NCBI, GenBank, Release 159.0 as of April 15, 2007*
*EC Numbers are from KEGG, Release 42.0 as of April 2007 (plus daily updates up to and including the date for this patent)*

| | | | | | |
|---|---|---|---|---|---|
| | umuC | DNA polymerase V, subunit | ABC42261 | 2.7.7.7 | | | |
| | NADH:NADPH transhydrogenase (alpha and beta subunits) (pntA, pntB) | | | | Over-express | increase output efficiency | *Escherichia coli* |
| | | | P07001, P0AB70 | 1.6.1.2 | express | increase output efficiency | *Shigella flexneri* |

Concentrations of free fatty acids (FFA) and fatty acid ethyl esters (FAEE) produced from three individual colonies of C41 (DE3, ΔfadEΔfabR)/ pETDuet-1-tesA + pCDFDuet-1-fadD +pHZ1.97_atfA2 t

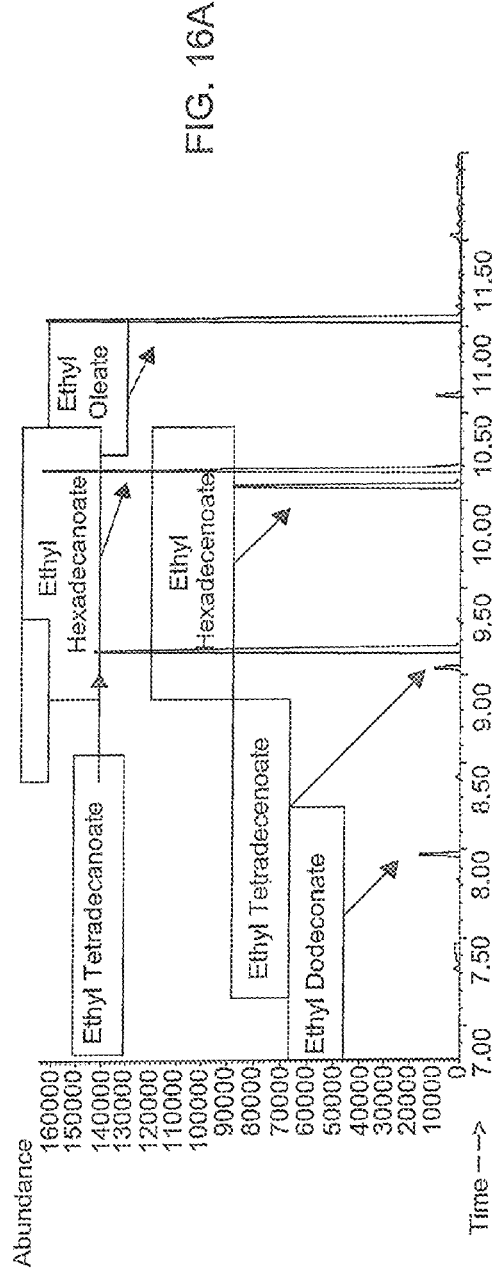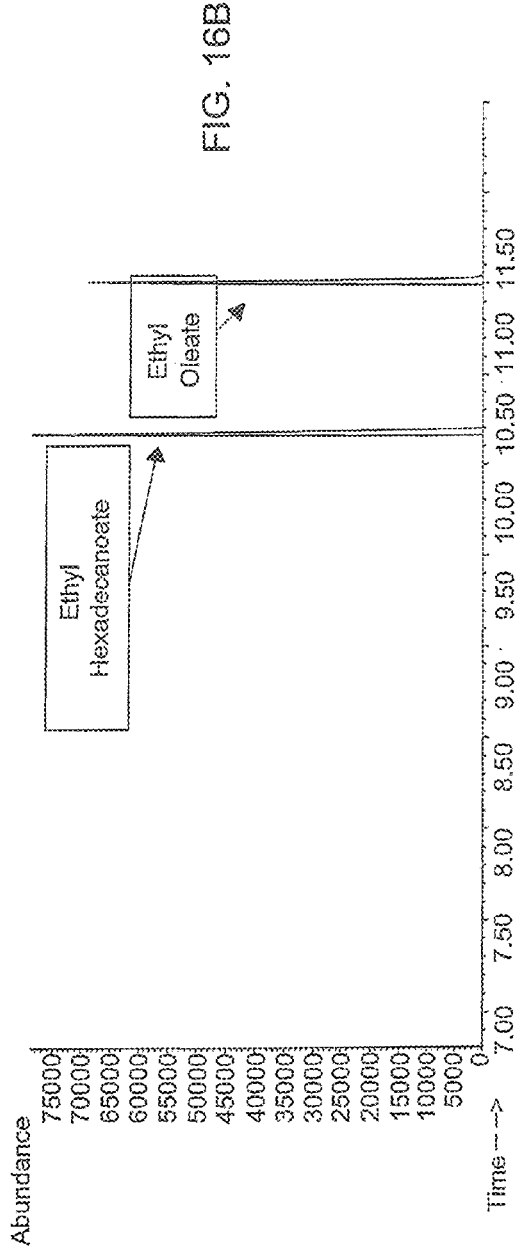

Figure 18

SEQ ID NO: 1 – DNA sequence of expression vector pOP-80.

CACTATACCAATTGAGATGGGCTAGTCAATGATAATTACTAGTCCTTTTCCTTTGAGT
TGTGGGTATCTGTAAATTCTGCTAGACCTTTGCTGGAAAACTTGTAAATTCTGCTAG
ACCCTCTGTAAATTCCGCTAGACCTTTGTGTGTTTTTTTTGTTTATATTCAAGTGGTTA
TAATTTATAGAATAAAGAAAGAATAAAAAAAGATAAAAAGAATAGATCCCAGCCCT
GTGTATAACTCACTACTTTAGTCAGTTCCGCAGTATTACAAAAGGATGTCGCAAACG
CTGTTTGCTCCTCTACAAAACAGACCTTAAAACCCTAAAGGCGTCGGCATCCGCTTA
CAGACAAGCTGTGACCGTCTCCGGGAGCTGCATGTGTCAGAGGTTTTCACCGTCATC
ACCGAAACGCGCGAGGCAGCAGATCAATTCGCGCGCGAAGGCGAAGCGGCATGCA
TTTACGTTGACACCATCGAATGGTGCAAAACCTTTCGCGGTATGGCATGATAGCGCC
CGGAAGAGAGTCAATTCAGGGTGGTGAATGTGAAACCAGTAACGTTATACGATGTC
GCAGAGTATGCCGGTGTCTCTTATCAGACCGTTTCCCGCGTGGTGAACCAGGCCAGC
CACGTTTCTGCGAAAACGCGGGAAAAAGTGGAAGCGGCGATGGCGGAGCTGAATTA
CATTCCCAACCGCGTGGCACAACAACTGGCGGGCAAACAGTCGTTGCTGATTGGCG
TTGCCACCTCCAGTCTGGCCCTGCACGCGCCGTCGCAAATTGTCGCGGCGATTAAAT
CTCGCGCCGATCAACTGGGTGCCAGCGTGGTGGTGTCGATGGTAGAACGAAGCGGC
GTCGAAGCCTGTAAAGCGGCGGTGCACAATCTTCTCGCGCAACGCGTCAGTGGGCT
GATCATTAACTATCCGCTGGATGACCAGGATGCCATTGCTGTGGAAGCTGCCTGCAC
TAATGTTCCGGCGTTATTTCTTGATGTCTCTGACCAGACACCCATCAACAGTATTATT
TTCTCCCATGAAGACGGTACGCGACTGGGCGTGGAGCATCTGGTCGCATTGGGTCAC
CAGCAAATCGCGCTGTTAGCGGGCCCATTAAGTTCTGTCTCGGCGCGTCTGCGTCTG
GCTGGCTGGCATAAATATCTCACTCGCAATCAAATTCAGCCGATAGCGGAACGGGA
AGGCGACTGGAGTGCCATGTCCGGTTTTCAACAAACCATGCAAATGCTGAATGAGG
GCATCGTTCCCACTGCGATGCTGGTTGCCAACGATCAGATGGCGCTGGGCGCAATGC
GCGCCATTACCGAGTCCGGGCTGCGCGTTGGTGCGGATATCTCGGTAGTGGGATACG
ACGATACCGAAGACAGCTCATGTTATATCCCGCCGTTAACCACCATCAAACAGGATT
TTCGCCTGCTGGGGCAAACCAGCGTGGACCGCTTGCTGCAACTCTCTCAGGGCCAGG
CGGTGAAGGGCAATCAGCTGTTGCCCGTCTCACTGGTGAAAAGAAAAACCACCCTG
GCGCCCAATACGCAAACCGCCTCTCCCCGCGCGTTGGCCGATTCATTAATGCAGCTG
GCACGACAGGTTTCCCGACTGGAAAGCGGGCAGTGAGCGCAACGCAATTAATGTAA
GTTAGCGCGAATTGATCTGGTTTGACAGCTTATCATCGACTGCACGGTGCACCAATG
CTTCTGGCGTCAGGCAGCCATCGGAAGCTGTGGTATGGCTGTGCAGGTCGTAAATCA
CTGCATAATTCGTGTCGCTCAAGGCGCACTCCCGTTCTGGATAATGTTTTTGCGCCG
ACATCATAACGGTTCTGGCAAATATTCTGAAATGAGCTGTTGACAATTAATCATCCG
GCTCGTATAATGTGTGGAATTGTGAGCGGATAACAATTTCACACAGGAAACAGCGC
CGCTGAGAAAAAGCGAAGCGGCACTGCTCTTTAACAATTTATCAGACAATCTGTGTG
GGCACTCGACCGGAATTATCGATTAACTTTATTATTAAAAATTAAAGAGGTATATAT
TAATGTATCGATTAAATAAGGAGGAATAAACCATGGATCCGAGCTCGAGATCTGCA
GCTGGTACCATATGGGAATTCGAAGCTTGGGCCCGAACAAAAACTCATCTCAGAAG
AGGATCTGAATAGCGCCGTCGACCATCATCATCATCATCATTGAGTTTAAACGGTCT
CCAGCTTGGCTGTTTTGGCGGATGAGAGAAGATTTTCAGCCTGATACAGATTAAATC
AGAACGCAGAAGCGGTCTGATAAAACAGAATTTGCCTGGCGGCAGTAGCGCGGTGG

Figure 18 (cont).

```
TCCCACCTGACCCCATGCCGAACTCAGAAGTGAAACGCCGTAGCGCCGATGGTAGT
GTGGGGTCTCCCCATGCGAGAGTAGGGAACTGCCAGGCATCAAATAAAACGAAAGG
CTCAGTCGAAAGACTGGGCCTTTCGTTTTATCTGTTGTTTGTCGGTGAACGCTCCT
GACGCCTGATGCGGTATTTTCTCCTTACGCATCTGTGCGGTATTTCACACCGCATATG
GTGCACTCTCAGTACAATCTGCTCTGATGCCGCATAGTTAAGCCAGCCCCGACACCC
GCCAACACCCGCTGACGAGCTTAGTAAAGCCCTCGCTAGATTTTAATGCGGATGTTG
CGATTACTTCGCCAACTATTGCGATAACAAGAAAAAGCCAGCCTTTCATGATATATC
TCCCAATTTGTGTAGGGCTTATTATGCACGCTTAAAAATAATAAAAGCAGACTTGAC
CTGATAGTTTGGCTGTGAGCAATTATGTGCTTAGTGCATCTAACGCTTGAGTTAAGC
CGCGCCGCGAAGCGGCGTCGGCTTGAACGAATTGTTAGACATTATTTGCCGACTACC
TTGGTGATCTCGCCTTTCACGTAGTGGACAAATTCTTCCAACTGATCTGCGCGCGAG
GCCAAGCGATCTTCTTCTTGTCCAAGATAAGCCTGTCTAGCTTCAAGTATGACGGGC
TGATACTGGGCCGGCAGGCGCTCCATTGCCCAGTCGGCAGCGACATCCTTCGGCGCG
ATTTTGCCGGTTACTGCGCTGTACCAAATGCGGGACAACGTAAGCACTACATTTCGC
TCATCGCCAGCCCAGTCGGGCGGCGAGTTCCATAGCGTTAAGGTTTCATTTAGCGCC
TCAAATAGATCCTGTTCAGGAACCGGATCAAAGAGTTCCTCCGCCGCTGGACCTACC
AAGGCAACGCTATGTTCTCTTGCTTTTGTCAGCAAGATAGCCAGATCAATGTCGATC
GTGGCTGGCTCGAAGATACCTGCAAGAATGTCATTGCGCTGCCATTCTCCAAATTGC
AGTTCGCGCTTAGCTGGATAACGCCACGGAATGATGTCGTCGTGCACAACAATGGTG
ACTTCTACAGCGCGGAGAATCTCGCTCTCTCCAGGGGAAGCCGAAGTTTCCAAAAG
GTCGTTGATCAAAGCTCGCCGCGTTGTTTCATCAAGCCTTACGGTCACCGTAACCAG
CAAATCAATATCACTGTGTGGCTTCAGGCCGCCATCCACTGCGGAGCCGTACAAATG
TACGGCCAGCAACGTCGGTTCGAGATGGCGCTCGATGACGCCAACTACCTCTGATA
GTTGAGTCGATACTTCGGCGATCACCGCTTCCCTCATGATGTTTAACTTTGTTTTAGG
GCGACTGCCCTGCTGCGTAACATCGTTGCTGCTCCATAACATCAAACATCGACCCAC
GGCGTAACGCGCTTGCTGCTTGGATGCCCGAGGCATAGACTGTACCCCAAAAAAAC
AGTCATAACAAGCCATGAAAACCGCCACTGCGCCGTTACCACCGCTGCGTTCGGTCA
AGGTTCTGGACCAGTTGCGTGAGCGCATACGCTACTTGCATTACAGCTTACGAACCG
AACAGGCTTATGTCCACTGGGTTCGTGCCTTCATCCGTTTCCACGGTGTGCGTCACCC
GGCAACCTTGGGCAGCAGCGAAGTCGAGGCATTTCTGTCCTGGCTGGCGAACGAGC
GCAAGGTTTCGGTCTCCACGCATCGTCAGGCATTGGCGGCCTTGCTGTTCTTCTACG
GCAAGGTGCTGTGCACGGATCTGCCCTGGCTTCAGGAGATCGGAAGACCTCGGCCG
TCGCGGCGCTTGCCGGTGGTGCTGACCCCGGATGAAGTGGTTCGCATCCTCGGTTTT
CTGGAAGGCGAGCATCGTTTGTTCGCCCAGCTTCTGTATGGAACGGGCATGCGGATC
AGTGAGGGTTTGCAACTGCGGGTCAAGGATCTGGATTTCGATCACGGCACGATCATC
GTGCGGGAGGGCAAGGGCTCCAAGGATCGGGCCTTGATGTTACCCGAGAGCTTGGC
ACCCAGCCTGCGCGAGCAGGGGAATTAATTCCCACGGGTTTTGCTGCCCGCAAACG
GGCTGTTCTGGTGTTGCTAGTTTGTTATCAGAATCGCAGATCCGGCTTCAGCCGGTTT
GCCGGCTGAAAGCGCTATTTCTTCCAGAATTGCCATGATTTTTTCCCCACGGGAGGC
GTCACTGGCTCCCGTGTTGTCGGCAGCTTTGATTCGATAAGCAGCATCGCCTGTTTCA
GGCTGTCTATGTGTGACTGTTGAGCTGTAACAAGTTGTCTCAGGTGTTCAATTTCATG
TTCTAGTTGCTTTGTTTTACTGGTTTCACCTGTTCTATTAGGTGTTACATGCTGTTCAT
CTGTTACATTGTCGATCTGTTCATGGTGAACAGCTTTGAATGCACCAAAAACTCGTA
AAAGCTCTGATGTATCTATCTTTTTACACCGTTTTCATCTGTGCATATGGACAGTTT
TCCCTTTGATATGTAACGGTGAACAGTTGTTCTACTTTTGTTTGTTAGTCTTGATGCTT
```

Figure 18 (cont).

CACTGATAGATACAAGAGCCATAAGAACCTCAGATCCTTCCGTATTTAGCCAGTATG
TTCTCTAGTGTGGTTCGTTGTTTTTGCGTGAGCCATGAGAACGAACCATTGAGATCAT
ACTTACTTTGCATGTCACTCAAAAATTTTGCCTCAAAACTGGTGAGCTGAATTTTTGC
AGTTAAAGCATCGTGTAGTGTTTTTCTTAGTCCGTTATGTAGGTAGGAATCTGATGTA
ATGGTTGTTGGTATTTTGTCACCATTCATTTTTATCTGGTTGTTCTCAAGTTCGGTTAC
GAGATCCATTTGTCTATCTAGTTCAACTTGGAAAATCAACGTATCAGTCGGGCGGCC
TCGCTTATCAACCACCAATTTCATATTGCTGTAAGTGTTTAAATCTTTACTTATTGGT
TTCAAAACCCATTGGTTAAGCCTTTTAAACTCATGGTAGTTATTTTCAAGCATTAACA
TGAACTTAAATTCATCAAGGCTAATCTCTATATTTGCCTTGTGAGTTTTCTTTTGTGTT
AGTTCTTTTAATAACCACTCATAAATCCTCATAGAGTATTTGTTTTCAAAAGACTTAA
CATGTTCCAGATTATATTTTATGAATTTTTTTAACTGGAAAAGATAAGGCAATATCTC
TTCACTAAAAACTAATTCTAATTTTTCGCTTGAGAACTTGGCATAGTTTGTCCACTGG
AAAATCTCAAAGCCTTTAACCAAAGGATTCCTGATTTCCACAGTTCTCGTCATCAGC
TCTCTGGTTGCTTTAGCTAATACACCATAAGCATTTTCCCTACTGATGTTCATCATCT
GAGCGTATTGGTTATAAGTGAACGATACCGTCCGTTCTTTCCTTGTAGGGTTTTCAAT
CGTGGGGTTGAGTAGTGCCACACAGCATAAAATTAGCTTGGTTTCATGCTCCGTTAA
GTCATAGCGACTAATCGCTAGTTCATTTGCTTTGAAAACAACTAATTCAGACATACA
TCTCAATTGGTCTAGGTGATTTTAAT

Figure 19

**SEQ ID NO: 2 – DNA sequence of *E. coli* codon-optimized gene *fadD35* from *Mycobacterium tuberculosis* HR7Rv.**

CC<u>ATG</u>GCAGCAGCGGAAGTGGTTGATCCAAATCGTCTGAGCTATGATCGTGGCCCGAGCGCGCCGAGCCTGTTGGAGAGCACCA
TCGGTGCAAACCTGGCCGCTACGGCGGCCCGTTACGGCCACCGCGAGGCCCTGGTGGACATGGTCGCACGCCGTCGCTTCAATTA
TAGCGAGCTGCTGACGGATGTTCACCGTTTGGCTACGGGCCTGGTGCGTGCTGGTATTGGCCCAGGCGACCGTGTGGGTATTTGG
GCGCCGAATCGTTGGGAGTGGGTTCTGGTCCAGTATGCAACGGCGGAGATTGGTGCGATCCTGGTTACGATTAACCCGGCTTATC
GCGTGCGTGAGGTTGAATACGCGCTGCGTCAATCTGGCGTCGCGATGGTCATTGCGGTTGCGTCCTTCAAGGACGCTGATTACGC
TGCGATGCTGGCGGAGGTTGGTCCGCGTTGCCCGGACCTGGCTGACGTGATCCTGTTGGAAAGCGACCGTTGGGACGCACTGGC
AGGTGCCGAGCCGGATCTGCCGGCGCTGCAGCAGACCGCTGCCCGCCTGGATGGTTCCGATCCGGTTAACATTCAATACACCAGC
GGTACGACCGCGTACCCGAAAGGTGTTACGCTGAGCCACCGCAATATCCTGAATAACGGTTATTTGGTTGGTGAGCTGTTGGGTT
ATACGGCGCAGGATCGTATTTGCATCCCGGTGCCGTTCTACCACTGCTTTGGTATGGTCATGGGCAACTTGGCGGCGACCTCCCA
CGGTGCGGCGATGGTTATTCCGGCGCCAGGTTTCGACCCAGCGGCTACGCTGCGCGCGGTGCAAGATGAACGCTGTACGTCTCTG
TACGGCGTTCCGACCATGTTTATTGCAGAACTGGGTCTGCCGGATTTCACCGATTACGAGCTGGGTTCTTTGCGTACCGGCATCAT
GGCAGGCGCAGCGTGTCCGGTTGAAGTCATGCGTAAAGTGATCAGCCGTATGCACATGCCGGGTGTCAGCATTTGCTACGGTATG
ACCGAGACGAGCCCGGTGAGCACCCAAACCCGTGCGGACGATAGCGTGGACCGTCGTGTGGGCACCGTTGGCCGCGTCGGCCCG
CACCTGGAAATTAAAGTTGTTGACCCAGCGACCGGCGAAACCGTTCCGCGCGGTGTTGTTGGCGAATTTTGCACGCGTGGCTACT
CTGTCATGGCGGGTTATTGGAATGACCCGCAGAAAACGGCAGAGGTGATCGACGCTGATGGTTGGATGCATACCGGTGACCTGG
CGGAAATGGACCCGAGCGGTTACGTTCGTATTGCAGGCCGCATTAAAGACCTGGTGGTTCGTGGCGGTGAGAACATTAGCCCGC
GTGAAATTGAGGAGCTGCTGCATACCCATCCGGACATCGTTGATGGTCACGTGATCGGTGTTCCGGATGCGAAATATGGCGAAG
AGCTGATGGCAGTTGTGAAGCTGCGTAATGATGCGCCGGAGTTGACGATTGAACGCCTGCGTGAGTATTGCATGGGTCGCATCGC
ACGCTTTAAAATCCCGCGCTACTTGTGGATCGTTGACGAGTTCCCGATGACCGTGACCGGCAAGGTCCGTAAGGTCGAGATGCGT
CAGCAGGCATTGGAATATCTGCGTGGTCAACAG<u>TAA</u>GAATTC

Figure 20

SEQ ID NO: 3 – DNA sequence of E. coli codon-optimized gene fadD1 from Pseudomonas aeruginosa PAO1.

TCATGATCGAGAATTTTTGGAAGGACAAGTATCCGGCAGGTATTGCAGCAGAAATTAATCCGGATCAGTATCGAATATTCTGA
GCGTCCTGAAGGAGAGCTGCCAACGTTTTGGCAGCAAGGCGGGTTTACGACTTGGTAAGAACTTGGATCGAAGACCTTGACCTATGGTGAGCTGTA
CAAACTGTCTGGCGACTTCGCAGGTACCTGCAGGTAACCTGCAACATACGATCGAAACCGGTGATCGTATTGCCGTTGCCGTGCCGAAC
GTTCTGCAGTACCGGATCGTTGTCTTCCGGCGCATGCGTGCGGGTCTCGATCGGGTGGTGAACACGAAACCGTTGTATACGGCGCTG
AGTTGGAACACCAGTTAAACAGGTGATTGTCACCGAGGTGGGACATTCTGCACCGGGCAAAAGCGGGTGGTTTGTTGGCTAAATATGCC
GAAGACCGGTGTTAAACAGGTGATTGTCACCGAGGTGGGGACATTCTGCACCGAGGCCAAGCGTTTCATTGTCAAGTTCGTCGTC
AAACACATTAAGAAGATGCCCGGCTATTCCCTGCCGACAGTTGACCGGGCCGATGCACTGCCGTGTCAGCAAG
AGTTCCAAGAAGCGGCACCGCAGGCAGCGTCGCTAACCTGGTCGCTAACATGTTGCGTTTACCTTCCACTGTAAAGCGTGATGGGCGTGAACGAGGGGTGCGAAAT
GATGCTGACTCATCGTACCCTGGTCGCTAACATGTTATGCGTTTACCTTCCACTGTGATCTATGATGCTGACGGTAATCATAACATTC
CTTGATTGCCCGGTTGCCGCTGTATCACCATTTATGCGAGCATGCTCAGTGGAAGTTCAGGCACTGAAGCGTCAGGCCATGCGGCTG
TGATCACCAATCCGCGGCGACCTGCAATAATGAGACCTTCCGTAAGCTGGACTTAGCGCTGAAGCTGAAGCTGGCCATGCCGCCGAAGTACGCT
GTTCGCGCTCTGTGCAATGCGGGGAAACTGGAAAGAGGTCACGGGCTGCTATTTCGAGGGTTATGTCGAGGGTTATGGTGACCGAAACGGCCCGGTG
CAGGTGGCCAGGGCCAGCCGGGTCAACCGGTTCAGAACGTTCCCCTGGGCAGCGGGCCGTCACCATCCGGTCGTATTCCGGTCGTCGAGTTGGGTCGTCAAGCTTGTAAGGGCTACTGCCAGGCCAGG
GTTCCGGTCAAGAAGTTCCCTGGCAGCCGCCGGTTCAGAACATTGACAAGTTGGCCACCATCCGGCCGTATTCCGGTCGTCAAGGGCTACTGGCCACCGAG
ACGGTCAAGAAGGACGAGATTCGAGAACGCTGATGGTTGGTTGAAAACCGGGATATTGCAATTATTCAAGAAGACGGCTATATGCGCA
AGGCAACGGACGAGATTCGTAAGAAGACATGATTTTGGTTTGAAAACCGGGTTCAACGTTTACCCGGATGAAAAGAGGGGGGGAGTGTAATCAAGGTTTTCGTTGTGAAGCCGGG
TTGTCGATCGTAAGAAGACATGATTTTGGTTTGAAAACCGGGTTCAACGTTTACCCGGATGAAAAGAGGGGGGGGAGTGTAATCAAGGTTTTCGTTGTGAAGCCGGG
GGGTGTGCTCAATGCCAGCAGCAGGTCATGCGGATCGTATCCGGTATCCGGTATGGCAGCATAGCAGATAACCCGGCAGGCATAATGCAGATAACCGGTACAAGCGCACATGCAGATAACCGGTACAAGCGCACCGAAGCAGTGGAGTTCCG
TGCGACCCTGACCAAAGAGCAGGTCATGCGGATCGTATCCGGTATCCGGTATGGCAGCATAGCAGATAACCCGGTACAAGCGCACCGAAGCAGTGGAGTTCCG
TGATAGCCTGCCAACGACCAATGTTGCAAGATTTTGCGGTCGTGAGCTGCCGATGAAGAGCTGAAAAAGGCAGGCCAGAAGTA
AGAATTC

Figure 21

SEQ ID NO: 4 – the BsyAI.BspHIF primer based on the DNA sequence deposited at NCBI with the accession code NC_000964.

CATCATGAATCTTGTTTC

Figure 22

SEQ ID NO: 5 – the BsyhflEcoR primer based on the DNA sequence deposited at NCBI with the accession code NC_000964.

CGGAATTCTTATTGGGGCAAAATATC

Figure 23

SEQ ID NO: 6 — DNA sequence of the *Bacillus subtilis yhfL* gene.

TCATGAATCTTGTTTCAAAATTGGAAGAAACAGCATCGAGAAGCCCGACACAGCATCGCATGCTGAGTGCAGGTTTAAAGATCACATGATGA
CGTATCAAGAGCTGAATGAATATATTCAGCGATTGCCGAACGGATTGGCCGCCTTCAGGAAGCCGGTATGGAGAAAGGGGACCATTAGCTT
TGCTGCTTGCTCAATTCGCCTGATTTTATCATCGCGTTTTTGGCGTTTAAAAGCTGGGATCGTAGTTGTTCCCATCAATCCGTTGT
ACACGCCGACAGAAATTGGTTATATGCTGACAAATGGCGAATGTAAAGCAATCGTGGCGTTAGCCAGTTTTGCGCTTTATGA
GAGCATGCATGAATCGCTGCCAAAGGTTGAGCTCGTCATTTTATGCCAGACGGAGGCCGAGCCGAAGCTGCGACCCAGA
GGTCAGGATGAAAATGACAACGTTTGCAAAAATATTGCGCCGCTAAACAAAACCAAGAACCTGTACCTGATCA
TACCGGGTTATTTTATATCGTCAGGCTATTTGGGAATGAGAGGACAATGAAGGACGATGCTGCGCTCTTCCCATGTGTCAGCAATGC
CAAGGATGTCGCAGGCTATTTGCCACCGTGAATCGAGCGGCGTGTGCCTACAAGTGATGAGCCTCAATTCAGTCGGCATCTGTTTGTTAA
GCAGCAGGCGACCATTTTTCGGCATTCGGAGGCGGCGTCCATGCAGTGCGTTGCTGACAGGCAGAAAGCGGGCTCCATGG
TCTTCGATCCGGCTGTGCATTTCGGAAGGCTCTCCGGAAGCATCACCGTCACGTTGCTTTAACCCGTTGACAGGGGCAGAAAGCGGGCGAATTGATCGT
TTTTGGAAGGCTACGGCGTCTCCGAAGCATCACCGTCACGGTCGTAGATCGTATAAATGCGATGGCGCATGAAAAGACAGAGCATTAAAGATCATGGAGGATACAATGT
GACAAGTATCTTACATGTGATGAAGGGCTATTAGAGGGTCTGTCAGTGGCTGCTGTACAACGCGTCATTGTTACATTCCGGACGTCAAGGAGCGGTTGTCATCGCGTCGTGCCGGGACCCCAAAG
GAAAGGCCCAATGGCAAGACGGTGGAGGGAGGGAGGTAAAGGGATATGTGTGCCATTGCGCCATTACGTTTCTGACGATATTCGAAATGCGACGGGGAAAATGCTCAGACGGGCAC
TGAGAGATATTTGCCCCAATAAGAATTC

Figure 24

SEQ ID NO: 7 – the Scfaa3pPciF primer designed based on the DNA sequence deposited at NCBI with the accession code NC_001141.
CGACATGTCCGAACAACAC

Figure 25

SEQ ID NO: 8 -- the Scfaa3pPciI primer designed based on the DNA sequence deposited at NCBI with the accession code NC_001141.
GCAAGCTTCTAAGAATTTCTTTG

Figure 26

SEQ ID NO: 9 – DNA sequence of the *faa3p* structural gene from *Saccharomyces cerevisiae*.

TCA<u>ATG</u>AGTCTCGGATCGTCCCTGGCTGCAGAGCTATCCGAAAGGCGTTCCCGCCGAAATGGACGTCAACGAATTCCATTCGGTCGC
CTCGGTCTTCGACGCGTTCCGTGCGGCGAAATTCCGGACGTCCGCCTACTCCAGCTTCGGCAGTTCCTCACCTATGGTGAGACG
GACGGCTGGTCACCCAGTTCGCCGCGCCTACTCCGGGGTGAGCTCAAGAAGGTGACCGGTCACCCGGTCCGATGATGCCCA
ACTGCCTGCAGTACCCGGTGCGCCATCCTTCGGCGGCGTCCTGGTTGATGCCGGTCAGCGTCAACCCGGCTGTACACCGCGCG
CGAACTCAAGCACCAGCTGGTTGATGCGGGTCAGCGGCGTCAGCCGACAACTCGGGCGACACCGTCGGGACACTCGTGCT
CGCCGATACACCGGTCAACGTGTGCCCAACTACCACATCAAGGGCGCGCCTTCAAGCGGCGTCAAGTCGGCAGCGCCA
GAAGTACATCAAGAAGATGGTGCCCAACTACCACATCAAGGGCGCGCCTTCAAGCGGCGTCAAGTCGGCAGCGCCA
CGGCTTCCCGCCGGTCGAGATCGCAACCGACAACATGCAGCAGCGTGCCGCCTGCCTGGCTTACGCCCGCCTGCAACCGCCA
GATGCTGACCAACCGCTGCCCTGCCGCGACAACCGCAGCGGTCAACCGCCGTCGTGCCAACGGCTGGTCTTATGAAGTTCGGTGGCTGCAAC
AGTGATCATCACTGCCCCTGCCGCGACAACCGCAGCGGTCAACCGCAACGCAACGAACTGAAGAGCTCAAGGGCACCGCTCATGCCATCACCCGCTCAAC
ACGCTGATCATCAACCCAACCGCGACAACCGGCTGCTCAACGACGGCTTCAACGAGGCTCAAGAAGGGCACCGCTCATGCCATCACCCGCTCAAC
ACGCGTTCAACTGCCGGTCAACTCCGGCCGAAGATGGACTTCTCTCCGGTCAGAAGGTCACCGGGTGAAGCCTATGCCCTGGCCGGGCCCATGG
CGGTGCAACGCCGTCAACCGGAATGGTCCGAGTACAACGTGGGGAGGCGTCAACGAGCGTCAAGCCTATGCCGTGGCCGGGCCCATGG
CCGCGGCCTGCATCAATCGCTCACCGGCGGAGCGCTCAAGGGCCGCCATGTGCTGCACACCGGCGAAGCCTACTGGCC
GGACGACAACGGCAACATCCGGCGGCCAAGCGCCACCGCCACGCCAAGAAGGACATCGGCCGCAGTAATGAAGGCTACTGGCC
AGCGTCCGGAAGAAACGCCGGCGAAGCGCCATCAACCGCCACCGCCAAGAGGGCACATCGGCCGAATGCCGAAGACATGAGAACAGGC
TTCTTCTACATGTCGACGCAACTGGTCAACCCGAAGAATGGCGCGGAAGTCCGGATCCTGTGTCCGGACGATAACGTGGATCCGAACAAAGTCCGAATGCCGAAGAAAGTCGGGACGTGTACCGGCAAAAGTCCGGACGTAAGTCCGAATGTACCGGAGCGCAAGAACATGCCGGGCAAACCTGACCGGTTACAAGCACCCCAGAATCGTA
CGATGATGCCGGGGTGCTGACCTGACCGTGCTGACCTGACCGGCAAAATGGCCGGGGCAAACCTGACCGGTTACAAGCACCCCAGAATCGTA
AGAAGGACCCGAAGGAGCTGCCGAAGACGTCCGGCAAGATCCTCGGCAAGATCCTCGGCAAGATCCTCGGCAAGACGTCCTGAGCGCCGCGCCCCGC<u>GTA</u>AGAATTC
GAATTCCGAAGGAGCTGCCGAAGACCGTCGGCAAGATCCTCGGCAAGTCCGGCAAGTCGGCAAGTCGGAGCTGCCGAGCTGCCGAGCTGCCCCGCC<u>GTA</u>AGAATTC

Figure 27

SEQ ID NO: 10 – the Smprk59BspF primer based on the DNA sequence deposited at NCBI with the accession code NZ_AAVZ01090044.

AGTCATGAGTCTGGATCG

Figure 28

SEQ ID NO: 11 – the Smprk59HindR primer based on the DNA sequence deposited at NCBI with the accession code NZ_AAVZ01000044.

GGAAGCTTACGGGGCGGGCG

Figure 29

SEQ ID NO: 12 – the primer PrkBsp

GCGAACGGCCTGGTCTTTATGAAGTTCGGTGG

Figure 30

SEQ ID NO: 13 – DNA sequence of the gene encoding the protein ZP_01644857 from *Stenotrophomonas maltophilia* R551-3.

TCATGAGTCTCGGATCGTCCGTCCCTGGCTGCAGAGCTATCCGAAAGGCGTTCCCGCCGAAATCGACGTCAACGAATTCCATTCGGTCGC
CTCGGTCTTCGACGCTTCCGTCGCGAAATTCCGCGACGTCCCGCCTACTCCAGTTCGGCAAGTTCCTCACCTATGGTGAGACG
GACGCGGTCGTCACCCAGTTCGCGCGCTACCTGCTGGTGAGCTCAAGTCAACGGCCTGATCCGGTCGCCCTGATGATGCCCA
ACTGCCTGCAGTACCGGGTGCCACTTCGGCGTGCGCGCCCGCCGTCCCCGGGTCAACGGTCAACCGGTCACCGGCGG
CGAACTCAAGCACCAGCTGGTTGATGCCGGAGCGTCAGCGCCCTGTGGTGTCGACAACTCGGCGACACCGTCGAACAGGTCAT
CGCCGATACACCGGTCAAGCAAGTGGTCCAACTACCACACTACAAGGGCCGGCGACCTGCTCGGCGCCAAGGGCGATCGTCAACTTCGTGCT
GAAGTACAATCAAGAAGATGGTCCCAACTACCACACGAGACATTGCCTTCAAGCAGGGCGCTCAAGTCGTGGGCAGCCCCA
CGGCGTTCCGCCGGTCGAGATCGAACCTGCGCAACACGAGCAGGCGTCAGTACACCGGGGACCACCGCGTGGCCAAGGGTGC
GATGCTGACCAACGCAACCTGATCGCGCGTGCTACCAGCGGAACATCTTCGCATTGACGCGAACGGCTTCGGTGGTGCAAC
AGTGATCATCATGACCAAGACGATCAACCCGGGCCTTGTCGTAAAGGAGCTCGATGAAGGCGCCCTACTCACCGGCGTCAAC
CACCTGATCATCGAACAAAGGGCCTGTCAACCGCGAACCGGCTTCGACGAGATCGAGCTTCTTCGTTCAAGTTCAACTCCGTCAAC
ACGGTGTTCAAGGCCTGCCGTGCCGAACCGGCTCAATCCGGTCAAGCGCTCACCGCCCGGTGAAGAAGGTCACCCGGTGGGCATGG
CGGTCGAACGTGCCGTGCCGGAACCGGCTCAATCCGGTCACCTGGCCTGGTCGAAGCTATGGCCTGAAGCCTGTACGATCCTGCATCAA
GGACGACAACGGCAAGACGCAACATCTGGCCTGGGCGACGCGCCATGCGTGCATCAAGGGCCCGACATGGCGAAGATGGACGAACAGGGC
AGCGTCCGGAAGAAAACCGCCTGGAAGTCGTGCTGCTAAGGACCCTCGGTGTCCGGACGAAAAGTCCGGCGCAAACCTGACCGGTCATCG
TTCTTCTACATCGTCGACGGCGTGCTGCTAAGGACCTCGATGATCCTGGTGTCCGGAACATGACCGGCTCAACGTGTACCCGAAGTGTTCAAGACGTCATCG
CGATGATGCGGGGGCGTGCTGGAACGCCGAAGCCGAAGCCAGCCGAAATGGCCGGCAAATGTCGGCGCGCAAAGTCCGGCGAAGTGGTCAAGGTCGTGATCGTGA
AGAAGGACCCGAAACCTGACCGGGCCGGTGCTGCGCCTGAAAGGACCCAAGACCTGGGGCGCCAAGACCTCCCCGGGAAACGACCCGAAGCCCAAGGTGCTGATACGCCGCCCGCCCGTAAGAATCGTA
GAATTCCGAAAAGGACCTGCCGAAGAGACTCGGCAAGACCAAGGTCGGCAAGATCCTCCGTGCGGGTGCTGCTGATACGCCGCCCCCGTAAGAATTC

Figure 31

SEQ ID NO: 14 – Protein sequence of ZP_01644857 from *Stenotrophomonas multophilia* ATCC 17679.

MSLDRPWLQSYPKGVPAEIDVNEFHSVASVFDASVAKFRDRPAYSSFGKVLTYGETDALVTQFAAYLLGELKLKKGDRVALMAPNC
LQYFVATFGVLRAGLTVVNVNPLYTARELKHQLVDAGVSALVVVDNFGDTVEQVIADTPVKHVVTTGLGDLLGAKGAIVNFVLKYI
KKMVPNYHIKGAVRFKQALKLGSRHALPPVEIDHDDIAFLQYTGGTTGVAKGAMLTNRNLIANMQQASAWLSTSGIEPGKEVIITALP
LYHIFALTANGLVFMKPGGCNHLITNPRDMKGFVKELKGTRFTAIITGVNTLFNGLLNTPGFDEIDFSSVKFTLGGGMAVQRAVAERWK
KVTGVTLVEAYGLTETSPAACINPLTLPEYNGAIGLPIPSTDACIKDDNGNILALGEVGELCIKGPQVMKGYWQRPEETATAIDADGWL
HTGDMAKMDEQGFFYIVDRKKKDMILVSGFNVYPNEVEDVIAMMPGVLEVAAVGVPDEKSGEVVKVVIVKKDPNLTAEMVKEHARA
NLTGYKHPRIVEFRKELPKTNVGKILRRELRDTPA

SEQUENCE LISTING

```
<160> NUMBER OF SEQ ID NOS: 56

<210> SEQ ID NO 1
<211> LENGTH: 5903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cactatacca attgagatgg gctagtcaat gataattact agtcctttc ctttgagttg      60 tgggtatctg taaattctgc tagacctttg ctggaaaact tgtaaattct gctagaccct     120
ctgtaaattc cgctagacct ttgtgtgttt tttttgttta tattcaagtg gttataattt     180
atagaataaa gaaagaataa aaaaagataa aaagaataga tcccagccct gtgtataact     240
cactacttta gtcagttccg cagtattaca aaaggatgtc gcaaacgctg tttgctcctc     300
tacaaaacag accttaaaac cctaaaggcg tcggcatccg cttacagaca agctgtgacc     360
gtctccggga gctgcatgtg tcagaggttt tcaccgtcat caccgaaacg cgcgaggcag     420
cagatcaatt cgcgcgcgaa ggcgaagcgg catgcattta cgttgacacc atcgaatggt     480
gcaaaacctt tcgcggtatg gcatgatagc gcccggaaga gagtcaattc agggtggtga     540
atgtgaaacc agtaacgtta tacgatgtcg cagagtatgc cggtgtctct tatcagaccg     600
tttcccgcgt ggtgaaccag gccagccacg tttctgcgaa aacgcgggaa aaagtggaag     660
cggcgatggc ggagctgaat tacattccca accgcgtggc acaacaactg gcgggcaaac     720
agtcgttgct gattggcgtt gccacctcca gtctggccct gcacgcgccg tcgcaaattg     780
tcgcggcgat taaatctcgc gccgatcaac tgggtgccag cgtggtggtg tcgatggtag     840
aacgaagcgg cgtcgaagcc tgtaaagcgg cggtgcacaa tcttctcgcg caacgcgtca     900
gtgggctgat cattaactat ccgctggatg accaggatgc cattgctgtg gaagctgcct     960
gcactaatgt tccggcgtta tttcttgatg tctctgacca gacacccatc aacagtatta    1020
ttttctccca tgaagacggt acgcgactgg gcgtggagca tctggtcgca ttgggtcacc    1080
agcaaatcgc gctgttagcg ggcccattaa gttctgtctc ggcgcgtctg cgtctggctg    1140
```

```
gctggcataa atatctcact cgcaatcaaa ttcagccgat agcggaacgg aaggcgact    1200 ggagtgccat gtccggtttt caacaaacca tgcaaatgct gaatgagggc atcgttccca   1260
ctgcgatgct ggttgccaac gatcagatgg cgctgggcgc aatgcgcgcc attaccgagt   1320
ccgggctgcg cgttggtgcg atatctcgg tagtgggata cgacgatacc gaagacagct    1380
catgttatat cccgccgtta accaccatca aacaggattt tcgcctgctg gggcaaacca   1440
gcgtggaccg cttgctgcaa ctctctcagg gccaggcgt gaagggcaat cagctgttgc    1500
ccgtctcact ggtgaaaaga aaaaccaccc tggcgcccaa tacgcaaacc gcctctcccc   1560
gcgcgttggc cgattcatta atgcagctgg cacgacaggt tccccgactg aaagcgggc    1620 agtgagcgca acgcaattaa tgtaagttag cgcgaattga tctggtttga cagcttatca   1680
tcgactgcac ggtgcaccaa tgcttctggc gtcaggcagc catcggaagc tgtggtatgg   1740
ctgtgcaggt cgtaaatcac tgcataattc gtgtcgctca aggcgcactc ccgttctgga   1800
taatgttttt tgcgccgaca tcataacggt tctggcaaat attctgaaat gagctgttga   1860
caattaatca tccggctcgt ataatgtgtg gaattgtgag cggataacaa tttcacacag   1920
gaaacagcgc cgctgagaaa aagcgaagcg gcactgctct ttaacaattt atcagacaat   1980
ctgtgtgggc actcgaccgg aattatcgat taactttatt attaaaaatt aaagaggtat   2040
atattaatgt atcgattaaa taaggaggaa taaaccatgg atccgagctc gagatctgca   2100
gctggtacca tatgggaatt cgaagcttgg gcccgaacaa aaactcatct cagaagagga   2160
tctgaatagc gccgtcgacc atcatcatca tcatcattga gtttaaacgg tctccagctt   2220
ggctgttttg gcggatgaga aagattttc agcctgatac agattaaatc agaacgcaga    2280
agcggtctga taaaacagaa tttgcctggc ggcagtagcg cggtggtccc acctgacccc   2340
atgccgaact cagaagtgaa acgccgtagc gccgatggta gtgtggggtc tccccatgcg   2400
agagtaggga actgccaggc atcaaataaa acgaaaggct cagtcgaaag actgggcctt   2460
tcgttttatc tgttgtttgt cggtgaacgc tctcctgacg cctgatgcgg tattttctcc   2520
ttacgcatct gtgcggtatt tcacaccgca tatggtgcac tctcagtaca atctgctctg   2580
atgccgcata gttaagccag ccccgacacc cgccaacacc cgctgacgag cttagtaaag   2640
ccctcgctag atttttaatgc ggatgttgcg attacttcgc caactattgc gataacaaga   2700
aaaagccagc ctttcatgat atatctccca atttgtgtag gcttattat gcacgcttaa    2760 aaataataaa agcagacttg acctgatagt ttggctgtga gcaattatgt gcttagtgca   2820
tctaacgctt gagttaagcc gcgccgcgaa gcggcgtcgg cttgaacgaa ttgttagaca   2880
ttatttgccg actaccttgg tgatctcgcc tttcacgtag tggacaaaatt cttccaactg   2940 atctgcgcg gaggccaagc gatcttcttc ttgtccaaga taagcctgtc tagcttcaag    3000
tatgacgggc tgatactggg ccggcaggcg ctccattgcc cagtcggcag cgacatcctt   3060
cggcgcgatt ttgccggtta ctgcgctgta ccaaatgcgg gacaacgtaa gcactacatt   3120
tcgctcatcg ccagcccagt cgggcggcga gttccatagc gttaaggttt catttagcgc   3180
ctcaaataga tcctgttcag gaaccggatc aaagagttcc tccgccgctg gacctaccaa   3240
ggcaacgcta tgttctcttg cttttgtcag caagatagcc agatcaatgt cgatcgtggc   3300
tggctcgaag atacctgcaa gaatgtcatt gcgctgccat tctccaaatt gcagttcgcg   3360
cttagctgga taacgccacg gaatgatgtc gtcgtgcaca acaatggtga cttctacagc   3420
gcggagaatc tcgctctctc caggggaagc cgaagtttcc aaaaggtcgt tgatcaaagc   3480
```

-continued

| | | | | |
|---|---|---|---|---|
| tcgccgcgtt | gtttcatcaa | gccttacggt | caccgtaacc | agcaaatcaa tatcactgtg | 3540 |
| tggcttcagg | ccgccatcca | ctgcggagcc | gtacaaatgt | acggccagca acgtcggttc | 3600 |
| gagatggcgc | tcgatgacgc | caactacctc | tgatagttga | gtcgatactt cggcgatcac | 3660 |
| cgcttccctc | atgatgttta | actttgtttt | agggcgactg | ccctgctgcg taacatcgtt | 3720 |
| gctgctccat | aacatcaaac | atcgacccac | ggcgtaacgc | gcttgctgct tggatgcccg | 3780 |
| aggcatagac | tgtaccccaa | aaaaacagtc | ataacaagcc | atgaaaaccg ccactgcgcc | 3840 |
| gttaccaccg | ctgcgttcgg | tcaaggttct | ggaccagttg | cgtgagcgca tacgctactt | 3900 |
| gcattacagc | ttacgaaccg | aacaggctta | tgtccactgg | gttcgtgcct tcatccgttt | 3960 |
| ccacggtgtg | cgtcacccgg | caaccttggg | cagcagcgaa | gtcgaggcat ttctgtcctg | 4020 |
| gctggcgaac | gagcgcaagg | tttcggtctc | cacgcatcgt | caggcattgg cggccttgct | 4080 |
| gttcttctac | ggcaaggtgc | tgtgcacgga | tctgccctgg | cttcaggaga tcggaagacc | 4140 |
| tcggccgtcg | cggcgcttgc | cggtggtgct | gaccccggat | gaagtggttc gcatcctcgg | 4200 |
| ttttctggaa | ggcgagcatc | gtttgttcgc | ccagcttctg | tatggaacgg gcatgcggat | 4260 |
| cagtgagggt | ttgcaactgc | gggtcaagga | tctggatttc | gatcacggca cgatcatcgt | 4320 |
| gcgggagggc | aagggctcca | aggatcgggc | cttgatgtta | cccgagagct ggcacccag | 4380 |
| cctgcgcgag | caggggaatt | aattcccacg | ggttttgctg | cccgcaaacg ggctgttctg | 4440 |
| gtgttgctag | tttgttatca | gaatcgcaga | tccggcttca | gccggtttgc cggctgaaag | 4500 |
| cgctatttct | tccagaattg | ccatgatttt | ttccccacgg | gaggcgtcac tggctcccgt | 4560 |
| gttgtcggca | gctttgattc | gataagcagc | atcgcctgtt | tcaggctgtc tatgtgtgac | 4620 |
| tgttgagctg | taacaagttg | tctcaggtgt | tcaatttcat | gttctagttg ctttgtttta | 4680 |
| ctggtttcac | ctgttctatt | aggtgttaca | tgctgttcat | ctgttacatt gtcgatctgt | 4740 |
| tcatggtgaa | cagctttgaa | tgcaccaaaa | actcgtaaaa | gctctgatgt atctatcttt | 4800 |
| tttacaccgt | tttcatctgt | gcatatggac | agttttccct | ttgatatgta acggtgaaca | 4860 |
| gttgttctac | ttttgtttgt | tagtcttgat | gcttcactga | tagatacaag agccataaga | 4920 |
| acctcagatc | cttccgtatt | tagccagtat | gttctctagt | gtggttcgtt gttttttgcgt | 4980 |
| gagccatgag | aacgaaccat | tgagatcata | cttactttgc | atgtcactca aaaattttgc | 5040 |
| ctcaaaactg | gtgagctgaa | ttttttgcagt | taaagcatcg | tgtagtgttt ttcttagtcc | 5100 |
| gttatgtagg | taggaatctg | atgtaatggt | tgttggtatt | ttgtcaccat tcatttttat | 5160 |
| ctggttgttc | tcaagttcgg | ttacgagatc | catttgtcta | tctagttcaa cttggaaaat | 5220 |
| caacgtatca | gtcgggcggc | ctcgcttatc | aaccaccaat | ttcatattgc tgtaagtgtt | 5280 |
| taaatctttta | cttattggtt | tcaaaaccca | ttggttaagc | cttttaaact catggtagtt | 5340 |
| attttcaagc | attaacatga | acttaaattc | atcaaggcta | atctctatat ttgccttgtg | 5400 |
| agttttcttt | tgtgttagtt | cttttaataa | ccactcataa | atcctcatag agtatttgtt | 5460 |
| ttcaaaagac | ttaacatgtt | ccagattata | ttttatgaat | ttttttaact ggaaaagata | 5520 |
| aggcaatatc | tcttcactaa | aaactaattc | taatttttcg | cttgagaact tggcatagtt | 5580 |
| tgtccactgg | aaaatctcaa | agcctttaac | caaaggattc | ctgatttcca cagttctcgt | 5640 |
| catcagctct | ctggttgctt | tagctaatac | accataagca | ttttccctac tgatgttcat | 5700 |
| catctgagcg | tattggttat | aagtgaacga | taccgtccgt | tctttccttg tagggttttc | 5760 |
| aatcgtgggg | ttgagtagtg | ccacacagca | taaaattagc | ttggtttcat gctccgttaa | 5820 |
| gtcatagcga | ctaatcgcta | gttcatttgc | tttgaaaaca | actaattcag acatacatct | 5880 | caattggtct aggtgatttt aat                                              5903

<210> SEQ ID NO 2
<211> LENGTH: 1652
<212> TYPE: DNA
<213> ORGANISM: Mycobacterium tuberculosis

<400> SEQUENCE: 2
ccatggcagc agcggaagtg gttgatccaa atcgtctgag ctatgatcgt ggcccgagcg      60
cgccgagcct gttggagagc accatcggtg caaacctggc cgctacggcg cccgttacg     120
gccaccgcga ggccctggtg gacatggtcg cacgccgtcg cttcaattat agcgagctgc     180
tgacggatgt tcaccgtttg gctacgggcc tggtgcgtgc tggtattggc ccaggcgacc     240
gtgtggggtat ttgggcgccg aatcgttggg agtgggttct ggtccagtat gcaacggcgg     300
agattggtgc gatcctggtt acgattaacc cggcttatcg cgtgcgtgag gttgaatacg     360
cgctgcgtca atctggcgtc gcgatggtca ttgcggttgc gtccttcaag gacgctgatt     420
acgctgcgat gctggcggag gttggtccgc gttgcccgga cctggctgac gtgatcctgt     480
tggaaagcga ccgttgggac gcactggcag gtgccgagcc ggatctgccg gcgctgcagc     540
agaccgctgc ccgcctggat ggttccgatc cggttaacat tcaatacacc agcggtacga     600
ccgcgtaccc gaaaggtgtt acgctgagcc accgcaatat cctgaataac ggttatttgg     660
ttggtgagct gttgggttat acggcgcagg atcgtatttg catcccggtg ccgttctacc     720
actgctttgg tatggtcatg ggcaacttgg cggcgacctc ccacggtgcg gcgatggtta     780
ttccggcgcc aggtttcgac ccagcggcta cgctgcgcgc ggtgcaagat gaacgctgta     840
cgtctctgta cggcgttccg accatgtttta ttgcagaact gggtctgccg gatttcaccg     900
attacgagct gggttctttg cgtaccggca tcatggcagg cgcagcgtgt ccggttgaag     960
tcatgcgtaa agtgatcagc cgtatgcaca tgccgggtgt cagcatttgc tacggtatga    1020
ccgagacgag cccggtgagc acccaaaccc gtgcggacga tagcgtggac cgtcgtgtgg    1080
gcaccgttgg ccgcgtcggc ccgcacctgg aaattaaagt tgttgaccca gcgaccggcg    1140
aaaccgttcc gcgcggtgtt gttggcgaat tttcacgcg tggctactct gtcatggcgg    1200
gttattggaa tgacccgcag aaaacggcag aggtgatcga cgctgatggt tggatgcata    1260
ccggtgacct ggcggaaatg gacccgagcg gttacgttcg tattgcaggc cgcattaaag    1320
acctggtggt tcgtggcggt gagaacatta gcccgcgtga aattgaggag ctgctgcata    1380
cccatccgga catcgttgat ggtcacgtga tcggtgttcc ggatgcgaaa tatggcgaag    1440
agctgatggc agttgtgaag ctgcgtaatg atgcgccgga gttgacgatt gaacgcctgc    1500
gtgagtattg catgggtcgc atcgcacgct ttaaaatccc gcgctacttg tggatcgttg    1560
acgagttccc gatgaccgtg accggcaagg tccgtaaggt cgagatgcgt cagcaggcat    1620
tggaatatct gcgtggtcaa cagtaagaat tc                                  1652

<210> SEQ ID NO 3
<211> LENGTH: 1697
<212> TYPE: DNA
<213> ORGANISM: Pseudomonas aeruginosa

<400> SEQUENCE: 3
tcatgatcga gaatttttgg aaggacaagt atccggcagg tattgcagca gaaattaatc      60
cggatcagta tccgaatatt ctgagcgtcc tgaaggagag ctgccaacgt tttgcgacca     120

-continued

```
agccggcgtt tacgaacttg ggtaagacct tgacctatgg tgagctgtac aaactgtctg    180
gcgacttcgc agcgtacctg caacaacata ccgatctgaa accgggtgat cgtattgccg    240
ttcagctgcc gaacgttctg cagtacccga tcgttgtctt cggcgcaatg cgtgcgggtc    300
tgatcgtggt gaacacgaac ccgttgtata cggcgcgtga gttggaacac cagtttaatg    360
atagcggcgc aaaagcggtg gtttgtttgg ctaatatggc ccacctggtt gaaggtgttt    420
tgccgaagac cggtgttaaa caggtgattg tcaccgaggt gggcgacatt ctgccaccgc    480
tgaagcgttt cattgtcaat ttcgtcgtca aacacattaa gaagatggtc ccggcctatt    540
ccctgccgca ggccacgaag ttgaccgatg cactggcccg tggtgcaggc aagagcttcc    600
aagaagcggc accgcaggca gacgacgtcg cggtgctgca gtacaccggc ggtaccacgg    660
gcgtcgccaa gggtgcgatg ctgacccatc gtaacctggt cgctaacatg ttgcagtgta    720
aagcgctgat gggtgcgaac ctgaacgagg gttgcgaaat cttgattgcc ccgttgccgc    780
tgtatcacat ttatgcgttt accttccact gtatggctat gatgctgacg ggtaatcata    840
acattctgat caccaatccg cgcgacctgc cgagcatgct gaaggacctg ggtcagtgga    900
agttcacggg tttcgtgggt ctgaatacgc tgttcgtcgc gctgtgcaat aatgagacct    960
tccgtaagct ggactttagc gcactgaagc tgaccctgag cggcggcatg gcgctgcagc   1020
tggccacggc ggaacgttgg aaagaggtca cgggctgcgc tatttgcgag ggttatggta   1080
tgaccgaaac ggccccggtg gtttccgtca acccgtttca gaacattcaa gttggcacca   1140
tcggtattcc ggtgccaagc accttgtgta aggttattgg cgatgacggt caagaagttc   1200
cgctgggcga gcgcggtgag ttgtgcgtca agggtccgca ggttatgaag ggctactggc   1260
agcgccagga ggcaacggac gagattctgg acgctgatgg ttggttgaaa accggcgata   1320
ttgcaattat tcaagaagac ggctatatgc gcattgtcga tcgtaagaaa gacatgattt   1380
tggttagcgg tttcaacgtt tacccgaatg aattggaaga tgttttggcg accttgccgg   1440
gtgtgctgca atgcgcagcg atcggtatcc cggatgaaaa gagcggcgag tctatcaagg   1500 tttcgttgt tgtgaagccg ggtgcgaccc tgaccaaaga gcaggtcatg cagcatatgc   1560
acgataacct gaccggctac aaacgcccga aagcagtgga gttccgtgat agcctgccaa   1620
cgaccaatgt tggcaagatt ttgcgtcgtg agctgcgcga tgaagagctg aaaaaggcag   1680
gccagaagta agaattc                                                  1697
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catcatgaat cttgtttc                                                    18

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggaattctt attggggcaa aatatc                                           26

<210> SEQ ID NO 6
<211> LENGTH: 1550
<212> TYPE: DNA
<213> ORGANISM: Bacillus subtilis

<400> SEQUENCE: 6

| | | | | | |
|---|---|---|---|---|---|
| tcatgaatct | tgtttcaaaa | ttggaagaaa | cagcatctga | gaagcccgac agcatcgcat | 60 |
| gcaggtttaa | agatcacatg | atgacgtatc | aagagctgaa | tgaatatatt cagcgatttg | 120 |
| cggacggcct | tcaggaagcc | ggtatggaga | aggggdacca | tttagctttg ctgcttggca | 180 |
| attcgcctga | ttttatcatc | gcgttttttg | gcgctttaaa | agctgggatc gtagttgttc | 240 |
| ccatcaatcc | gttgtacacg | ccgacagaaa | ttggttatat | gctgacaaat ggcgatgtaa | 300 |
| aggcaatcgt | gggcgttagc | cagcttttgc | cgctttatga | gagcatgcat gaatcgctgc | 360 |
| caaaggttga | gctcgtcatt | ttatgccaga | cgggggaggc | cgagccggaa gctgcggacc | 420 |
| cagaggtcag | gatgaaaatg | acaacgtttg | caaaaatatt | gcggccgaca tctgccgcta | 480 |
| aacaaaacca | agaacctgta | cctgatgata | ccgcggttat | tttatatacg tcaggaacga | 540 |
| ctggaaaacc | gaaaggcgcg | atgctgacac | atcagaattt | gtacagcaat gccaacgatg | 600 |
| tcgcaggcta | tttgggaatg | gatgagaggg | acaatgtggt | ctgcgctctt cccatgtgtc | 660 |
| acgtgttttg | tttaaccgtc | tgtatgaatg | caccgctgat | gagcggcgca actgtattga | 720 |
| ttgagcctca | attcagtccg | gcatctgttt | ttaagcttgt | taagcagcag caggcgacca | 780 |
| tttttgccgg | tgtgcctaca | atgtataact | acttgtttca | gcatgaaaac ggaaagaaag | 840 |
| atgattttc | ttcgatccgg | ctgtgcattt | cgggaggcgc | gtccatgcca gtcgcgttgc | 900 |
| tgacggcgtt | tgaagaaaaa | ttcggtgtta | ccattttgga | aggctacggg ctctcggaag | 960 |
| catcacccgt | cacgtgcttt | aacccgtttg | acaggggcag | aaagccgggc tccatcggga | 1020 |
| caagtatctt | acatgtcgaa | aacaaggtcg | tagatccgct | cggacgcgag ctgcccgctc | 1080 |
| accaggtcgg | cgaattgatc | gtgaaaggcc | ccaatgtgat | gaagggctat tataaaatgc | 1140 |
| cgatggaaac | agagcatgca | ttaaaagacg | ggtggcttta | tacggggggac ttggcaagac | 1200 |
| gggatgagga | cggctatttt | tacattgttg | accggaaaaa | agacatgatc attgtaggag | 1260 |
| gatacaatgt | gtatccgcgg | gaggtggagg | aggtgctgta | cagccatccg gacgtcaagg | 1320 |
| aggcggttgt | catcggcgtg | ccggaccccc | aaagcgggga | agcggtaaag ggatatgtgg | 1380 |
| tgccgaaacg | ctctggggta | acagaggagg | acatcatgca | gcactgcgaa aagcatctgg | 1440 |
| caaaatacaa | gcggcctgcc | gccattacgt | ttcttgacga | tattccgaaa aatgcgacgg | 1500 |
| ggaaaatgct | cagacgggca | ctgagagata | ttttgcccca | ataagaattc | 1550 |

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgacatgtcc gaacaacac                                                    19

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gcaagcttct aagaattttc tttg                                          24

<210> SEQ ID NO 9
<211> LENGTH: 1685
<212> TYPE: DNA
<213> ORGANISM: Saccharomyces cerevisiae

<400> SEQUENCE: 9
tcatgagtct ggatcgtccc tggctgcaga gctatccgaa aggcgttccc gccgaaatcg    60
acgtcaacga attccattcg gtcgcctcgg tcttcgacgc ttccgtcgcg aaattccgcg   120
accgtcccgc ctactccagc ttcggcaagg tcctcaccta tggtgagacg gacgcgctgg   180
tcacccagtt cgccgcctac ctgctgggtg agctcaagct caagaagggt gaccgcgtcg   240
ccctgatgat gcccaactgc ctgcagtacc cggtggccac cttcggcgtg ctgcgcgccg   300
gcctgaccgt ggtcaacgtc aacccgctgt acaccgcgcg cgaactcaag caccagctgg   360
ttgatgccgg cgtcagcgcc ctggtggtgg tcgacaactt cggcgacacc gtcgaacagg   420
tcatcgccga tacaccggtc aagcacgtgg tcaccaccgg cctgggcgac ctgctcggcg   480
ccaagggcgc gatcgtcaac ttcgtgctga agtacatcaa gaagatggtg cccaactacc   540
acatcaaggg cgccgtccgc ttcaagcagg cgctcaagct gggcagccgc cacgcgcttc   600
cgccggtcga gatcgaccac gacgacattg ccttcctgca gtacaccggc gggaccaccg   660
gcgtggccaa gggtgcgatg ctgaccaacc gcaacctgat cgccaacatg cagcaggcgt   720
cagcgtggct gtccacctcc ggcatcgagc cgggcaagga agtgatcatc actgccctgc   780
cgctgtacca catcttcgca ttgaccgcga acggcctggt cttatgaag ttcggtggct   840
gcaaccacct gatcaccaac ccacgcgaca tgaagggctt cgtaaaggag ctcaagggca   900
cccgcttcac tgccatcacc ggcgtcaaca cgctgttcaa cggcctgctc aacaccccgg   960
gcttcgacga gatcgacttc tcttcggtca agttcaccct gggcggcggc atggcggtgc  1020
aacgtgccgt ggccgaacgc tggaagaagg tcaccggcgt gaccctggtc gaagcctatg  1080
gcctgaccga gacctcgccc gcggcctgca tcaatccgct caccctgccc gagtacaacg  1140
gtgccatcgg cctgccgatc ccgtctaccg atgcctgcat caaggacgac aacggcaaca  1200
tcctggcgct gggcgaagtg ggcgagctgt gcatcaaggg cccgcaggta atgaagggct  1260
actggcagcg tccggaagaa accgccaccg ccatcgatgc ggacggctgg ctgcacaccg  1320
gcgacatggc gaagatggac gaacagggct tcttctacat cgtcgaccgc aagaaggaca  1380
tgatcctggt gtccggcttc aacgtgtacc cgaatgaggt cgaagacgtc atcgggatga  1440
tgccgggcgt gctggaagtc gccgccgtcg gtgtccggcga cgaaaagtcc ggcgaagtgg  1500
tcaaggtcgt gatcgtgaag aaggacccga acctgaccgc ggaaatggtc aaggaacatg  1560
cgcgggcaaa cctgaccggt tacaagcacc ccagaatcgt agaattccga aaggagctgc  1620
cgaagaccaa cgtcggcaag atcctccgtc gcgagctgcg tgatacgccc gccccgtaag  1680
aattc                                                               1685

<210> SEQ ID NO 10
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 10
agtcatgagt ctggatcg                                                   18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggaagcttac ggggcgggcg                                                 20

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgaacggcc tggtctttat gaagttcggt gg                                   32

<210> SEQ ID NO 13
<211> LENGTH: 1685
<212> TYPE: DNA
<213> ORGANISM: Stenotrophomonas maltophilia

<400> SEQUENCE: 13
tcatgagtct ggatcgtccc tggctgcaga gctatccgaa aggcgttccc gccgaaatcg      60
acgtcaacga attccattcg gtcgcctcgg tcttcgacgc ttccgtcgcg aaattccgcg     120
accgtcccgc ctactccagc ttcggcaagg tcctcaccta tggtgagacg gacgcgctgg     180
tcacccagtt cgccgcctac ctgctgggtg agctcaagct caagaagggt gaccgcgtcg     240
ccctgatgat gcccaactgc ctgcagtacc cggtggccac cttcggcgtg ctgcgcgccg     300
gcctgaccgt ggtcaacgtc aacccgctgt acaccgcgcg cgaactcaag caccagctgg     360
ttgatgccgg cgtcagcgcc ctggtggtgg tcgacaactt cggcgacacc gtcgaacagg     420
tcatcgccga tacaccggtc aagcacgtgg tcaccaccgg cctgggcgac ctgctcggcg     480
ccaagggcgc gatcgtcaac ttcgtgctga agtacatcaa gaagatggtg cccaactacc     540
acatcaaggg cgccgtccgc ttcaagcagg cgctcaagct gggcagccgc cacgcgcttc     600
cgccggtcga gatcgaccac gacgacattg ccttcctgca gtacaccggc gggaccaccg     660
gcgtggccaa gggtgcgatg ctgaccaacc gcaacctgat cgccaacatg cagcaggcgt     720
cagcgtggct gtccacctcc ggcatcgagc cgggcaagga agtgatcatc actgccctgc     780
cgctgtacca catcttcgca ttgaccgcga acggcctggt ctttatgaag ttcggtggct     840
gcaaccacct gatcaccaac ccacgcgaca tgaagggctt cgtaaaggag ctcaagggca     900
cccgcttcac tgccatcacc ggcgtcaaca cgctgttcaa cggcctgctc aacacccgg      960 gcttcgacga gatcgacttc tcttcggtca agttcaccct gggcggcggc atggcggtgc    1020
aacgtgccgt ggccgaacgc tggaagaagg tcaccggcgt gacctggtc gaagcctatg    1080 gcctgaccga gacctcgccc gcggcctgca tcaatccgct caccctgccc gagtacaacg    1140
```

```
gtgccatcgg cctgccgatc ccgtctaccg atgcctgcat caaggacgac aacggcaaca    1200
tcctggcgct gggcgaagtg ggcgagctgt gcatcaaggg cccgcaggta atgaagggct    1260
actggcagcg tccggaagaa accgccaccg ccatcgatgc ggacggctgg ctgcacaccg    1320
gcgacatggc gaagatggac gaacagggct tcttctacat cgtcgaccgc aagaaggaca    1380
tgatcctggt gtccggcttc aacgtgtacc cgaatgaggt cgaagacgtc atcgcgatga    1440
tgccgggcgt gctggaagtc gccgccgtcg gtgtcccgga cgaaaagtcc ggcgaagtgg    1500
tcaaggtcgt gatcgtgaag aaggacccga acctgaccgc ggaaatggtc aaggaacatg    1560
cgcgggcaaa cctgaccggt tacaagcacc ccagaatcgt agaattccga aggagctgc     1620 cgaagaccaa cgtcggcaag atcctccgtc gcgagctgcg tgatacgccc gccccgtaag    1680
aattc                                                                1685
```

<210> SEQ ID NO 14
<211> LENGTH: 557
<212> TYPE: PRT
<213> ORGANISM: Stenotrophomonas maltophilia

<400> SEQUENCE: 14

```
Met Ser Leu Asp Arg Pro Trp Leu Gln Ser Tyr Pro Lys Gly Val Pro
1               5                   10                  15

Ala Glu Ile Asp Val Asn Glu Phe His Ser Val Ala Ser Val Phe Asp
            20                  25                  30

Ala Ser Val Ala Lys Phe Arg Asp Arg Pro Ala Tyr Ser Ser Phe Gly
        35                  40                  45

Lys Val Leu Thr Tyr Gly Glu Thr Asp Ala Leu Val Thr Gln Phe Ala
    50                  55                  60

Ala Tyr Leu Leu Gly Glu Leu Lys Leu Lys Gly Asp Arg Val Ala
65                  70                  75                  80

Leu Met Met Pro Asn Cys Leu Gln Tyr Pro Val Ala Thr Phe Gly Val
                85                  90                  95

Leu Arg Ala Gly Leu Thr Val Val Asn Val Asn Pro Leu Tyr Thr Ala
            100                 105                 110

Arg Glu Leu Lys His Gln Leu Val Asp Ala Gly Val Ser Ala Leu Val
        115                 120                 125

Val Val Asp Asn Phe Gly Asp Thr Val Glu Gln Val Ile Ala Asp Thr
    130                 135                 140

Pro Val Lys His Val Val Thr Thr Gly Leu Gly Asp Leu Leu Gly Ala
145                 150                 155                 160

Lys Gly Ala Ile Val Asn Phe Val Leu Lys Tyr Ile Lys Lys Met Val
                165                 170                 175

Pro Asn Tyr His Ile Lys Gly Ala Val Arg Phe Lys Gln Ala Leu Lys
            180                 185                 190

Leu Gly Ser Arg His Ala Leu Pro Pro Val Glu Ile Asp His Asp Asp
        195                 200                 205

Ile Ala Phe Leu Gln Tyr Thr Gly Gly Thr Thr Gly Val Ala Lys Gly
    210                 215                 220

Ala Met Leu Thr Asn Arg Asn Leu Ile Ala Asn Met Gln Gln Ala Ser
225                 230                 235                 240

Ala Trp Leu Ser Thr Ser Gly Ile Glu Pro Gly Lys Glu Val Ile Ile
                245                 250                 255

Thr Ala Leu Pro Leu Tyr His Ile Phe Ala Leu Thr Ala Asn Gly Leu
            260                 265                 270
```

Val Phe Met Lys Phe Gly Gly Cys Asn His Leu Ile Thr Asn Pro Arg
            275                 280                 285

Asp Met Lys Gly Phe Val Lys Glu Leu Lys Gly Thr Arg Phe Thr Ala
        290                 295                 300

Ile Thr Gly Val Asn Thr Leu Phe Asn Gly Leu Leu Asn Thr Pro Gly
305                 310                 315                 320

Phe Asp Glu Ile Asp Phe Ser Ser Val Lys Phe Thr Leu Gly Gly Gly
                325                 330                 335

Met Ala Val Gln Arg Ala Val Ala Glu Arg Trp Lys Lys Val Thr Gly
            340                 345                 350

Val Thr Leu Val Glu Ala Tyr Gly Leu Thr Glu Thr Ser Pro Ala Ala
        355                 360                 365

Cys Ile Asn Pro Leu Thr Leu Pro Glu Tyr Asn Gly Ala Ile Gly Leu
    370                 375                 380

Pro Ile Pro Ser Thr Asp Ala Cys Ile Lys Asp Asp Asn Gly Asn Ile
385                 390                 395                 400

Leu Ala Leu Gly Glu Val Gly Glu Leu Cys Ile Lys Gly Pro Gln Val
                405                 410                 415

Met Lys Gly Tyr Trp Gln Arg Pro Glu Glu Thr Ala Thr Ala Ile Asp
            420                 425                 430

Ala Asp Gly Trp Leu His Thr Gly Asp Met Ala Lys Met Asp Glu Gln
        435                 440                 445

Gly Phe Phe Tyr Ile Val Asp Arg Lys Lys Asp Met Ile Leu Val Ser
    450                 455                 460

Gly Phe Asn Val Tyr Pro Asn Glu Val Glu Asp Val Ile Ala Met Met
465                 470                 475                 480

Pro Gly Val Leu Glu Val Ala Ala Val Gly Val Pro Asp Glu Lys Ser
                485                 490                 495

Gly Glu Val Val Lys Val Val Ile Val Lys Lys Asp Pro Asn Leu Thr
            500                 505                 510

Ala Glu Met Val Lys Glu His Ala Arg Ala Asn Leu Thr Gly Tyr Lys
        515                 520                 525

His Pro Arg Ile Val Glu Phe Arg Lys Glu Leu Pro Lys Thr Asn Val
    530                 535                 540

Gly Lys Ile Leu Arg Arg Glu Leu Arg Asp Thr Pro Ala
545                 550                 555

<210> SEQ ID NO 15
<211> LENGTH: 66
<212> TYPE: DNA
<213> ORGANISM: Escherichia coli

<400> SEQUENCE: 15
tttattccga actgatcgga cttgttcagc gtacacgtgt tagctatcct gcgtgcttca      60
ataaaa                                                                66

<210> SEQ ID NO 16
<211> LENGTH: 66
<212> TYPE: DNA
<213> ORGANISM: Escherichia coli

<400> SEQUENCE: 16
tctttaaatg gctgatcgga cttgttcggc gtacaagtgt acgctattgt gcattcgaaa     60
cttact                                                               66

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcatatgcgc ccattacatc cg                                              22

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcctaggagg gctaatttag ccctttagtt                                      30

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atagtttagc ggccgcaaat cgagctggat caggatta                             38

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aggattcaga catcgtgatg taatgaaaca agcaaatcaa gataga                    46

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cgcggatccg aatcactacg ccactgttcc                                      30

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttgatttgct tgtttcatta catcacgatg tctgaatcct tg                        42

```
<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atatgacgtc ggcatccgct tacagaca                                          28

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aattcttaag tcaggagagc gttcaccgac aa                                     32

<210> SEQ ID NO 25
<211> LENGTH: 8
<212> TYPE: PRT
<213> ORGANISM: Unknown
<220> FEATURE:
<223> OTHER INFORMATION: Description of Unknown: ADP-1 motif peptide
<220> FEATURE:
<221> NAME/KEY: MOD_RES
<222> LOCATION: (4)..(4)
<223> OTHER INFORMATION: Any amino acid

<400> SEQUENCE: 25

His His Ala Xaa Val Asp Gly Val
1               5

<210> SEQ ID NO 26
<211> LENGTH: 6
<212> TYPE: PRT
<213> ORGANISM: Unknown
<220> FEATURE:
<223> OTHER INFORMATION: Description of Unknown: ADP-1 motif peptide

<400> SEQUENCE: 26

Asn Asp Val Val Leu Ala
1               5

<210> SEQ ID NO 27
<211> LENGTH: 7
<212> TYPE: PRT
<213> ORGANISM: Unknown
<220> FEATURE:
<223> OTHER INFORMATION: Description of Unknown: ADP-1 motif peptide
<220> FEATURE:
<221> NAME/KEY: MOD_RES
<222> LOCATION: (5)..(5)
<223> OTHER INFORMATION: Any amino acid

<400> SEQUENCE: 27

Gly Ala Leu Arg Xaa Tyr Leu
1               5

<210> SEQ ID NO 28
<211> LENGTH: 7
<212> TYPE: PRT
<213> ORGANISM: Unknown
<220> FEATURE:
<223> OTHER INFORMATION: Description of Unknown: ADP-1 motif peptide
```

<220> FEATURE:
<221> NAME/KEY: MOD_RES
<222> LOCATION: (3)..(3)
<223> OTHER INFORMATION: Any amino acid

<400> SEQUENCE: 28

Pro Leu Xaa Ala Met Val Pro
1 5

<210> SEQ ID NO 29
<211> LENGTH: 7
<212> TYPE: PRT
<213> ORGANISM: Unknown
<220> FEATURE:
<223> OTHER INFORMATION: Description of Unknown: ADP-1 motif peptide

<400> SEQUENCE: 29

Ile Ser Asn Val Pro Gly Pro
1 5

<210> SEQ ID NO 30
<211> LENGTH: 9
<212> TYPE: PRT
<213> ORGANISM: Unknown
<220> FEATURE:
<223> OTHER INFORMATION: Description of Unknown: ADP-1 motif peptide
<220> FEATURE:
<221> NAME/KEY: MOD_RES
<222> LOCATION: (6)..(6)
<223> OTHER INFORMATION: Any amino acid

<400> SEQUENCE: 30

Arg Glu Pro Leu Tyr Xaa Asn Gly Ala
1 5

<210> SEQ ID NO 31
<211> LENGTH: 8
<212> TYPE: PRT
<213> ORGANISM: Mycobacterium bovis

<400> SEQUENCE: 31

His His Ser Leu Ile Asp Gly Tyr
1 5

<210> SEQ ID NO 32
<211> LENGTH: 6
<212> TYPE: PRT
<213> ORGANISM: Mycobacterium bovis

<400> SEQUENCE: 32

Asn Asp Val Ala Leu Ala
1 5

<210> SEQ ID NO 33
<211> LENGTH: 7
<212> TYPE: PRT
<213> ORGANISM: Mycobacterium bovis

<400> SEQUENCE: 33

Gly Gly Leu Arg Arg Phe Leu
1 5

<210> SEQ ID NO 34
<211> LENGTH: 7
<212> TYPE: PRT
<213> ORGANISM: Mycobacterium bovis

<400> SEQUENCE: 34

Ser Leu Ile Val Val Leu Pro
1 5

<210> SEQ ID NO 35
<211> LENGTH: 7
<212> TYPE: PRT
<213> ORGANISM: Mycobacterium bovis

<400> SEQUENCE: 35

Val Ser Asn Val Pro Gly Pro
1 5

<210> SEQ ID NO 36
<211> LENGTH: 9
<212> TYPE: PRT
<213> ORGANISM: Mycobacterium bovis

<400> SEQUENCE: 36

Glu Asp Val Leu Tyr Leu Arg Gly Ser
1 5

<210> SEQ ID NO 37
<211> LENGTH: 8
<212> TYPE: PRT
<213> ORGANISM: Mycobacterium gilvum

<400> SEQUENCE: 37

His His Ala Leu Val Asp Gly Tyr
1 5

<210> SEQ ID NO 38
<211> LENGTH: 6
<212> TYPE: PRT
<213> ORGANISM: Mycobacterium gilvum

<400> SEQUENCE: 38

Asn Asp Val Ala Leu Ala
1 5

<210> SEQ ID NO 39
<211> LENGTH: 7
<212> TYPE: PRT
<213> ORGANISM: Mycobacterium gilvum

<400> SEQUENCE: 39

Gly Gly Leu Arg Lys Phe Leu
1 5

<210> SEQ ID NO 40
<211> LENGTH: 7
<212> TYPE: PRT
<213> ORGANISM: Mycobacterium gilvum

<400> SEQUENCE: 40

Ser Leu Ile Ala Phe Leu Pro
1 5

<210> SEQ ID NO 41
<211> LENGTH: 7
<212> TYPE: PRT
<213> ORGANISM: Mycobacterium gilvum

<400> SEQUENCE: 41

```
Val Ser Asn Val Pro Gly Pro
1               5

<210> SEQ ID NO 42
<211> LENGTH: 9
<212> TYPE: PRT
<213> ORGANISM: Mycobacterium gilvum

<400> SEQUENCE: 42

Arg Glu Pro Leu Tyr Phe Asn Gly Ser
1               5

<210> SEQ ID NO 43
<211> LENGTH: 8
<212> TYPE: PRT
<213> ORGANISM: Mycobacterium vanbaalenii

<400> SEQUENCE: 43

His His Ala Leu Val Asp Gly Tyr
1               5

<210> SEQ ID NO 44
<211> LENGTH: 6
<212> TYPE: PRT
<213> ORGANISM: Mycobacterium vanbaalenii

<400> SEQUENCE: 44

Asn Asp Val Ala Leu Ala
1               5

<210> SEQ ID NO 45
<211> LENGTH: 7
<212> TYPE: PRT
<213> ORGANISM: Mycobacterium vanbaalenii

<400> SEQUENCE: 45

Gly Gly Leu Arg Lys Phe Leu
1               5

<210> SEQ ID NO 46
<211> LENGTH: 7
<212> TYPE: PRT
<213> ORGANISM: Mycobacterium vanbaalenii

<400> SEQUENCE: 46

Ser Leu Ile Ala Phe Leu Pro
1               5

<210> SEQ ID NO 47
<211> LENGTH: 7
<212> TYPE: PRT
<213> ORGANISM: Mycobacterium vanbaalenii

<400> SEQUENCE: 47

Val Ser Asn Val Pro Gly Pro
1               5

<210> SEQ ID NO 48
<211> LENGTH: 9
<212> TYPE: PRT
<213> ORGANISM: Mycobacterium vanbaalenii

<400> SEQUENCE: 48

Arg Glu Pro Leu Tyr Phe Asn Gly Ser
1               5
```

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tcatatgcgc ccattacatc cg                                              22

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tcctaggagg gctaatttag ccctttagtt                                      30

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
atagtttagc ggccgcaaat cgagctggat caggatta                             38

<210> SEQ ID NO 52
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
aggattcaga catcgtgatg taatgaaaca agcaaatcaa gataga                    46

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cgcggatccg aatcactacg ccactgttcc                                      30

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ttgatttgct tgtttcatta catcacgatg tctgaatcct tg                        42

```
<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atatgacgtc ggcatccgct tacagaca                                          28

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aattcttaag tcaggagagc gttcaccgac aa                                     32
```

ENHANCED PRODUCTION OF FATTY ACID DERIVATIVES

CROSS-REFERENCE TO RELATED APPLICATIONS

This application is a continuation of U.S. patent application Ser. No. 13/099,986, filed May 3, 2011 and issued on Oct. 9, 2012 as U.S. Pat. No. 8,283,143, which is a continuation of U.S. patent application Ser. No. 12/278,960, filed Aug. 8, 2008 and issued on Feb. 7, 2012 as U.S. Pat. No. 8,110,670, which is the National Stage of International Application No. PCT/US2008/58788, filed Mar. 28, 2008, which claims the benefit of U.S. Provisional Application No. 60/908,547, filed Mar. 28, 2007, and U.S. Provisional Application No. 60/989,798, filed Nov. 21, 2007; and said U.S. Ser. No. 12/278,960, now U.S. Pat. No. 8,110,670 is a continuation-in-part of International Application No. PCT/US2007/011923, filed May 18, 2007, which claims the benefit of U.S. Provisional Application No. 60/801,995, filed May 19, 2006, U.S. Provisional Application No. 60/802,016, filed May 19, 2006, and U.S. Provisional Application No. 60/908,547, filed Mar. 28, 2007, all of which are herein expressly incorporated by reference in their entirety.

TECHNICAL FIELD

Genetically engineered cells and microorganisms are provided that produce products from the fatty acid biosynthetic pathway (i.e., fatty alcohols), as well as methods of their use. The products are particularly useful as biofuels.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 34,203 Byte ASCII (Text) file named "LS00004 PCT-US CON2 SL.txt," created on Mar. 11, 2014.

BACKGROUND

Developments in technology have been accompanied by an increased reliance on fuel sources. Such fuel sources are becoming increasingly limited and difficult to acquire. With the burning of fossil fuels taking place at an unprecedented rate, it is likely that the world's fuel demand will soon outweigh current fuel supplies.

As a result, efforts have been directed toward harnessing sources of renewable energy, such as sunlight, water, wind, and biomass. The use of biomasses to produce new sources of fuel which are not derived from petroleum sources, (i.e., biofuel) has emerged as one alternative option. Biofuel is a biodegradable, clean-burning combustible fuel which can be comprised of alkanes and esters. An exemplary biofuel is biodiesel. Biodiesel can be used in most internal combustion diesel engines in either a pure form, which is referred to as "neat" biodiesel, or as a mixture in any concentration with regular petroleum diesel.

Biodiesel offers a number of interesting and attractive beneficial properties compared to petroleum-based diesel, including reduced emissions (e.g., carbon monoxide, sulphur, aromatic hydrocarbons, soot particles, etc.) during combustion. Biodiesel also maintains a balanced carbon dioxide cycle because it is based on renewable biological materials. Biodiesel is non-toxic, completely biodegradable, and very safe due to its high flash point and low flammability. Furthermore, biodiesel provides good lubrication properties, thereby reducing wear and tear on engines.

Current methods of making biodiesel involve transesterification of triacylglycerides from vegetable oil feedstocks, such as rapeseed in Europe, soybean in North America, and palm oil in South East Asia. Industrial-scale biodiesel production is thus geographically and seasonally restricted to areas where vegetable oil feedstocks are produced. The transesterification process leads to a mixture of fatty esters which can be used as biodiesel. An undesirable byproduct of the transesterification process is glycerin. To be usable as biodiesel, the fatty esters must be further purified from the heterogeneous product. This increases costs and the amount of energy required for fatty ester production and, ultimately, biodiesel production as well. Furthermore, vegetable oil feedstocks are inefficient sources of energy because they require extensive acreage for cultivation. For example, the yield of biodiesel from rapeseed is only 1300 L/hectare because only the seed oil is used for biodiesel production, and not the rest of the rapeseed biomass. Additionally, cultivating some vegetable oil feedsocks, such as rapeseed and soybean, requires frequent crop rotation to prevent nutrient depletion of the land.

Therefore, there is a need for an economically- and energy-efficient biofuel and method of making biofuels from renewable energy sources, such as biomass.

SUMMARY

This invention relates to the production of fatty acid derivatives from recombinant cells. Generally, the fatty acid derivatives are produced by expressing or over-expressing at least one gene encoding a fatty acid derivative enzyme. In addition, a gene encoding an acyl-CoA dehydrogenase enzyme can be modified in the recombinant cell such that expression of the gene is attenuated.

In one aspect, the invention provides a recombinant cell comprising at least one of (a) at least one gene encoding a fatty acid derivative enzyme, which gene is modified such that the gene is over-expressed, and (b) a gene encoding an acyl-CoA dehydrogenase enzyme, which gene is modified such that expression of the gene is attenuated. The modified gene encoding a fatty acid derivative enzyme gene may be a gene encoding an acyl-CoA synthase, a thioesterase, an ester synthase, an alcohol acyltransferase, an alcohol dehydrogenase, an acyl-CoA reductase, or a fatty-alcohol forming acyl-CoA reductase. In one embodiment, the modified gene encodes an acyl-CoA synthase, a thioesterase or an ester synthase. In some embodiments, the acyl-CoA synthase and a thioesterase and/or an ester synthase are modified. In some embodiments, the cell also comprises a gene encoding a transport protein.

The recombinant or host cell of the invention may be a *Saccharomyces cerevisiae*, *Candida lipolytica*, *E. coli*, *Arthrobacter*, *Rhodotorula glutinins*, *Acinetobacter*, *Candida lipolytica*, *Botryococcus braunii*, *Vibrio furnissii*, *Micrococcus leuteus*, *Stenotrophomonas maltophilia* or *Bacillus subtilis* cell, e.g., an *Arthrobacter* AK 19, *Acinetobacter* sp. strain M-1, *E. coli* B, *E. coli* C, *E. coli* K or *E. coli* W cell. In other embodiments, the recombinant cell is a cyanobacteria cell, e.g., a *Synechocystis* sp. PCC6803 or *Synechococcus elongatus* PCC7942 cell. In still other embodiments, the recombinant cell is a plant, animal or human cell. Alternatively, the recombinant cell is a microorganism cell from a bacteria, yeast, or filamentous fungi.

In a second aspect, the invention provides a recombinant cell capable of producing a fatty acid derivative, wherein the cell is modified to include at least one exogenous nucleic acid sequence encoding a fatty acid derivative enzyme. The exogenous nucleic acid sequence may encode an acyl-CoA synthase, a thioesterase, an ester synthase, an alcohol acyltransferase, an alcohol dehydrogenase, an acyl-CoA reductase or a fatty-alcohol forming acyl-CoA reductase. In some embodiments, the cell is modified to include at least two exogenous nucleic acid sequences encoding a fatty acid derivative enzyme, e.g., a first exogenous nucleic acid sequences encodes an acyl-CoA synthase and a second exogenous nucleic acid sequence encodes a thioesterase or an ester synthase. In other embodiments, the gene encoding a fatty acid derivative enzyme is modified to optimize a codon for expression in the recombinant cell.

In one embodiment, the recombinant cell comprises a modified gene encoding an acyl-CoA synthase, such as fadD, fadK, BH3103, yhfL, Pfl-4354, EAV15023, fadD1, fadD2, RPC_4074, fadDD35, fadDD22, faa3p or the gene encoding the protein ZP_01644857. Examples of the acyl-CoA synthase genes are fadDD35 from *M. tuberculosis* HR7Rv [NP_217021], yhfL from *B. subtilis* [NP_388908], fadD1 from *P. aeruginosa* PAO1 [NP_251989], the gene encoding the protein ZP_01644857 from *Stenotrophomonas maltophilia* R551-3, or faa3p from *Saccharomyces cerevisiae* [NP_012257].

In a second embodiment, the recombinant cell comprises a modified gene encoding a thioesterase, such as tesA, 'tesA, tesB, fatB, fatB2, fatB3, fatB [M141T], fatA or fatA1.

In a third embodiment, the recombinant cell comprises a modified gene encoding an ester synthase, such as an ester synthase gene obtained from *Acinetobacter* spp., *Alcanivorax borkumensis, Arabidopsis thaliana, Saccharomyces cerevisiae, Homo sapiens, Simmondsia chinensis, Mortierella alpina, Cryptococcus curvatus, Alcanivorax jadensis, Alcanivorax borkumensis. Acinetobacter* sp. HO1-N or *Rhodococcus opacus*. Examples of ester synthase genes include wax/dgat, a bifunctional ester synthase/acyl-CoA:diacylglycerol acyltransferase from *Simmondsia chinensis, Acinetobacter* sp. strain ADP1, *Alcanivorax borkumensis, Pseudomonas aeruginosa, Fundibacter jadensis, Arabidopsis thaliana*, or *Alkaligenes eutrophus*.

In one embodiment, the recombinant cell of the invention further comprises at least one of a pdh, panK, aceEF, fabH, fabD, fabG, acpP, and fabF gene that is modified to be expressed or overexpressed. In a second embodiment, the recombinant cell further comprises at least one of a fadE, gpsA, IdhA, pflB, adhE, pta, poxB, ackA, and ackB gene that is modified such that expression of the gene is attenuated. In a third embodiment, the recombinant cell further comprises at least one modified gene of plsB and sfa.

In other embodiments, the gene encoding an acyl-CoA dehydrogenase enzyme is deleted.

Recombinant cells according to the invention produce more acyl-CoA relative to a non-recombinant cell, e.g., an otherwise identical non-recombinant cell or a cell of similar lineage and phenotype.

The invention further provides compositions produced by the recombinant cells disclosed herein. The compositions comprising fatty acid derivatives produced from a recombinant cell may comprising less than or equal to about 50 ppm arsenic, about 30 ppm, about 25 ppm, or between about 10-50 ppm arsenic; less than or equal to about 200 ppm calcium, about 150 ppm calcium, about 119 ppm calcium or between about 50-200 ppm calcium; less than or equal to about 200 ppm chlorine, about 150 ppm chlorine, about 119 ppm chlorine or between about 50-200 ppm chlorine; less than or equal to about 50 ppm copper, about 30 ppm copper, about 23 ppm copper, or between about 10-50 ppm copper; less than or equal to about 300 ppm iron, about 200 ppm iron, about 136 ppm iron, or between about 50-250 ppm iron; less than or equal to about 50 ppm lead, about 30 ppm lead, about 25 ppm lead, or between about 10-50 ppm lead; less than or equal to about 50 ppm manganese, about 30 ppm manganese, about 23 ppm manganese, or between about 10-50 ppm manganese; less than or equal to about 50 ppm magnesium, about 30 ppm magnesium, about 23 ppm magnesium, or between about 10-50 ppm magnesium; less than or equal to about 0.5 ppm mercury, about 0.1 ppm mercury, about 0.06 ppm mercury or between about 0.01-0.2 ppm mercury; less than or equal to about 50 ppm molybdenum, about 30 ppm molybdenum, about 23 ppm molybdenum or between about 10-50 ppm molybdenum; less than or equal to about 2% nitrogen; about 1% nitrogen, about 0.5% nitrogen, or between about 0.1-1% nitrogen; less than or equal to about 200 ppm potassium, about 150 ppm potassium, about 103 ppm potassium, or between about 50-200 ppm potassium; less than or equal to about 300 ppm sodium, 200 ppm sodium, about 140 ppm sodium, or between about 50-300 ppm sodium; less than or equal to about 1 ppm sulfur, less than or equal to about 1% sulfur, about 0.14% sulfur, or between about 0.05-0.3% sulfur; less than or equal to about 50 ppm zinc, about 30 ppm zinc, about 23 ppm zinc, or between about 10-50 ppm zinc; or less than or equal to about 700 ppm phosphorus, about 500 ppm phosphorus, about 350 ppm phosphorus, or between about 100-700 ppm phosphorus.

In one aspect, the composition produced by a recombinant cell of the invention comprises a fatty acid having a double bond at position 7 in the carbon chain (between $C_7$ and $C_8$) from the reduced end of the fatty acid derivative. In some embodiments, the composition comprises $C_5$-$C_{25}$ fatty esters, or $C_{10}$-$C_{20}$ fatty esters, or $C_{12}$-$C_{18}$ fatty esters. In other embodiments, the fatty acid derivatives comprise straight chain fatty acid derivatives, branched chain fatty acid derivatives, cyclic moieties. In still other embodiments, the fatty acid derivatives are unsaturated (e.g., monounsaturated) or saturated.

In other aspects, the composition comprises a fatty ester that is produced from an alcohol and an acyl-CoA, wherein the alcohol is at least about 1, about 2, about 3, about 4, about 5, about 6, about 7, about 8, about 10, about 12, about 14, about 16, or about 18 carbons in length, and the acyl-CoA is at least about 2, about 4, about 6, about 8, about 10, about 12, about 14, about 16, about 18, about 20, about 22, about 24, or about 26 carbons in length. In some embodiments, the alcohol and acyl-CoA from which the fatty ester are produced vary by about 2, about 4, about 6, about 8, about 10, about 12 or about 14 carbon atoms.

In one embodiment, the composition produced by a recombinant cell of this invention has a fraction of modern carbon of about 1.003 to about 1.5.

In other aspects, the invention provides a method for producing fatty acid derivatives in a recombinant cell comprising a) obtaining a recombinant cell; b) culturing the recombinant cell, and c) producing fatty acid derivatives.

In further aspects, the invention provides a method of increasing production of fatty acid derivatives in a recombinant cell comprising introducing an exogenous nucleic acid encoding a fatty acid derivative enzyme into the recombinant cell, and expressing the exogenous nucleic acid, wherein expression of the nucleic acid in the recombinant cell results in increased production of fatty acid derivatives relative to a non-recombinant cell, e.g., an otherwise identical non-recombinant cell or a cell of similar lineage and phenotype. In some embodiments, the exogenous nucleic acid encodes an acyl-CoA synthase, a thioesterase or an ester synthase. In other embodiments, exogenous nucleic acid encoding an acyl-CoA synthase, a thioesterase and an ester synthase are introduced into the recombinant cell. In other embodiments, a method for increasing the production level of fatty acid derivatives in a recombinant cell is provided, the method comprising: introducing a nucleic acid construct into a host cell, the nucleic acid construct comprising (a) a nucleic acid sequence encoding a fatty acid derivative enzyme of SEQ ID NO:2, SEQ ID NO:3, SEQ ID NO: 6, SEQ ID NO:9 or SEQ ID NO:13, and (b) regulatory sequences for expression of the nucleic acid sequence; expressing the nucleic acid sequence; and obtaining the fatty acid derivatives.

In still further aspects, the invention provides a recombinant construct comprising a nucleic acid sequence encoding a fatty acid derivative enzyme, wherein the nucleic acid sequence is modified to over-express the gene encoding a fatty acid derivative enzyme. In one embodiment, the nucleic acid sequence is modified to over-express the gene encoding an acyl-CoA synthase, a thioesterase, or an ester synthase. In a second embodiment, the nucleic acid sequence is modified to over-express (1) the gene encoding an acyl-CoA synthase, and (2) the gene encoding a thioesterase or an ester synthase. In a third embodiment, the nucleic acid sequence is modified to over-express the gene encoding (1) an acyl-CoA synthase, (2) a thioesterase, and (3) an ester synthase. In a fourth embodiment, the construct further comprises a nucleic acid sequence encoding an acyl-CoA dehydrogenase which is modified such that expression of the acyl-CoA dehydrogenase is attenuated. Vectors comprising these recombinant constructs are also provided by the invention. In some embodiments, the vector further comprises a structural gene providing for selection of transformed cells.

In another aspect, the invention provides a method for increasing production of fatty acid derivatives in a host cell, comprising: transforming the host cell with a nucleotide sequence so that the host cell expresses or over-expresses a fatty acid derivative enzyme gene, wherein the production of fatty acid derivatives in the host cell has been increased relative to a cell that has not been transformed. In such a method, the host cells may be harvested and lysed to obtain the fatty acid derivatives that have been produced. Alternatively, the host cell is transformed with a nucleotide sequence encoding a transport protein and the host cell releases the fatty acid derivatives extracellularly.

In still another aspect, the invention provides a vector comprising a nucleic acid sequence encoding a fatty acid derivative enzyme operably linked to a promoter that is functional in a host cell, wherein the nucleic acid sequence comprises a first nucleic acid sequence encoding an acyl-CoA synthase and a second nucleic acid sequence encoding a thioesterase or ester synthase. The vector may further comprise a nucleic acid sequence encoding a transport protein. In one embodiment, the second nucleic acid sequence encodes a thioesterase and the vector further comprises a third nucleic acid sequence encoding an ester synthase. In a second embodiment, the vector further comprises a nucleic acid sequence encoding a transport protein.

In a still further aspect, the invention provides a method of producing fatty acid derivatives comprising: (a) providing a host cell comprising the vector of the invention, and (b) culturing the host cell to produce fatty acid derivatives. In some embodiments, a supernatant from the culturing of the host cell is collected to obtain the fatty acid derivatives that have been produced. Fatty acid derivatives produced by such methods are also provided by the invention.

In one aspect, fatty acid derivatives produced in accordance with the invention may be used as biofuel compositions. The fatty acid derivatives may be used as a biodiesel, fatty alcohol, fatty ester, triacylglyceride, gasoline or jet fuel.

In another aspect, the compositions produced by a recombinant cell of the invention comprise fatty esters and free fatty acids. For example, in one embodiment, the percentage of free fatty acids by weight is at least about 1%, about 2%, about 3%, about 4%, about 5%, about 6%, about 7%, about 8%, about 9%, about 10%, about 15%, about 20%, or about 25%. In another embodiment, the percentage of fatty esters produced by weight is at least about 50%, about 55%, about 60%, about 65%, about 70%, about 75%, about 80%, about 85%, or about 90%. In a further embodiment, the ratio of fatty esters to free fatty acids is about 10:1, about 9:1, about 8:1, about 7:1, about 5:1, about 2:1 or about 1:1.

In one embodiment, the composition produced in accordance with the invention includes a fatty ester, wherein the fatty ester is at least one of: ethyl dodecanoate, ethyl tridecanoate, ethyl tetradecanoate, ethyl pentadecanoate, ethyl cis-9-hexadecenoate, ethyl hexadecanoate, ethyl heptadecanoate, ethyl cis-11-octadecenoate, ethyl octadecanoate, or a combination thereof.

In a second embodiment, the composition produced in accordance with the invention includes a free fatty acid, wherein the free fatty acid is at least one of: dodecanoic acid, tetradecanoic acid, pentadecanoic acid, cis-9-hexadecenoic acid, hexadecanoic acid, cis-11-octadecenoic acid, or combinations thereof.

The compositions of these embodiments may also be used as biofuels, for example, as a biodiesel, fatty alcohol, fatty ester, triacylglyceride, gasoline or jet fuel.

In some embodiments, the compositions disclosed herein contain a percentage by weight of $C_{12}$ free fatty acids relative to the total free fatty acids of at least about 5%, 10%, or 15%. In other embodiments, the compositions disclosed herein contain a percentage by weight of $C_{14}$ free fatty acids relative to the total free fatty acids of at least about 20%, 30%, or 40%. In other embodiments, the compositions disclosed herein contain a percentage by weight of $C_{15}$ free fatty acids relative to the total free fatty acids of at least about 1% or 2%. In other embodiments, the compositions disclosed herein contain a percentage by weight of $C_{16}$ free fatty acids relative to the total free fatty acids of at least about 20%, 30%, or 40%. In other embodiments, the compositions disclosed herein contain a percentage by weight of $C_{18}$ free fatty acids relative to the total free fatty acids of at least about 15%, 20%, or 25%.

In some embodiments, the compositions disclosed herein contain a percentage by weight of $C_{12}$ fatty esters relative to the total fatty esters of at least about 1%, 2%, or 3%. In other embodiments, the compositions disclosed herein contain a percentage by weight of $C_{14}$ fatty esters relative to the total fatty esters of at least about 10%, 15%, or 20%. In other embodiments, the compositions disclosed herein contain a percentage by weight of $C_{16}$ fatty esters relative to the total fatty esters of at least about 30%, 40%, or 50%. In other embodiments, the compositions disclosed herein contain a percentage by weight of $C_{18}$ fatty esters relative to the total fatty esters of at least about 20%, 30%, or 40%.

BRIEF DESCRIPTION OF THE FIGURES

FIG. 1 is a table identifying various genes that can be over-expressed or attenuated to increase fatty acid derivative production. The table also identifies various genes that can be modulated to alter the structure of the fatty acid derivative product. Some of the genes that are used to alter the structure of the fatty acid derivative will also increase the production of fatty acid derivatives.

FIG. 9A is a GC-MS spectrum showing ethyl acetate extract of strain C41(DE3, ΔfadE/pHZ1.43)/pRSET B+pAS004.114B) wherein the pHZ1.43 plasmid expressed ADP1 ester synthase (EC 2.3.1.20, 2.3.1.75). FIG. 9B is a GC-MS spectrum showing ethyl acetate extract of strain C41 (DE3, ΔfadE/pHZ1.43)/pRSET B+pAS004.114B) wherein the pHZ1.43 plasmid expressed SAAT. FIG. 9C is a GC-MS spectrum showing acetyl acetate extract of strain C41(DE3, ΔfadE/pHZ1.43)/pRSET B+pAS004.114B) wherein the pHZ1.43 plasmid did not contain ADP1 (ester synthase) or SAAT. FIG. 9D is a GC-MS spectrum showing the mass spectrum and fragmentation pattern of $C_8C_8$ produced by C41(DE3, ΔfadE/pHZ1.43)/pRSET B+pAS004.114B wherein the pHZ1.43 plasmid expressed SAAT).

FIG. 15 discloses SEQ ID NOS 15 and 16, respectively, in order of appearance.

FIG. 16A and FIG. 16B are chromatograms depicting GC/MS analysis. FIG. 16A is a chromatogram depicting the ethyl extract of the culture of *E. coli* LS9001 strain transformed with plasmids pCDFDuet-1-fadD-WSadp1, pETDuet-1-'tesA. FIG. 16B is a chromatogram depicting ethyl hexadecanoate and ethyl oleate used as reference.

FIG. 18 is SEQ ID NO: 1, the full DNA sequence of the pOP-80 plasmid.

FIG. 19 is SEQ ID NO: 2, the DNA sequence for the *E. coli* codon-optimized fadD35 gene (accession code NP_217021).

FIG. 20 is SEQ ID NO: 3, the DNA sequence for the *E. coli* codon-optimized fadD1 gene (accession code NP_251989).

FIG. 21 is SEQ ID NO: 4, the BsyhfLBspHIF primer based on the DNA sequence deposited at NCBI with the accession code NC_000964.

FIG. 22 is SEQ ID NO: 5, the BsyhfLEcoR primer based on the DNA sequence deposited at NCBI with the accession code NC_000964.

FIG. 23 is SEQ ID NO: 6, the DNA sequence for the yhfL gene from *Bacillus subtilis*.

FIG. 24 is SEQ ID NO: 7, the Scfaa3pPciF primer based on the DNA sequence deposited at NCBI with the accession code NC_001141.

FIG. 25 is SEQ ID NO: 8, the Scfaa3pPcil primer based on the DNA sequence deposited at NCBI with the accession code NC_001141.

FIG. 26 is SEQ ID NO: 9, the DNA sequence for the FAA3 gene from *Saccharomyces cerevisiae* (NP_012257).

FIG. 27 is SEQ ID NO: 10, the Smprk59BspF primer based on the DNA sequence deposited at NCBI with the accession code NZ_AAVZ01000044.

FIG. 28 is SEQ ID NO: 11, the Smprk59HindR primer based on the DNA sequence deposited at NCBI with the accession code NZ_AAVZ01000044.

FIG. 29 is SEQ ID NO: 12, the PrkBsp primer.

FIG. 30 is SEQ ID NO: 13, the DNA sequence encoding the protein ZP_01644857 from *Stenotrophomonas maltophilia* R551-3.

FIG. 31 is SEQ ID NO: 14, the protein sequence of ZP_01644857 from *Stenotrophomonas maltophilia* ATCC 17679.

ABBREVIATIONS AND TERMS

Figure 2:
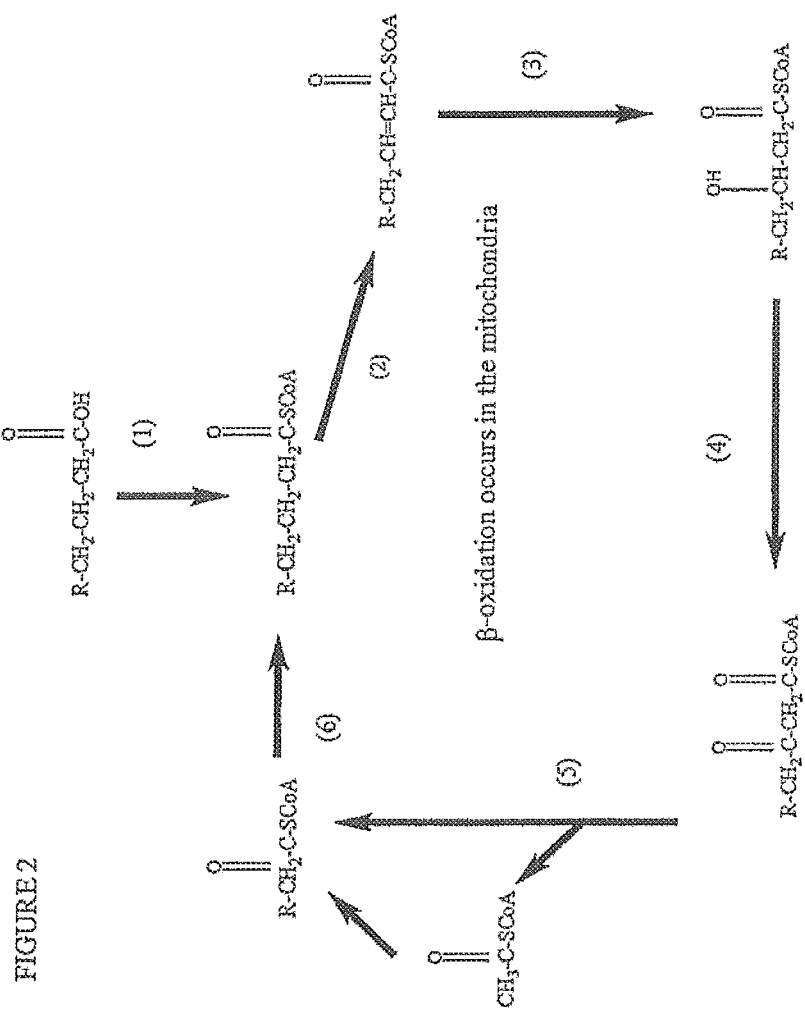
FIG. 2 is a diagram illustrating the beta-oxidation pathway, including steps catalyzed by the following enzymes (1) acyl-CoA synthase (EC 6.2.1.-), (2) acyl-CoA dehydrogenase (EC 1.3.99.3), (3) enoyl-CoA hydratase (EC 4.2.1.17), (4) 3-hydroxybutyryl-CoA epimerase (EC 5.1.2.3), and (5) 3-ketoacyl-CoA thiolase (EC 2.3.1.16). This final reaction of the β-oxidation cycle, releases acetyl-CoA and an acyl-CoA fatty acid two carbons shorter, ready to go through β-oxidation reactions again.

The following explanations of terms and methods are provided to better describe the present disclosure and to guide those of ordinary skill in the art in the practice of the present disclosure. As used herein, the singular forms "a" or "an" or "the" include plural references unless the context clearly dictates otherwise. For example, reference to "a cell" or "the cell" includes one or a plurality of such cells. The term "or" refers to a single element of stated alternative elements or a combination of two or more elements, unless the context clearly indicates otherwise. For example, the phrase "thioesterase activity or fatty alcohol-forming acyl-CoA reductase activity" refers to thioesterase activity, fatty alcohol forming acyl-CoA reductase activity, or a combination of both thioesterase activity and fatty alcohol forming acyl-CoA reductase activity. Additionally, throughout the specification, a reference may be made using an abbreviated gene name or enzyme name, but it is understood that such an abbreviated gene or enzyme name represents the genus of genes or enzymes. For example "fadD" refers to a gene encoding the enzyme "FadD," as well as genes encoding acyl-CoA synthase (EC 6.2.1.-). Such gene names include all genes encoding the same peptide and homologous enzymes having the same physiological function, and enzyme names include all peptides that catalyze the same fundamental chemical reaction or have the same activity. FIG. 1 provides various abbreviated gene and peptide names, descriptions of their activities, and their enzyme classification numbers. These can be used to identify other members of the class of enzymes having the associated activity and their associated genes, which can be used to produce fatty acid derivatives.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Accession Numbers: The accession numbers throughout this description are derived from the NCBI database (National Center for Biotechnology Information) maintained by the National Institute of Health, U.S.A. The accession numbers are as provided in the database on Mar. 27, 2007.

Enzyme Classification Numbers (EC): EC numbers are established by the Nomenclature Committee of the International Union of Biochemistry and Molecular Biology (NC-IUBMB). The EC numbers provided herein are derived from the KEGG Ligand database, maintained by the Kyoto Encyclopedia of Genes and Genomics, sponsored in part by the University of Tokyo. The EC numbers are as provided in the database on Mar. 27, 2007.

Attenuate: To weaken, reduce or diminish. In one example, the sensitivity of a particular enzyme to feedback inhibition or inhibition caused by a composition that is not a product or a reactant (non-pathway specific feedback) is reduced such that the enzyme activity is not impacted by the presence of a compound. In another example, the expression of fabH gene is temperature sensitive and its sequence can be altered to decrease the sensitivity to temperature fluctuations. Expression of the fabH gene can be attenuated when branched amino acids are desired. In another example, an enzyme that has been modified to be less active can be referred to as attenuated.

A functional modification of the sequence encoding an enzyme can be used to attenuate expression of an enzyme. Sequence modifications may include, for example, a mutation, deletion or insertion of one or more nucleotides in a gene sequence or a sequence controlling the transcription or translation of a gene sequence, which modification results in reduction or inhibition of production of the gene product, or renders the gene product non-functional. For example, functional deletion of fabR in E. coli reduces the repression of the fatty acid biosynthetic pathway and allows E. coli to produce more unsaturated fatty acids (UFAs). In some instances a functional deletion is described as a knock-out mutation.

Other methods are available for attenuating expression of an enzyme. For example, attenuation can be accomplished by modifying the sequence encoding the gene as described above; placing the gene under the control of a less active promoter, expressing interfering RNA, ribozymes or antisense sequences that target the gene of interest; by changing the physical or chemical environment, such as temperature, pH, or solute concentration, such that the optimal activity of the gene or gene product is not realized; or through any other technique known in the art.

Biofuel: The term "biofuel" refers to any fuel derived from biomass.

Biomass is a biological material that can be converted into a biofuel. One exemplary source of biomass is plant matter. For example, corn, sugar cane, and switchgrass can be used as biomass. Another non-limiting example of biomass is animal matter, for example cow manure. Biomass also includes waste products from industry, agriculture, forestry, and households. Examples of such waste products which can be used as biomass are fermentation waste, straw, lumber, sewage, garbage and food leftovers. Biomass also includes sources of carbon, such as carbohydrates (e.g., sugars).

Biofuels can be substituted for petroleum based fuels. For example, biofuels are inclusive of transportation fuels (e.g., gasoline, diesel, jet fuel, etc.), heating fuels, and electricity-generating fuels. Biofuels are a renewable energy source. Non-limiting examples of biofuels are biodiesel, hydrocarbons (e.g., alkanes, alkenes, alkynes, or aromatic hydrocarbons), and alcohols derived from biomass.

Biodiesel: Biodiesel is a biofuel. Biodiesel can be a substitute of diesel, which is derived from petroleum. Biodiesel can be used in internal combustion diesel engines in either a pure form, which is referred to as "neat" biodiesel, or as a mixture in any concentration with petroleum-based diesel.

Biodiesel can be comprised of hydrocarbons or esters. In one embodiment, biodiesel is comprised of fatty esters, such as fatty acid methyl esters (FAME) or fatty acid ethyl esters (FAEE). In a preferred embodiment, these FAME and FAEE are comprised of fatty acyl moieties having a carbon chain length of about 8-20, 10-18, or 12-16 carbons in length. Fatty esters used as biodiesel may contain carbon chains which are saturated or unsaturated.

Biocrude: Biocrude is a biofuel. Biocrude can be used as a substitute for petroleum based fuels. In addition, biocrude, like petroleum crude, can be converted into other fuels, for example gasoline, diesel, jet fuel, or heating oil. Moreover, biocrude, like petroleum crude, can be converted into other industrially useful chemicals for use in, for example, pharmaceuticals, cosmetics, consumer goods, industrial processes, etc.

Biocrude may include, for example, hydrocarbons, hydrocarbon products, fatty acid esters, and/or aliphatic ketones. In a preferred embodiment, biocrude is comprised of hydrocarbons, for example aliphatic (e.g., alkanes, alkenes, alkynes) or aromatic hydrocarbons.

Carbon source: Generally refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, gases (e.g., CO and $CO_2$), etc. These include, for example, various monosaccharides such as glucose, fructose, mannose and galactose; oligosaccharides such as fructo-oligosaccharide and galacto-oligosaccharide; polysaccharides such as xylose, and arabinose; disaccharides such as sucrose, maltose and turanose; cellulosic material such as methyl cellulose and sodium carboxymethyl cellulose; saturated or unsaturated fatty acid esters such as succinate, lactate and acetate; alcohols such as ethanol, etc., or mixtures thereof.

The carbon source can additionally be a product of photosynthesis, including, but not limited to glucose.

Cloud point of a fluid: The temperature at which dissolved solids are no longer completely soluble, precipitating as a second phase giving the fluid a cloudy appearance. This term is relevant to several applications with different consequences.

In the petroleum industry, cloud point refers to the temperature below which wax or other heavy hydrocarbons crystallizes in a crude oil, refined oil or fuel to form a cloudy appearance. The presence of solidified waxes influences the flowing behavior of the fluid, the tendency to clog fuel filters/injectors etc., the accumulation of wax on cold surfaces (e.g., pipeline or heat exchanger fouling), and even the emulsion characteristics with water. Cloud point is an indication of the tendency of the oil to plug filters or small orifices at cold operating temperatures.

The cloud point of a nonionic surfactant or glycol solution is the temperature where the mixture starts to phase separate and two phases appear, thus becoming cloudy. This behavior is characteristic of non-ionic surfactants containing polyoxyethylene chains, which exhibit reverse solubility versus temperature behavior in water and therefore "cloud out" at some point as the temperature is raised. Glycols demonstrating this behavior are known as "cloud-point glycols" and are used as shale inhibitors. The cloud point is affected by salinity, being generally lower in more saline fluids.

Cloud point lowering additive: An additive which may be added to a composition to decrease or lower the cloud point of a solution, as described above.

Detectable: Capable of having an existence or presence ascertained. For example, production of a product from a reactant (e.g., the production of C18 fatty acids) is detectable using the methods provided below.

Endogenous: As used herein, with reference to a nucleic acid molecule and a particular cell or microorganism, "endogenous" refers to a nucleic acid sequence or peptide that is in the cell and was not introduced into the cell using recombinant engineering techniques. For example, a gene that was present in the cell when the cell was originally isolated from nature. A gene is still considered endogenous if the control sequences, such as a promoter or enhancer sequences that activate transcription or translation, have been altered through recombinant techniques.

Ester synthase: An ester synthase is a peptide capable of producing fatty esters. More specifically, an ester synthase is a peptide which converts a thioester to a fatty ester. In a preferred embodiment, the ester synthase converts the thioester, acyl-CoA, to a fatty ester.

In an alternate embodiment, an ester synthase uses a thioester and an alcohol as substrates to produce a fatty ester. Ester synthases are capable of using short and long chain acyl-CoAs as substrates. In addition, ester synthases are capable of using short and long chain alcohols as substrates.

Non-limiting examples of ester synthases are wax synthases, wax-ester synthases, acyl-CoA:alcohol transacylases, acyltransferases, and fatty acyl-coenzyme A:fatty alcohol acyltransferases. Exemplary ester synthases are classified in enzyme classification number EC 2.3.1.75. Exemplary GenBank Accession Numbers are provided in FIG. 1.

Exogenous: As used herein, with reference to a nucleic acid molecule and a particular cell, "exogenous" refers to any nucleic acid molecule that does not originate from that particular cell as found in nature. For example, "exogenous DNA" could refer to a DNA sequence that was inserted within the genomic DNA sequence of a microorganism, or an extra chromosomal nucleic acid sequence that was introduced into the microorganism. Thus, a non-naturally-occurring nucleic acid molecule is considered to be exogenous to a cell once introduced into the cell. A nucleic acid molecule that is naturally-occurring also can be exogenous to a particular cell. For example, an entire coding sequence isolated from an *E. coli* DH5alpha cell is an exogenous nucleic acid with respect to a second *E. coli* DH5alpha cell once that coding sequence is introduced into the second *E. coli* DH5alpha cell, even though both cells are DH5alpha cells.

Expression: The process by which the inheritable information in a gene, such as the DNA sequence, is made into a functional gene product, such as protein or RNA.

Several steps in the gene expression process may be modulated, including the transcription step, the translational step, and the post-translational modification of the resulting protein. Gene regulation gives the cell control over its structure and function, and it is the basis for cellular differentiation, morphogenesis and the versatility and adaptability of any organism. Gene regulation may also serve as a substrate for evolutionary change, since control of the timing, location, and amount of gene expression can have a profound effect on the functions (actions) of the gene in the organism.

Expressed genes include genes that are transcribed into messenger RNA (mRNA) and then translated into protein, as well as genes that are transcribed into types of RNA, such as transfer RNA (tRNA), ribosomal RNA (rRNA), and regulatory RNA that are not translated into protein.

Fatty ester: A fatty ester is an ester. In a preferred embodiment, a fatty ester is any ester made from a fatty acid, for example a fatty acid ester.

In one embodiment, a fatty ester contains an A side (i.e., the carbon chain attached to the carboxylate oxygen) and a B side (i.e., the carbon chain comprising the parent carboxylate). In a preferred embodiment, when the fatty ester is derived from the fatty acid biosynthetic pathway, the A side is contributed by an alcohol, and the B side is contributed by a fatty acid.

Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied in the fermentation broth in instances where the fatty ester is produced by an organism. Alternatively, a carboxylic acid, such as a fatty acid or acetic acid, can be supplied exogenously in instances where the fatty ester is produced by an organism that can also produce alcohol.

The carbon chains comprising the A side or B side can be of any length. In one embodiment, the A side of the ester is at least about 1, 2, 3, 4, 5, 6, 7, 8, 10, 12, 14, 16, or 18 carbons in length. The B side of the ester is at least about 4, 6, 8, 10, 12, 14, 16, 18, 20, 22, 24, or 26 carbons in length. The A side and/or the B side can be straight or branched chain. The branched chains may have one or more points of branching. In addition, the branched chains may include cyclic branches.

Furthermore, the A side and/or B side can be saturated or unsaturated. If unsaturated, the A side and/or B side can have one or more points of unsaturation.

In one embodiment, the fatty ester is produced biosynthetically. In this embodiment, first the fatty acid is "activated." Non-limiting examples of "activated" fatty acids are acyl-CoA, acyl ACP, and acyl phosphate. Acyl-CoA can be a direct product of fatty acid biosynthesis or degradation. In addition, acyl-CoA can be synthesized from a free fatty acid, a CoA, and an adenosine nucleotide triphosphate (ATP). An example of an enzyme which produces acyl-CoA is acyl-CoA synthase After the fatty acid is activated, it can be readily transferred to a recipient nucleophile. Exemplary nucleophiles are alcohols, thiols, or phosphates.

In another embodiment, the fatty ester can be derived from a fatty acyl-thioester and an alcohol.

In one embodiment, the fatty ester is a wax. The wax can be derived from a long chain alcohol and a long chain fatty acid. In another embodiment, the fatty ester is a fatty acid thioester, for example fatty acyl Coenzyme A (CoA). In other embodiments, the fatty ester is a fatty acyl panthothenate, an acyl acyl carrier protein (ACP), or a fatty phosphate ester.

Fatty esters have many uses. For examples, fatty esters can be used as a biofuel or a surfactant.

Fatty acid derivative: The term "fatty acid derivative" includes products made in part from the fatty acid biosynthetic pathway of the production host organism. "Fatty acid derivative" also includes products made in part from acyl-ACP or acyl-ACP derivatives. The fatty acid biosynthetic pathway includes fatty acid synthase enzymes which can be engineered as described herein to produce fatty acid derivatives, and in some examples can be expressed with additional enzymes to produce fatty acid derivatives having desired carbon chain characteristics. Exemplary fatty acid derivatives include for example, short and long chain alcohols, hydrocarbons, and fatty alcohols and esters, including waxes, fatty acid esters, or fatty esters.

Fatty acid derivative enzymes: All enzymes that may be expressed or over-expressed in the production of fatty acid derivatives are collectively referred to herein as fatty acid derivative enzymes. These enzymes may be part of the fatty acid biosynthetic pathway. Non-limiting examples of fatty acid derivative synthases include fatty acid synthases, thioesterases, acyl-CoA synthases, acyl-CoA reductases, alcohol dehydrogenases, alcohol acyltransferases, fatty alcohol-forming acyl-CoA reductase, and ester synthases. Fatty acid derivative enzymes convert a substrate into a fatty acid derivative. In some examples, the substrate may be a fatty acid derivative which the fatty acid derivative enzyme converts into a different fatty acid derivative.

Fatty alcohol forming peptides: Peptides capable of catalyzing the conversion of acyl-CoA to fatty alcohol, including fatty alcohol forming acyl-CoA reductase (FAR, EC 1.1.1.*), acyl-CoA reductase (EC 1.2.1.50) or alcohol dehydrogenase (EC 1.1.1.1). Additionally, one of ordinary skill in the art will appreciate that some fatty alcohol forming peptides will catalyze other reactions as well. For example, some acyl-CoA reductase peptides will accept other substrates in addition to fatty acids. Such non-specific peptides are, therefore, also included. Nucleic acid sequences encoding fatty alcohol forming peptides are known in the art and such peptides are publicly available. Exemplary GenBank Accession Numbers are provided in FIG. 1.

Fraction of modern carbon: Fraction of modern carbon ($f_M$) is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

Hydrocarbon: includes chemical compounds that contain the elements carbon (C) and hydrogen (H). All hydrocarbons consist of a carbon backbone and atoms of hydrogen attached to that backbone. Sometimes, the term is used as a shortened form of the term "aliphatic hydrocarbon." There are essentially three types of hydrocarbons: (1) aromatic hydrocarbons, which have at least about one aromatic ring; (2) saturated hydrocarbons, also known as alkanes, which lack double, triple or aromatic bonds; and (3) unsaturated hydrocarbons, which have one or more double or triple bond between carbon atoms and include: alkenes (e.g., dienes) and alkynes.

Isolated: An "isolated" biological component (such as a nucleic acid molecule, protein, or cell) is a biological component that has been substantially separated or purified away from other biological components in which the biological component naturally occurs, such as other chromosomal and extra-chromosomal DNA sequences; chromosomal and extra-chromosomal RNA; and proteins. Nucleic acid molecules and proteins that have been "isolated" include nucleic acid molecules and proteins purified by standard purification methods. The term embraces nucleic acid molecules and proteins prepared by recombinant expression in a production host cell as well as chemically synthesized nucleic acid molecules and proteins.

In one example, isolated refers to a naturally-occurring nucleic acid molecule that is not contiguous with both of the sequences with which it is directly adjacent to (i.e., the sequence on the 5' end and the sequence on the 3' end) in the naturally-occurring genome of the organism from which it is derived.

Microorganism: Includes prokaryotic and eukaryotic microbial species from the domains Archaea, Bacteria and Eucarya, the latter including yeast and filamentous fungi, protozoa, algae, or higher Protista. The terms "microbial cells" and "microbes" are used interchangeably with the term microorganism.

Nucleic Acid Molecule: Encompasses both RNA and DNA sequences including, without limitation, cDNA, genomic DNA sequences, and mRNA. The term ncludes synthetic nucleic acid molecules, such as those that are chemically synthesized or recombinantly produced. The nucleic acid molecule can be double-stranded or single-stranded. When single-stranded, the nucleic acid molecule can be the sense strand or the antisense strand. In addition, a nucleic acid molecule can be circular or linear.

Operably linked: A first nucleic acid sequence is operably linked to a second nucleic acid sequence when the first nucleic acid sequence is placed in a functional relationship to the second nucleic acid sequence. For instance, a promoter is operably linked to a coding sequence if the promoter is in a position to affect the transcription or expression of the coding sequence. Generally, operably linked DNA sequences are contiguous and may join two protein coding regions, in the same reading frame. Configurations of separate genes which are operably linked and are transcribed in tandem as a single messenger RNA are denoted as operons. Placing genes in close proximity, for example in a plasmid vector, under the transcriptional regulation of a single promoter, constitutes a synthetic operon.

ORF (open reading frame): A series of nucleotide triplets (i.e., codons) coding for amino acids without any termination codons. These sequences are usually translatable into a peptide.

Over-express: When a peptide is present in a greater concentration in a recombinant host cell compared to its concentration in a non-recombinant host cell of the same species. Over-expression can be accomplished using any method known in the art. For example, over-expression can be caused by altering the control sequences in the genomic DNA sequence of a host cell, introducing one or more coding sequences into the genomic DNA sequence, altering one or more genes involved in the regulation of gene expression (e.g., deleting a repressor gene or producing an active activator), amplifying the gene at a chromosomal location (tandem repeats), introducing an extra chromosomal nucleic acid sequence, increasing the stability of the RNA transcribed via introduction of stabilizing sequences, and combinations thereof.

Examples of recombinant microorganisms that over-produce a peptide include microorganisms that express nucleic acid sequences encoding acyl-CoA synthases (EC 6.2.1.-). Other examples include microorganisms that have had exogenous promoter sequences introduced upstream to the endogenous coding sequence of a thioesterase peptide (EC 3.1.2.-). Over-expression also includes elevated rates of translation of a gene compared to the endogenous translation rate for that gene. Methods of testing for over-expression are well known in the art. For example, transcribed RNA levels can be assessed using rtPCR and protein levels can be assessed using SDS page gel analysis.

Partition coefficient: The partition coefficient, P, is defined as the equilibrium concentration of a compound in an organic phase divided by the concentration at equilibrium in an aqueous phase (e.g., fermentation broth). In one embodiment of the bi-phasic system described herein, the organic phase is formed by the fatty acid derivative during the production process. However, in some examples, an organic phase can be provided, such as by providing a layer of octane, to facilitate product separation. When describing a two phase system, the partition coefficient, P, is usually discussed in terms of log P. A compound with a log P of 1 would partition 10:1 to the organic phase. A compound with a log P of −1 would partition 1:10 to the organic phase. By choosing an appropriate fermentation broth and organic phase, a fatty acid derivative with a high log P value will separate into the organic phase even at very low concentrations in the fermentation vessel.

Production host: A production host is a cell used to produce the products disclosed herein. As disclosed herein, the production host is modified to express or over-express selected genes, or to have attenuated expression of selected genes. Non-limiting examples of production hosts include plant, animal, human, bacteria, yeast, or filamentous fungi cells.

Promoters and enhancers: Transcriptional control signals in eukaryotes comprise "promoter" and "enhancer" elements. Promoters and enhancers consist of short arrays of DNA sequences which interact specifically with cellular proteins involved in transcription (Maniatis et al., *Science* 236:1237, 1987). Promoter and enhancer elements have been isolated from a variety of eukaryotic sources including genes in yeast, insect, mammalian and plant cells. Promoter and enhancer elements that have been isolated from viruses. Analogous control elements, such as promoters and enhancers, are also found in prokaryotes. The selection of a particular promoter and enhancer depends on the cell type used to express the protein of interest. Some eukaryotic and prokaryotic promoters and enhancers have a broad production host cell range while others are functional in a limited subset of production host cells (see, e.g., Voss et al., *Trends Biochem. Sci.,* 11:287, 1986; and Maniatis et al., 1987 supra).

The terms "promoter element," "promoter," or "promoter sequence" refer to a DNA sequence that functions as a switch which activates the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Purified: The term "purified" refers to molecules that are removed from their natural environment by, for example, isolation or separation. "Substantially purified" molecules are at least about 60% free, preferably at least about 75% free, and more preferably at least about 90% free from other components with which they are naturally associated. As used herein, the term "purified" or "to purify" also refers to the removal of contaminants from a sample. For example, the removal of contaminants can result in an increase in the percentage of fatty acid derivatives of interest in a sample. For example, after fatty acid derivatives are expressed in plant, bacterial, yeast, or mammalian production host cells, the fatty acid derivatives are purified by the removal of production host cell proteins. After purification, the percentage of fatty acid derivatives in the sample is increased.

The term purified does not require absolute purity; rather, it is intended as a relative term. Thus, for example, a purified fatty acid derivative preparation is one in which the product is more concentrated than the product is in its environment within a cell. For example, a purified fatty ester is one that is substantially separated from cellular components (e.g., nucleic acids, lipids, carbohydrates, and other peptides) that can accompany it. In another example, a purified fatty ester preparation is one in which the fatty ester is substantially free from contaminants, such as those that might be present following fermentation.

For example, a fatty ester is purified when at least about 50% by weight of a sample is composed of the fatty ester. In another example when at least about 60%, 70%, 80%, 85%, 90%, 92%, 95%, 98%, or 99% or more by weight of a sample is composed of the fatty ester.

Recombinant: A recombinant nucleic acid molecule is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules, such as genetic engineering techniques. Recombinant is also used to describe nucleic acid molecules that have been artificially manipulated, but contain the same regulatory sequences and coding regions that are found in the organism from which the nucleic acid was isolated. A recombinant protein is a protein derived from a recombinant nucleic acid molecule.

A recombinant or transformed cell is one into which a recombinant nucleic acid molecule has been introduced, such as an acyl-CoA synthase encoding nucleic acid molecule, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA sequence by electroporation, lipofection, and particle gun acceleration.

Sequence identity: The similarity between two nucleic acid sequences or between two amino acid sequences is expressed in terms of the level of sequence identity shared between the sequences. Sequence identity is typically expressed in terms of percentage identity. The higher the percentage identity, the more similar the two sequences. For the purposes of this application, the terms "identity" and "similarity" are interchangeable.

Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237 244, 1988; Higgins & Sharp, *CABIOS* 5:151-153, 1989; Corpet et al., *Nucleic Acids Research* 16:10881-10890, 1988; Huang et al., *CABIOS* 8:155-165, 1992; and Pearson et al., *Methods in Molecular Biology* 24:307-331, 1994. Altschul et al., *J. Mol. Biol.* 215: 403-410, 1990, presents a detailed consideration of sequence alignment methods and homology calculations.

The NCBI Basic Local Alignment Search Tool (BLAST™; Altschul et al., *J. Mol. Biol.* 215:403-410, 1990) is available from several sources, including the National Center for Biotechnology Information (NBCI, Bethesda, Md.), for use in connection with the sequence analysis programs blastp, blastn, blastx, tblastn and tblastx. BLAST™ can be accessed on the Internet at the NBCI website. As used herein, sequence identity is commonly determined with the BLAST™ software set to default parameters. For example, blastn (version 2.0) software can be used to determine sequence identity between two nucleic acid sequences using default parameters (e.g., expect=10, matrix=BLOSUM62, filter=DUST (Tatusov and Lipmann, in preparation as of Dec. 1, 1999; and Hancock and Armstrong, *Comput. Appl. Biosci.* 10:67-70, 1994), gap existence cost=11, per residue gap cost=1, and lambda ratio=0.85). For comparison of two polypeptides, blastp (version 2.0) software can be used with default parameters (e.g., expect 10, filter=SEG (Wootton and Federhen, *Computers in Chemistry* 17:149-163, 1993), matrix=BLOSUM62, gap existence cost=11, per residue gap cost=1, lambda=0.85).

For comparisons of nucleic acid sequences, the "Blast 2 sequences" function of the BLAST™ (Blastn) program is employed using the default BLOSUM62 matrix set to default parameters (e.g., cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least about 45%, at least about 60%, at least about 70%, at least about 75%, at least about 80%, at least about 85%, at least about 90%, at least about 95%, or at least about 98%, or at least about 99% sequence identity.

For comparisons of amino acid sequences of greater than about 30 amino acids, the "Blast 2 sequences" function of the BLAST™ program is employed using the default BLOSUM62 matrix set to default parameters (e.g., gap existence cost of 11, and a per residue gap cost of 1). When aligning short peptides (e.g., fewer than around 30 amino acids), the alignment should be performed using the Blast 2 sequences function, employing the PAM30 matrix set to default parameters (e.g., open gap 9, extension gap 1 penalties). Proteins with even greater similarity to the reference sequences will show increasing percentage identities when assessed by this method, such as at least about 35%, at least about 45%, at least about 50%, at least about 60%, at least about 80%, at least about 85%, at least about 90%, at least about 95%, at least about 98%, or at least about 99% sequence identity to the sequences.

Surfactants: Substances capable of reducing the surface tension of a liquid in which they are dissolved. They are typically composed of a water-soluble head and a hydrocarbon chain or tail. The water soluble head is hydrophilic and can be either ionic or nonionic. The hydrocarbon chain is hydrophobic. Surfactants are used in a variety of products, including detergents and cleaners, and are also used as auxiliaries for textiles, leather and paper, in chemical processes, in cosmetics and pharmaceuticals, in the food industry and in agriculture. In addition, they can be used to aid in the extraction and isolation of crude oils which are found hard to access environments or in water emulsions.

There are four types of surfactants characterized by varying uses. Anionic surfactants have detergent-like activity and are generally used for cleaning applications. Cationic surfactants contain long chain hydrocarbons and are often used to treat proteins and synthetic polymers or are components of fabric softeners and hair conditioners. Amphoteric surfactants also contain long chain hydrocarbons and are typically used in shampoos. Non-ionic surfactants are generally used in cleaning products.

Synthase: A synthase is an enzyme which catalyzes a synthesis process. As used herein, the term synthase includes synthases and synthetases.

Transport protein: A protein that facilitates the movement of one or more compounds in and/or out of an organism or organelle. In some embodiments, an exogenous DNA sequence encoding an ATP-Binding Cassette (ABC) transport protein will be functionally expressed by the production host so that the production host exports the fatty acid derivative into the culture medium. ABC transport proteins are found in many organisms, such as *Caenorhabditis elegans, Arabidopsis thalania, Alcaligenes eutrophus* (later renamed *Ralstonia eutropha*), or *Rhodococcus erythropolis*. Non-limiting examples of ABC transport proteins include CER5, AtMRP5, AmiS2 and AtPGP1. In a preferred embodiment, the ABC transport protein is CER5 (e.g., AY734542).

In other embodiments, the transport protein is an efflux protein selected from: AcrAB, TolC, or AcrEF from *E. coli* or tll1618, tll1619, and tll0139 from *Thermosynechococcus elongatus* BP-1.

In further embodiments, the transport protein is a fatty acid transport protein (FATP) selected from *Drosophila melanogaster, Caenorhabditis elegans, Mycobacterium tuberculosis,* or *Saccharomyces cerevisiae* or any one of the mammalian FATPs well known in the art.

Under conditions that permit product production: Any fermentation conditions that allow a production host to produce a desired product, such as acyl-CoA or fatty acid derivatives such as fatty acids, hydrocarbons, fatty alcohols, waxes, or fatty esters. Fermentation conditions usually comprise many parameters. Exemplary conditions include, but are not limited to, temperature ranges, levels of aeration, and media composition. Each of these conditions, individually and in combination, allows the production host to grow.

Exemplary mediums include broths or gels. Generally, the medium includes a carbon source, such as glucose, fructose, cellulose, or the like, that can be metabolized by the microorganism directly. In addition, enzymes can be used in the medium to facilitate the mobilization (e.g., the depolymerization of starch or cellulose to fermentable sugars) and subsequent metabolism of the carbon source.

To determine if the culture conditions permit product production, the production host can be cultured for about 4, 8, 12, 24, 36, or 48 hours. During culturing or after culturing, samples can be obtained and analyzed to determine if the culture conditions permit product production. For example, the production hosts in the sample or the medium in which the production hosts were grown can be tested for the presence of the desired product. When testing for the presence of a product, assays, such as, but not limited to, TLC, HPLC, GC/FID, GC/MS, LC/MS, MS, as well as those provided in the examples below, can be used.

Vector: A nucleic acid molecule as introduced into a cell, thereby producing a transformed cell. A vector can include nucleic acid sequences that permit it to replicate in the cell, such as an origin of replication. A vector can also include one or more selectable marker genes or other genetic elements known in the art.

Wax: Wax is comprised of fatty esters. In a preferred embodiment, the fatty ester contains an A side and a B side comprised of medium to long carbon chains.

In addition to fatty esters, a wax may comprise other components. For example, wax can also comprise hydrocarbons, sterol esters, aliphatic aldehydes, alcohols, ketones, beta-diketones, triacylglycerols, etc.

DETAILED DESCRIPTION

Many cells microorganisms can utilize fatty acids as energy sources and, therefore, contain β-oxidation pathways that metabolize fatty acids to make energy. Surprisingly, it was found that over-expressing a peptide having acyl-CoA synthase activity (the first enzymatic activity found in the β-oxidation pathway), and/or attenuating other genes in the beta oxidation pathway, could increase the amount of acyl-CoA produced, while maintaining the viability of the cell or microorganism. Similarly, over-expressing a peptide having acyl-CoA synthase activity in combination with over-expression of peptides that form fatty acid derivatives can improve fatty acid derivative production.

Fatty acid derivatives are useful as biofuels and specialty chemicals, which can be used to make additional products such as nutritional supplements, polymers, paraffin replacements, and personal care products. Furthermore, the teachings disclosed herein allow for the production of fatty acid derivatives with particular branch points, levels of saturation, and carbon chain length.

Non-limiting examples of microorganisms which can be used as production hosts to produce fatty acid derivatives include bacteria, yeast, or filamentous fungi. Further non-limiting examples of suitable production hosts include plant, animal, or human cells.

Alcohols (short chain, long chain, branched, or unsaturated) can be produced by the production hosts described herein. Such alcohols can be used as fuels directly or they can be used to create a fatty ester. Fatty esters, alone or in combination with other fatty acid derivatives described herein, are useful as fuels.

Similarly, hydrocarbons produced from the production hosts described herein can be used as biofuels. Such hydrocarbon-based fuels can be designed to contain branch points, defined degrees of saturation, and specific carbon lengths. When used as biofuels alone or in combination with other fatty acid derivatives, the hydrocarbons can be combined with additives or other traditional fuels (e.g., alcohols, diesel derived from triglycerides, and petroleum-based fuels).

The centane number (CN), viscosity, melting point, and heat of combustion for various fatty esters have been characterized in Knothe, *Fuel Processing Technology* 86:1059-1070, 2005, which is herein incorporated by reference in its entirety. A production host can be engineered to produce any of the fatty esters described in Knothe, using the teachings provided herein.

I. Production of Fatty Acid Derivatives and Modifications for Increasing Production The production host used to produce acyl-CoA and/or fatty acid derivatives can be recombinantly modified to include nucleic acid sequences that over-express peptides. For example, the production host can be modified to increase the production of acyl-CoA and reduce the catabolism of fatty acid derivatives and intermediates in the fatty acid biosynthetic pathway, such as acyl-CoA, or to reduce feedback inhibition at specific points in the fatty acid biosynthetic pathway. In addition to modifying the genes described herein, additional cellular resources can be diverted to over-produce fatty acids, for example, the lactate, succinate and/or acetate pathways can be attenuated, and acetyl-CoA carboxylase (acc) can be over-expressed. The modifications to the production host described herein can be through genomic alterations, addition of recombinant expression systems, or combinations thereof.

The fatty acid biosynthetic pathways involved are illustrated in FIG. 2 through FIG. 6. Subsections A-G below describe the steps in these pathways. Different steps in the pathway are catalyzed by different enzymes. Each step is a potential place for overexpression of the gene to produce more enzyme and thus drive the production of more fatty acids and fatty acid derivatives. Genes encoding enzymes required for the pathway may also be recombinantly added to a production host lacking such enzymes. Finally, steps that would compete with the pathway leading to production of fatty acids and fatty acid derivatives can be attenuated or blocked in order to increase the production of the desired products.

A. Acetyl-CoA—Malonyl-CoA to Acyl-ACP

Fatty acid synthase (FAS) is a group of peptides that catalyze the initiation and elongation of acyl chains (Marrakchi et al., *Biochemical Society*, 30:1050-1055, 2002). The acyl carrier protein (ACP) along with the enzymes in the FAS pathway control the length, degree of saturation, and branching of the fatty acids produced. The steps in this pathway are catalyzed by enzymes of the fatty acid biosynthesis (fab) and acetyl-CoA carboxylase (acc) gene families. Depending upon the desired product, one or more of these genes can be attenuated or over-expressed (see FIG. 1 for a detailed description of the enzymatic activity of each enzyme and its enzyme classification number).

1. Fatty Acid Biosynthetic Pathway: Acetyl-CoA or Malonyl-CoA to Acyl-ACP

Figure 3:
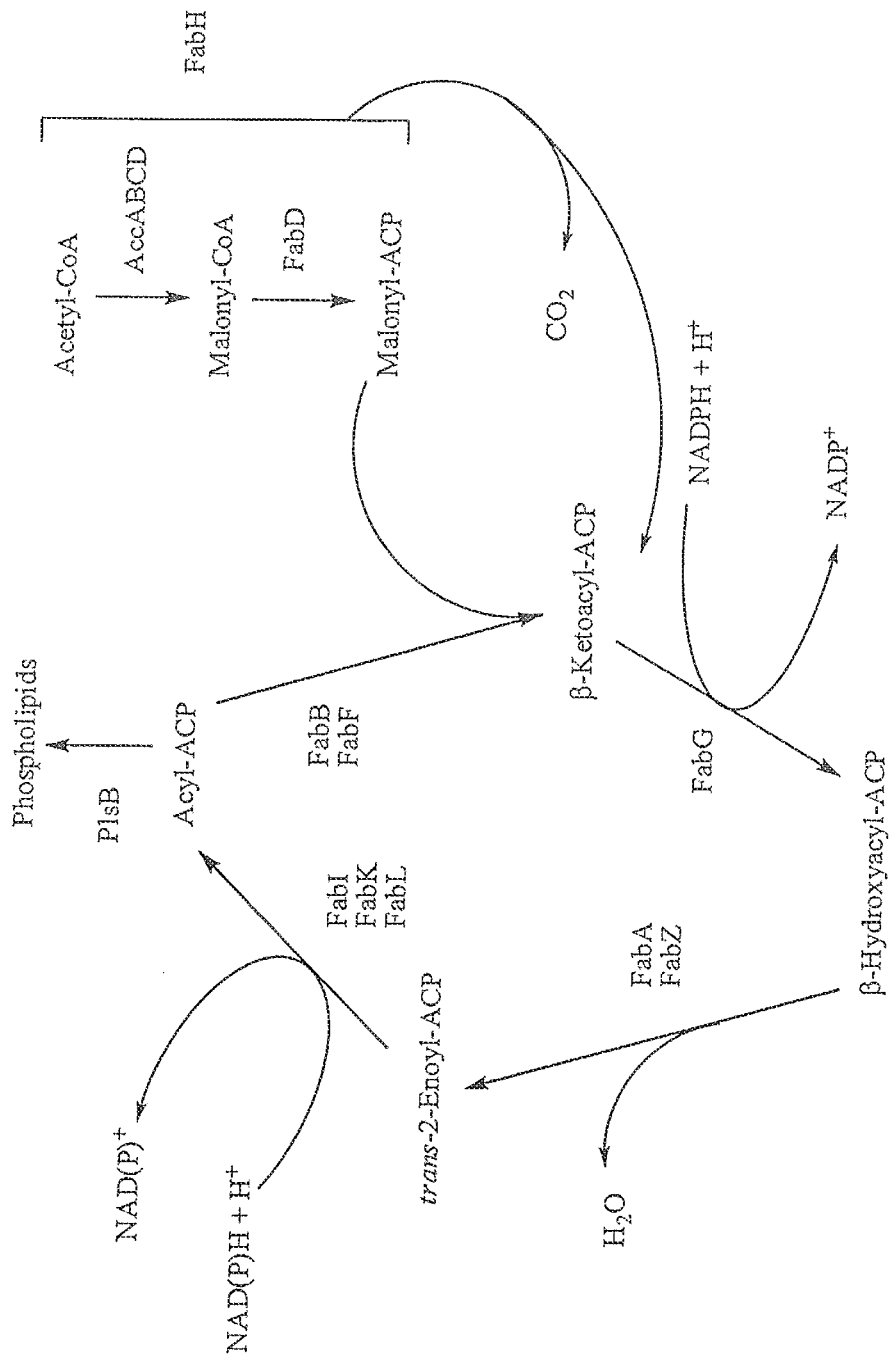
FIG. 3 is a diagram illustrating the FAS biosynthetic pathway.

The fatty acid biosynthetic pathway in the production host uses the precursors acetyl-CoA and malonyl-CoA (FIG. 3). The steps in this pathway are catalyzed by enzymes of the fatty acid biosynthesis (fab) and acetyl-CoA carboxylase (acc) gene families. This pathway is described in Heath et al., *Prog. Lipid Res.* 40(6):467-97 (2001), which is incorporated herein by reference in its entirety.

Acetyl-CoA is carboxylated by acetyl-CoA carboxylase (Acc, a multisubunit enzyme encoded by four separate genes, accABCD), to form malonyl-CoA. The malonate group is transferred to ACP by malonyl-CoA:ACP transacylase (FabD) to form malonyl-ACP. A condensation reaction then occurs, where malonyl-ACP merges with acetyl-CoA, resulting in β-ketoacyl-ACP. β-ketoacyl-ACP synthase III (FabH) initiates the FAS cycle, while β-ketoacyl-ACP synthase I (FabB) and β-ketoacyl-ACP synthase II (FabF) are involved in subsequent cycles.

Next, a cycle of steps is repeated until a saturated fatty acid of the appropriate length is made. First, the β-ketoacyl-ACP is reduced by NADPH to form β-hydroxyacyl-ACP. This step is catalyzed by β-ketoacyl-ACP reductase (FabG). β-hydroxyacyl-ACP is then dehydrated to form trans-2-enoyl-ACP. β-hydroxyacyl-ACP dehydratase/isomerase (FabA) or β-hydroxyacyl-ACP dehydratase (FabZ) catalyze this step. NADPH-dependent trans-2-enoyl-ACP reductase I, II, or III (FabI, FabK, and FabL, respectively) reduces trans-2-enoyl-ACP to form acyl-ACP. Subsequent cycles are started by the condensation of malonyl-ACP with acyl-ACP by β-ketoacyl-ACP synthase I or β-ketoacyl-ACP synthase II (FabB and FabF, respectively).

2. Modifications to the Fatty Acid Biosynthetic Pathway to Increase Acyl-ACP Production Production host organisms may be engineered to overproduce acetyl-CoA and malonyl-CoA. Such production host organisms include plant, animal, or human cells. Microorganisms such as bacteria, yeast, or filamentous fungi can be used as production hosts. Non-limiting examples of microorganisms that may be used as production hosts include *E. coli, Saccharomyces cerevisiae, Candida lipolytica, E. coli, Arthrobacter* AK 19, *Rhodotorula glutinins, Acinetobacter* sp. strain M-1, *Candida lipolytica*, and other oleaginous microorganisms. Several different modifications can be made, either in combination or individually, to the production host to obtain increased acetyl-CoA/malonyl-CoA/fatty acid and fatty acid derivative production.

For example, to increase acetyl-CoA production, one or more of the following genes could be expressed in a production host: pdh, panK, aceEF (encoding the E1p dehydrogenase component and the E2p dihydrolipoamide acyltransferase component of the pyruvate and 2-oxoglutarate dehydrogenase complexes), fabH, fabD, fabG, acpP, fabF. In other examples, additional DNA sequence encoding fatty-acyl-CoA reductases and aldehyde decarbonylases could be expressed in the production host. It is well known in the art that a plasmid containing one or more of the aforementioned genes, all under the control of a constitutive, or otherwise controllable promoter, can be constructed. Exemplary GenBank accession numbers for these genes are: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

Additionally, the expression levels of fadE, gpsA, ldhA, pflb, adhE, pta, poxB, ackA, and/or ackB can be reduced or knocked-out in the engineered microorganism by transformation with conditionally replicative or non-replicative plasmids containing null or deletion mutations of the corresponding genes, or by substituting promoter or enhancer sequences. Exemplary GenBank accession numbers for these genes are: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting engineered production hosts will have increased acetyl-CoA production levels when grown in an appropriate environment.

Moreover, malonyl-CoA overproduction can be affected by engineering the production host as described above with accABCD (e.g., accession number AAC73296, EC 6.4.1.2) included in the plasmid synthesized de novo. Fatty acid overproduction can be achieved by further including a DNA sequence encoding lipase (e.g., Accession numbers CAA89087, CAA98876) in the plasmid synthesized de novo.

As a result, in some examples, acetyl-CoA carboxylase is over-expressed to increase the intracellular concentration thereof by at least about 2-fold, preferably at least about 5-fold, or more preferably at least about 10-fold, relative to native expression levels.

In addition, the plsB (e.g., Accession number AAC77011) D311E mutation can be used to increase the amount of available acyl-CoA.

In addition, over-expression of a sfa gene (suppressor of FabA, e.g., Accession number AAN79592) can be included in the production host to increase production of monounsaturated fatty acids (Rock et al., *J. Bacteriology* 178:5382-5387, 1996).

B. Acyl-ACP to Fatty Acid

1. Fatty Acid Biosynthetic Pathway: Acyl-ACP to Fatty Acids

As described above, acetyl-CoA and malonyl-CoA are processed in several steps to form acyl-ACP chains. The enzyme sn-glycerol-3-phosphate acyltransferase (PlsB) catalyzes the transfer of an acyl group from acyl-ACP or acyl-CoA to the sn-1 position of glycerol-3-phosphate. Thus, PlsB is a key regulatory enzyme in phospholipid synthesis, which is part of the fatty acid pathway. Inhibiting PlsB leads to an increase in the levels of long chain acyl-ACP, which feedback will inhibit early steps in the pathway (e.g., accABCD, fabH, and fabI). Uncoupling of this regulation, for example by thioesterase overexpression, leads to increased fatty acid production. The tes and fat gene families express thioesterase. FabI is also inhibited in vitro by long-chain acyl-CoA.

2. Modifications to the Fatty Acid Biosynthetic Pathway to Produce Desired Fatty Acids To engineer a production host for the production of a homogeneous population of fatty acid derivatives, one or more endogenous genes can be attenuated or functionally deleted and, as a result, one or more thioesterases can be expressed. For example, $C_{10}$ fatty acid derivatives can be produced by attenuating thioesterase $C_{18}$ (e.g., accession numbers AAC73596 and POADA1), which uses $C_{18:1}$-ACP and expressing thioesterase $C_{10}$ (e.g., accession number Q39513), which uses $C_{10}$-ACP. This results in a relatively homogeneous population of fatty acid derivatives that have a carbon chain length of 10. In another example, $C_{14}$ fatty acid derivatives can be produced by attenuating endogenous thioesterases that produce non-$C_{14}$ fatty acids and expressing the thioesterase accession number Q39473 (which uses $C_{14}$-ACP). In yet another example, $C_{12}$ fatty acid derivatives can be produced by expressing thioesterases that use $C_{12}$-ACP (for example, accession number Q41635) and attenuating thioesterases that produce non-$C_{12}$ fatty acids. Acetyl-CoA, malonyl-CoA, and fatty acid overproduction can be verified using methods known in the art, for example by using radioactive precursors, HPLC, and GC-MS subsequent to cell lysis. Non-limiting examples of thioesterases useful in the claimed methods and production hosts are listed in Table 1.

TABLE 1

Thioesterases

| Accession Number | Source Organism | Gene | Preferential product produced |
|---|---|---|---|
| AAC73596 | *E. coli* | tesA without leader sequence | $C_{18:1}$ |

TABLE 1-continued

Thioesterases

| Accession Number | Source Organism | Gene | Preferential product produced |
|---|---|---|---|
| AAC73555 | E. coli | tesB | |
| Q41635, AAA34215 | Umbellularia california | fatB | $C_{12:0}$ |
| Q39513; AAC49269 | Cuphea hookeriana | fatB2 | $C_{8:0}$-$C_{10:0}$ |
| AAC49269; AAC72881 | Cuphea hookeriana | fatB3 | $C_{14:0}$-$C_{16:0}$ |
| Q39473, AAC49151 | Cinnamonum camphorum | fatB | $C_{14:0}$ |
| CAA85388 | Arabidopsis thaliana | fatB [M141T]* | $C_{16:1}$ |
| NP 189147; NP 193041 | Arabidopsis thaliana | fatA | $C_{18:1}$ |
| CAC39106 | Bradyrhiizobium japonicum | fatA | $C_{18:1}$ |
| AAC72883 | Cuphea hookeriana | fatA | $C_{18:1}$ |
| AAL79361 | Helianthus annus | fatA1 | |

*Mayer et al., BMC Plant Biology 7: 1-11, 2007

C. Fatty Acid to Acyl-CoA

1. Conversion of Fatty Acids to Acyl-COA

Acyl-CoA synthase (ACS) esterifies free fatty acids to acyl-CoA by a two-step mechanism. The free fatty acid first is converted to an acyl-AMP intermediate (an adenylate) through the pyrophosphorolysis of ATP. The activated carbonyl carbon of the adenylate is then coupled to the thiol group of CoA, releasing AMP and the acyl-CoA final product. See Shockey et al., Plant. Physiol. 129:1710-1722, 2002.

The E. coli ACS enzyme FadD and the fatty acid transport protein FadL are essential components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which bind to the transcription factor FadR and derepress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that will result in different end-products. See Caviglia et al., J. Biol. Chem. 279(12):1163-1169, 2004.

2. Modifications to Increase Conversion of Fatty Acids to Acyl-CoA

Production hosts can be engineered using known peptides to produce fatty acids of various lengths which can be converted to acyl-CoA. One method of making fatty acid derivatives involves increasing the expression of, or expressing more active forms of, one or more acyl-CoA synthase peptides (EC 6.2.1.-).

A list of acyl-CoA synthases that can be expressed to produce acyl-CoA and fatty acid derivatives is shown in Table 2. These Acyl-CoA synthases were examined to optimize any pathway that uses fatty-acyl-CoAs as substrates. Using bioinformatics and synthetic genes, heterologous fadD genes were expressed in production strains and evaluated for their capacity to produce biodiesel and potentially biocrude.

TABLE 2

Acyl-CoA synthases

| Gene Name/Locus | Source | NCBI ID | % Identity to E. coli FadD | % Similarity to E. coli FadD |
|---|---|---|---|---|
| fadD | E. coli | NP_416319 | — | — |
| fadK | E. coli | YP_416216 | 45 | 27 |
| fadD | Acinetobacter sp. ADP1 | YP_045024 | 51 | 70 |
| fadD | Haemophilus influenza RdKW20 | NP_438551 | 64 | 78 |
| BH3103 | Bacillus halodurans C-125 | NP_243969 | 40 | 58 |
| yhfL | Bacillus subtilis | NP_388908 | 39 | 57 |
| Pfl-4354 | Pseudomonas fluorescens Pfo-1 | YP_350082 | 52 | 71 |
| EAV15023 | Comamonas testosterone KF-1 | ZP_01520072 | 55 | 72 |
| fadD1 | Pseudomonas aeruginosa | NP_251989 | 54 | 72 |
| fadD2 | Pseudomonas aeruginosa PAO1 | NP_251990 | 55 | 72 |
| fadD | Rhizobium etli CFN42 | YP_533919 | 55 | 72 |
| RPC_4074 | Rhodopseudomonas palustris Bis B18 | YP_533919 | 56 | 72 |
| fadD1 | Rasltonia Solanacearum GMI 1000 | NP_520978 | 56 | 72 |
| fadDD35 | Mycobacterium tuberculosis H37Rv | NP_217021 | 28 | 46 |
| fadDD22 | Mycobacterium tuberculosis H37Rv | NP_217464 | 23 | 42 |
| PRK0059 | Stenotrophomon as Maltophilia R551-3 | ZP_01644857 | 59 | 75 |

Based on their degree of similarity to *E. coli* FadD, the following homologous genes were selected to be synthesized and evaluated:

fadDD35 from *M. tuberculosis* HR7Rv [NP_217021].

yhfL from *B. subtilis* [NP_388908]. fadD1 from *P. aeruginosa* PAO1 [NP_251989].

fadD homolog, Faa3p from *Saccharomyces cerevisiae* [NP_012257].

Additional fatty acid acyl-CoA synthases from eukaryotic organisms which can be used to produce acyl-CoA, as well as fatty acid derivatives, include those described in Shockey et al., *Plant. Physiol.* 129: 1710-1722, 2002 (Arabidopsis), Caviglia et al., *J. Biol. Chem.* 279: 1163-1169, 2004 (rat), and Knoll et al., *J. Biol. Chem.* 269(23):16348-56, 1994 (yeast). Gene sequences encoding these synthetases are known in the art. See, e.g., Johnson et al., *J. Biol. Chem.* 269: 18037-18046, 1994; Shockey et al., *Plant. Physiol.* 129: 1710-1722, 2002; Black et al., *J. Biol. Chem.* 267: 25513-25520, 1992. These eukaryotic acyl-CoA synthases, despite their lack of high homology to *E. coli* fadD sequences, can complement FadD activity in *E. coli* fadD knockouts.

D. Acyl-CoA to Fatty Alcohol

1. Conversion of Acyl-CoA to Fatty Alcohol

Acyl-CoA is reduced to a fatty aldehyde by NADH-dependent acyl-CoA reductase (e.g., Acr1). The fatty aldehyde is then reduced to a fatty alcohol by NADPH-dependent alcohol dehydrogenase (e.g., YqhD). Alternatively, fatty alcohol forming acyl-CoA reductase (FAR) catalyzes the reduction of an acyl-CoA into a fatty alcohol and CoASH. FAR uses NADH or NADPH as a cofactor in this four-electron reduction. Although the alcohol-generating FAR reactions proceed through an aldehyde intermediate, a free aldehyde is not released. Thus, the alcohol-forming FARs are distinct from those enzymes that carry out two-electron reductions of acyl-CoA and yield free fatty aldehyde as a product. (See Cheng and Russell, *J. Biol. Chem.*, 279(36):37789-37797, 2004; Metz et al., *Plant Physiol.*, 122:635-644, 2000).

2. Modifications to Increase Conversion of Acyl-CoA to Fatty Alcohol

Production hosts can be engineered using known polypeptides to produce fatty alcohols from acyl-CoA. One method of making fatty alcohols involves increasing the expression of, or expressing more active forms of, fatty alcohol forming acyl-CoA reductases (encode by a gene such as acr1 from FAR, EC 1.2.1.50/1.1.1) or acyl-CoA reductases (EC 1.2.1.50) and alcohol dehydrogenase (EC 1.1.1.1). Exemplary GenBank Accession Numbers are provided in FIG. 1.

Fatty alcohols can be described as hydrocarbon-based surfactants. For surfactant production, the production host is modified so that it produces a surfactant from a renewable carbon source. Such a production host includes a first exogenous DNA sequence encoding a protein capable of converting a fatty acid to a fatty aldehyde and a second exogenous DNA sequence encoding a protein capable of converting a fatty aldehyde to an alcohol. In some examples, the first exogenous DNA sequence encodes a fatty acid reductase. In one embodiment, the second exogenous DNA sequence encodes mammalian microsomal aldehyde reductase or long-chain aldehyde dehydrogenase. In a further example, the first and second exogenous DNA sequences are from *Arthrobacter* AK 19, *Rhodotorula glutinins*, *Acinetobacter* sp. strain M-1, or *Candida lipolytica*. In one embodiment, the first and second heterologous DNA sequences are from a multienzyme complex from *Acinetobacter* sp. strain M-1 or *Candida lipolytica*.

Additional sources of heterologous DNA sequences encoding fatty acid to long chain alcohol converting proteins that can be used in surfactant production include, but are not limited to, *Mortierella alpina* (ATCC 32222), *Cryptococcus curvatus*, (also referred to as *Apiotricum curvatum*), *Alcanivorax jadensis* (T9T=DSM 12718=ATCC 700854), *Acinetobacter* sp. Hβ1-N (ATCC 14987) and *Rhodococcus opacus* (PD630 DSMZ 44193).

In one example, the fatty acid derivative is a saturated or unsaturated surfactant product having a carbon chain length of about 6 to about 36 carbon atoms, about 8 to about 30 carbon atoms, about 10 to about 26 carbon atoms, about 12 to about 20 carbon atoms, or about 12 to about 16 carbon atoms. In another example, the surfactant product has a carbon chain length of about 10 to about 18 carbon atoms, or about 12 to about 14 carbon atoms.

Appropriate production hosts for producing surfactants can be either eukaryotic or prokaryotic microorganisms. Exemplary production hosts include *Arthrobacter* AK 19, *Rhodotorula glutinins*, *Acinetobacter* sp strain M-1, *Arabidopsis thalania*, *Candida lipolytica*, *Saccharomyces cerevisiae*, and *E. coli* engineered to express acetyl-CoA carboxylase. Production hosts which demonstrate an innate ability to synthesize high levels of surfactant precursors in the form of lipids and oils, such as *Rhodococcus opacus*, *Arthrobacter* AK 19, and *Rhodotorula glutinins E. coli* engineered to express acetyl CoA carboxylase, and other oleaginous bacteria, yeast, and fungi can also be used.

E. Fatty Alcohols to Fatty Esters

Production hosts can be engineered using known polypeptides to produce fatty esters of various lengths. One method of making fatty esters includes increasing the expression of, or expressing more active forms of, one or more alcohol O-acetyltransferase peptides (EC 2.3.1.84). These peptides catalyze the acetylation of an alcohol by converting an acetyl-CoA and an alcohol to a CoA and an ester. In some examples, the alcohol O-acetyltransferase peptides can be expressed in conjunction with selected thioesterase peptides, FAS peptides, and fatty alcohol forming peptides, thus allowing the carbon chain length, saturation, and degree of branching to be controlled. In some cases, the bkd operon can be coexpressed to enable branched fatty acid precursors to be produced.

As used herein, alcohol O-acetyltransferase peptides include peptides in enzyme classification number EC 2.3.1.84, as well as any other peptide capable of catalyzing the conversion of acetyl-CoA and an alcohol to form a CoA and an ester. Additionally, one of ordinary skill in the art will appreciate that alcohol O-acetyltransferase peptides will catalyze other reactions.

For example, some alcohol O-acetyltransferase peptides will accept other substrates in addition to fatty alcohols or acetyl-CoA thioester, such as other alcohols and other acyl-CoA thioesters. Such non-specific or divergent-specificity alcohol O-acetyltransferase peptides are, therefore, also included. Alcohol O-acetyltransferase peptide sequences are publicly available. Exemplary GenBank Accession Numbers are provided in FIG. 1. Assays for characterizing the activity of particular alcohol O-acetyltransferase peptides are well known in the art. O-acyltransferases can be engineered to have new activities and specificities for the donor acyl group or acceptor alcohol moiety. Engineered enzymes can be generated through well-documented rational and evolutionary approaches.

F. Acyl-CoA to Fatty Esters

1. Production of Fatty Esters

Fatty esters are synthesized by acyl-CoA:fatty alcohol acyltransferase (e.g., ester synthase), which conjugate a long chain fatty alcohol to a fatty acyl-CoA via an ester linkage.

Ester synthases and encoding genes are known from the jojoba plant and the bacterium *Acinetobacter* sp. strain ADP1 (formerly *Acinetobacter calcoaceticus* ADP1). The bacterial ester synthase is a bifunctional enzyme, exhibiting ester synthase activity and the ability to form triacylglycerols from diacylglycerol substrates and fatty acyl-CoAs (acyl-CoA: diglycerol acyltransferase (DGAT) activity). The gene wax/dgat encodes both ester synthase and DGAT. See Cheng et al., *J. Biol. Chem.* 279(36):37798-37807, 2004; Kalscheuer and Steinbuchel, *J. Biol. Chem.* 278:8075-8082, 2003. Ester synthases may also be used to produce certain fatty esters which can be used as a fuel, such as biodiesel, as described herein.

2. Modifications to Produce Fatty Esters

The production of fatty esters, including waxes, from acyl-CoA and alcohols, can be engineered using known polypeptides. One method of making fatty esters includes increasing the expression of, or expressing more active forms of, one or more ester synthases (EC 2.3.1.20, 2.3.1.75). Ester synthase peptide sequences are publicly available. Exemplary GenBank Accession Numbers are provided in FIG. 1. Methods to identify ester synthase activity are provided in U.S. Pat. No. 7,118,896, which is herein incorporated by reference in its entirety.

In particular examples, if the desired product is an ester-based biofuel, the production host is modified so that it produces an ester generated from a renewable energy source. Such a production host includes an exogenous DNA sequence encoding an ester synthase that is expressed so as to confer upon said production host the ability to synthesize a saturated, unsaturated, or branched fatty ester from a renewable energy source. In some embodiments, the organism can also express DNA sequence encoding the following exemplary proteins: fatty acid elongases, acyl-CoA reductases, acyltransferases, ester synthases, fatty acyl transferases, diacylglycerol acyltransferases, acyl-coA wax alcohol acyltransferases. In an alternate embodiment, the organism expresses a DNA sequence encoding a bifunctional ester synthase/acyl-CoA: diacylglycerol acyltransferase. For example, the bifunctional ester synthase/acyl-CoA: diacylglycerol acyltransferase can be selected from the multienzyme complexes from *Simmondsia chinensis, Acinetobacter* sp. strain ADP1 (formerly *Acinetobacter calcoaceticus* ADP1), *Alcanivorax borkumensis, Pseudomonas aeruginosa, Fundibacter jadensis, Arabidopsis thaliana*, or *Alcaligenes eutrophus* (later renamed *Ralstonia eutropha*). In one embodiment, the fatty acid elongases, acyl-CoA reductases or wax synthases are from a multienzyme complex from *Alcaligenes eutrophus* (later renamed *Ralstonia eutropha*) or other organisms known in the literature to produce esters, such as wax or fatty esters.

Additional sources of heterologous DNA sequence encoding ester synthesis proteins useful in fatty ester production include, but are not limited to, *Mortierella alpina* (e.g., ATCC 32222), *Cryptococcus curvatus* (also referred to as *Apiotricum curvatum*), *Alcanivorax jadensis* (for example T9T=DSM 12718=ATCC 700854), *Acinetobacter* sp. HO1-N, (e.g., ATCC 14987) and *Rhodococcus opacus* (e.g., PD630, DSMZ 44193).

Useful production hosts for producing fatty esters can be either eukaryotic or prokaryotic microorganisms. Non-limiting examples of production hosts for producing fatty esters include *Saccharomyces cerevisiae, Candida lipolytica, E. coli Arthrobacter* AK 19, *Rhodotorula glutinins, Acinetobacter* sp. strain M-1, *Candida lipolytica*, and other oleaginous microorganisms.

In one example, the ester synthase from *Acinetobacter* sp. ADP1 at locus AAO17391 (described in Kalscheuer and Steinbuchel, *J. Biol. Chem.* 278:8075-8082, 2003, herein incorporated by reference) is used. In another example, the ester synthase from *Simmondsia chinensis* at locus AAD38041 is used.

Optionally, an ester exporter such as a member of the FATP family can be used to facilitate the release of esters into the extracellular environment. A non-limiting example of an ester exporter that can be used is fatty acid (long chain) transport protein CG7400-PA, isoform A, from *Drosophila melanogaster*, at locus NP_524723.

G. Acyl-ACP, Acyl-CoA to Hydrocarbon

1. Hydrocarbons from Particular Microorganisms

A diversity of microorganisms are known to produce hydrocarbons, such as alkanes, olefins, and isoprenoids. Many of these hydrocarbons are derived from fatty acid biosynthesis. The production of these hydrocarbons can be controlled by controlling the genes associated with fatty acid biosynthesis in the native production hosts.

For example, hydrocarbon biosynthesis in the algae *Botryococcus braunii* occurs through the decarbonylation of fatty aldehydes. The fatty aldehydes are produced by the reduction of fatty acyl—thioesters by fatty acyl-CoA reductase. Thus, the structure of the final alkanes can be controlled by engineering *B. braunii* to express specific genes, such as thioesterases, which control the chain length of the fatty acids being channeled into alkane biosynthesis. Expressing the enzymes that result in branched chain fatty acid biosynthesis in *B. braunii* will result in the production of branched chain alkanes. Introduction of genes affecting the production of desaturation of fatty acids will result in the production of olefins. Further combinations of these genes can provide further control over the final structure of the hydrocarbons produced.

To produce higher levels of the native or engineered hydrocarbons, the genes involved in the biosynthesis of fatty acids and their precursors or the degradation to other products can be expressed, over-expressed, or attenuated. Each of these approaches can be applied to the production of alkanes in *Vibrio furnissii* M1 and other *Vibrio furnissii* strains, which produce alkanes through the reduction of fatty alcohols. In addition to *Vibrio furnissii*, other alkane producing organisms that utilize the fatty acid pathway could be used.

Each of these approaches can also be applied to the production of the olefins produced by many strains of *Micrococcus leuteus, Stenotrophomonas maltophilia*, and related microorganisms. These microorganisms produce long chain olefins that are derived from the head to head condensation of fatty acid precursors. Controlling the structure and level of the fatty acid precursors using the methods described herein will result in formation of olefins of different chain length, branching, and levels of saturation.

Cyanobacteria can also be used as production hosts for the production of fatty acid derivatives such as fatty alcohols, fatty esters, and hydrocarbons. For example, *Synechocystis* sp. PCC6803 and *Synechococcus elongatus* PCC7942 can serve as production hosts and can be engineered using standard molecular biology techniques (Thiel, *Genetic analysis of cyanobacteria*, in 1 THE MOLECULAR BIOLOGY OF CYANOBACTERIA, ADVANCES IN PHOTOSYNTHESIS AND RESPIRATION 581-611 (Kluwer Academic Publishers 1994); Koksharova & Wolk, *Appl. Microbiol. Biotechnol.*, 58: 123-137, 2002). Fatty acid biosynthesis genes can be easily identified and isolated in these organisms (see Table 18).

Furthermore, many cyanobacteria are natural producers of hydrocarbons, such as heptadecane, and therefore contain hydrocarbon biosynthesis genes which can be deregulated and over-expressed in conjunction with manipulating their fatty acid biosynthesis genes to increase hydrocarbon production.

Unlike other bacteria, some cyanobacteria (e.g., *Synechocystis* sp. PCC6803) contain polyunsaturated fatty acids in their lipids (Murata, *Plant cell Physiol.*, 33: 933-941, 1992), and thus have the inherent capability to produce polyunsaturated fatty acid derivatives. Most importantly, cyanobacteria are photosynthetic organisms that synthesize all of their cellular carbon by harvesting sun light and fixing carbon dioxide. Therefore, fatty acid derivatives produced in cyanobacteria are directly derived from $CO_2$.

2. Hydrocarbons from Reduction of Primary Alcohols

Hydrocarbons can also be produced using evolved oxidoreductases for the reduction of primary alcohols. Primary fatty alcohols are known to be used to produce alkanes in microorganisms, such as *Vibrio furnissii* M1 (Park, *J. Bacteriol.*, 187:1426-1429, 2005). One example of an oxidoreductase which can be used to produce hydrocarbons from fatty alcohols is NAD(P)H-dependent oxidoreductase. Synthetic NAD(P)H dependent oxidoreductases can be produced through the use of evolutionary engineering and can be expressed in production hosts to produce fatty acid derivatives.

The process of "evolving" a fatty alcohol reductase to have the desired activity is well known (Kolkman and Stemmer, *Nat. Biotechnol.* 19:423-8, 2001; Ness et al., *Adv Protein Chem.* 55:261-92, 2000; Minshull and Stemmer, *Curr. Opin. Chem. Biol.* 3:284-90, 1999; Huisman and Gray, *Curr. Opin. Biotechnol.* 13:352-8, 2002; U.S. Patent Pub. No. 2006/0195947.

A library of NAD(P)H dependent oxidoreductases is generated by standard methods, such as error prone PCR, site-specific random mutagenesis, site specific saturation mutagenesis, or site directed specific mutagenesis. Additionally, a library can be created through the "shuffling" of naturally occurring NAD(P)H dependent oxidoreductase encoding sequences. The library is expressed in a suitable production host, such as *E. coli*. Individual colonies expressing a different member of the oxidoreductase library are then analyzed for expression of an oxidoreductase that can catalyze the reduction of a fatty alcohol.

For example, each cell can be assayed as a whole cell bioconversion, a cell extract, or a permeabilized cell. Enzymes purified from the cell can be analyzed as well. Fatty alcohol reductases are identified by spectrophotometrically or fluorometrically monitoring the fatty alcohol-dependent oxidation of NAD(P)H. Production of alkanes is monitored by GC-MS, TLC, or other methods.

An oxidoreductase identified in this manner is used to produce alkanes, alkenes, and related branched hydrocarbons. This is achieved either in vitro or in vivo. The latter is achieved by expressing the evolved fatty alcohol reductase gene in an organism that produces fatty alcohols, such as those described herein. The fatty alcohols act as substrates for the alcohol reductase, which produces alkanes. Other oxidoreductases can also be engineered to catalyze this reaction, such as those that use molecular hydrogen, glutathione, FADH, or other reductive coenzymes.

H. Release of Fatty Acid Derivatives—Transport Proteins

Transport proteins export fatty acid derivatives out of the production host. Many transport and efflux proteins serve to excrete a large variety of compounds, and can naturally be modified to be selective for particular types of fatty acid derivatives. Non-limiting examples of suitable transport proteins are ATP-Binding Cassette (ABC) transport proteins, efflux proteins, and fatty acid transporter proteins (FATP). Additional non-limiting examples of suitable transport proteins include the ABC transport proteins from organisms such as *Caenorhabditis elegans, Arabidopsis thalania, Alkaligenes eutrophus, Rhodococcus erythropolis*. Exemplary ABC transport proteins which could be used are CER5, AtMRP5, AmiS2, or AtPGP1. In a preferred embodiment, the ABC transport proteins is CER5 (e.g., AY734542)). See also transport proteins identified in FIG. 1. Vectors containing genes that express suitable transport proteins can be inserted into the protein production host to increase the release of fatty acid derivatives.

Production hosts can also be chosen for their endogenous ability to release fatty acid derivatives. The efficiency of product production and release into the fermentation broth can be expressed as a ratio of intracellular product to extracellular product. In some examples, the ratio can be about 5:1, 4:1, 3:1, 2:1, 1:1, 1:2, 1:3, 1:4, or 1:5.

II. Selection of Carbon Chain Characteristics of Fatty Acid Derivatives

Fatty acid derivatives with particular branch points, levels of saturation, carbon chain length, and ester characteristics can be produced as desired. Microorganisms that naturally produce particular derivatives can be chosen. Alternatively, genes that express enzymes that will produce particular fatty acid derivatives can be inserted into the production host microorganism. FIG. 1 provides non-limiting examples of enzymes that can be used alone or in combination to make fatty acid derivatives with desired characteristics.

In some examples, the expression of exogenous FAS genes originating from different species or engineered variants can be introduced into the production host to result in the biosynthesis of fatty acids that are structurally different (in length, branching, degree of unsaturation, etc.) from those of the native production host. These heterologous gene products can also be chosen or engineered to be unaffected by the natural regulatory mechanisms in the production host cell, and therefore allow for control of the production of the desired commercial product. For example, the FAS enzymes from *Bacillus subtilis, Saccharomyces cerevisiae, Streptomyces* spp., *Ralstonia, Rhodococcus, Corynebacteria, Brevibacteria, Mycobacteria*, oleaginous yeast, and the like can be expressed in the production host. The expression of such exogenous enzymes will alter the structure of the fatty acid produced.

When a production host is engineered to produce a fatty acid with a specific level of unsaturation, branching, or carbon chain length, the resulting engineered fatty acid can be used in the production of fatty acid derivatives. Fatty acid derivatives generated from such production hosts can display the characteristics of the engineered fatty acid.

For example, a production host can be engineered to make branched, short chain fatty acids, which may then be used by the production host to produce branched, short chain fatty alcohols. Similarly, a hydrocarbon can be produced by engineering a production host to produce a fatty acid having a defined level of branching, unsaturation, and/or carbon chain length, thus, producing a homogeneous hydrocarbon population. Additional steps can be employed to improve the homogeneity of the resulting product. For example, when an unsaturated alcohol, fatty ester, or hydrocarbon is desired, the production host organism can be engineered to produce low levels of saturated fatty acids and in addition can be modified to express an additional desaturase and thus lessen the production of saturated product.

A. Branched and Cyclic Moieties

1. Engineering Branched and Cyclic Fatty Acid Derivatives

Fatty acids are a key intermediate in the production of fatty acid derivatives. Fatty acid derivatives can be produced that contain branch points, cyclic moieties, and combinations thereof, by using branched or cyclic fatty acids to make the fatty acid derivatives.

For example, *E. coli* naturally produces straight chain fatty acids (sFAs). To engineer *E. coli* to produce branched chain fatty acids (brFAs), several genes that provide branched precursors (e.g., bkd operon) can be introduced into the production host and expressed to allow initiation of fatty acid biosynthesis from branched precursors (e.g., fabH). The bkd, ilv, icm, and fab gene families may be expressed or over-expressed to produce branched chain fatty acid derivatives. Similarly, to produce cyclic fatty acids, genes that provide cyclic precursors can be introduced into the production host and expressed to allow initiation of fatty acid biosynthesis from cyclic precursors. The ans, chc, and plm gene families may be expressed or over-expressed to produce cyclic fatty acids. FIG. 1 recites non-limiting examples of genes in these gene families that may be used in the present methods and production hosts.

Additionally, the production host can be engineered to express genes encoding proteins for the elongation of brFAs (e.g., ACP, FabF, etc.) and/or to delete or attenuate the corresponding *E. coli* genes that normally lead to sFAs. In this regard, endogenous genes that would compete with the introduced genes (e.g., fabH, fabF) are deleted or attenuated.

The branched acyl-CoA (e.g., 2-methyl-butyryl-CoA, isovaleryl-CoA, isobutyryl-CoA, etc.) are the precursors of brFA. In most microorganisms containing brFA, the brFA are synthesized in two steps from branched amino acids (e.g., isoleucine, leucine, and valine) (Kadena, *Microbiol. Rev.* 55:288, 1991). A production host can be engineered to express or over-express one or more of the enzymes involved in these two steps to produce brFAs, or to over-produce brFAs. For example, the production host may have an endogenous enzyme that can accomplish one step leading to brFA, therefore only genes encoding enzymes involved in the second step need to be introduced recombinantly.

2. Formation of Branched Fatty Acids and Branched Fatty Acid Derivatives

The first step in forming brFAs is the production of the corresponding α-keto acids by a branched-chain amino acid aminotransferase. Production hosts may endogenously include genes encoding such enzymes or such genes may be recombinantly introduced. *E. coli*, for example, endogenously expresses such an enzyme, IlvE (EC 2.6.1.42; GenBank accession YP_026247). In some production hosts, a heterologous branched-chain amino acid aminotransferase may not be expressed. However, *E. coli* IlvE or any other branched-chain amino acid aminotransferase (e.g., IlvE from *Lactococcus lactis* (GenBank accession AAF34406), IlvE from *Pseudomonas putida* (GenBank accession NP_745648), or IlvE from *Streptomyces coelicolor* (GenBank accession NP_629657)), if not endogenous, can be introduced. If the aminotransferase reaction is rate limiting in brFA biosynthesis in the chosen production host organism, then the aminotransferase can be over-expressed.

The second step is the oxidative decarboxylation of the α-ketoacids to the corresponding branched-chain acyl-CoA. This reaction can be catalyzed by a branched-chain α-keto acid dehydrogenase complex (bkd; EC 1.2.4.4.) (Denoya et al., *J. Bacteriol.* 177:3504, 1995), which consists of E1α/β (decarboxylase), E2 (dihydrolipoyl transacylase) and E3 (dihydrolipoyl dehydrogenase) subunits. These branched-chain α-keto acid dehydrogenase complexes are similar to pyruvate and α-ketoglutarate dehydrogenase complexes. Every microorganism that possesses brFAs and/or grows on branched-chain amino acids can be used as a source to isolate bkd genes for expression in production hosts such as, for example, *E. coli*. Furthermore, *E. coli* has the E3 component as part of its pyruvate dehydrogenase complex (lpd, EC 1.8.1.4, GenBank accession NP_414658), thus it can be sufficient to only express the E1 α/β and E2 bkd genes. Table 3 recites non-limiting examples of bkd genes from several microorganisms that can be recombinantly introduced and expressed in a production host to provide branched-chain acyl-CoA precursors. Microorganisms having such bkd genes can also be used as production hosts.

TABLE 3

Bkd genes from selected microorganisms

| Organism | Gene | GenBank Accession # |
|---|---|---|
| *Streptomyces coelicolor* | bkdA1 (E1α) | NP_628006 |
| | bkdB1 (E1β) | NP_628005 |
| | bkdC1 (E2) | NP_638004 |
| *Streptomyces coelicolor* | bkdA2 (E1α) | NP_733618 |
| | bkdB2 (E1β) | NP_628019 |
| | bkdC2 (E2) | NP_628018 |
| *Streptomyces avermitilis* | bkdA (E1a) | BAC72074 |
| | bkdB (E1b) | BAC72075 |
| | bkdC (E2) | BAC72076 |
| *Streptomyces avermitilis* | bkdF (E1α) | BAC72088 |
| | bkdG (E1β) | BAC72089 |
| | bkdH (E2) | BAC72090 |
| *Bacillus subtilis* | bkdAA (E1α) | NP_390288 |
| | bkdAB (E1β) | NP_390288 |
| | bkdB (E2) | NP_390288 |
| *Pseudomonas putida* | bkdA1 (E1α) | AAA65614 |
| | bkdA2 (E1β) | AAA65615 |
| | bkdC (E2) | AAA65617 |

In another example, isobutyryl-CoA can be made in a production host, for example in *E. coli*, through the coexpression of a crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, *J. Bacteriol.* 179:5157, 1997). Crotonyl-CoA is an intermediate in fatty acid biosynthesis in *E. coli* and other microorganisms. Non-limiting examples of ccr and icm genes from selected microorganisms are given in Table 4.

TABLE 4

Ccr and icm genes from selected microorganisms

| Organism | Gene | GenBank Accession # |
|---|---|---|
| *Streptomyces coelicolor* | Ccr | NP_630556 |
| | icmA | NP_629554 |
| | icmB | NP_630904 |
| *Streptomyces cinnamonensis* | ccr | AAD53915 |
| | icmA | AAC08713 |
| | icmB | AJ246005 |

In addition to expression of the bkd genes, the initiation of brFA biosynthesis utilizes β-ketoacyl-acyl-carrier-protein synthase III (FabH, EC 2.3.1.41) with specificity for branched chain acyl-CoAs (Li et al., *J. Bacteriol.* 187:3795-3799, 2005). Non-limiting examples of such FabH enzymes are listed in Table 5. fabH genes that are involved in fatty acid biosynthesis of any brFA-containing microorganism can be expressed in a production host. The Bkd and FabH enzymes from production hosts that do not naturally make brFA may not support brFA production, therefore Bkd and FabH can be expressed recombinantly. Vectors containing the bkd and fabH genes can be inserted into such a production host. Similarly, the endogenous level of Bkd and FabH production may not be sufficient to produce brFA, therefore, they can be over-expressed. Additionally, other components of fatty acid biosynthesis pathway can be expressed or over-expressed, such as acyl carrier proteins (ACPs) and β-ketoacyl-acyl-carrier-protein synthase II (fabF, EC 2.3.1.41) (non-limiting examples of candidates are listed in Table 5). In addition to expressing these genes, some genes in the endogenous fatty acid biosynthesis pathway may be attenuated in the production host. Genes encoding enzymes that would compete for substrate with the enzymes of the pathway that result in brFA production may be attenuated to increase brFA production. For example, in *E. coli* the most likely candidates to interfere with brFA biosynthesis are fabH (GenBank accession #NP_415609) and/or fabF genes (GenBank accession #NP_415613).

TABLE 5

FabH, ACP and fabF genes from selected microorganisms with brFAs

| Organism | Gene | GenBank Accession # |
|---|---|---|
| *Streptomyces coelicolor* | fabH1 | NP_626634 |
| | ACP | NP_626635 |
| | fabF | NP_626636 |
| *Streptomyces avermitilis* | fabH3 | NP_823466 |
| | fabC3 (ACP) | NP_823467 |
| | fabF | NP_823468 |
| *Bacillus subtilis* | fabH_A | NP_389015 |
| | fabH_B | NP_388898 |
| | ACP | NP_389474 |
| | fabF | NP_389016 |
| *Stenotrophomonas maltophilia* | SmalDRAFT_0818 (FabH) | ZP_01643059 |
| | SmalDRAFT_0821 (ACP) | ZP_01643063 |
| | SmalDRAFT_0822 (FabF) | ZP_01643064 |
| *Legionella pneumophila* | FabH | YP_123672 |
| | ACP | YP_123675 |
| | fabF | YP_123676 |

As mentioned above, branched chain alcohols can be produced through the combination of expressing genes that support brFA synthesis and alcohol synthesis. For example, when an alcohol reductase, such as Acr1 from *Acinetobacter baylyi* ADP1, is coexpressed with a bkd operon, *E. coli* can synthesize isopentanol, isobutanol or 2-methyl butanol. Similarly, when Acr1 is coexpressed with ccr/icm genes, *E. coli* can synthesize isobutanol.

3. Formation of Cyclic Fatty Acids and Cyclic Fatty Acid Derivatives

To convert a production host such as *E. coli* into an organism capable of synthesizing ω-cyclic fatty acids (cyFA), a gene that provides the cyclic precursor cyclohexylcarbonyl-CoA (CHC-CoA) (Cropp et al., *Nature Biotech.* 18:980-983, 2000) is introduced and expressed in the production host. A similar conversion is possible for other production hosts, for example, bacteria, yeast and filamentous fungi.

Non-limiting examples of genes that provide CHC-CoA in *E. coli* include: ansJ, ansK, ansL, chcA and ansM from the ansatrienin gene cluster of *Streptomyces collinus* (Chen et al., *Eur. J. Biochem.* 261: 98-107, 1999) or plmJ, plmK, plmL, chcA and plmM from the phoslactomycin B gene cluster of *Streptomyces* sp. HK803 (Palaniappan et al., *J. Biol. Chem.* 278:35552-35557, 2003) together with the chcB gene (Patton et al., *Biochem.* 39:7595-7604, 2000) from *S. collinus, S. avermitilis* or *S. coelicolor* (see Table 6 for GenBank accession numbers). The genes listed above in Table 5 can then be expressed to allow initiation and elongation of ω-cyclic fatty acids. Alternatively, the homologous genes can be isolated from microorganisms that make cyFA and expressed in *E. coli*.

TABLE 6

Genes for the synthesis of CHC-CoA

| Organism | Gene | GenBank Accession # |
|---|---|---|
| *Streptomyces collinus* | ansJK | U72144* |
| | ansL | |
| | chcA | |
| | ansM | |
| | chcB | AF268489 |
| *Streptomyces* sp. HK803 | pmlJK | AAQ84158 |
| | pmlL | AAQ84159 |
| | chcA | AAQ84160 |
| | pmlM | AAQ84161 |
| *Streptomyces coelicolor* | chcB/caiD | NP_629292 |
| *Streptomyces avermitilis* | chcB/caiD | NP_629292 |

*Only chcA is annotated in GenBank entry U72144, ansJKLM are according to Chen et al. (*Eur. J. Biochem.* 261: 98-107, 1999).

The genes listed in Table 5 (fabH, ACP and fabF) are sufficient to allow initiation and elongation of ω-cyclic fatty acids because they can have broad substrate specificity. If the coexpression of any of these genes with the ansJKLM/chcAB or pmlJKLM/chcAB genes from Table 5 does not yield cyFA, then fabH, ACP and/or fabF homologs from microorganisms that make cyFAs can be isolated (e.g., by using degenerate PCR primers or heterologous DNA sequence probes) and coexpressed. Table 7 lists non-limiting examples of microorganisms that contain ω-cyclic fatty acids.

TABLE 7

Non-limiting examples of microorganisms that contain ω-cyclic fatty acids

| Organism | Reference |
|---|---|
| *Curtobacterium pusillum* | ATCC19096 |
| *Alicyclobacillus acidoterrestris* | ATCC49025 |
| *Alicyclobacillus acidocaldarius* | ATCC27009 |
| *Alicyclobacillus cycloheptanicus** | Moore, *J. Org. Chem.* 62: pp. 2173, 1997. |

*Uses cycloheptylcarbonyl-CoA and not cyclohexylcarbonyl-CoA as precursor for cyFA biosynthesis.

B. Saturation

Fatty acids are a key intermediate in the production of fatty acid derivatives. The degree of saturation in fatty acid derivatives can be controlled by regulating the degree of saturation of the fatty acid intermediates. The sfa, gns, and fab families of genes can be expressed or over-expressed to control the saturation of fatty acids. FIG. 1 recites non-limiting examples of genes in these gene families that may be used in the present methods and production hosts.

Production hosts can be engineered to produce unsaturated fatty acids by engineering the production host to over-express fabB, or by growing the production host at low temperatures (e.g., less than 37° C.). FabB has preference to cis-δ³decenoyl-ACP and results in unsaturated fatty acid production in *E. coli*. Over-expression of fabB results in the production of a significant percentage of unsaturated fatty acids (de Mendoza et al., *J. Biol. Chem.*, 258:2098-101, 1983). fabB may be inserted into and expressed in production hosts not naturally having the gene. These unsaturated fatty acids can then be used as intermediates in production hosts that are engineered to produce fatty acid derivatives, such as fatty alcohols, fatty esters, waxes, olefins, alkanes, and the like.

Alternatively, the repressor of fatty acid biosynthesis, for example, fabR (GenBank accession NP_418398), can be deleted, which will also result in increased unsaturated fatty acid production in *E. coli* (Zhang et al., *J. Biol. Chem.* 277: 15558, 2002). Similar deletions may be made in other production hosts. Further increase in unsaturated fatty acids may be achieved, for example, by over-expression of fabM (trans-2, cis-3-decenoyl-ACP isomerase, GenBank accession DAA05501) and controlled expression of fabK (trans-2-enoyl-ACP reductase II, GenBank accession NP_357969) from *Streptococcus pneumoniae* (Marrakchi et al., *J. Biol. Chem.* 277: 44809, 2002), while deleting *E. coli* fabI (trans-2-enoyl-ACP reductase, GenBank accession NP_415804). Additionally, to increase the percentage of unsaturated fatty esters, the production host can also over-express fabB (encoding β-ketoacyl-ACP synthase I, Accessions: BAA16180, EC:2.3.1.41), sfa (encoding a suppressor of fabA, Accession: AAC44390), and gnsA and gnsB (both encoding secG null mutant suppressors, (i.e., cold shock proteins), Accession: ABD18647.1, AAC74076.1). In some examples, the endogenous fabF gene can be attenuated, thus increasing the percentage of palmitoleate ($C_{16:1}$) produced.

C. Chain Length and Ester Characteristics

1. Chain Length and Production of Odd-Numbered Chains

The methods described herein permit production of fatty esters and fatty acid derivatives of varied lengths. Chain length is controlled by thioesterase, which is produced by expression of the tes and fat gene families By expressing specific thioesterases, fatty acids and fatty acid derivatives having a desired carbon chain length can be produced. Non-limiting examples of suitable thioesterases are listed in FIG. 1. A gene encoding a particular thioesterase may be introduced into a production host so that a fatty acid or fatty acid derivative of a particular carbon chain length is produced. Expression of endogenous thioesterases should then be suppressed.

In one embodiment, the fatty acid derivative contain a carbon chain of about 4 to 36 carbon atoms, about 6 to 32 carbon atoms, about 10 to 30 carbon atoms, about 10 to 18 carbon atoms, about 24 to 32 carbon atoms, about 26 to 30 carbon atoms, about 26 to 32 carbon atoms, about 5 to 10 carbon atoms, about 10 to 16 carbon atoms, or about 12 to 18 carbon atoms. In an alternate embodiment, the fatty acid derivative contain a carbon chain less than about 20 carbon atoms, less than about 18 carbon atoms, or less than about 16 carbon atoms. In another embodiment, the fatty ester product is a saturated or unsaturated fatty ester product having a carbon atom content between 24 and 46 carbon atoms. In one embodiment, the fatty ester product has a carbon atom content between 24 and 32 carbon atoms. In another embodiment, the fatty ester product has a carbon content of 14 and 20 carbons. In another embodiment, the fatty ester is the methyl ester of $C_{18:1}$. In another embodiment, the fatty ester is the ethyl ester of $C_{16:1}$. In another embodiment, the fatty ester is the methyl ester of $C_{16:1}$. In yet another embodiment, the fatty ester is octadecyl ester of octanol.

Some microorganisms preferentially produce even- or odd-numbered carbon chain fatty acids and fatty acid derivatives. For example, *E. coli* normally produce even-numbered carbon chain fatty acids and fatty acid ethyl esters (FAEE). Surprisingly, the methods disclosed herein may be used to alter that production. For example, *E. coli* can be made to produce odd-numbered carbon chain fatty acids and FAEE.

2. Ester Characteristics

An ester includes what may be designated an "A" side and a "B" side. The B side may be contributed by a fatty acid produced from de novo synthesis in the production host organism. In some embodiments where the production host is additionally engineered to make alcohols, including fatty alcohols, the A side is also produced by the production host organism. In yet other embodiments, the A side can be provided in the medium. By selecting the desired thioesterase genes, the B side (and the A side when fatty alcohols are being made) can be designed to be have certain carbon chain characteristics. These characteristics include points of branching, unsaturation, and desired carbon chain lengths.

When particular thioesterase genes are selected, the A and B side will have similar carbon chain characteristics when they are both contributed by the production host using fatty acid biosynthetic pathway intermediates. For example, at least about 50%, 60%, 70%, or 80% of the fatty esters produced will have A sides and B sides that vary by about 2, 4, 6, 8, 10, 12, or 14 carbons in length. The A side and the B side can also display similar branching and saturation levels.

In addition to producing fatty alcohols for contribution to the A side, the production host can produce other short chain alcohols such as ethanol, propanol, isopropanol, isobutanol, and butanol for incorporation on the A side using techniques well known in the art. For example, butanol can be made by the production host organism. To create butanol producing cells, the LS9001 strain, for example, can be further engineered to express atoB (acetyl-CoA acetyltransferase) from *Escherichia coli* K12, β-hydroxybutyryl-CoA dehydrogenase from *Butyrivibrio fibrisolvens*, crotonase from *Clostridium beijerinckii*, butyryl CoA dehydrogenase from *Clostridium beijerinckii*, CoA-acylating aldehyde dehydrogenase (ALDH) from *Cladosporium fulvum*, and adhE encoding an aldehyde-alchol dehydrogenase of *Clostridium acetobutylicum* in the pBAD24 expression vector under the prpBCDE promoter system. Other production host organisms may be similarly modified to produce butanol or other short chain alcohols. For example, ethanol can be produced in a production host using the methods taught by Kalscheuer et al., *Microbiology* 152:2529-2536, 2006, which is herein incorporated by reference.

III. Genetic Engineering of Production Strain to Increase Fatty Acid Derivative Production Heterologous DNA sequences involved in a biosynthetic pathway for the production of fatty acid derivatives can be introduced stably or transiently into a production host cell using techniques well known in the art (non-limiting examples include electroporation, calcium phosphate precipitation, DEAE-dextran mediated transfection, liposome-mediated transfection, conjugation, transduction, and genomic integration). For stable transformation, a DNA sequence can further include a selectable marker, including non-limiting examples such as antibiotic resistance and genes that complement auxotrophic deficiencies.

Various embodiments of this disclosure utilize an expression vector that includes a heterologous DNA sequence encoding a protein involved in a metabolic or biosynthetic pathway. Suitable expression vectors include, but are not limited to, viral vectors (such as baculovirus vectors), phage vectors (such as bacteriophage vectors), plasmids, phagemids, cosmids, fosmids, bacterial artificial chromosomes, viral vectors (e.g., viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors for specific production hosts of interest (such as *E. coli, Pseudomonas pisum*, and *Saccharomyces cerevisiae*).

Useful expression vectors can include one or more selectable marker genes to provide a phenotypic trait for selection of transformed production host cells. The selectable marker gene encodes a protein necessary for the survival or growth of transformed production host cells grown in a selective culture medium. Production host cells not transformed with the vector containing the selectable marker gene will not survive in the culture medium. Typical selection genes encode proteins that (a) confer resistance to antibiotics or other toxins (e.g., ampicillin, neomycin, methotrexate, or tetracycline); (b) complement auxotrophic deficiencies; or (c) supply critical nutrients not available from complex media (e.g., the gene encoding D-alanine racemate for Bacilli). In alternative embodiments, the selectable marker gene is one that encodes dihydrofolate reductase or confers neomycin resistance (for use in eukaryotic cell culture), or one that confers tetracycline or ampicillin resistance (for use in a prokaryotic production host cell, such as *E. coli*).

In the expression vector, the DNA sequence encoding the gene in the biosynthetic pathway is operably linked to an appropriate expression control sequence, (promoters, enhancers, and the like) to direct synthesis of the encoded gene product. Such promoters can be derived from microbial or viral sources, including CMV and SV40. Depending on the production host/vector system utilized, any number of suitable transcription and translation control elements can be used in the expression vector, including constitutive and inducible promoters, transcription enhancer elements, transcription terminators, etc. (see, e.g., Bitter et al., *Methods in Enzymology*, 153:516-544, 1987).

Suitable promoters for use in prokaryotic production host cells include, but are not limited to, promoters capable of recognizing the T4, T3, Sp6 and T7 polymerases, the $P_R$ and $P_L$ promoters of bacteriophage lambda, the trp, recA, heat shock, and lacZ promoters of *E. coli*, the alpha-amylase and the sigma-specific promoters of *B. subtilis*, the promoters of the bacteriophages of *Bacillus, Streptomyces* promoters, the int promoter of bacteriophage lambda, the bla promoter of the beta-lactamase gene of pBR322, and the CAT promoter of the chloramphenicol acetyl transferase gene. Prokaryotic promoters are reviewed by Glick, *J. Ind. Microbiol.* 1:277, 1987; Watson et al., MOLECULAR BIOLOGY OF THE GENE, 4th Ed. (1987), Benjamin Cummins (1987); and Sambrook et al., MOLECULAR CLONING: A LABORATORY MANUAL, 2nd Ed. (Cold Spring Harbor Laboratory Press 1989). Non-limiting examples of suitable eukaryotic promoters for use within a eukaryotic production host are viral in origin and include the promoter of the mouse metallothionein I gene (Hamer et al., *J. Mol. Appl. Gen.* 1:273, 1982); the TK promoter of herpes virus (McKnight, *Cell* 31:355, 1982); the SV40 early promoter (Benoist et al., *Nature (London)* 290:304, 1981); the cytomegalovirus promoter (Foecking et al., *Gene* 45:101, 1980); the yeast gal4 gene promoter (Johnston et al., *PNAS (USA)* 79:6971, 1982; Silver et al., *PNAS (USA)* 81:5951, 1984); and the IgG promoter (Orlandi et al., *PNAS (USA)* 86:3833, 1989).

The production host can be genetically modified with a heterologous DNA sequence encoding a biosynthetic pathway gene product that is operably linked to an inducible promoter. Inducible promoters are well known in the art. Non-limiting examples of suitable inducible promoters include promoters that are affected by proteins, metabolites, or chemicals. These include, but are not limited to: a bovine leukemia virus promoter, a metallothionein promoter, a dexamethasone-inducible MMTV promoter, an SV40 promoter, an MRP polIII promoter, a tetracycline-inducible CMV promoter (such as the human immediate-early CMV promoter) as well as those from the trp and lac operons.

In some examples, a production host is genetically modified with a heterologous DNA sequence encoding a biosynthetic pathway gene product that is operably linked to a constitutive promoter. Suitable constitutive promoters are known in the art and include constitutive adenovirus major late promoter, a constitutive MPSV promoter, or a constitutive CMV promoter.

In some examples, a modified production host is one that is genetically modified with an exogenous DNA sequence encoding a single protein involved in a biosynthesis pathway. In other embodiments, a modified production host is one that is genetically modified with exogenous DNA sequences encoding two or more proteins involved in a biosynthesis pathway, for example, the first and second enzymes in a biosynthetic pathway.

Where the production host is genetically modified to express two or more proteins involved in a biosynthetic pathway, those DNA sequences can each be contained in a single or in separate expression vectors. When those DNA sequences are contained in a single expression vector, in some embodiments, the nucleotide sequences will be operably linked to a common control element where the common control element controls expression of all of the biosynthetic pathway protein-encoding DNA sequences in the single expression vector (e.g., a promoter).

When a modified production host is genetically modified with heterologous DNA sequences encoding two or more proteins involved in a biosynthesis pathway, one of the DNA sequences can be operably linked to an inducible promoter, and one or more of the DNA sequences can be operably linked to a constitutive promoter.

In some embodiments, the intracellular concentration (e.g., the concentration of the intermediate in the genetically modified production host) of the biosynthetic pathway intermediate can be increased to further boost the yield of the final product. The intracellular concentration of the intermediate can be increased in a number of ways, including, but not limited to, increasing the concentration in the culture medium of a substrate for a biosynthetic pathway; increasing the catalytic activity of an enzyme that is active in the biosynthetic pathway; increasing the intracellular amount of a substrate (e.g., a primary substrate) for an enzyme that is active in the biosynthetic pathway; and the like.

In some examples, the fatty acid derivative or intermediate is produced in the cytoplasm of the production host. The cytoplasmic concentration can be increased in a number of ways, including, but not limited to, binding of the fatty acid to coenzyme A to form an acyl-CoA thioester. Additionally, the concentration of acyl-CoA can be increased by increasing the biosynthesis of CoA in the cell, such as by over-expressing genes associated with pantothenate biosynthesis (e.g., panD) or knocking out the genes associated with glutathione biosynthesis (e.g., glutathione synthase).

Regulatory sequences, coding sequences, and combinations thereof, can be introduced or altered in the chromosome of the production host. In some examples, the integration of the desired recombinant sequence into the production host genomic sequence does not require the use of a selectable marker such as an antibiotic. In some examples, the genomic alterations include changing the control sequence of the target genes by replacing the native promoter(s) with a promoter that is insensitive to regulation. There are numerous approaches for doing this. For example, Valle and Flores, *Methods Mol. Biol.* 267:113-122, 2006, describes a PCR-based method to over-express chromosomal genes in *E. coli*. Another approach is based on the use of single-strand oligonucleotides to create specific mutations directly in the chromosome, using the technology developed by Court et al., *Proc. Nat. Acad. Sci.* 100:15748-15753, 2003. This technology is based on the use of the over-expression of the Beta protein from the bacteriophage lambda to enhance genetic recombination. The advantages of this approach are that synthetic oligonucleotides 70 bases long (or more) can be used to create point mutations, insertions, and deletions, thus eliminating any cloning steps. Furthermore, the system is sufficiently efficient that no markers are necessary to isolate the desired mutations.

With this approach the regulatory region of a gene can be changed to create a stronger promoter and/or eliminate the binding site of a repressor. In such a manner, a desired gene can be overexpressed in the production host organism.

IV. Fermentation

A. Maximizing Production Efficiency

The production and isolation of fatty acid derivatives can be enhanced by employing specific fermentation techniques. One method for maximizing production while reducing costs is increasing the percentage of the carbon source that is converted to hydrocarbon products.

During normal cellular lifecycles carbon is used in cellular functions including producing lipids, saccharides, proteins, organic acids, and nucleic acids. Reducing the amount of carbon necessary for growth-related activities can increase the efficiency of carbon source conversion to output. This can be achieved by first growing microorganisms to a desired density, such as a density achieved at the peak of the log phase of growth. At such a point, replication checkpoint genes can be harnessed to stop the growth of cells. Specifically, quorum sensing mechanisms (reviewed in Camilli and Bassler *Science* 311:1113, 2006; Venturi *FEMS Microbio. Rev.* 30:274-291, 2006; and Reading and Sperandio *FEMS Microbiol. Lett.* 254:1-11, 2006, which references are incorporated by reference herein) can be used to activate genes such as p53, p21, or other checkpoint genes.

Genes that can be activated to stop cell replication and growth in *E. coli* include umuDC genes, the over-expression of which stops the progression from stationary phase to exponential growth (Murli et al., *J. of Bact.* 182:1127, 2000). UmuC is a DNA polymerase that can carry out translesion synthesis over non-coding lesions—the mechanistic basis of most UV and chemical mutagenesis. The umuDC gene products are used for the process of translesion synthesis and also serve as a DNA sequence damage checkpoint. The umuDC gene products include UmuC, UmuD, umuD', UmuD'$_2$C, UmuD'$_2$ and UmuD$_2$. Simultaneously, the product-producing genes could be activated, thus minimizing the need for replication and maintenance pathways to be used while the fatty acid derivative is being made. Production host microorganisms can also be engineered to express umuC and umuD from *E. coli* in pBAD24 under the prpBCDE promoter system through de novo synthesis of this gene with the appropriate end-product production genes.

The percentage of input carbons converted to fatty esters or hydrocarbon products is a cost driver. The more efficient the process is (i.e., the higher the percentage of input carbons converted to fatty esters or hydrocarbon products), the less expensive the process will be. For oxygen-containing carbon sources (e.g., glucose and other carbohydrate based sources), the oxygen must be released in the form of carbon dioxide. For every 2 oxygen atoms released, a carbon atom is also released leading to a maximal theoretical metabolic efficiency of ~34% (w/w) (for fatty acid derived products). This figure, however, changes for other hydrocarbon products and carbon sources. Typical efficiencies in the literature are approximately <5%. Production hosts engineered to produce hydrocarbon products can have greater than 1, 3, 5, 10, 15, 20, 25, and 30% efficiency. In one example, production hosts will exhibit an efficiency of about 10% to about 25%. In other examples, such production hosts will exhibit an efficiency of about 25% to about 30%. In other examples, such production hosts will exhibit >30% efficiency.

The production host can be additionally engineered to express recombinant cellulosomes, such as those described in PCT application number PCT/US2007/003736, incorporated herein by reference in its entirety, which could allow the production host to use cellulosic material as a carbon source. For example, the production host can be additionally engineered to express invertases (EC 3.2.1.26) so that sucrose can be used as a carbon source.

Similarly, the production host can be engineered using the teachings described in U.S. Pat. Nos. 5,000,000; 5,028,539; 5,424,202; 5,482,846; and 5,602,030 to Ingram et al., all incorporated herein by reference in their entirety, so that the production host can assimilate carbon efficiently and use cellulosic materials as carbon sources.

In one example, the fermentation chamber will enclose a fermentation that is undergoing a continuous reduction. In this instance, a stable reductive environment would be created. The electron balance would be maintained by the release of carbon dioxide (in gaseous form). Efforts to augment the NAD/H and NADP/H balance can also facilitate in stabilizing the electron balance.

The availability of intracellular NADPH can also be enhanced by engineering the production host to express an NADH:NADPH transhydrogenase. The expression of one or more NADH:NADPH transhydrogenase converts the NADH produced in glycolysis to NADPH which enhances the production of fatty acid derivatives.

B. Small-Scale Hydrocarbon Production

For small scale hydrocarbon product production, *E. coli* BL21(DE3) cells harboring pBAD24 (with ampicillin resistance and the end-product synthesis pathway) as well as pUMVC1 (with kanamycin resistance and the acetyl CoA/malonyl CoA over-expression system) are incubated overnight in 2 L flasks at 37° C. shaken at >200 rpm in 500 mL LB medium supplemented with 75 μg/mL ampicillin and 50 μg/ml kanamycin until cultures reach an OD$_{600}$ of >0.8. Upon achieving an OD$_{600}$ of >0.8, cells are supplemented with 25 mM sodium proprionate (pH 8.0) to activate the engineered gene systems for production, and to stop cellular proliferation by activating UmuC and UmuD proteins. Induction is performed for 6 hours at 30° C. After incubation, the media is examined for hydrocarbon product using GC-MS.

C. Large-Scale Hydrocarbon Production

For large scale product production, the engineered production hosts are grown in batches of 10 L, 100 L, or larger; fermented; and induced to express desired products based on the specific genes encoded in the appropriate plasmids.

For example, *E. coli* BL21(DE3) cells harboring pBAD24 (with ampicillin resistance and the end-product synthesis pathway) as well as pUMVC1 (with kanamycin resistance and the acetyl-CoA/malonyl-CoA over-expression system) are incubated from a 500 mL seed culture for 10 L fermentations (5 L for 100 L fermentations) in LB media (glycerol free) with 50 μg/mL kanamycin and 75 μg/mL ampicillin at 37° C., shaken at >200 rpm, until cultures reach an OD$_{600}$ of >0.8 (typically 16 hours). Media is continuously supplemented to maintain 25 mM sodium proprionate (pH 8.0) to activate the engineered gene systems for production, and to stop cellular proliferation by activating umuC and umuD proteins. Media is continuously supplemented with glucose to maintain a concentration 25 g/100 mL.

After the first hour of induction, aliquots of no more than 10% of the total cell volume are removed each hour and allowed to sit without agitation to allow the hydrocarbon product to rise to the surface and undergo a spontaneous phase separation. The hydrocarbon component is then collected and the aqueous phase returned to the reaction chamber. The reaction chamber is operated continuously. When the $OD_{600}$ drops below 0.6, the cells are replaced with a new batch grown from a seed culture.

For wax ester production, the wax esters are isolated, washed briefly in 1 M HCl to split the ester bond, and returned to pH 7 with extensive washing with distilled water.

V. Post-Production Processing

The fatty acid derivatives produced during fermentation can be separated from the fermentation media. Any technique known for separating fatty acid derivatives from aqueous media can be used. One exemplary separation process provided herein is a two phase (bi-phasic) separation process. This process involves fermenting the genetically engineered production hosts under conditions sufficient to produce a fatty acid derivative, allowing the derivative to collect in an organic phase, and separating the organic phase from the aqueous fermentation broth. This method can be practiced in both a batch and continuous fermentation setting.

Bi-phasic separation uses the relative immiscibility of fatty acid derivatives to facilitate separation. Immiscible refers to the relative inability of a compound to dissolve in water and is defined by the compounds partition coefficient. One or ordinary skill in the art will appreciate that by choosing a fermentation broth and organic phase such that the fatty acid derivative being produced has a high log P value, the fatty acid derivative will separate into the organic phase, even at very low concentrations in the fermentation vessel.

The fatty acid derivatives produced by the methods described herein will be relatively immiscible in the fermentation broth, as well as in the cytoplasm. Therefore, the fatty acid derivative will collect in an organic phase either intracellularly or extracellularly. The collection of the products in the organic phase will lessen the impact of the fatty acid derivative on cellular function, and will allow the production host to produce more product.

The fatty alcohols, fatty esters, waxes, and hydrocarbons produced as described herein allow for the production of homogeneous compounds wherein at least about 60%, 70%, 80%, 90%, or 95% of the fatty alcohols, fatty esters, and waxes produced will have carbon chain lengths that vary by less than about 6, less than about 4 carbons, or less than about 2 carbons. These compounds can also be produced so that they have a relatively uniform degree of saturation, for example at least about 60%, 70%, 80%, 90%, or 95% of the fatty alcohols, fatty esters, hydrocarbons and waxes will be monounsaturated, diunsaturated, or triunsaturated. These compounds can be used directly as fuels, personal care additives, or nutritional supplements. These compounds can also be used as feedstock for subsequent reactions for example transesterification, hydrogenation, catalytic cracking (via hydrogenation, pyrolisis, or both), or epoxidation reactions to make other products.

The fatty alcohols, fatty esters, waxes, and hydrocarbons produced as described herein contain low levels of unwanted or undesired elements, including, but not limited to, heavy metals. In some embodiments, the fatty alcohols, fatty esters, waxes, and hydrocarbons produced as described herein will contain less than about 50 ppm arsenic; less than about 300 ppm calcium; less than about 200 ppm chlorine; less than about 50 ppm cobalt; less than about 50 ppm copper; less than about 300 ppm iron; less than about 2% by weight water; less than about 50 ppm lead; less than about 50 ppm manganese; less than about 0.2 ppm mercury; less than about 50 ppm molybdenum; less than about 1% by weight nitrogen; less than about 200 ppm potassium; less than about 300 ppm sodium; less than about 3% by weight sulfur; less than 50 ppm zinc; or less than 700 ppm phosphorus.

In some embodiments, the fatty alcohols, fatty esters, waxes, and hydrocarbons produced as described herein will contain between about 50% and about 90% carbon; between about 5% and about 25% hydrogen; or between about 5% and about 25% oxygen. In other embodiments, the fatty alcohols, fatty esters, waxes, and hydrocarbons produced as described herein will contain between about 65% and about 85% carbon; between about 10% and about 15% hydrogen; or between about 10% and about 20% oxygen.

VI. Fuel Compositions

The fatty acid derivatives described herein can be used as fuel. One of ordinary skill in the art will appreciate that, depending upon the intended purpose of the fuel, different fatty acid derivatives can be produced and used. For example, a branched fatty acid derivative may be desirable for automobile fuel that is intended to be used in cold climates.

Using the methods described herein, fuels comprising relatively homogeneous fatty acid derivatives that have desired fuel qualities can be produced. Such fatty acid derivative-based fuels can be characterized by carbon fingerprinting, and their lack of impurities when compared to petroleum derived fuels or biodiesel derived from triglyceride. The fatty acid derivative-based fuels can also be combined with other fuels or fuel additives to produce fuels having desired properties.

The production hosts and methods disclosed herein can be used to produce free fatty acids and fatty esters. In some embodiments, the percentage of free fatty acids in the product produced by the production host is at least about 1%, 2%, 3%, 4%, 5%, 6%, 7%, 8%, 9%, 10%, 15%, 20%, or 25%. In some embodiments, the percentage of fatty esters in the product produced by the production host is at least about 50%, 55%, 60%, 65%, 70%, 75%, 80%, 85%, or 90%. In some embodiments, the ratio of fatty esters to free fatty acids in the product produced by the production host is about 10:1, 9:1, 8:1, 7:1, 5:1, 2:1, or 1:1. In other embodiments, the fatty ester produced by the production host is ethyl dodecanoate, ethyl tridecanoate, ethyl tetradecanoate, ethyl pentadecanoate, ethyl cis-9-hexadecenoate, ethyl hexadecanoate, ethyl heptadecanoate, ethyl cis-11-octadecenoate, ethyl octadecanoate, or combinations thereof. In other embodiments, the free fatty acid produced by the production host is dodecanoic acid, tetradecanoic acid, pentadecanoic acid, cis-9-hexadecenoic acid, hexadecanoic acid, cis-11-octadecenoic acid, or combinations thereof.

A. Carbon Fingerprinting

Biologically produced fatty acid derivatives represent a new source of fuels, such as alcohols, diesel, and gasoline. Some biofuels made using fatty acid derivatives have not been produced from renewable sources and are new compositions of matter. These new fuels can be distinguished from fuels derived form petrochemical carbon on the basis of dual carbon-isotopic fingerprinting. Additionally, the specific source of biosourced carbon (e.g., glucose vs. glycerol) can be determined by dual carbon-isotopic fingerprinting (see U.S. Pat. No. 7,169,588, which is herein incorporated by reference in its entirety, in particular, see col. 4, line 31, to col. 6, line 8).

The fatty acid derivatives and the associated biofuels, chemicals, and mixtures may be completely distinguished from their petrochemical derived counterparts on the basis of $^{14}C$ ($f_M$) and dual carbon-isotopic fingerprinting.

The fatty acid derivatives described herein have utility in the production of biofuels and chemicals. The new fatty acid derivative-based products provided by the instant invention additionally may be distinguished on the basis of dual carbon-isotopic fingerprinting from those materials derived solely from petrochemical sources. The ability to distinguish these products is beneficial in tracking these materials in commerce. For example, fuels or chemicals comprising both "new" and "old" carbon isotope profiles may be distinguished from fuels and chemicals made only of "old" materials. Thus, the instant materials may be followed in commerce or identified in commerce as a biofuel on the basis of their unique profile. In addition, other competing materials can be identified as being biologically derived or derived from a petrochemical source.

In some examples, a biofuel composition is made that includes a fatty acid derivative having $\delta^{13}C$ of from about −10.9 to about −15.4, wherein the fatty acid derivative accounts for at least about 85% of biosourced material (i.e., derived from a renewable resource such as cellulosic materials and sugars) in the composition. In other examples, the biofuel composition includes a fatty acid derivative having the formula:

$$X-(CH(R))_n CH_3$$

wherein X represents $CH_3$, $-CH_2OR^1$; $-C(O)OR^2$; or $-C(O)NR^3R^4$;

R is, for each n, independently absent, H or a lower aliphatic;

n is an integer from about 8 to about 34, preferably from about 10 to about 24; and $R^1$, $R^2$, $R^3$ and $R^4$ independently are selected from H or a lower alkyl.

Typically, when R is lower aliphatic, R represents a branched, unbranched or cyclic lower alkyl or lower alkenyl moiety. Exemplary R groups include, without limitation, methyl, isopropyl, isobutyl, sec-butyl, cyclopentenyl, and the like. The fatty acid derivative is additionally characterized as having a $\delta^{13}C$ of from about −10.9 to about −15.4, and the fatty acid derivative accounts for at least about 85% of biosourced material in the composition. In some examples the fatty acid derivative in the biofuel composition is characterized by having a fraction of modern carbon ($f_M$ $^{14}C$) of at least about 1.003, 1.010, or 1.5.

B. Impurities

The fatty acid derivatives described herein are useful for making biofuels. These fatty acid derivatives are made directly from fatty acids and not from the chemical processing of triglycerides. Accordingly, fuels comprising the disclosed fatty acid derivatives will contain fewer impurities than are normally associated with biofuels derived from triglycerides, such as fuels derived from vegetable oils and fats.

The crude fatty acid derivative biofuels described herein (prior to mixing the fatty acid derivative with other fuels such as petroleum-based fuels) will contain less transesterification catalyst than petrochemical diesel or biodiesel. For example, the fatty acid derivative can contain less than about 2%, 1.5%, 1.0%, 0.5%, 0.3%, 0.1%, 0.05%, or 0% of a transesterification catalyst or an impurity resulting from a transesterification catalyst.

Non-limiting examples of transesterification catalysts include hydroxide catalysts, such as NaOH, KOH, and LiOH; and acidic catalysts, such as mineral acid catalysts and Lewis acid catalysts. Non-limiting examples of catalysts and impurities resulting from transesterification catalysts include tin, lead, mercury, cadmium, zinc, titanium, zirconium, hafnium, boron, aluminum, phosphorus, arsenic, antimony, bismuth, calcium, magnesium, strontium, uranium, potassium, sodium, lithium, and combinations thereof.

Similarly, the crude fatty acid derivative biofuels described herein (prior to mixing the fatty acid derivative with other fuels such as petrochemical diesel or biodiesel) will contain less glycerol (or glycerin) than biofuels made from triglycerides. For example, the fatty acid derivative can contain less than about 2%, 1.5%, 1.0%, 0.5%, 0.3%, 0.1%, 0.05%, or 0% by weight of glycerol.

The crude biofuel derived from fatty acid derivatives will also contain less free alcohol (i.e., alcohol that is used to create the ester) than biodiesel made from triglycerides. This is due in part to the efficiency of utilization of the alcohol by the production host. For example, the fatty acid derivative will contain less than about 2%, 1.5%, 1.0%, 0.5%, 0.3%, 0.1%, 0.05%, or 0% by weight of free alcohol.

Biofuel derived from the disclosed fatty acid derivatives can be additionally characterized by its low concentration of sulfur compared to petroleum derived diesel. For example, biofuel derived from fatty acid derivatives can have less than about 2%, 1.5%, 1.0%, 0.5%, 0.3%, 0.1%, 0.05%, or 0% by weight of sulfur.

C. Additives

Fuel additives are used to enhance the performance of a fuel or engine. For example, fuel additives can be used to alter the freezing/gelling point, cloud point, lubricity, viscosity, oxidative stability, ignition quality, octane level, and flash point. In the United States, all fuel additives must be registered with Environmental Protection Agency. The names of fuel additives and the companies that sell the fuel additives are publicly available by contacting the EPA or by viewing the agency's website. One of ordinary skill in the art will appreciate that the fatty acid derivatives described herein can be mixed with one or more fuel additives to impart a desired quality.

The fatty acid derivatives described herein can be mixed with other fuels such as biodiesel derived from triglycerides, various alcohols such as ethanol and butanol, and petroleum-derived products such as gasoline or diesel.

In some examples, a fatty acid derivative with a low gel point, such as $C_{16:1}$ ethyl ester or $C_{18:1}$ ethyl ester, is produced. This low gel point fatty acid derivative can be mixed with biodiesel made from triglycerides to reduce gel point of the resulting fuel when compared to the biodiesel made from triglycerides. Similarly, a fatty acid derivative, such as $C_{16:1}$ ethyl ester or $C_{18:1}$ ethyl ester, can be mixed with petroleum-derived diesel to provide a mixture that is at least about, and often greater than, 5% by weight of biodiesel. In some examples, the mixture includes at least about 10%, 15%, 20%, 30%, 40%, 50%, 60% by weight of the fatty acid derivative.

For example, a biofuel composition can be made that includes at least about 5%, 10%, 20%, 30%, 40%, 50%, 60%, 70%, 80%, 85%, 90% or 95% of a fatty acid derivative that includes a carbon chain that is 8:0, 10:0, 12:0, 14:0, 14:1, 16:0, 16:1, 18:0, 18:1, 18:2, 18:3, 20:0, 20:1, 20:2, 20:3, 22:0, 22:1 or 22:3. Such biofuel compositions can additionally include at least one additive selected from a cloud point lowering additive that can lower the cloud point to less than about 5° C., or 0° C.; a surfactant; a microemulsion; at least about 5%, 10%, 15%, 20%, 30%, 40%, 50%, 60%, 70% or 80%, 85%, 90%, or 95% diesel fuel from triglycerides; petroleum-derived gasoline; or diesel fuel from petroleum.

EXAMPLES

The examples that follow illustrate the engineering of production hosts to produce specific fatty acid derivatives. The biosynthetic pathway involved in the production of fatty acid derivatives are illustrated in the figures.

For example, FIG. 3 is a diagram of the FAS pathway showing the enzymes directly involved in the synthesis of acyl-ACP. To increase the production of fatty acid derivatives, such as waxes, fatty esters, fatty alcohols, and hydrocarbons one or more of the enzymes in FIG. 3 can be over expressed or mutated to reduce feedback inhibition to increase the amount of acyl-ACP produced. Additionally, enzymes that metabolize the intermediates to make non-fatty acid based products (side reactions) can be functionally deleted or attenuated to increase the flux of carbon through the fatty acid biosynthetic pathway. In the examples below, many production hosts are described that have been modified to increase fatty acid production.

Figure 4:
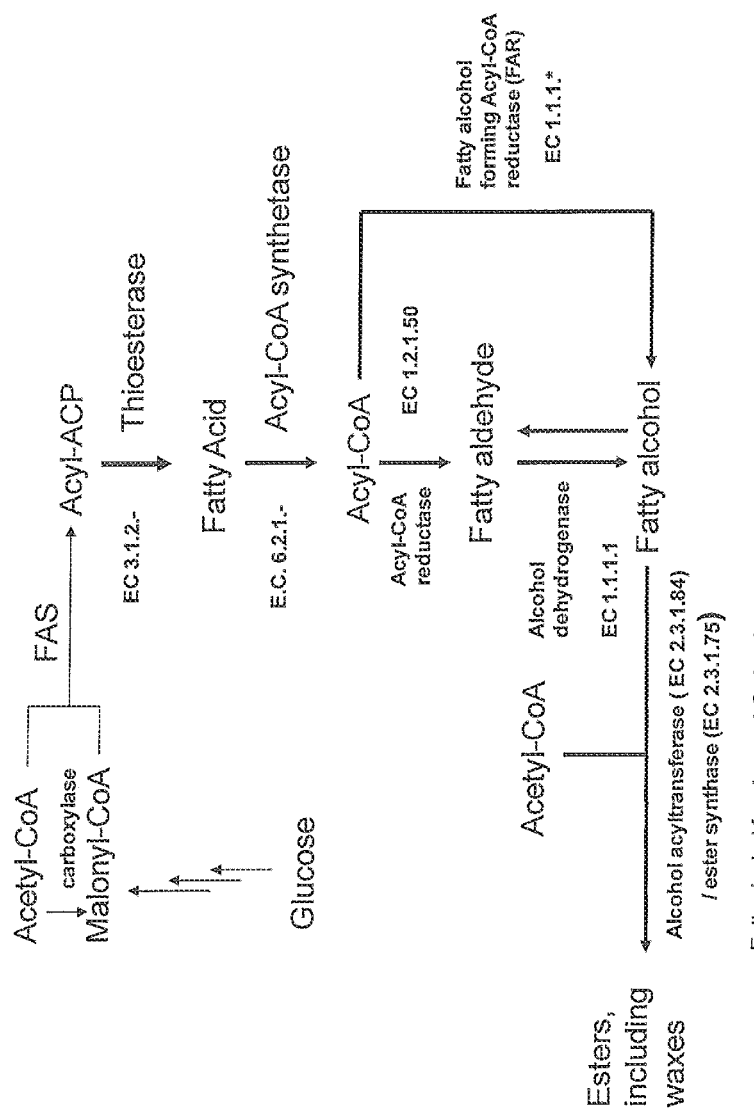
FIG. 4 is a diagram illustrating biosynthetic pathways that produce fatty esters depending upon the substrates provided.
Figure 5:
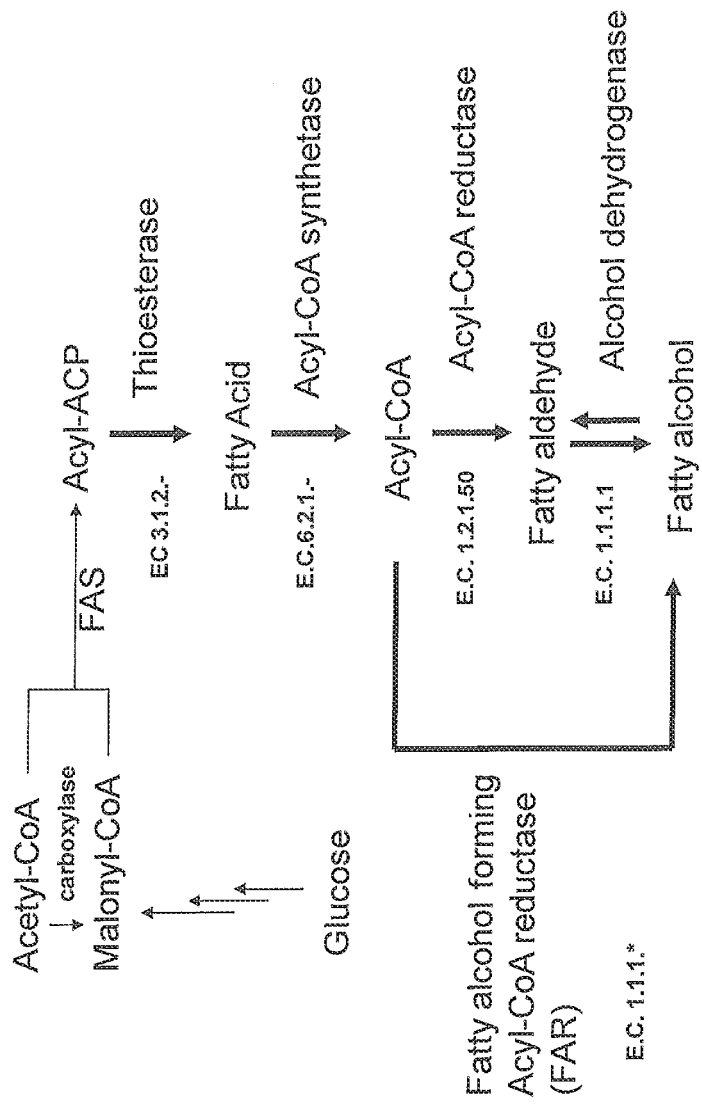
FIG. 5 is a diagram illustrating biosynthetic pathways that produce fatty alcohols.
Figure 6:
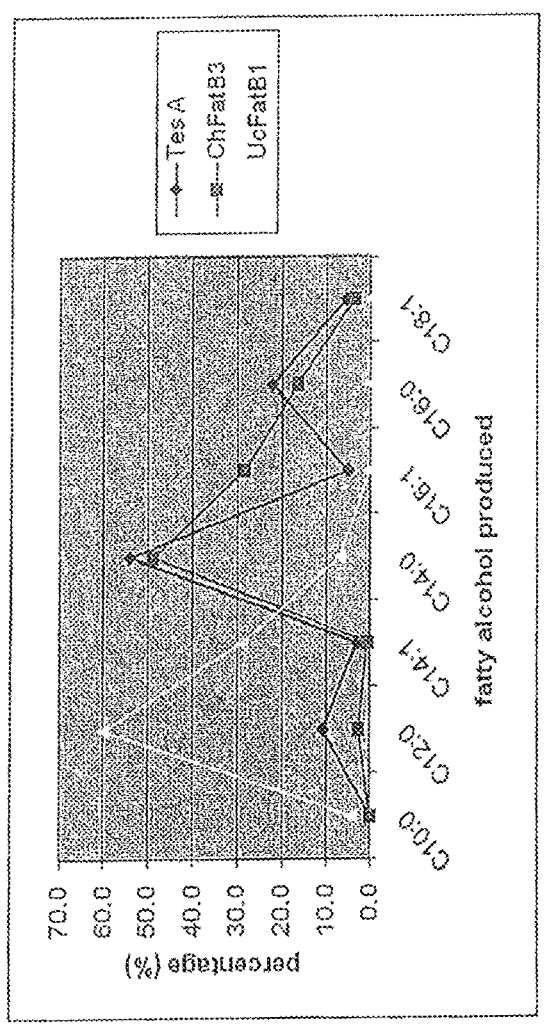
FIG. 6 is a diagram illustrating biosynthetic pathways that produce fatty esters.

FIG. 4, FIG. 5, and FIG. 6 show biosynthetic pathways that can be engineered to make fatty alcohols and fatty esters, respectively. As illustrated in FIG. 5, the conversion of each substrate (e.g., acetyl-CoA, malonyl-CoA, acyl-ACP, fatty acid, and acyl-CoA) to each product (e.g., acetyl-CoA, malonyl-CoA, acyl-ACP, fatty acid, and acyl-CoA) can be accomplished using several different polypeptides that are members of the enzyme classes indicated.

The examples below describe microorganisms that have been engineered or can be engineered to produce specific fatty alcohols, waxes, fatty esters, and hydrocarbons.

Example 1

Production Host Construction

An exemplary production host is LS9001. LS9001 was produced by modifying C41(DE3) from Over-express.com (Saint Beausine, France) to knock-out the fadE gene (acyl-CoA dehydrogenase).

Briefly, the fadE knock-out strain of *E. coli* was made using primers YafV_NotI and Ivry_O1 to amplify about 830 bp upstream of fadE and primers Lpcaf_ol and LpcaR_Bam to amplify about 960 bp downstream of fadE. Overlap PCR was used to create a construct for in-frame deletion of the complete fadE gene. The fadE deletion construct was cloned into the temperature-sensitive plasmid pKOV3, which contained a sacB gene for counterselection, and a chromosomal deletion of fadE was made according to the method of Link et al., *J. Bact.* 179:6228-6237, 1997. The resulting strain was not capable of degrading fatty acids and fatty acyl-CoAs. This knock-out strain is herein designated as ΔfadE.

Additional modifications that were included in a production host include introducing a plasmid carrying the four genes which are responsible for acetyl-CoA carboxylase activity in *E. coli* (accA, accB, accC, and accD, Accessions: NP_414727, NP_417721, NP_417722, NP_416819, EC 6.4.1.2). The accABCD genes were cloned in two steps as bicistronic operons into the NcoI/HindIII and NdeI/AvrII sites of pACYCDuet-1 (Novagen, Madison, Wis.), and the resulting plasmid was termed pAS004.126.

Additional modifications that were included in a production host include the following: over-expression of aceEF (encoding the E1p dihydrogase component and the E2p dihydrolipoamide acyltransferase component of the pyruvate and 2-oxoglutarate dehydrogenase complexes); and fabH/fabD/fabG/acpP/fabF (encoding FAS) from *E. coli, Nitrosomonas europaea* (ATCC 19718), *Bacillus subtilis, Saccharomyces cerevisiae, Streptomyces* spp, *Ralstonia, Rhodococcus, Corynebacteria, Brevibacteria, Mycobacteria,* and oleaginous yeast. Similarly, production hosts were engineered to express accABCD (encoding acetyl co-A carboxylase) from *Pisum savitum*. However, when the production host is also producing butanol it is less desirable to express the *Pisum savitum* homolog.

In some production hosts, genes were knocked out or attenuated using the method of Link, et al., *J. Bacteriol.* 179:6228-6237, 1997. Genes that were knocked out or attenuated include gpsA (encoding biosynthetic sn-glycerol 3-phosphate dehydrogenase, accession NP_418065, EC: 1.1.1.94); ldhA (encoding lactate dehydrogenase, accession NP_415898, EC: 1.1.1.28); pflb (encoding formate acetyltransferase 1, accessions: P09373, EC: 2.3.1.54); adhE (encoding alcohol dehydrogenase, accessions: CAA47743, EC: 1.1.1.1, 1.2.1.10); pta (encoding phosphotransacetylase, accessions: NP_416800, EC: 2.3.1.8); poxB (encoding pyruvate oxidase, accessions: NP_415392, EC: 1.2.2.2); ackA (encoding acetate kinase, accessions: NP_416799, EC: 2.7.2.1) and combinations thereof.

Similarly, the PlsB[D311E] mutation was introduced into LS9001 to attenuate plsB using the method described in Example 1 for the fadE deletion. This mutation decreased the amount of carbon diverted to phospholipid production (see FIG. 1). An allele encoding PlsB[D311E] was made by replacing the GAC codon for aspartate 311 with a GAA codon for glutamate. The altered allele was made by gene synthesis and the chromosomal plsB wildtype allele was exchanged for the mutant plsB[D311E] allele using the method of Link et al. (see above).

For the commercial production of fatty acid derivatives via fermentation, the production host internal regulatory pathways were optimized to produce more of the desired products. In many instances, this regulation was diminished by over-expressing certain enzymes. Some examples are shown in Table 8.

TABLE 8

Additional genes that can be optimized for fatty acid derivative production

| Enzymatic Activity | EC Number | Example of *E. coli* gene(s) (or other microorganism) |
|---|---|---|
| Pantetheine-phosphate adenylyltransferase | 2.7.7.3 | coaD |
| dephospho-CoA kinase | 2.7.1.24 | coaE |
| Biotin-[acetyl-CoA-carboxylase] ligase | 6.3.4.15 | birA |
| Carbonic anhydrase | 4.2.1.1 | cynT, can (yadF) |
| apo-[acyl carrier protein] | None | acpP |
| holo-[acyl-carrier-protein] synthase | 2.7.8.7 | acpS, acpT |
| Pyruvate dehydogenase complex | 1.2.4.1 | aceF |
|  | 2.3.1.12 | aceE |
|  | 1.8.1.4 | lpd |
| NAD Kinase | 2.7.1.23 | nadK (yfjB) |
| Pyruvate-ferredoxin oxidoreductase | 1.2.7.1 | porA (*Desulfovobrio vulgaris* DP4) |

Example 2

Production Host Modifications

The following plasmids were constructed for the expression of various proteins that are used in the synthesis of fatty acid derivatives. The constructs were made using standard molecular biology methods. All the cloned genes were put under the control of IPTG-inducible promoters (e.g., T7, tac, or lac promoters).

The 'tesA gene (thioesterase A gene accession NP_415027 without leader sequence (Cho and Cronan, *J. Biol. Chem.*, 270:4216-9, 1995, EC: 3.1.1.5, 3.1.2.-)) of *E.* coli was cloned into NdeI/AvrII digested pETDuet-1 (pET-Duet-1 described herein is available from Novagen, Madison, Wis.). Genes encoding for FatB-type plant thioesterases (TEs) from *Umbellularia californica*, *Cuphea hookeriana*, and *Cinnamonum camphorum* (accessions: UcFatB1=AAA34215, ChFatB2=AAC49269, ChFatB3=AAC72881, CcFatB=AAC49151) were individually cloned into three different vectors: (i) NdeI/AvrII digested pETDuet-1; (ii) XhoI/HindIII digested pBluescript KS+ (Stratagene, La Jolla, Calif., to create N-terminal lacZ:: TE fusion proteins); and (iii) XbaI/HindIII digested pMAL-c2X (New England Lab, Ipswich, Mass.) (to create n-terminal malE::TE fusions). The fadD gene (encoding acyl-CoA synthase) from *E. coli* was cloned into a NcoI/HindIII digested pCDFDuet-1 derivative, which contained the acr1 gene (acyl-CoA reductase) from *Acinetobacter baylyi* ADP1 within its NdeI/AvrII sites. Table 9 provides a summary of the plasmids generated to make several exemplary production strains. One of ordinary skill in the art will appreciate that different plasmids and genomic modifications can be used to achieve similar strains.

TABLE 9

Summary of plasmids used in production hosts

| Plasmid | Source Organism Gene Product | Accession No., EC number |
|---|---|---|
| pETDuet-1-tesA | *E. coli* TesA | Accessions: NP_415027, EC: 3.1.1.5, 3.1.2.- |
| pETDuet-1-TEuc pBluescript-TEuc pMAL-c2X-TEuc | *Umbellularia californica* UcFatB1 | Q41635 AAA34215 |
| pETDuet-1-TEch pBluescript-TEch pMAL-c2X-TEch | *Cuphea hookeriana* ChFatB2 ChFatB3 | ABB71581 AAC49269 AAC72881 |
| pETDuet-1-TEcc pBluescript-TEcc TEci | *Cinnamonum camphorum* CcFabB | AAC49151 |
| pETDuet-1-atFatA3 | *Arabidopsis thaliana* | NP_189147 |
| pETDuet-1-HaFatA1 | *Helianthus annuus* | AAL769361 |
| pCDFDuet-1-fadD-acr1 | *E. coli* | fadD: Accessions NP_416319, EC 6.2.1.3 acr1: Accessions YP_047869 |
| pETDuet-1-tesA | *E. coli* TesA | Accessions: NP_415027, EC: 3.1.1.5, 3.1.2.- |
| pETDuet-1-TEuc pBluescript-TEuc pMAL-c2X-TEuc | *Umbellularia californica* UcFatB1 | Q41635 AAA34215 |
| pETDuet-1-TEch pBluescript-TEch pMAL-c2X-TEch | *Cuphea hookeriana* ChFatB2 ChFatB3 | ABB71581 AAC49269 AAC72881 |
| pETDuet-1-TEcc pBluescript-TEcc TEci | *Cinnamonumcamphorum* CcFatB | AAC49151 |
| pCDFDuet-1-fadD-acr1 | *E. coli* | fadD: Accessions NP_416319, EC 6.2.1.3 acr1: Accessions YP_047869 |

The chosen expression plasmids contain compatible replicons and antibiotic resistance markers to produce a four-plasmid expression system. Therefore, LS9001 can be co-transformed with: (i) any of the TE-expressing plasmids; (ii) the FadD-expressing plasmid, which also expresses Acr1; and (iii) ester synthase expression plasmid. When induced with IPTG, the resulting strain will produce increased concentrations of fatty alcohols from carbon sources such as glucose.

Example 3

Production of Fatty Alcohol in the Recombinant *E. coli* Strain

Fatty alcohols were produced by expressing a thioesterase gene and an acyl-CoA reductase gene exogenously in a production host. More specifically, plasmids pCDFDuet-1-fadD-acr1 (acyl-CoA reductase) and pETDuet-1-'tesA (thioesterase) were transformed into *E. coli* strain LS9001 (described in Example 1) and corresponding transformants were selected in LB plates supplemented with 100 mg/L of spectinomycin and 50 mg/L of carbenicillin. Four transformants of LS9001/pCDFDuet-1-fadD-acr1 were independently inoculated into 3 mL of M9 medium supplemented with 50 mg/L of carbenicillin and 100 mg/L of spectinomycin. The samples containing the transformants were grown in at 25° C. in a shaker (250 rpm) until they reached 0.5 $OD_{600}$. Next, 1.5 mL of each sample was transferred into a 250 mL flask containing 30 mL of the M9 medium described above. The resulting culture was grown at 25° C. in a shaker until the culture reached between 0.5-1.0 $OD_{600}$. IPTG was then added to a final concentration of 1 mM. Cell growth continued for 40 hours.

The cells were then spun down at 4000 rpm. The cell pellets were suspended in 1.0 mL of methanol. 3 mL of ethyl acetate was then mixed with the suspended cells. 3 mL of $H_2O$ was then added to the mixture. Next, the mixture was sonicated for 20 minutes. The resulting sample was centrifuged at 4000 rpm for 5 minutes. Then the organic phase (the upper phase), which contained fatty alcohol, was subjected to GC/MS analysis. The total alcohol (including tetradecanol, hexadecanol, hexadecenol and octadecenol) yield was about 1-10 mg/L. When an *E. coli* strain carrying only empty vectors was cultured in the same way, fatty alcohols yields of only 0.2-0.5 mg/L were measured in the ethyl acetate extract.

Example 4

Production of Fatty Acids (FA) and Fatty Acid Ethyl Esters (FAEE) Containing Odd-Numbered Carbon Chains without Heavy Metals 1. Production of Biodiesel Sample #23-30

Biodiesel sample #23-30 ("sample #23-30") was produced by the bioreactor cultivation of an *E. coli* strain (C41 DE3 ΔfadE ΔfabR 'TesA fadD adp1ws) engineered to produce fatty esters. A two-stage inoculum protocol was utilized for expansion of the culture. The first stage consisted of the inoculation of 50 mL LB media (supplemented with 100 μg/L carbenicillin and 100 μg/L spectinomycin) in a 250 mL baffled shake flask with a 1 mL frozen stock vial of the *E. coli* ester production strain. This seed flask was incubated at 37° C. for seven hours (final $OD_{600}$=4.5 AU, pH 6.7), after which 3 mL of the primary culture was transferred to each of three 2 L baffled flasks containing 350 mL buffered F1 minimal medium, also containing 100 μg/L carbenicillin and 100 μg/L spectinomycin. The shake flask buffer used was Bis-Tris propane at a final concentration of 200 mM (pH 7.2). These secondary seed flasks were incubated at 37° C. for eighteen hours (final $OD_{600}$=12 AU, pH 5.5) and the contents used to inoculate three 14 L bioreactors with a starting volume of 6.5 liters of buffered F1 minimal medium following inoculation. These bioreactors also contained 100 μg/L carbenicillin and 100 g/L spectinomycin.

These 14 L bioreactors were initially cultivated at 37° C., and the dissolved oxygen level was maintained at 30% of saturation, using the agitation and oxygen enrichment cascade loops. The pH of the cultivation was maintained at 7.2, using 1 M $H_2SO_4$ and anhydrous ammonia gas. A nutrient feed consisting primarily of 43% (w/v) glucose was initiated when the original 5 g/L charge in the basal medium was exhausted. The glucose solution feed rate was then manually tuned for the duration of the run to keep the residual glucose at a low (but non-zero) value for the duration of the fermentation. Cultures were induced with 1 mM IPTG (final concentration) when the optical density of the culture reached a value of 30 AU. At this induction point, the bioreactor cultivation temperature was reduced to 30° C., and approximately 15 mL/L (on a 6.5 to 7 liter volume basis) of ethanol was added to the culture and monitored by HPLC throughout. Additional ethanol was added periodically to the bioreactors to maintain the residual concentration at around 20 mL/L The bioreactors were harvested after approximately 60 hours of cultivation, with approximately 10 L of the broth harvested from each of the three bioreactors.

These harvest broths were combined and extracted with an equivalent volume of ethyl acetate with stiffing at room temperature for two hours. The broth extract was then centrifuged (3500 rpm, 30 minutes) to separate the liquid layers, followed by the removal of the organic layer for further processing. The ethyl acetate was almost completely removed (<0.3% residual, by GC/FID) from this organic layer by rotary evaporation (Btichi, R-200), leaving approximately 90 mL of a dark, oily liquid. This liquid was referred to as sample #23-30.

2. Quantification of FA and FAEE in Sample #23-30

GC-MS was performed using an Agilent 5975B MSD system equipped with a 30m×0.25 mm (0.10 µm film) DB-5 column. The column temperature was 3 min isothermal at 100° C. The column was programmed to rise from 100° C. to 320° C. at a rate of 20° C./min. When the final temperature was reached, the column remained isothermal for 5 minutes at 320° C. The injection volume was 1 µL. The carrier gas, helium, was released at 1.3 mL/min. The mass spectrometer was equipped with an electron impact ionization source. The ionization source temperature was set at 300° C. FAEE standards (e.g., ethyl dodecanoate, ethyl tetradecanoate, ethyl cis-9-hexadecenoate, ethyl hexadecanoate, ethyl octadecanoate, all >99%); fatty acid methyl ester (FAME) standards (e.g., methyl dodecanoate, methyl tetradecanoate, methyl pentadecanoate, methyl cis-9-hexadecenoate, methyl hexadecanoate, methyl cis-11-octadecenoate, all >99%); trimethylsilyl diazomethane (TMSD, 2 M in hexane); hydrochloric acid (37%); methanol (>99.9%); and ethyl acetate (>99.9%) were purchased from Sigma-Aldrich and used without further purification.

Sample #23-30 was derivatized by adding 50 µL trimethylsilyldiazomethane (TMSD), 8 µL HCl, and 36 µL methanol to 1 mL of sample (1 mg/mL in ethyl acetate). The mixture was incubated at room temperature for 1 hour.

Prior to quantitation, the FAEE and FAME in sample #23-30 were identified using two methods. First, the GC retention time of each compound was compared to the retention time of a known standard. Second, identification of each compound was confirmed by matching the compound's mass spectrum to a standard's mass spectrum in the mass spectra library.

When a standard for a FAEE or FAME was available, the quantification of the FAEE or FAME was determined by generating a calibration curve (concentration vs. instrument response). A linear relationship between the instrument response and the analyte concentration was then obtained. The concentration of the compound in the sample was determined by taking its instrument response and referring to the calibration curve.

When a standard for an FAEE was not available, an average instrument response was used to determine the compound's concentrations. The slope and the intercept for all existing calibration curves were averaged. From these averages, a linear relationship between concentration and instrument response was determined The concentration of unknown compounds was then determined by referencing its instrument response to the linear relationship between instrument response and concentration using Equation 1.

concentration=(instrument response−average intercept)/average slope  Equation 1

After identifying and quantifying the FAME, the concentration of the associated free fatty acids was determined based upon the concentration of FAME and the molecular weight ratio of FA to FAME. Finally, the concentration of FAEE and FA in mg/L was converted into percentage in the biodiesel sample (w/w %).

The concentrations of FAEE and FA in sample #23-30 are listed in Table 10. The total concentration of FAEEs and FAs was 80.7%. The rest of the unknown compounds may be analyzed by LC/MS/MS method. Ethyl pentadecanoate, ethyl cis-9-hexadecenoate, ethyl hexadecanoate and ethyl cis-11-octadecenoate were the major component of sample #23-30.

TABLE 10

Percentage of FAEE and FA in sample #23-30

| Name | Structure | MW | Percentage, % |
|------|-----------|------|---------------|
| Ethyl dodecanoate | 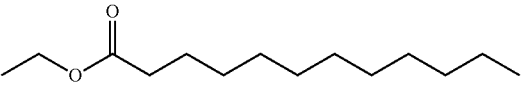 [SMILES: CCCCCCCCCCCC(=O)OCC] | 228.2 | 1.82 ± 0.03 |
| Ethyl tridecanoate | 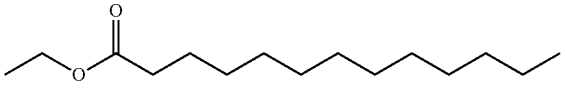 [SMILES: CCCCCCCCCCCCC(=O)OCC] | 242.2 | 0.16 ± 0.01 |
| Ethyl tetradecanoate | 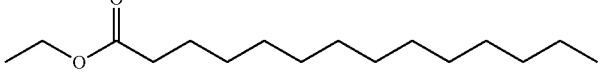 | 256.2 | 12.88 ± 0.16 |

TABLE 10-continued

Percentage of FAEE and FA in sample #23-30

| Name | Structure | MW | Percentage, % |
|---|---|---|---|
| Ethyl pentadecanoate | 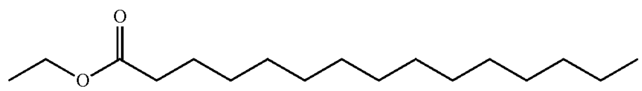 [SMILES: CCCCCCCCCCCCCCC(=O)OCC] | 270.3 | 0.62 ± 0.02 |
| Ethyl cis-9-hexadecenoate | 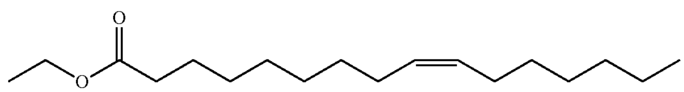 [SMILES: CCCCCC/C=C\CCCCCCCC(=O)OCC] | 282.3 | 24.12 ± 0.20 |
| Ethyl hexadecanoate | 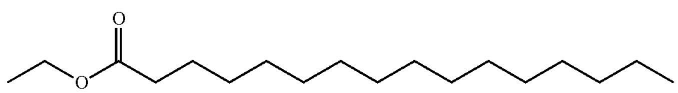 [SMILES: CCCCCCCCCCCCCCCC(=O)OCC] | 284.3 | 9.04 ± 0.11 |
| Ethyl heptadecanoate | 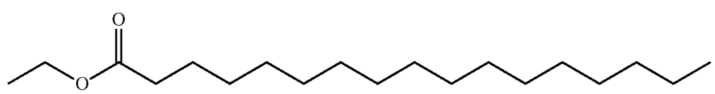 [SMILES: CCCCCCCCCCCCCCCCC(=O)OCC] | 298.3 | 0.11 ± 0.01 |
| Ethyl cis-11-octadecenoate | 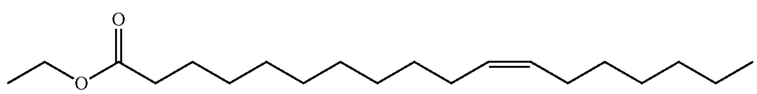 [SMILES: CCCCCC/C=C\CCCCCCCCCC(=O)OCC] | 310.3 | 23.09 ± 0.33 |
| Ethyl octadecanoate | 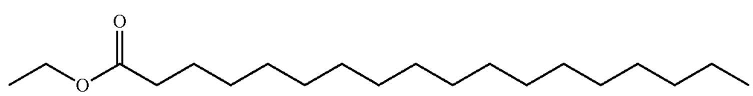 [SMILES: CCCCCCCCCCCCCCCCCC(=O)OCC] | 312.3 | 0.19 ± 0.03 |
| Dodecanoic acid | 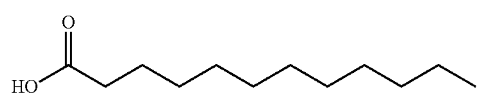 | 200.2 | 0.94 ± 0.02 |
| Tetradecanoic acid | 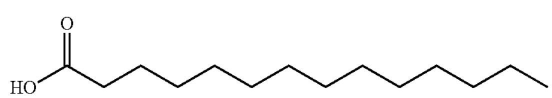 [SMILES: CCCCCCCCCCCCCC(=O)O] | 228.2 | 2.63 ± 0.03 |
| Pentadecanoic acid | 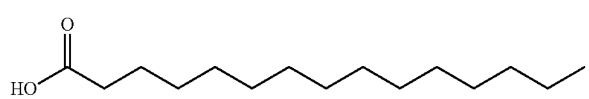 [SMILES: CCCCCCCCCCCCCCC(=O)O] | 242.2 | 0.10 ± 0.01 |
| cis-9-hexadecenoic acid | 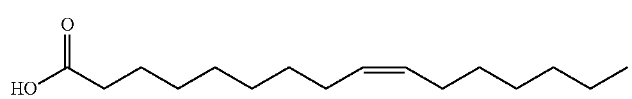 [SMILES: CCCCCC/C=C\CCCCCCCC(=O)O] | 254.2 | 1.97 ± 0.01 |
| Hexadecanoic acid | 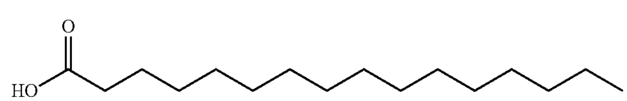 [SMILES: CCCCCCCCCCCCCCCC(=O)O] | 256.2 | 1.01 ± 0.01 |
| cis-11-octadecenoic acid | 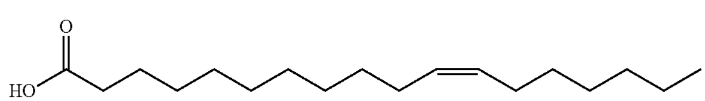 [SMILES: CCCCCC/C=C\CCCCCCCCCC(=O)O] | 282.3 | 2.00 ± 0.02 |

*Percentage is w/w %.

Surprisingly, sample #23-30 contained odd-numbered FA and FAEE. Further analysis, such as LC/MS/MS, may be performed to confirm that these odd-numbered carbon chain fatty acids were produced by *E. coli* and did not come from the *E. coli*'s own lipids.

3. Quantitative Elemental Analysis of Sample #23-30

Heavy metals are known to poison the catalysts used in catalytic cracking. To measure the levels of heavy metals in sample #23-30, sample #23-30 was sent to Galbraith Laboratories, Inc. for quantitative elemental analysis of arsenic, calcium, carbon, chlorine, cobalt, copper, hydrogen, iron, Karl Fisher water, lead, manganese, magnesium, mercury, molybdenum, nitrogen, potassium, sodium, sulfur, zinc, oxygen, and phosphorus. Preparatory and analytical methods are described below. Results are shown in Table 11. All amounts in Table 11 were below the level of quantitation (LOQ) except for carbon (73.38%), chlorine (91 ppm), hydrogen (12.1%), Karl Fisher water (0.998%), mercury (0.057 ppm), oxygen (14.53%), and phosphorus (343 ppm). Therefore, sample #23-30 did not contain high levels of the heavy metals that were measured.

Method G-52, Rev 6: Microwave Digestion of Samples for Metals Analysis

An appropriate amount of sample was weighed into a microwave vessel to the nearest 0.001 g. The appropriate reagents were then added to the microwave vessel. If a visible reaction was observed the reaction was allowed to cease before capping the vessel. The vessel was then sealed and placed in the microwave according to the manufacture's directions. The temperature of each vessel reached a minimum of 180±10° C. in 5 minutes. It remained at a minimum of 180±10° C. for 10 minutes. At the end of the microwave program the vessels were allowed to cool for a minimum of 5 minutes before removal. The vessels were then uncapped and transferred to volumetric flasks for analysis by the proper technique.

Method G-55, Rev 3: Parr Oxygen Bomb Combustion for the Determination of Halogens Samples were weighed into a combustion cup, and Mineral oil was added as a combustion aid. For chlorine (Cl) and bromine (Br) measurements, 1% hydrogen peroxide solution was added into the bomb. For sulfur (S) measurements, 0.01 N sodium hydroxide solution was added. The sample and cup were sealed into a Parr oxygen combustion bomb along with a suitable absorbing solution. The bomb was purged with oxygen, then pressurized to 25-30 atm of oxygen pressure, and ignited. Afterwards, the contents of the bomb were well mixed and transferred to a beaker for subsequent analysis.

Method G-30B, Rev 7: Wet Ash Digestion of Inorganic and Organic Compounds for Metals Analysis The sample was charred using $H_2SO_4$. If analyzing for metals that form insoluble sulfates, $HClO_4$ and $HNO_3$ were used to char the organic material. After charring the sample, $HNO_3$ was added and the sample was refluxed to solubilize the metals present. If the solution became cloudy, HCl was added to aid complete digestion. HF could be used if silicon was present in the sample but only if silicon was not an analyte of interest. All HF used was restricted to Teflon vessels. The clear digestate was quantitatively transferred to a Class A volumetric flask and brought to final volume. The sample was then analyzed.

Method ME-4A Rev 2: Determination of Anions Suppressed by Ion Chromatography

| | |
|---|---|
| Instrument | Dionex Model DX500 |
| Chromatograph Column | Dionex IonPac AS9-SC 4 × 250 mm |
| Eluent 2.4 mM $Na_2CO_3$ | 1.8 mM $NaHCO_3$ |
| Preparation | Aqueous samples may be analyzed as is. Water-soluble samples are typically transferred by weight to a known volume. Other solid materials that are not water-soluble may be extracted to determine extractable quantities of various anions or combusted to determine total quantities of an element such as Cl or Br. |
| Calibration | Standards to bracket sample concentration. 0.2 mg/L-4.0 mg/L |
| Sample Intro | Auto injection (Hitachi Model AS7200) |
| Determination | Conductivity detection/linear regression |
| Quantitation Limit | Typically 0.2 mg/L in solution. |
| Interferences | Anions with similar retention times; overlapping peaks from major constituent anions. |

Method S-300 Rev 7: Determination of Water by Coulometric Titration (Karl Fischer)

This method combined coulometry with the Karl Fischer titration. The sample was mixed with an amine-methanol mixture containing predominantly iodide ion (I−) and sulfur dioxide. The iodine produced at the anode through the electrolysis was allowed to react with water. In such cases, iodine was produced in direct proportion to the quantity of electricity according to Faraday's Law. Also, because 1 mole of water stoichiometrically reacts with 1 mole of iodine, 1 mg of water was equivalent to 10.71 coulombs of electricity. Utilizing this principle, the Moisture Meter determined the amount of water directly from the number of coulombs required for the electrolysis. This procedure included both direct introduction and a vaporizer pre-treatment technique.

| | |
|---|---|
| Preparation | Weigh to obtain 100 µg to 3 mg H2O; Protect samples from atmospheric moisture during weighing and transfer. |
| Instrument | Mitsubishi Moisture Meter MCl Model CA-06 (Inst. #569) Mitsubishi Moisture Vaporizer, Model CA/VA-06 (Inst. #568) |
| Control | Sodium tartrate monohydrate (15.66%); Frequency: every 10 samples, one each day minimum, 95-105% recovery |
| Sample Intro | A. Entry port, Direct transfer; capillary, syringe, or scoop B. Furnace, tin capsules (Water Vaporizer VA-06); Temperature varies, 200° C. is default value used for standards. Most samples analyzed at 160° C. Other temperatures upon request. |
| Determination | Coulometric titration of Karl Fischer reagent via automatic titrator |
| Quantitation Limit | 100 µg $H_2O$ |

| Precision & Accuracy | RSD | RE | INSTR# |
|---|---|---|---|
| Sodium Tartrate Monohydrate | 1.35% | −0.54% | 569 |
| | 1.34% | −2.13% | 568 |

| | |
|---|---|
| Equations | $(2I^- - 2e^- \rightarrow I_2)$; $(I_2 + SO_2 + 3C_5H_5N + H_2O \rightarrow 2C_5H_5NHI + C_5H_5NSO_3)$ µg $H_2O$/spl wt (g) = ppm $H_2O$ µg$H_2O$ × 0.1/spl wt (mg) = % $H_2$) |
| Interferences | (direct transfer only) free alkali; oxidizing, reducing agent; mercaptans |

Method E16-2, rev 9 (Trace E16-2A): Sulfur Determination Using the LECO SC-432DR The SC-432DR Sulfur Analyzer is a non-dispersive infrared, digitally controlled instrument designed to measure sulfur content in a variety of organic and inorganic materials. The sample was combusted at 1350+50° C. in an atmosphere of pure oxygen. The sulfur was oxidized to sulfur dioxide and quantitated by infrared absorption. The SC-432DR was equipped with two detectors, a high-range and a low-range infrared cell.

| | |
|---|---|
| Instrument | LECO SC-432DR Sulfur Analyzer |
| Sample Intro | Weigh sample to nearest 0.01 mg. Weigh samples directly into sample boat tared on electronic balance. Weight automatically transferred to SC432 database. Cover sample with LECO Com-Cat combustion accelerator as called for by sample type. |
| Calibration | Three conditioners of 5-10 mg cystine. Seven calibration standards of 30-175 mg NIST SRM 8415 Whole Egg Powder (0.512% S). Internal calibration using a quadratic regressed curve. |
| Control | NIST SRM 1549 Milk Powder (0.351%); others to match sample type. Frequency: one for every ten samples. |

| | |
|---|---|
| Determination | Combustion in $O_2$ atmosphere at 1350° C. Determination of resulting $SO_2$ by infrared detector. |
| Quantitation Limit | 0.08 mg S |
| Calculations | Internal |

| Precision & Accuracy | RSD (%) | Mean Recovery (%) |
|---|---|---|
| (milk powder) | 2.60 | 97.97 |

Method ME-2, Rev 14: Carbon, Hydrogen, and Nitrogen Determination

This instrument burns sample in pure oxygen at 950° C. under static conditions to produce combustion products of $CO_2$, $H_2O$, and $N_2$. The PE-240 automatically analyzes these products in a self-integrating, steady state thermal conductivity analyzer. Tungstic anhydride may be added to aid combustion. An extended combustion time (e.g., burn hard mode) may be employed for difficult to combust samples.

| | |
|---|---|
| Instrument | PerkinElmer 240 Elemental Analyzer (Instrument # 409, 410) |
| Sample intro | Weigh 1.0-2.5 mg into Al capsule; crimp (see GLI Procedure G-6) for liquids; washed with solvent prior to weighing upon request |
| Decomposition | Combustion at ≥950° C., reduction at ≥675° C. = $CO_2$, $H_2O$, $N_2$ |
| Calibration | Cyclohexanone-2,4-dinitropheylhydrazone (1-2.5 mg) |
| Control | s-1409, 2-1410: Cyclohexanone-2,4-dinitropheylhydrazone (51.79% C, 5.07% H, 20.14% N) |
| Determination | $CO_2$, $H_2O$, $N_2$ by thermal conductivity analyzer |
| Quantitation | 0.5% C, 0.5% H, 0.5% N |

| | Instrument #409 | | | Instrument #410 | | |
|---|---|---|---|---|---|---|
| Precision & accuracy | C | H | N | C | H | N |
| RSD % | 0.28 | 1026 | 0.39 | 0.35 | 1.12 | 0.41 |
| Mean recovery (%) | 99.94 | 101.25 | 99.86 | 100.13 | 100.40 | 100.04 |

| | |
|---|---|
| Interferences | Metals and some halogens cause incomplete combustion. Combustion aids and/or an extended combustion time can be used to alleviate this problem. |
| Calculations | Instrument calculates & prints w/w results for % C, % H, and % N. For samples crimped in an aluminum capsule, the % N is corrected with a factor; (μV/μg sample/K) × 100 = % Element, where K = calibration = μV/μg of C, or H, or N |

Method ME-70, Rev 4: Inductively Coupled Plasma Atomic Emission Spectrometry

This method describes multi-elemental determinations by ICP-AES using simultaneous optical systems and axial or radial viewing of the plasma. The instrument measures characteristic emission spectra by optical spectrometry. Samples are nebulized and the resulting aerosol is transported to the plasma torch. Element-specific emission spectra are produced by radio-frequency inductively coupled plasma. The spectra are dispersed by a grating spectrometer, and the intensities of the emission lines are monitored by photosensitive devices. Background correction is required for trace element determination. Background must be measured adjacent to analyte lines on samples during analysis. The position selected for the background-intensity measurement, on either or both sides of the analytical line, will be determined by the complexity of the spectrum adjacent to the analyte line. In one mode of analysis, the position used should be as free as possible from spectral interference and should reflect the same change in background intensity as occurs at the analyte wavelength measured. Background correction is not required in cases of line broadening where a background correction measurement would actually degrade the analytical result.

| | |
|---|---|
| Instrument | ICP-OES Optima 5300, 3300DV and 4300DV, or equivalent |
| Decomposition | Prior to analysis, samples must be acidified or digested using appropriate Sample Preparation Methods. |
| Calibration | 0.01 ppm-60 ppm plus matrix specific calibrations |
| Sample Intro | Peristaltic pump, cross flow nebulizer, gemcone nebulizer, scott ryton spray chamber and quartz cylonic spray chamber |
| Determination | Atomic emission by radio frequency inductively coupled plasma of element-specific emission spectra through a grating spectrometer monitored by photosensitive devices. |
| Quantitation Limit | Element and calibration specific ranging from 0.01-2 ppm |
| Precision & Accuracy | ±10% RSD |
| Interferences | Spectral, chemical, physical, memory |
| Calculations | wt % = (fc × v/10 × D)/spl<br>ppm = (fc × v × D)/SPL |

| |
|---|
| -continued |
| Where fc = final concentration in μg/mL; v = sample volume in mL; D = dilution factor; spl = sample mass in mg; SPL = sample mass in g |

Method E80-2, Rev 4: Determination of Mercury (Automated Cold Vapor Technique)

This procedure is based on EPA SW846 Method 7471A. Cold Vapor Atomic Absorption is based on the general theory of atomic absorption, which holds that free atoms of the analyte absorb energy from a lamp source that is proportional to the concentration of analyte. By using a lamp containing the metal to be measured, the exact wavelength needed for absorption is produced and interferences are greatly reduced. Cold Vapor Atomic Absorption uses this principle, and the mercury atoms are liberated by reducing mercury ions with Tin (II) Chloride ($SnCl_2$). Nitrogen gas carries the atoms through an optical cell, with the Hg lamp on one end and the detector on the other end. Because the cold vapor method is employed, instead of a flame method, undigested organic compounds are an interference concern, because of their wide band of absorption wavelengths.

| Instrument | PerkinElmer FIMS 400 Automated Mercury Analyzer or equivalent |
|---|---|
| Decomposition | Variable, usually microwave digestion or permanganate hot water bath digestion |
| Calibration | 0.1-5.0 μg/L |
| Sample Introduction | Autosampler, peristaltic pump |
| Determination | Primary wavelength 253.7 nm, using a solid state detector |
| Detection Limit | Varies with preparation method and sample matrix |
| Precision & Accuracy | For microwave digestion:    For MnO$_4^-$ digestion: |
| RE | −2.47%            4.90% |
| RSD | 7.48%            5.20% |
| Interferences | Undigested organic compounds |
| Calculations | ppb Hg = (μg/L in solution × volume (mL) × dilution factor) / sample weight (g) |

TABLE 11

Quantitative elemental analysis of sample #23-30

| Element | Preparation Method | Analytical Method | Result |
|---|---|---|---|
| Arsenic | G-52 | ME-70 | <25 ppm |
| Calcium | G-30B | ME-70 | <119 ppm |
| Carbon | N/A | ME-2 | 73.38% |
| Chlorine | G-55 | ME-4A | 91 ppm |
| Cobalt | G-30B | ME-70 | <23 ppm |
| Copper | G-30B | ME-70 | <23 ppm |
| Hydrogen | N/A | ME-2 | 12.1% |
| Iron | G-30B | ME-70 | <136 ppm |
| Karl Fisher water | N/A | S-300 | 0.998% |
| Lead | G-52 | ME-70 | <25 ppm |
| Manganese | G-30B | ME-70 | <23 ppm |
| Magnesium | G-30B | ME-70 | <23 ppm |
| Mercury | G-52 | E80-2 | 0.057 ppm |
| Molybdenum | G-30B | ME-70 | <23 ppm |
| Nitrogen | N/A | ME-2 | <0.5% |
| Potassium | G-30B | ME-70 | <103 ppm |
| Sodium | G-30B | ME-70 | <140 ppm |
| Sulfur | N/A | E16-2A | <0.140% |
| Zinc | G-30B | ME-70 | <23 ppm |
| Oxygen | N/A | Subtraction* | 14.53% |
| Phosphorus | G-30B | ME-70 | 343 ppm |

Results presented as "<" are below LOQ.
*Oxygen content was determined by subtracting the observed results for all other elements from 100%.

Example 5

Production and Release of Fatty Alcohol from Production Host

Acr1 (acyl-CoA reductase) was expressed in *E. coli* grown on glucose as the sole carbon and energy source. The *E. coli* produced small amounts of fatty alcohols such as dodecanol ($C_{12:0}$—OH), tetradecanol ($C_{14:0}$—OH) and hexadecanol ($C_{16:0}$—OH). In other samples, FadD (acyl-CoA synthase) was expressed together with acr1 in *E. coli*. A five-fold increase in fatty alcohol production was observed.

Figure 7:
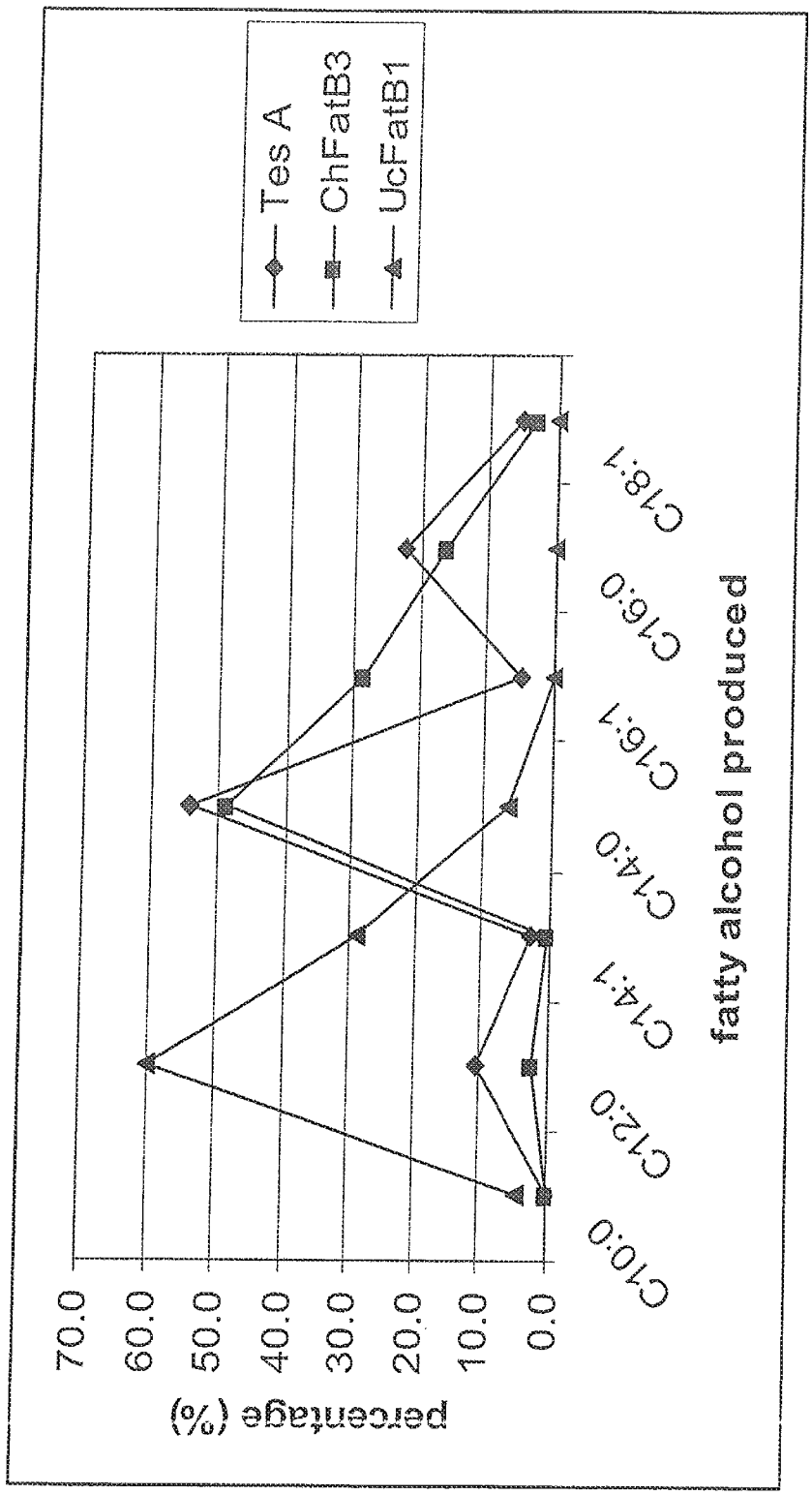
FIG. 7 is a graph depicting fatty alcohol production by the strain, described in Example 5, co-transformed with pCDF-Duet-1-fadD-acr1 and plasmids containing various thioesterase genes. Saturated $C_{10}$, $C_{12}$, $C_{14}$, $C_{16}$ and $C_{18}$ fatty alcohol were identified.

In other samples, acr1, fadD, and accABCD (acetyl-CoA carboxylase) (plasmid carrying accABCD constructed as described in Example 1) were expressed along with various individual thioesterases (TEs) in wild-type *E. coli* C41 (DE3) and an *E. coli* C41 (DE3 ΔfadE, a strain lacking acyl-CoA dehydrogenase). This resulted in additional increases in fatty alcohol production and modulation of the profiles of fatty alcohols (see FIG. 7). For example, over-expression of *E. coli* 'tesA (pETDuet-1-'tesA) in this system achieved approximately a 60-fold increase in $C_{12:0}$—OH, $C_{14:0}$—OH and $C_{16:0}$—OH, with $C_{14:0}$—OH being the major fatty alcohol. A very similar result was obtained when the ChFatB3 enzyme (FatB3 from *Cuphea hookeriana* in pMAL-c2X-TEcu) was expressed. When the UcFatB 1 enzyme (FatB1 from *Umbellularia californicain* in pMAL-c2X-TEuc) was expressed, fatty alcohol production increased approximately 20-fold and $C_{12:0}$—OH was the predominant fatty alcohol.

Figure 8:
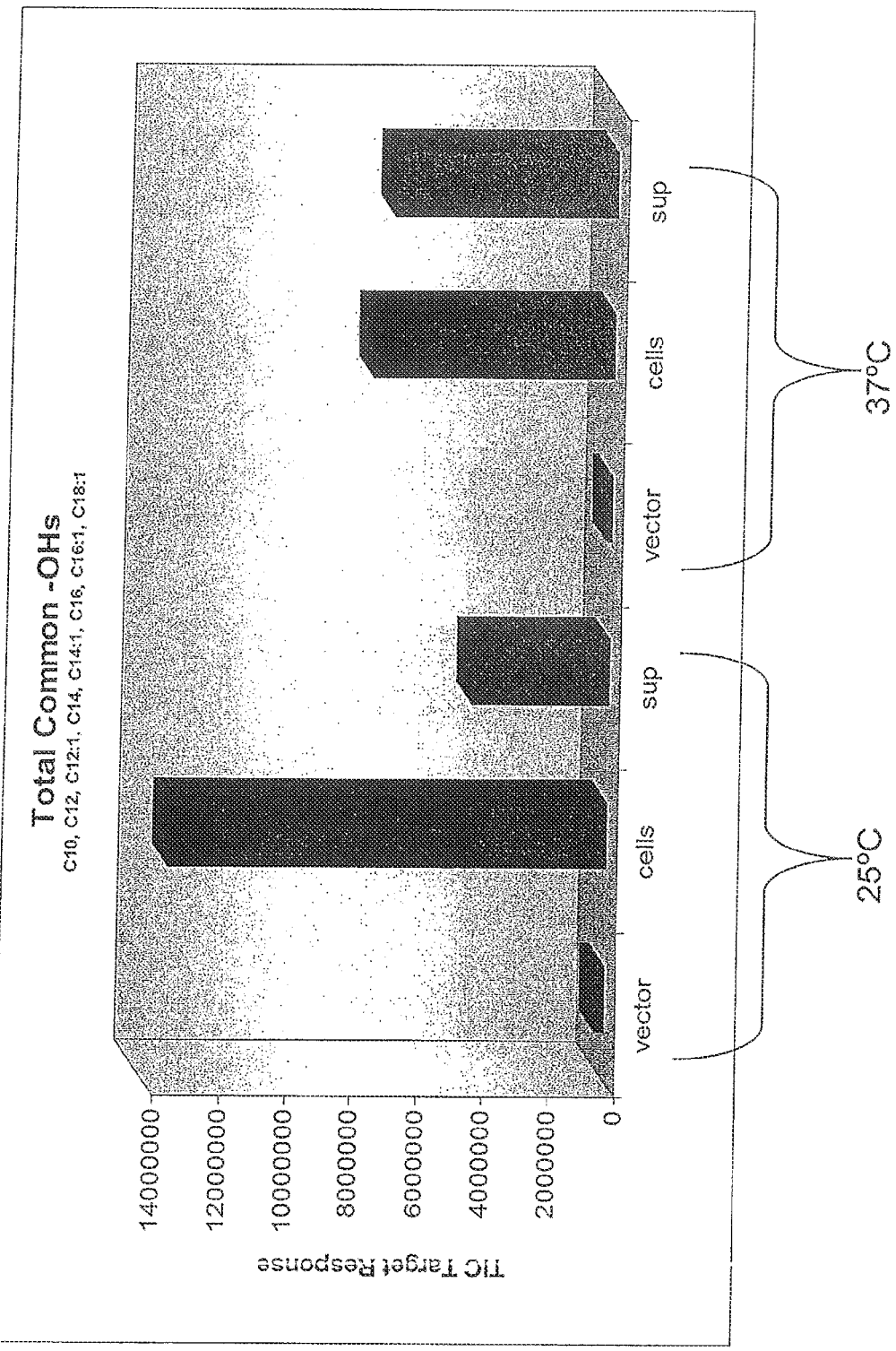
FIG. 8 is a graph depicting the release of fatty alcohols from the production strain. Approximately 50% of the fatty alcohol produced was released from the cells when they were grown at 37° C.
Figure 9A:
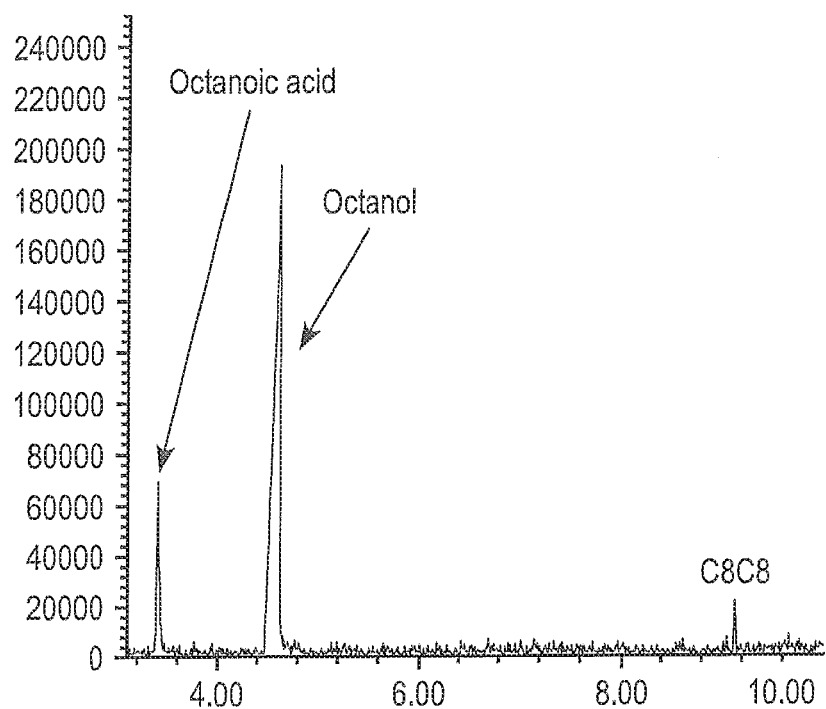
FIG. 9A-D are plots depicting GS-MS spectra of octyl octanoate ($C_8C_8$) produced by a production host expressing alcohol acetyl transferase (AATs, EC 2.3.1.84) and production hosts expressing ester synthase (EC 2.3.1.20, 2.3.1.75).
Figure 9B:
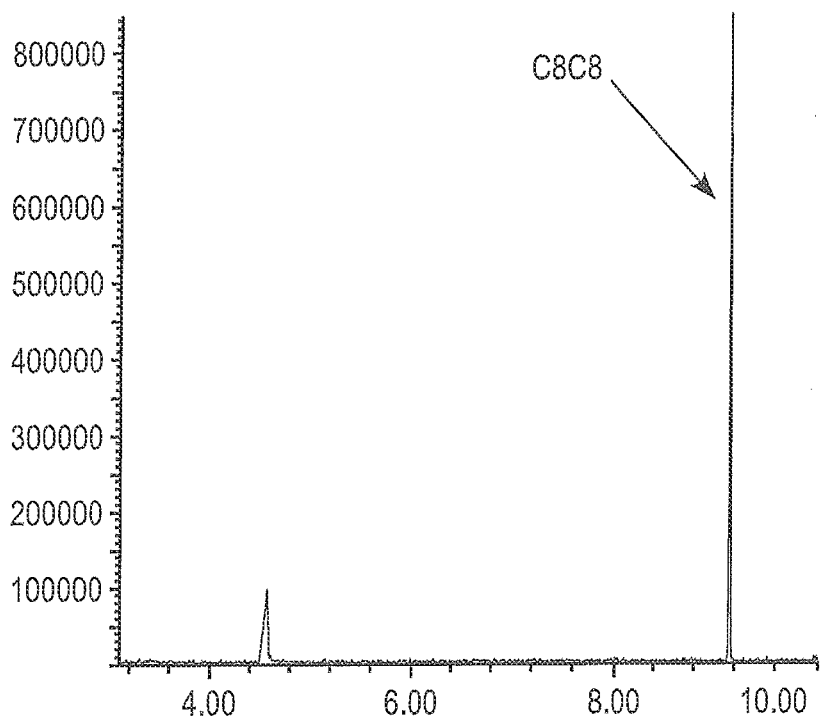
Figure 9C:
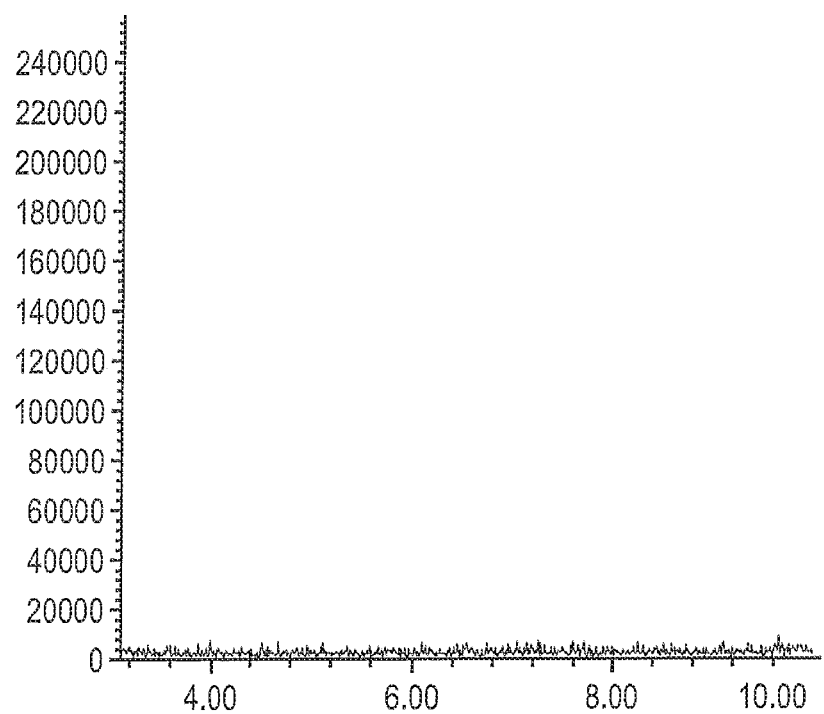
Figure 9D:
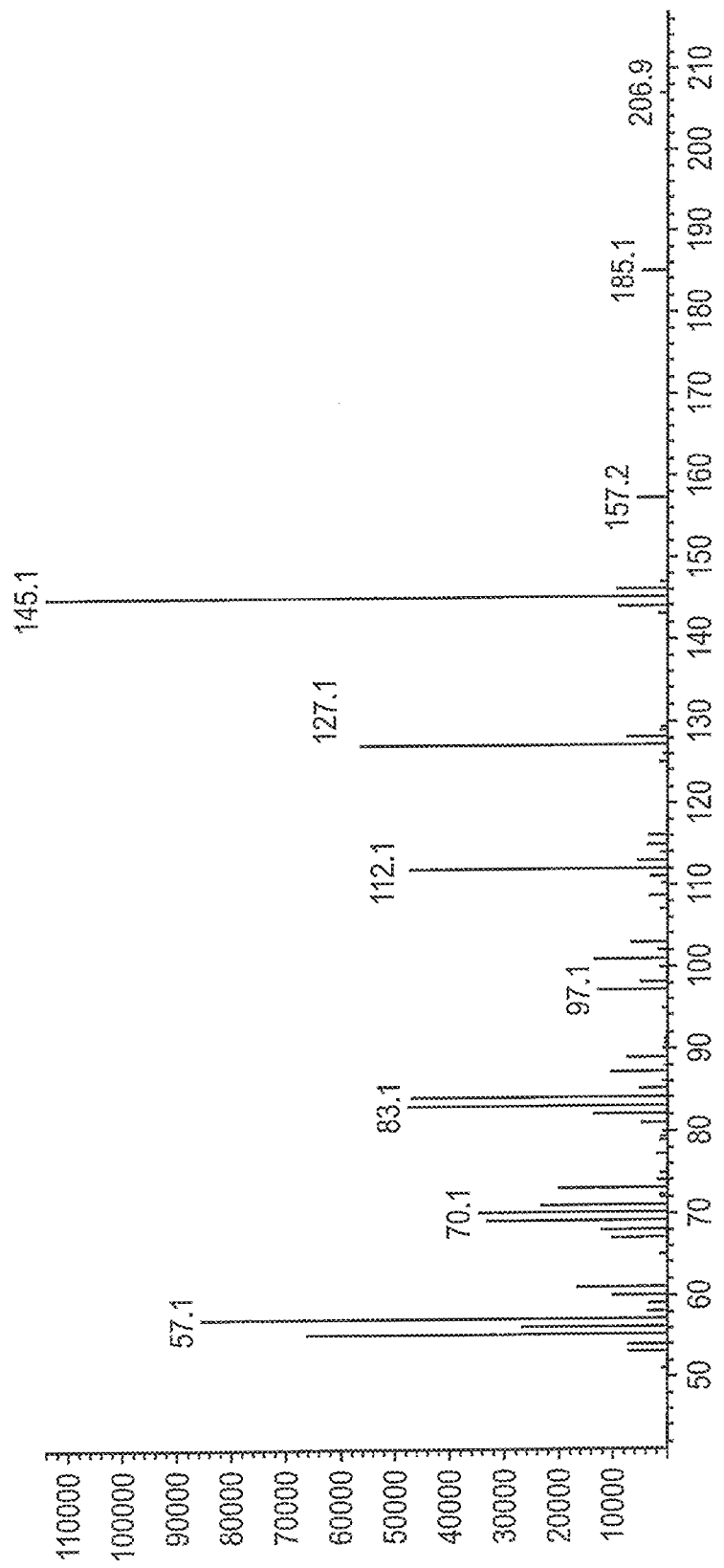

Expression of ChFatB3 and UcFatB 1 also led to the production of significant amounts of the unsaturated fatty alcohols $C_{16:1}$—OH and $C_{14:1}$—OH, respectively. The presence of fatty alcohols was also found in the supernatant of samples generated from the expression of tesA (FIG. 8). At 37° C., approximately equal amounts of fatty alcohols were found in the supernatant and in the cell pellet. Whereas at 25° C., approximately 25% of the fatty alcohols were found in the supernatant.

Example 6

Production of Fatty Alcohol Using a Variety of Acyl-CoA Reductases

This example describes fatty alcohol production using a variety of acyl-CoA reductases. Fatty alcohols can be the final product. Alternatively, the production host cells can additionally express/over-express ester synthases to produce fatty esters.

Each of four genes encoding fatty acyl-CoA reductases (Table 12) from various sources were codon-optimized for *E. coli* expression and synthesized by Codon Devices, Inc. (Cambridge, Mass.). Each of the synthesized genes was cloned as a NdeI-AvrII fragment into pCDFDuet-1-fadD (described in Example 3). Each of the plasmids carrying these acyl-CoA reductase genes with the *E. coli* fadD gene was transformed into *E. coli* strain C41 (DE) strain, which was purchased from Over-expression.com.

The recombinant strains were grown in 3 mL of LB broth (supplemented with 100 mg/L of spectinomycin) at 37° C. overnight. 0.3 mL of the overnight culture was transferred to 30 mL of fresh M9 medium (with 100 mg/L of spectinomycin) and grown at 25° C. When the cultures reached $OD_{600}$ of 0.5, IPTG was added to obtain a final concentration of 1 mM. Each culture was fed 0.1% of one of three fatty acids dissolved in $H_2O$ at pH 7.0. The three fatty acids fed were sodium dodecanoate, sodium myristate, or sodium palmitate.

A culture without the addition of fatty acid was also included as a control. After induction the cultures were grown at the same temperature for an additional 40 hours at 25° C.

The quantification of fatty alcohol yield at the end of fermentation was performed using GC-MS as described above in Example 3 and Example 4. The resulting fatty alcohol produced from the corresponding fatty acid is shown in Table 13. The results showed that three acyl-CoA reductases—Acr1, AcrM and BmFAR—could convert all three fatty acids into corresponding fatty alcohols. The results also showed that hFAR and JjFAR had activity when myristate and palmitate were the substrates. However, there was little to no activity when dodecanoate was the substrate. mFAR1 and mFAR2 only showed low activity with myristate and showed no activity with the other two fatty acids.

TABLE 12

Acyl-CoA reductases

| Acyl-coA reductase | Protein ID accession number | Protein sources |
|---|---|---|
| mFAR1 | AAH07178 | *Mus musculus* |
| mFAR2 | AAH55759 | *Mus musculus* |
| JjFAR | AAD38039 | *Simmondsia chinensis* |
| BmFAR | BAC79425 | *Bombyx mori* |
| Acr1 | AAC45217 | *Acinetobacter baylyi* ADP1 |
| AcrM | BAB85476 | *Acinetobacter* sp. M1 |
| hFAR | AAT42129 | *Homo sapiens* |

TABLE 13

Fatty alcohol production

| | | Peak Area[c] | | |
|---|---|---|---|---|
| E. coli C41 (DE3) | Acyl-CoA reductase genes | Dodecanoate/ dodecanol[b] | Myristate/ tetra-decanol[b] | Palmitate/ hexa-decanol[b] | No fatty acid feeding[a]/ hexa-decanol |
| mFAR1 | 7,400 | 85,700 | 8,465 | 70,900 |
| mFAR2 | 2,900 | 14,100 | 32,500 | 25,800 |
| JjFAR | 5,200 | 8,500 | 53,112 | 33,800 |
| BmFAR | 35,800 | 409,000 | 407,000 | 48,770 |
| acr1 | 202,000 | 495,000 | 1,123,700 | 58,515 |
| acrM | 42,500 | 189,000 | 112,448 | 36,854 |
| hFAR1 | 5,050 | 59,500 | 109,400 | 94,400 |
| vector control | 4,000 | 1,483 | 32,700 | 27,500 |
| media control | 10,700 | 1,500 | 25,700 | 25,000 |

Note:
[a]Only hexadecanol was quantified in this case.
[b]Fatty acid fed/fatty alcohol produced.
[c]The area peak of fatty alcohol produced.

Example 7

Medium Chain Fatty Esters

Alcohol acetyl transferases (AATs, EC 2.3.1.84), which is responsible for acyl acetate production in various plants, can be used to produce medium chain length fatty esters, such as octyl octanoate, decyl octanoate, decyl decanoate, and the like. Fatty esters, synthesized from medium chain alcohol (such as $C_6$ and $C_8$) and medium chain acyl-CoA (or fatty acids, such as $C_6$ and $C_8$) have a relatively low melting point. For example, hexyl hexanoate has a melting point of −55° C. and octyl octanoate has a melting point of −18° C. to −17° C. The low melting points of these compounds make them good candidates for use as biofuels.

Example 8

Medium Chain Fatty Esters

In this example, an SAAT gene encoding a thioesterase was co-expressed in a production host *E. coli* C41(DE3, ΔfadE) with fadD from *E. coli* and acr1 (alcohol reductase from *A. baylyi* ADP1). Octanoic acid was provided in the fermentation broth. This resulted in the production of octyl octanoate. Similarly, when the ester synthase gene from *A. baylyi* ADP1 was expressed in the production host instead of the SAAT gene, octyl octanoate was produced.

A recombinant SAAT gene was synthesized by DNA 2.0 (Menlo Park, Calif. 94025). The synthesized DNA sequence was based on the published gene sequence (accession number AF193789), but modified to eliminate the NcoI site. The synthesized SAAT gene (as a BamHI-HindIII fragment) was cloned in pRSET B (Invitrogen, Carlsbad, Calif.), linearized with BamHI and HindIII. The resulting plasmid, pHZ1.63A was cotransformed into an *E. coli* production host with pAS004.114B, which carries a fadD gene from *E. coli* and acr1 gene from *A. baylyi* ADP1. The transformants were grown in 3 mL of M9 medium with 2% glucose. After IPTG induction and the addition of 0.02% octanoic acid, the culture was continued at 25° C. for 40 hours. 3 mL of acetyl acetate was then added to the whole culture and mixed several times with a mixer. The acetyl acetate phase was analyzed by GC/MS.

Surprisingly, no acyl acetate was observed in the acetyl acetate extract. However, octyl octanoate was observed. However, the control strain without the SAAT gene (C41 (DE3, ΔfadE)/pRSET B+pAS004.114B) did not produce octyl octanoate. Furthermore, the strain (C41(DE3, ΔfadE)/ pHZ1.43 B+pAS004.114B) in which the ester synthase gene from *A. baylyi* ADP1 was carried by pHZ1.43 produced octyl octanoate (see FIG. 9A-D).

The finding that SAAT activity produces octyl octanoate makes it possible to produce medium chain fatty esters, such as octyl octanoate and octyl decanoate, which have low melting point and are good candidates for use as biofuels to replace triglyceride based biodiesel.

Example 9

Production of Fatty Esters in *E. coli* Strain LS9001

Fatty esters were produced by engineering an *E. coli* production host to express a fatty alcohol forming acyl-CoA reductase, thioesterase, and an ester synthase. Thus, the production host produced both the A and the B side of the ester and the structure of both sides was influenced by the expression of the thioesterase gene.

Ester synthase from *A. baylyi* ADP1 (termed WSadp1, accessions AA017391, EC 2.3.175) was amplified with the following primers using genomic DNA sequence from *A. baylyi* ADP1 as the template: (1) WSadp1_NdeI, 5'-TCATAT-GCGCCCATTACATCCG-3' (SEQ ID NO: 49) and (2) WSadp1_Avr, 5'-TCCTAGGAGGGCTAATTTAGCCCTT-TAGTT-3' (SEQ ID NO: 50).

The PCR product was digested with NdeI and AvrII and cloned into pCOALDeut-1 to give pHZ 1.43. The plasmid carrying WSadp1 was then co-transformed into *E. coli* strain LS9001 with both pETDuet-1 'tesA and pCDFDuet-1-fadD-acr1 and transformants were selected in LB plates supplemented with 50 mg/L of kanamycin, 50 mg/L of carbenicillin and 100 mg/L of spectinomycin.

Three transformants were inoculated in 3 mL of LBKCS (LB broth supplement with 50 mg/L kanamycin, 50 mg/L carbenicillin, 100 mg/L spectinomycin, and 10 g/L glucose) and incubated at 37° C. in a shaker (250 rpm). When the cultures reached 0.5 $OD_{600}$, 1.5 mL of each culture was transferred into 250 mL flasks containing 50 mL LBKCS. The flasks were then incubated in a shaker (250 rpm) at 37° C. until the culture reached 0.5-1.0 $OD_{600}$. IPTG was then added to a final concentration of 1 mM. The induced cultures were incubated at 37° C. in a shaker (250 rpm) for another 40-48 hours.

The culture was then placed into 50 mL conical tubes and the cells were spun down at 3500×g for 10 minutes. The cell pellet was then mixed with 5 mL of ethyl acetate. The ethyl acetate extract was analyzed with GC/MS. The yield of fatty esters (including $C_{16}C_{16}$, $C_{14:1}C_{16}$, $C_{18:1}C_{18:1}$, $C_2C_{14}$, $C_2C_{16}$, $C_2C_{16:1}$, $C_{16}C_{16:1}$ and $C_2C_{18:1}$) was about 10 mg/L. When an E. coli strain only carrying empty vectors was cultured in the same way, only 0.2 mg/L of fatty esters was found in the ethyl acetate extract.

Example 10

Production and Release of Fatty-Ethyl Ester from Production Host

The LS9001 strain was transformed with plasmids carrying an ester synthase gene from A. baylyi (plasmid pHZ1.43), a thioesterase gene from Cuphea hookeriana (plasmid pMAL-c2X-TEcu) and a fadD gene from E. coli (plasmid pCDFDuet-1-fadD).

A control E. coli strain C41(DE3, ΔfadE) containing pCO-LADuet-1 (empty vector for the ester synthase gene), pMAL-c2X-TEuc (containing fatB from U. california) and pCDF-Duet-1-fadD (fadD gene from E. coli) failed to produce detectable amounts of fatty ethyl esters. The fatty esters were quantified using commercial palmitic acid ethyl ester as the reference.

Fatty esters were also made using the methods described herein except that methanol or isopropanol was added to the fermentation broth. The expected fatty esters were produced.

Example 11

The Influence of Various Thioesterases on the Composition of Fatty-Ethyl Esters Produced in Recombinant E. coli Strains The thioesterases FatB3 (C. hookeriana), TesA (E. coli), and FatB (U. california) were expressed simultaneously with ester synthase (A. baylyi). A plasmid, pHZ1.61, was constructed by replacing the NotI-AvrII fragment (carrying the acr1 gene) with the NotI-AvrII fragment from pHZ1.43 so that fadD and the ADP1 ester synthase were in one plasmid and both coding sequences were under the control of separate T7 promoter. The construction of pHZ1.61 made it possible to use a two plasmid system instead of the three plasmid system as described in Example 8. pHZ1.61 was then co-transformed into E. coli C41(DE3, ΔfadE) with one of the various plasmids carrying the different thioesterase genes stated above.

The total fatty acid ethyl esters (in both the supernatant and intracellular fatty acid ethyl fluid) produced by these transformants were evaluated using the technique described herein. The yields and the composition of fatty acid ethyl esters are summarized in Table 14.

TABLE 14

Yields (mg/L) and composition of fatty acid ethyl esters by recombinant E. coli C41(DE3, ΔfadE)/pHZ1.61 and plasmids carrying various thioesterase genes.

| Thioesterases | $C_2C_{10}$ | $C_2C_{12:1}$ | $C_2C_{12}$ | $C_2C_{14:1}$ | $C_2C_{14}$ | $C_2C_{16:1}$ | $C_2C_{16}$ | $C_2C_{18:1}$ | Total |
|---|---|---|---|---|---|---|---|---|---|
| 'TesA | 0.0 | 0.0 | 6.5 | 0.0 | 17.5 | 6.9 | 21.6 | 18.1 | 70.5 |
| ChFatB3 | 0.0 | 0.0 | 0.0 | 0.0 | 10.8 | 12.5 | 11.7 | 13.8 | 48.8 |
| ucFatB | 6.4 | 8.5 | 25.3 | 14.7 | 0.0 | 4.5 | 3.7 | 6.7 | 69.8 |
| pMAL | 0.0 | 0.0 | 0.0 | 0.0 | 5.6 | 0.0 | 12.8 | 7.6 | 26.0 |

Note:
'TesA, pETDuet-1-'tesA; chFatB3, pMAL-c2X-TEcu; ucFatB, pMAL-c2X-TEuc; pMAL, pMAL-c2X, the empty vector for thioesterase genes used in the study.

This recombinant strain was grown at 25° C. in 3 mL M9 medium with 50 mg/L kanamycin, 100 mg/L carbenicillin, and 100 mg/L of spectinomycin. After IPTG induction, the media was adjusted to a final concentration of 1% ethanol and 2% glucose.

The culture was allowed to grow for 40 hours after IPTG induction. The cells were separated from the spent medium by centrifugation at 3500×g for 10 minutes). The cell pellet was re-suspended with 3 mL of M9 medium. The cell suspension and the spent medium were then extracted with 1 volume of ethyl acetate. The resulting ethyl acetate phases from the cells suspension and the supernatant were subjected to GC-MS analysis.

Figure 10:
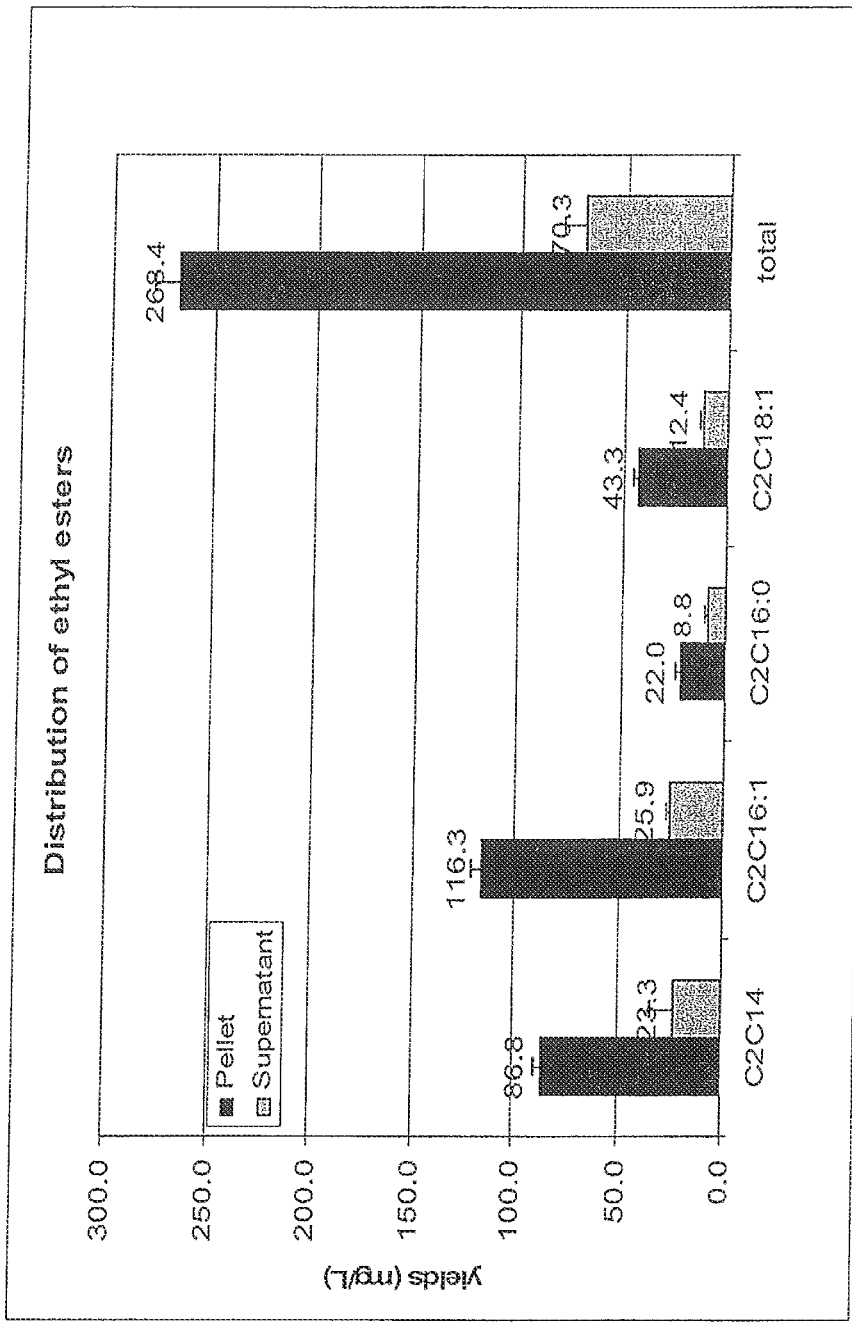
FIG. 10 is a graph depicting the distribution of ethyl esters made when the ester synthase from *A. baylyi* ADP1 (WSadp1) was co-expressed with thioesterase gene from *Cuphea hookeriana* in a production host.

The $C_{16}$ ethyl ester was the most prominent ester species (as expected for this thioesterase, see Table 1), and 20% of the fatty ester produced was released from the cell (see FIG. 10).

Example 12

Use of Various Ester Synthases to Produce Biofuel

Four genes encoding ester synthases were synthesized based on corresponding DNA sequences reported on NCBI GenBank with minor modifications. These modifications include the removal of internal NcoI, NdeI, HindIII and AvrII sites present without introducing changes to the corresponding amino acid sequence. The four genes of interest were synthesized with an NdeI site on the 5' end and an AvrII at the 3' end. The sequences were then cloned into the NdeI and AvrII site of pCOLADuet-1 (Novagene) to produce pHZ1.97-376, pHZ1.97-377, pHZ1.97-atfA1 and pHZ1.97-atfA2. The plasmids carrying each of the four genes of interest along with the respective GenBank accession numbers and the GenPeptide accessions numbers are listed in Table 15 below.

TABLE 15

Ester synthases

| Plasmids | LS9 ID | DNA sequence original sources | GenBank # | GenPeptide accession # |
|---|---|---|---|---|
| pHZ1.97-376 | FES376(376) | Marinobacter aquaeolei VT8 | CP000514.1 | ABM17275 |
| pHZ1.97-377 | FES377(377) | Marinobacter aquaeolei VT8 | CP000514.1 | ABM20141 |
| pHZ1.97-atfA1 | FESA1 (AtfA1) | Alcanivorax borkumensis SK2 | NC_008260.1 | YP_694462 |
| pHZ1.97-atfA2 | FESA2 (AtfA2) | Alcanivorax borkumensis SK2 | NC_008260.1 | YP_693524 |

Each of the four plasmids was transformed into E. coli C41 (DE3, ΔfadEΔfabR)/pETDuet-1-tesA+pCDFDuet-1-fadD. Three transformants from each transformation were picked for fermentation to test their ability to synthesize fatty acid ethyl esters. The fermentation was performed as described in Example 9, but with two different temperatures, either at 25° C. or 37° C. Strain C41 (DE3, ΔfadEΔfabR)/pETDuet-1-tesA+pCDPDuet-1-fadD+pHZ1.43 (expressing ADP1 ester synthase) was used as a positive control and C41 (DE3, ΔfadEΔfabR)/pETDuet-1-tesA+pCDFDuet-1-fadD as a negative control.

Figure 11:
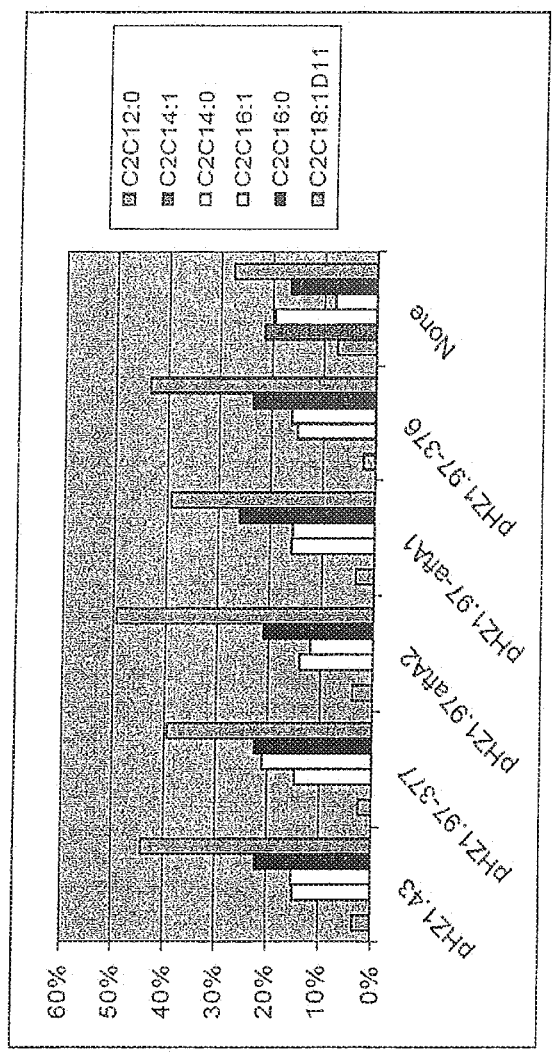
FIG. 11 is a graph depicting the production of ethyl esters by various ester synthases at 25° C. The ethyl esters were produced by recombinant *E. coli* strains carrying various ester synthase genes. The recombinant strains were 1. C41 (DE3, ΔfadEΔfabR)/pETDuet-1-tesA+pCDFDuet-1-fadD with 1 pHZ1.43; 2. pHZ1.97_377; 3. pHZ1.97_atfA2; 4. pHZ1.97_376; 5. pHZ1.97_atfA1; 6. No plasmids (control).
Figure 12:
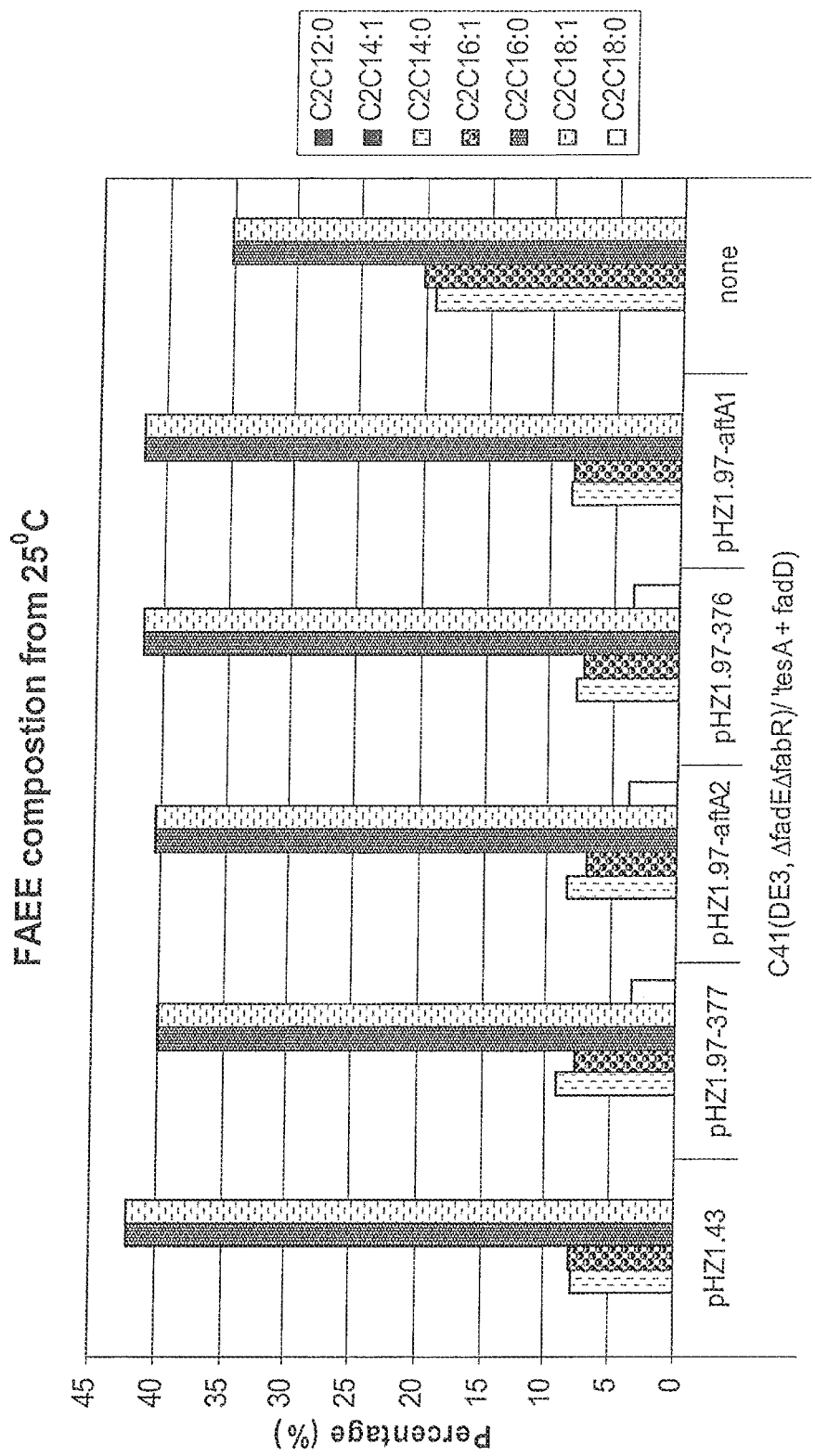
FIG. 12 is a graph depicting the acyl composition of fatty acid ethyl esters (FAEE) produced from various *E. coli* strains. The recombinant strains are 1. C41 (DE3, ΔfadEΔfabR)/pETDuet-1-tesA+pCDFDuet-1-fadD with 1 pHZ1.43; 2. pHZ1.97_377; 3. pHZ1.97_atfA2; 4. pHZ1.97_376; 5. pHZ1.97_atfA1; 6. No plasmids (control).

The expression of each of the four ester synthase genes in the E. coli strain with attenuated fadE and fabR activity and over-expressing 'tesA and fadD enabled each strain to produce around 250 mg/L of FAEE at 25° C. This is the same amount produced by the positive control that expressed ADP1. In contrast, the negative control strain produced less than 50 mg/L FAEE in the same condition (FIG. 11) at 25° C. The fatty acyl composition of FAEE produced from these four ester synthases is similar to that from ADP1 ester synthases (FIG. 12).

Figure 13:
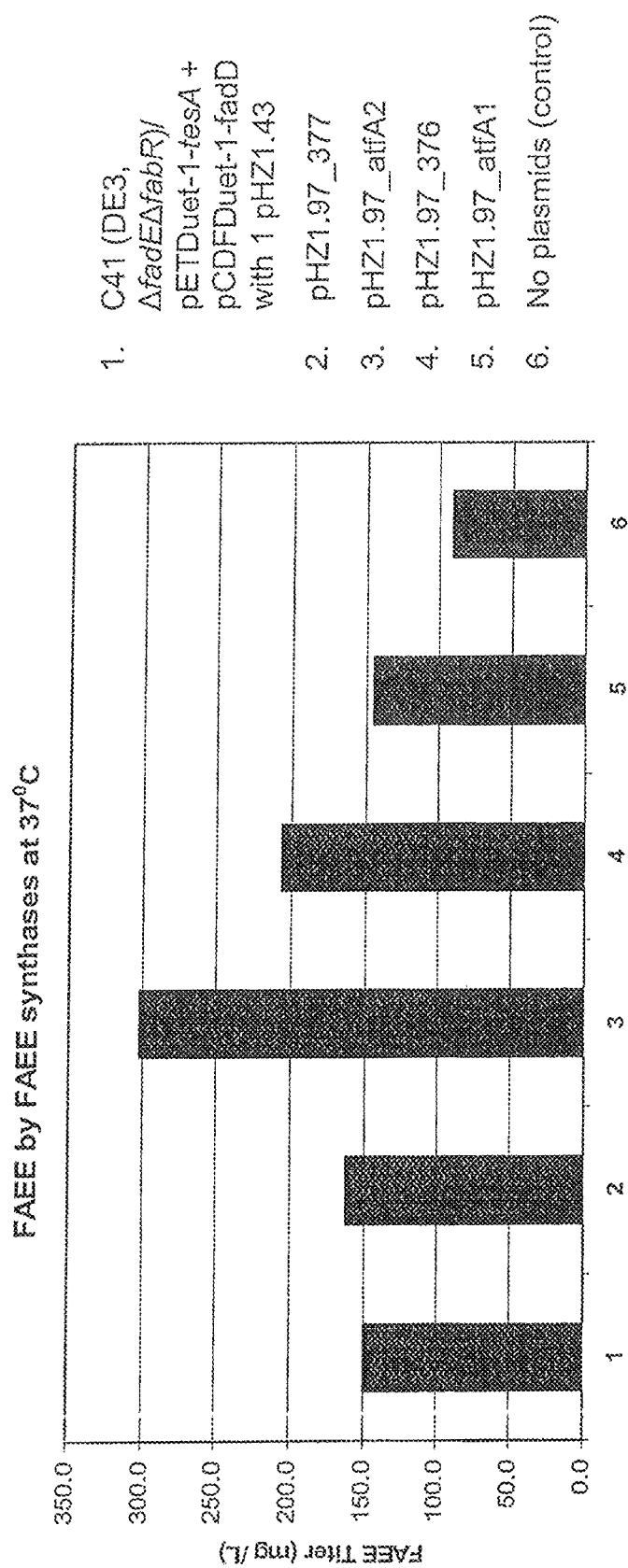
FIG. 13 is a graph depicting the production of ethyl esters by various ester synthases at 37° C. The ethyl esters were produced by recombinant *E. coli* strains carrying various ester synthase genes. The recombinant strains were 1. C41 (DE3, ΔfadEΔfabR)/pETDuet-1-tesA+pCDFDuet-1-fadD with 1 pHZ1.43; 2. pHZ1.97_377; 3. pHZ1.97_atfA2; 4. pHZ1.97_376; 5. pHZ1.97_atfA1; 6. No plasmids (control).
Figure 14:
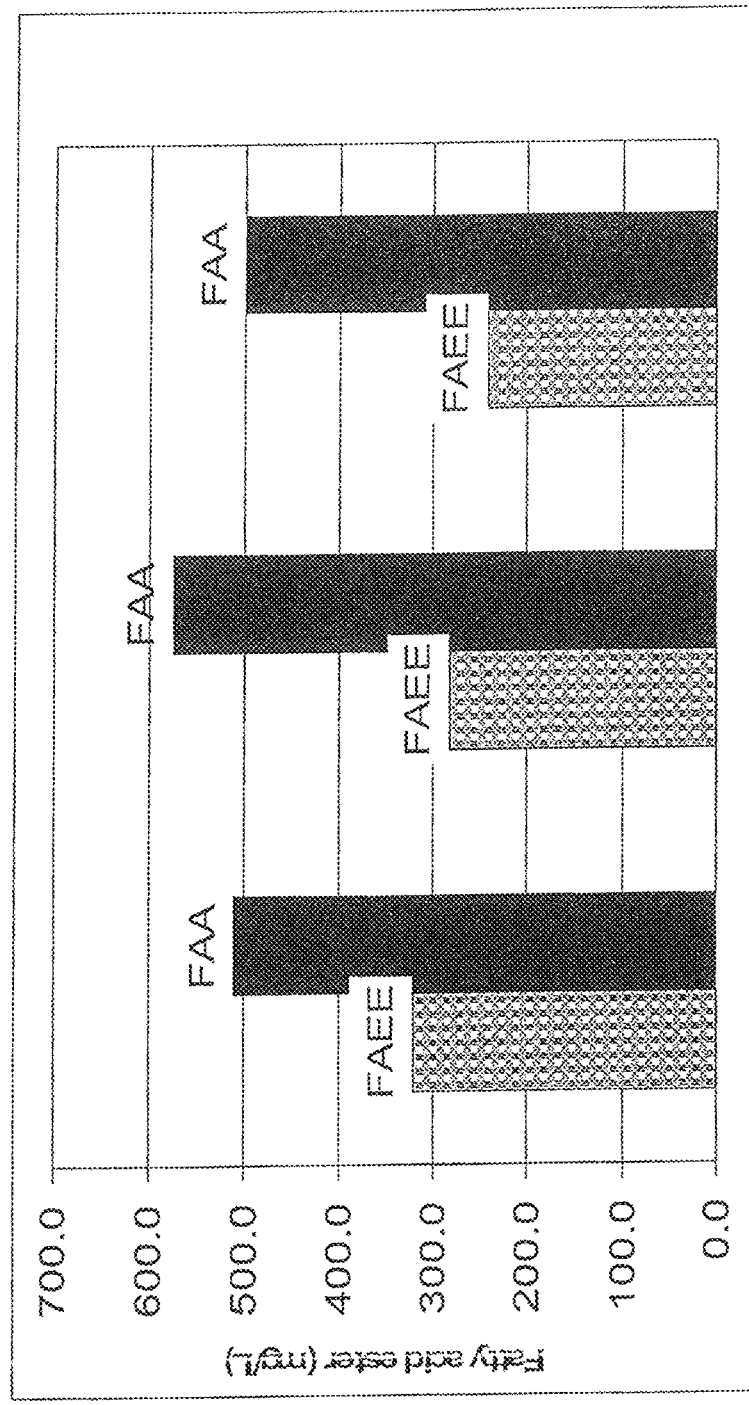
FIG. 14 is a graph depicting concentrations of free fatty acids (FFA) and fatty acid ethyl esters (FAEE) produced from three individual colonies from the transformants, C41 (DE3, ΔfadEΔfabR)/pETDuet-1-tesA+pCDFDuet-1-fadD+ pHZ1.97_atfA2 t. The FFA was converted to fatty acid ethyl ester (FAEE) and quantified by GC/MS.

Results from fermentations performed at 37° C. indicated that strains carrying pHZ1.97_aftA2 and strains carrying pHZ1.97_376 produced more FAEE than the positive control carrying pHZ1.43 (FIG. 13). The strains carrying pHZ1.97_aftA2 and the strains carrying pHZ1.97_376 also produced large amount of free fatty acid. Whereas the strain carrying pHZ.143 did not accumulate free fatty acid (FIG. 14). The results showed that these four ester synthases are capable of accepting ethanol and a broad range of acyl-CoA as substrates.

Example 13

Use of Eukaryotic Ester Synthase to Produce Biofuel

This example describes the cloning and expression of an ester synthase from Saccharomyces cerevisiae. Plasmids were generated using standard molecular biology techniques.

TABLE 16

Plasmids with eeb1

| Given Name | Vector Backbone | Construction |
|---|---|---|
| pGL10.59 | pCOLADuet-1 (Novagen) | eeb1* gene inserted between BamHI and HindIII sites (KanR) |
| pGL10.104 | pMAL c2x (NEB) | eeb1* gene inserted between BamHI and HindIII sites (AmpR) |
| pMAL-c2X-TEuc | pMAL c2x (NEB) | See Table 8 above |
| pCDFDuet-1-acr1 | pCDFDuet-1 (Novagen) | See Table 8 above |

*The Saccharomyces cerevisiae gene eeb1 (GenBank accession number YPL095C) was PCR-amplifed from S. cerevisiae genomic DNA sequence using primers introducing 5' BamHI and 3' HindIII sites.

An E. coli C41 (DE3 ΔfadE) production host was used to express the various plasmids. The E. coli cells were grown on M9 minimal media (6 g/L $Na_2HPO_4$, 3 g/L $KH_2PO_4$, 0.5 g/L NaCl, 1 g/L $NH_4Cl$, 1 mg/L thiamine (vit. B1), 1 mM $MgSO_4$, 0.1 mM $CaCl_2$, 0.4% (w/v) or 2% (w/v) glucose, as indicated). All fatty acid stock solutions were prepared by dissolving the fatty acid sodium or potassium salt in distilled deionized water at pH 7.0. Octanoic acid stock was purchased from Sigma, St. Louis, Mo.

Fermentations were performed using the C41 (DE3 ΔfadE) strain containing plasmids pCDFDuet-1-acr1, pMAL-c2X-TEuc (ucFatB), and pGL10.59 (eeb1). The control strain was C41 (DE3 ΔfadE) strain carrying pCDFDuet-1-acr1, pMAL-c2X-TEuc, and the empty pCOLADuet-1 vector. Three colonies from each transformation were used to inoculate M9+0.4% glucose starter cultures supplemented with carbenicillin (100 μg/mL), spectinomycin (100 μg/mL), and kanamycin (50 μg/mL). The cultures were allowed to grow at 37° C. overnight. Production cultures were established by making a 1:100 dilution of starter culture to inoculate 3 mL M9 media+0.4% glucose. The production cultures were allowed to grow at 37° C. until $OD_{600}$=0.6 before being induced with 1 mM IPTG, fed 1% ethanol, and cultured for an additional 40 hours at 25° C. Whole cell cultures were extracted with an equal volume of ethyl acetate by vortexing vigorously for 30 seconds. The organic phase was taken and run on the GC/MS using the method alkane_1_splitless_ctc.m for FAEE detection, which is described above in Example 4, part 2, "Quantification of FA and FAEE in sample #23-30."

No FAEE peaks could be detected in any of the samples. In order to determine whether Eeb1 was being properly expressed, IPTG-induced and uninduced cultures were analyzed by SDS-PAGE. No bands corresponding to the size of Eeb1 (~52 kDa) could be detected. This suggests that for this particular plasmid system, Eeb1 is not well-expressed.

Additional expression experiments were preformed using a different expression vector. The gene was cloned into the vector pMALc2x, which expresses the target protein as a maltose binding protein (MBP) fusion. SDS-PAGE analysis of whole-cell lysates revealed that cultures induced with 1 mM IPTG yielded an appropriately-sized band corresponding to the Eeb1-MBP fusion (~92 kDa). The band was not present in uninduced cells.

Eeb1 enzymatic activity was assessed using the C41 (DE3 ΔfadE) E. coli strain carrying plasmids pCDFDuet-1-acr1 and pGL10.104 (eeb1). A C41 (DE3 ΔfadE) with pCDFDuet-1-acr1 and pMALc2x served as the control strain. Three colonies were picked from each transformation and used to inoculate M9+0.4% glucose overnight starter cultures supplemented with carbenicillin (100 μg/mL) and spectinomycin (100 μg/mL). A 1:100 dilution of the starter cultures was used to inoculate 10 mL M9+0.4% glucose production cultures. The production cultures were allowed to grow at 37°

C. until $OD_{600}$=0.4-0.5 before inducing with 1 mM IPTG, feeding 1% ethanol, and feeding octanoic acid (0.01% or 0.02% final volume) or decanoic acid (0.02% final volume). Fermentations were allowed to continue for 24 hours at 25° C. Extractions were carried out by adding 1/10 volume of 12 M HCl and an equal volume of ethyl acetate to the culture and vortexing for 30 seconds. Samples were analyzed by GC/MS as described above.

GC/MS data revealed a peak corresponding to the octanoic acid ethyl ester could be detected for cells expressing Eeb1 and fed octanoic acid and ethanol. The vector control strain also showed a $C_2C_8$ peak, albeit a smaller peak than that of the Eeb1 expressing cells.

Cells fed 0.02% decanoic acid did not grow well, therefore the following studies were conducted using 0.01% or 0.005% decanoic acid. To test the ability of Eeb1 to utilize alcohols other than ethanol in the synthesis of fatty acid esters, fermentations were carried out using the same strain: C41 (DE3 ΔfadE) with pCDFDuet-1-acr1 and pGL10.104. Cells were cultured as previously described. At induction, the cells were fed 0.02% octanoic acid along with either 1% methanol, ethanol, propanol, or isopropanol. Cells were also fed 0.01% or 0.005% decanoic acid and 1% ethanol. Fermentations were continued post-induction for 24 hours at 25° C. For GC/MS, cultures were spun down to separate the pellet and the supernatant. The pellet was resuspended in an equal volume of fresh M9+0.4% glucose media. Both the resuspended pellet and supernatant samples were extracted as described above and analyzed by GC/MS.

All of the supernatant samples contained large amounts of fatty acid and no fatty acid esters were detected. Similarly, the vector control pellet samples contained no peaks. However, cells fed C10 fatty acid showed peaks identified as decanoic acid.

The pellet samples derived from the cells expressing Eeb1 and fed $C_8$ fatty acid and propanol or ethanol showed small peaks corresponding to the propyl or ethyl esters. No peaks were detected for the cells fed methanol or isopropanol. Cultures fed 0.01% or 0.005% C10 fatty acid and ethanol also produced the $C_2C_{10}$ FAEE, which was present in the pellet samples.

The results indicated that Eeb1 was capable of synthesizing FAEEs using octanoic or decanoic acids and was also able to use methanol to generate the octanoic methyl ester. However, these compounds are highly volatile and GC/MS data may not accurately reflect the true titers. To more accurately measure product formation a hexadecane overlay was used to facilitate the capture of these more volatile FAEE.

Eeb1 activity using various fatty acid substrates was assessed using strain C41 (DE3 ΔfadE) with pCDFDuet-1-acr1 and pGL10.104 while feeding different chain-length fatty acids. Cells were cultured as before, but were induced at $OD_{600}$=0.8-0.9 so as to promote better cell growth post-induction. At this point, cells were fed 1% ethanol and 0.02% C8 fatty acid or 0.01% of the following fatty acids: C10, C12, C14, and C16. Cultures fed $C_8$ or $C_{10}$ fatty acids were overlaid with 20% total volume hexadecane. Fermentations were carried out for an additional 24 hours at 25° C. For product analysis, whole cultures (without separating the supernatant from the pellet) were extracted as before, with 1/10 volume of HCl and a volume of ethyl acetate equal to the culture. Hexadecane samples were injected directly into the GC/MS using the program hex_1_splitless_ctc.m, which is described above in Example 4, part 2, "Quantification of FA and FAEE in sample #23-30."

None of the vector controls showed any FAEE peaks. For the $C_8$- and $C_{10}$-fed cells, large $C_2C_8$ and $C_2C_{10}$ peaks could be detected in the hexadecane samples, but not in the ethyl acetate samples. This demonstrated that hexadecane was able to successfully trap the volatile FAEEs. For the rest of the ethyl acetate samples, small peaks could be detected for $C_2C_{12}$ and $C_2C_{14}$ FAEEs, but none for $C_2C_{16}$. Thus, Eeb1 generated ethyl esters using fatty acids with chain lengths from $C_8$ to $C_{14}$. Eeb1 favored $C_8$ and $C_{10}$ over the longer-chain fatty acids.

Example 14

Figure 15:
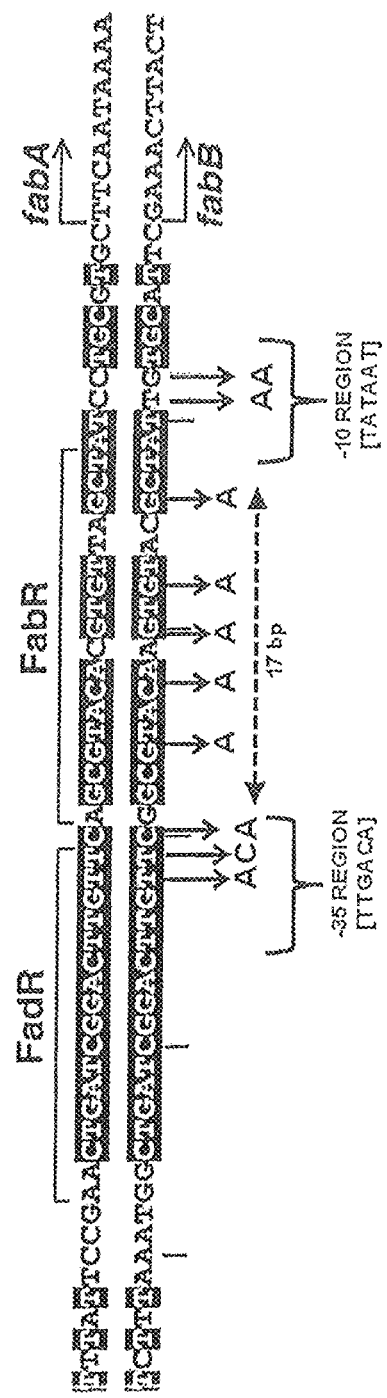
FIG. 15 is a diagram depicting the control region for FabA and FabB. The FadR and FabR consensus binding sites are shown in bold. Vertical arrows indicate the positions where mutations can be made to alter fabA expression. The proposed base for each position is also indicated by the brackets. The two regions that constitute the −35 and −10 regions of the typical *E. coli* promoter are indicated by the brackets. The proposed mutations that make the promoter closer to the consensus promoter sequence are also shown.

Genomic Integration of Recombinant Sequences to Make a Host Strain that Over-Expresses *E. coli* fabA and/or fabB Genes It is known that the product of the fabR gene acts as a repressor of the expression of the fabA and fabB genes. It is also known that FadR works as an activator of the same genes. The FabR and predicted consensus binding sequences were previously published by Zhang et al., *J. Biol. Chem.* 277: 15558-15565, 2002. The consensus binding sequences and their location as they relate to the fabA and fabB genes from *E. coli* is shown in FIG. 15.

A fabR knock-out strain of *E. coli* was created. Primers TrmA_R-_NotI and FabR_FOP were used to amplify approximately 1000 bp upstream of fabR, and primers SthA_F_Bam and FabR_ROP were used to amplify approximately 1000 bp downstream of fabR (see Table D). Overlap PCR was applied to create a construct for in-frame deletion of the complete fabR gene. The fabR deletion construct was cloned into the temperature-sensitive plasmid pKOV3, which contained SacB for counterselection, and a chromosomal deletion of fabR was made according to the method of Church and coworkers (Link et al., *J. Bact.* 179:6228-6237, 1997).

TABLE 17 fabR knock-out primers

| Primer Name | Primer Sequence (5' to 3') |
|---|---|
| TrmA_R-_Not | ATAGTTTAGCGGCCGCAAATCGAGCTGGATCAGGATTA (SEQ ID NO: 51) |
| FabR_FOP | AGGATTCAGACATCGTGATGTAATGAAACAAGCAAAT CAAGATAGA (SEQ ID NO: 52) |
| SthA_F_Bam | CGCGGATCCGAATCACTACGCCACTGTTCC (SEQ ID NO: 53) |
| FabR_ROP | TTGATTTGCTTGTTTCATTACATCACGATGTCTGAAT CCTTG (SEQ ID NO: 54) |

Example 15

Production Host Construction

Table 18 identifies the homologues of many of the genes described herein which are known to be expressed in microorganisms that produce biodiesels, fatty alcohols, and hydrocarbons. To increase fatty acid production and, therefore, hydrocarbon production in production hosts such as those identified in Table 18, heterologous genes can be expressed, such as those from *E. coli*. One of ordinary skill in the art will also appreciate that genes that are endogenous to the microorganisms provided in Table 18 can also be expressed, overexpressed, or attenuated using the methods described herein.

Moreover, genes that are described in Table 18 can be expressed, over-expressed, or attenuated in production hosts that endogenously produce hydrocarbons to allow for the production of specific hydrocarbons with defined carbon chain length, saturation points, and branch points.

TABLE 18

Hydrocarbon production hosts

| Organism | Gene Name | Accession No./Seq ID/Loci | EC No. |
|---|---|---|---|
| *Desulfovibrio desulfuricans* G20 | accA | YP_388034 | 6.4.1.2 |
| *Desulfovibrio desulfuricans* G22 | accC | YP_388573/YP_388033 | 6.3.4.14, 6.4.1.2 |
| *Desulfovibrio desulfuricans* G23 | accD | YP_388034 | 6.4.1.2 |
| *Desulfovibrio desulfuricans* G28 | fabH | YP_388920 | 2.3.1.180 |
| *Desulfovibrio desulfuricans* G29 | fabD | YP_388786 | 2.3.1.39 |
| *Desulfovibrio desulfuricans* G30 | fabG | YP_388921 | 1.1.1.100 |
| *Desulfovibrio desulfuricans* G31 | acpP | YP_388922/YP_389150 | 3.1.26.3, 1.6.5.3, 1.6.99.3 |
| *Desulfovibrio desulfuricans* G32 | fabF | YP_388923 | 2.3.1.179 |
| *Desulfovibrio desulfuricans* G33 | gpsA | YP_389667 | 1.1.1.94 |
| *Desulfovibrio desulfuricans* G34 | ldhA | YP_388173/YP_390177 | 1.1.1.27, 1.1.1.28 |
| *Erwinia (micrococcus) amylovora* | accA | 942060-943016 | 6.4.1.2 |
| *Erwinia (micrococcus) amylovora* | accB | 3440869-3441336 | 6.4.1.2 |
| *Erwinia (micrococcus) amylovora* | accC | 3441351-3442697 | 6.3.4.14, 6.4.1.2 |
| *Erwinia (micrococcus) amylovora* | accD | 2517571-2516696 | 6.4.1.2 |
| *Erwinia (micrococcus) amylovora* | fadE | 1003232-1000791 | 1.3.99.- |
| *Erwinia (micrococcus) amylovora* | plsB(D311E) | 333843-331423 | 2.3.1.15 |
| *Erwinia (micrococcus) amylovora* | aceE | 840558-843218 | 1.2.4.1 |
| *Erwinia (micrococcus) amylovora* | aceF | 843248-844828 | 2.3.1.12 |
| *Erwinia (micrococcus) amylovora* | fabH | 1579839-1580789 | 2.3.1.180 |
| *Erwinia (micrococcus) amylovora* | fabD | 1580826-1581749 | 2.3.1.39 |
| *Erwinia (micrococcus) amylovora* | fabG | CAA74944 | 1.1.1.100 |
| *Erwinia (micrococcus) amylovora* | acpP | 1582658-1582891 | 3.1.26.3, 1.6.5.3, 1.6.99.3 |
| *Erwinia (micrococcus) amylovora* | fabF | 1582983-1584221 | 2.3.1.179 |
| *Erwinia (micrococcus) amylovora* | gpsA | 124800-125810 | 1.1.1.94 |
| *Erwinia (micrococcus) amylovora* | ldhA | 1956806-1957789 | 1.1.1.27, 1.1.1.28 |

TABLE 18-continued

Hydrocarbon production hosts

| Organism | Gene Name | Accession No./Seq ID/Loci | EC No. |
|---|---|---|---|
| *Kineococcus radiotolerans* SRS30216 | accA | ZP_00618306 | 6.4.1.2 |
| *Kineococcus radiotolerans* SRS30216 | accB | ZP_00618387 | 6.4.1.2 |
| *Kineococcus radiotolerans* SRS30216 | accC | ZP_00618040/ZP_00618387 | 6.3.4.14, 6.4.1.2 |
| *Kineococcus radiotolerans* SRS30216 | accD | ZP_00618306 | 6.4.1.2 |
| *Kineococcus radiotolerans* SRS30216 | fadE | ZP_00617773 | 1.3.99.- |
| *Kineococcus radiotolerans* SRS30216 | plsB(D311E) | ZP_00617279 | 2.3.1.15 |
| *Kineococcus radiotolerans* SRS30216 | aceE | ZP_00617600 | 1.2.4.1 |
| *Kineococcus radiotolerans* SRS30216 | aceF | ZP_00619307 | 2.3.1.12 |
| *Kineococcus radiotolerans* SRS30216 | fabH | ZP_00618003 | 2.3.1.180 |
| *Kineococcus radiotolerans* SRS30216 | fabD | ZP_00617602 | 2.3.1.39 |
| *Kineococcus radiotolerans* SRS30216 | fabG | ZP_00615651 | 1.1.1.100 |
| *Kineococcus radiotolerans* SRS30216 | acpP | ZP_00617604 | 3.1.26.3, 1.6.5.3, 1.6.99.3 |
| *Kineococcus radiotolerans* SRS30216 | fabF | ZP_00617605 | 2.3.1.179 |
| *Kineococcus radiotolerans* SRS30216 | gpsA | ZP_00618825 | 1.1.1.94 |
| *Kineococcus radiotolerans* SRS30216 | ldhA | ZP_00618879 | 1.1.1.28 |
| *Rhodospirillum rubrum* | accA | YP_425310 | 6.4.1.2 |
| *Rhodospirillum rubrum* | accB | YP_427521 | 6.4.1.2 |
| *Rhodospirillum rubrum* | accC | YP_427522/YP_425144/YP_427028/YP_426209/YP_427404 | 6.3.4.14, 6.4.1.2 |
| *Rhodospirillum rubrum* | accD | YP_428511 | 6.4.1.2 |
| *Rhodospirillum rubrum* | fadE | YP_427035 | 1.3.99.— |
| *Rhodospirillum rubrum* | aceE | YP_427492 | 1.2.4.1 |
| *Rhodospirillum rubrum* | aceF | YP_426966 | 2.3.1.12 |
| *Rhodospirillum rubrum* | fabH | YP_426754 | 2.3.1.180 |
| *Rhodospirillum rubrum* | fabD | YP_425507 | 2.3.1.39 |
| *Rhodospirillum rubrum* | fabG | YP_425508/YP_425365 | 1.1.1.100 |
| *Rhodospirillum rubrum* | acpP | YP_425509 | 3.1.26.3, 1.6.5.3, 1.6.99.3 |
| *Rhodospirillum rubrum* | fabF | YP_425510/YP_425510/YP_425285 | 2.3.1.179 |

TABLE 18-continued

Hydrocarbon production hosts

| Organism | Gene Name | Accession No./Seq ID/Loci | EC No. |
|---|---|---|---|
| Rhodospirillum rubrum | gpsA | YP_428652 | 1.1.1.94 |
| Rhodospirillum rubrum | ldhA | YP_426902/YP_428871 | 1.1.1.27 1.1.1.28 |
| Vibrio furnissii | accA | 1, 16 | 6.4.1.2 |
| Vibrio furnissii | accB | 2, 17 | 6.4.1.2 |
| Vibrio furnissii | accC | 3, 18 | 6.3.4.14, 6.4.1.2 |
| Vibrio furnissii | accD | 4, 19 | 6.4.1.2 |
| Vibrio furnissii | fadE | 5, 20 | 1.3.99.- |
| Vibrio furnissii | plsB(D311E) | 6, 21 | 2.3.1.15 |
| Vibrio furnissii | aceE | 7, 22 | 1.2.4.1 |
| Vibrio furnissii | aceF | 8, 23 | 2.3.1.12 |
| Vibrio furnissii | fabH | 9, 24 | 2.3.1.180 |
| Vibrio furnissii | fabD | 10, 25 | 2.3.1.39 |
| Vibrio furnissii | fabG | 11, 26 | 1.1.1.100 |
| Vibrio furnissii | acpP | 12, 27 | 3.1.26.3, 1.6.5.3, 1.6.99.3 |
| Vibrio furnissii | fabF | 13, 28 | 2.3.1.179 |
| Vibrio furnissii | gpsA | 14, 29 | 1.1.1.94 |
| Vibrio furnissii | ldhA | 15, 30 | 1.1.1.27, 1.1.1.28 |
| Stenotrophomonas maltophilia R551-3 | accA | ZP_01643799 | 6.4.1.2 |
| Stenotrophomonas maltophilia R551-3 | accB | ZP_01644036 | 6.4.1.2 |
| Stenotrophomonas maltophilia R551-3 | accC | ZP_01644037 | 6.3.4.14, 6.4.1.2 |
| Stenotrophomonas maltophilia R551-3 | accD | ZP_01644801 | 6.4.1.2 |
| Stenotrophomonas maltophilia R551-3 | fadE | ZP_01645823 | 1.3.99.- |
| Stenotrophomonas maltophilia R551-3 | plsB(D311E) | ZP_01644152 | 2.3.1.15 |
| Stenotrophomonas maltophilia R551-3 | aceE | ZP_01644724 | 1.2.4.1 |
| Stenotrophomonas maltophilia R551-3 | aceF | ZP_01645795 | 2.3.1.12 |
| Stenotrophomonas maltophilia R551-3 | fabH | ZP_01643247 | 2.3.1.180 |
| Stenotrophomonas maltophilia R551-3 | fabD | ZP_01643535 | 2.3.1.39 |
| Stenotrophomonas maltophilia R551-3 | fabG | ZP_01643062 | 1.1.1.100 |
| Stenotrophomonas maltophilia R551-3 | acpP | ZP_01643063 | 3.1.26.3 1.6.5.3, 1.6.99.3 |
| Stenotrophomonas maltophilia R551-3 | fabF | ZP_01643064 | 2.3.1.179 |
| Stenotrophomonas maltophilia R551-3 | gpsA | ZP_01643216 | 1.1.1.94 |
| Stenotrophomonas maltophilia R551-3 | ldhA | ZP_01645395 | 1.1.1.28 |
| Synechocystis sp. PCC6803 | accA | NP_442942 | 6.4.1.2 |
| Synechocystis sp. PCC6803 | accB | NP_442182 | 6.4.1.2 |
| Synechocystis sp. PCC6803 | accC | NP_442228 | 6.3.4.14, 6.4.1.2 |
| Synechocystis sp. PCC6803 | accD | NP_442022 | 6.4.1.2 |
| Synechocystis sp. PCC6803 | fabD | NP_440589 | 2.3.1.39 |
| Synechocystis sp. PCC6803 | fabH | NP_441338 | 2.3.1.180 |
| Synechocystis sp. PCC6803 | fabF | NP_440631 | 2.3.1.179 |
| Synechocystis sp. PCC6803 | fabG | NP_440934 | 1.1.1.100, 3.1.26.3 |
| Synechocystis sp. PCC6803 | fabZ | NP_441227 | 4.2.1.60 |
| Synechocystis sp. PCC6803 | fabI | NP_440356 | 1.3.1.9 |
| Synechocystis sp. PCC6803 | acp | NP_440632 | |
| Synechocystis sp. PCC6803 | fadD | NP_440344 | 6.2.1.3 |
| Synechococcus elongates PCC7942 | accA | YP_400612 | 6.4.1.2 |
| Synechococcus elongates PCC7942 | accB | YP_401581 | 6.4.1.2 |
| Synechococcus elongates PCC7942 | accC | YP_400396 | 6.3.4.14, 6.4.1.2 |
| Synechococcus elongates PCC7942 | accD | YP_400973 | 6.4.1.2 |
| Synechococcus elongates PCC7942 | fabD | YP_400473 | 2.3.1.39 |
| Synechococcus elongates PCC7942 | fabH | YP_400472 | 2.3.1.180 |
| Synechococcus elongates PCC7942 | fabF | YP_399556 | 2.3.1.179 |
| Synechococcus elongates PCC7942 | fabG | YP_399703 | 1.1.1.100, 3.1.26.3 |
| Synechococcus elongates PCC7942 | fabZ | YP_399947 | 4.2.1.60 |
| Synechococcus elongates PCC7942 | fabI | YP_399145 | 1.3.1.9 |
| Synechococcus elongates PCC7942 | acp | YP_399555 | |
| Synechococcus elongates PCC7942 | fadD | YP_399935 | 6.2.1.3 |

For Table 18, Accession Numbers are from GenBank, Release 159.0 as of Apr. 15, 2007, EC Numbers are from KEGG, Release 42.0 as of April 2007 (plus daily updates up to and including May 9, 2007), results for *Erwinia amylovora* strain Ea273 are taken from the Sanger sequencing center, completed shotgun sequence as of May 9, 2007, positions for *Erwinia* represent locations on the Sanger psuedo-chromosome, sequences from *Vibrio fumisii* M1 are from the LS9 VFM1 pseudochromosome, v2 build, as of Sep. 28, 2006, and include the entire gene, and may also include flanking sequence.

Example 16

Additional Exemplary Production Strains

Table 19 provides additional exemplary production strains. Two example biosynthetic pathways are described for producing fatty acids, fatty alcohols, and wax esters. For example, Table 19 provides Examples 1 and 2 that produce fatty acids. The production host strain used to produce fatty acids in Example 1 is a production host cell that is engineered to have the synthetic enzymatic activities indicated by the "x" marks in the rows which identify the genes (see "x" identifying acetyl-CoA carboxylase, thio-esterase, and acyl-CoA synthase activity). Production host cells can be selected from bacteria, yeast, and fungi. These genes can also be transformed into a production host cell that is modified to contain one or more of the genetic manipulations described in FIG. 1. As provided in Table 19, additional production hosts can be created using the indicated exogenous genes.

TABLE 19

Combination of genes useful for making genetically engineered production strains

| Peptide | Sources of genes | Genes | Fatty acids example 1 | Fatty acids example 2 | Fatty alcohols example 1 | Fatty alcohols example 2 | wax/fatty esters example 1 | wax/fatty esters example 2 |
|---|---|---|---|---|---|---|---|---|
| acetyl-CoA carboxylase | *E. coli* | accABCD | X | X | X | X | X | X |
| thio-esterase | *E. coli* | tesA | X |  | X |  | X | X |
|  | *Cinnamomum camphora* | ccFatB |  |  |  |  |  |  |
|  | *Umbellularia californica* | umFatB |  | X |  | X |  |  |
|  | *Cuphea hookeriana* | chFatB2 |  |  |  |  |  |  |
|  | *Cuphea hookeriana* | chFatB3 |  |  |  |  |  |  |
|  | *Cuphea hookerian* | chFatA |  |  |  |  |  |  |
|  | *Arabidopsis thaliana* | AtFatA1 |  |  |  |  |  |  |
|  | *Arabidopsis thaliana* | AtFatB1 [M141T] |  |  |  |  |  |  |
| acyl-CoA synthase | *E. coli* | fadD | X | X | X | X | X | X |
| acyl-CoA reductase | *Bombyx mori* | bFAR |  |  |  |  |  |  |
|  | *Acinetobacter baylyi* ADP1 | acr 1 |  |  | X |  | X |  |
|  | *Simmondsia chinensis* | jjFAR |  |  |  | X |  | X |
|  | *Triticum aestivum* | TTA1 |  |  |  |  |  |  |
|  | *Mus musculus* | mFAR1 |  |  |  |  |  |  |
|  | *MUS musculus* | mFAR2 |  |  |  |  |  |  |
|  | *Acinetpbacter sp.* M1 | acr M1 |  |  |  |  |  |  |
|  | *Homo sapiens* | hFAR |  |  |  |  |  |  |
| Ester synthase/ alcohol acyl-transferase | *Fundibacter jadensis* DSM 12178 | WST9 |  |  |  |  |  |  |
|  | *Acinetobacter sp.* HO1-N | WSHN |  |  |  |  | X |  |
|  | *Acinetobacter baylyl* ADP1 | WSadp1 |  |  |  |  |  | X |
|  | *Mus musculus* | mWS |  |  |  |  |  |  |
|  | *Homo sapiens* | hWS |  |  |  |  |  |  |
|  | *Fragaria x ananassa* | SAAT |  |  |  |  |  |  |
|  | *Malus x domestica* | MpAAT |  |  |  |  |  |  |
|  | *Simmondsia chinensis* | JjWS (AAD38041) |  |  |  |  |  |  |
| Decarbonylase | *Arabidopsis thaliana* | cer1 |  |  |  |  |  |  |
|  | *Oryzasativa* | cer1 |  |  |  |  |  |  |
| Transport protein | *Acinetobacter sp.* HO1-N | unknown |  |  |  |  | X | X |
|  | *Arabidopsis thaliana* | Cer5 |  |  |  |  |  |  |

Example 17

Use of Additional Acyl-CoA Synthases to Over Produce Acyl-CoA

Homologues to *E. coli* fadD can be expressed in *E. coli* by synthesizing codon-optimized genes of the desired sequence from *M tuberculosis* HR7Rv (NP_217021, FadDD35), *B. subtilis* (NP_388908, YhfL), *Saccharomyces cerevisiae* (NP_012257, Faa3p) and *P. aeruginosa* PAO1 (NP_251989). The synthetic genes can be designed to include NcoI and HindIII compatable overhangs. The acyl-CoA synthases can be then cloned into NcoI/HindIII digested pTrcHis2 vector (Invitrogen Corp., Carlsbad, Calif.) as described above and expressed in *E. coli* strain MG1655 ΔfadE. After expression in *E. coli*, acyl-CoA production will be increased.

Fatty acid derivatives such as FAEE can also be produced by co-tranformation of the *E. coli* strain MG1655 ΔfadE with various acyl-CoA synthases in the pTrcHis2 vector with a compatible plasmid derived from pCL1920, which contains the ester synthase from *A. baylyi* or the thioesterase gene from *Cuphea hookeriana*. The resulting production host will produce FAEE when cultured in media containing ethanol as described above.

Example 18

Use of Additional Acyl-CoA Synthases to Overproduce Acyl-CoA

The DNA sequences or protein sequences of numerous *E. coli* FadD homologs are known. However, the biochemical properties of only a few have been described. See, e.g., Knoll et al., *J. Biol. Chem.* 269(23):16348-56, 1994; Shockey et al., *Plant Physiol.* 132: 1065-1076, 2003. Furthermore, their capacity to be expressed in an active form at significant levels for commercial purposes is unknown. To explore the possibility of using heterologous acyl-CoA synthases for esters production, several acyl-CoA synthases genes were cloned and expressed as follows. Although this example describes transforming the production host with separate plasmids for the thioesterase, ester synthase, and acyl-CoA synthase genes, these genes may alternatively be incorporated together in one plasmid to transform the production host.

1) Construction of pOP-80 Plasmid

To over-express the genes, a low copy plasmid based on the commercial vector pCL1920 (Lerner & Inouye, (1990) NAR 18: 4631) carrying a strong transcriptional promoter was constructed by digesting pCL1920 with the restriction enzymes AflII and SfoI (New England BioLabs Inc. Ipswich, Mass.). Three DNA sequence fragments were produced by this digestion. The 3737 bp fragment was gel-purified using a gel-purification kit (Qiagen, Inc. Valencia, Calif.). In parallel, a DNA sequence fragment containing the trc-promoter and lacI region from the commercial plasmid pTrcHis2 (Invitrogen, Carlsbad, Calif.) was amplified by PCR using primers LF302 (5'-atatgacgtcGGCATCCGCTTACAGACA-3') (SEQ ID NO: 55) and LF303 (5'-aattcttaagTCAGGAGAGCGT-TCACCGACAA-3') (SEQ ID NO: 56). These two primers also introduced recognition sites for the ZraI and AflII enzymes, respectively, at the end of the PCR products. After amplification, the PCR products were purified using a PCR-purification kit (Qiagen, Inc. Valencia, Calif.) and digested with ZraI and AflII following the recommendations of the supplier (New England BioLabs Inc., Ipswich, Mass.). After digestion, the PCR product was gel-purified and ligated with the 3737 bp DNA sequence fragment derived from pCL1920.

Figure 17:
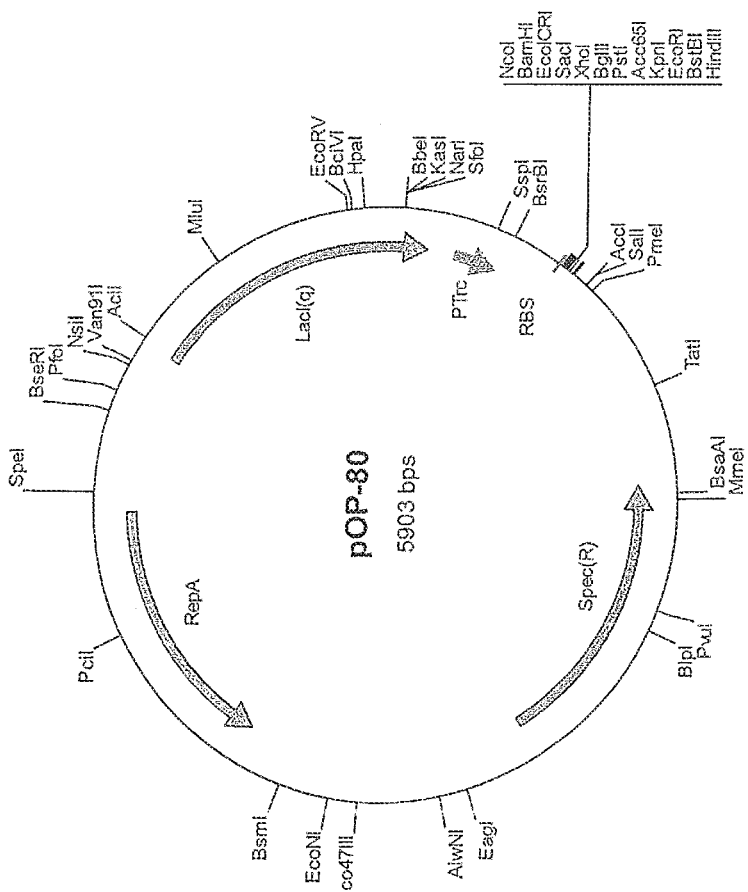
FIG. 17 is a map of the pOP-80 plasmid.

After transformation with the ligation mixture in TOP10 chemically competent cells (Invitrogen, Carlsbad, Calif.), transformants were selected on Luria agar plates containing 100 μg/mL spectinomycin. Many colonies were visible after overnight incubation at 37° C. Plasmids present in these colonies were purified, analyzed with restriction enzymes, and then sequenced. One plasmid produced in this way was retained, named pOP-80, and used for further expression experiments. A map of pOP-80 is shown in FIG. 17.

The DNA sequence of relevant regions of plasmid pOP-80 was corroborated. It was found that in the junctions were the 2 fragments were ligated, 3-4 bases at each end were missing, this was probably caused by an exonuclease activity contaminating one of the restriction enzymes. It is likely that these small deletions did not affect any relevant plasmid function. The resulting plasmid was used for all expression experiments described in this example. The full sequence of the plasmid is disclosed as SEQ ID NO: 1 (FIG. 18).

2) Cloning of fadD35 from *Mycobacterium tuberculosis* HR7Rv

An *E. coli* codon-optimized gene was synthesized by DNA 2.0 Inc. (Menlo Park, Calif.), using the protein sequence of the fadD35 gene deposited at NCBI with the accession code NP_217021. The synthetic gene contained a unique NcoI site at the 5'-end and a unique EcoRI site at the 3'-end. The synthetic gene was provided by DNA 2.0 Inc. cloned in plasmid pJ201:16084. The fad35 gene was released from this plasmid by digesting with NcoI and EcoRI. The sequence of this fragment is shown in SEQ ID NO: 1. The resulting DNA sequence fragment (SEQ ID NO: 2, FIG. 19) was ligated with pOP-80, which was previously digested with NcoI and EcoRI. The ligation mixture was transformed into TOP10 chemically competent cells (Invitrogen, Carlsbad, Calif.), which were then plated on Luria agar plates containing 100 μg/mL spectinomycin and incubated at 37° C. overnight. Colonies that appeared the next day were screened, and a strain containing the correct plasmid was identified. The plasmid was named pDS9.

3) Cloning of fadD1 from *Pseudomonas aeruginosa* PAO1

An *E. coli* codon-optimized gene was synthesized by DNA 2.0 Inc. (Menlo Park, Calif.) using the protein sequence of the fadD1 gene deposited at NCBI with the accession code NP_251989. The synthetic gene contained a unique BspHI site at the 5'-end and a unique EcoRI site at the 3'-end. The synthetic gene was provided by DNA 2.0, Inc. and cloned in plasmid pJ201:16083. The fadD1 gene was released from this plasmid by digesting with BspHI and EcoRI. The sequence of this fragment is shown in SEQ ID NO: 3 (FIG. 20). The resulting DNA sequence fragment was ligated with pOP-80, which was previously digested with NcoI and EcoRI. The ligation mixture was transformed into TOP10 chemically competent cells (Invitrogen, Carlsbad, Calif.), which were then plated on Luria agar plates containing 100 μg/mL spectinomycin and incubated at 37° C. overnight. Colonies that appeared the next day were screened. A strain containing the correct plasmid was identified. The plasmid was named pDS8.

4) Cloning of yhfL from *Bacillus subtilis*

The yhfL gene was amplified by PCR using *Bacillus subtilis* 1168 chromosomal DNA sequence as a template, and two primers designed based on the DNA sequence deposited at NCBI with the accession code NC_000964. The sequence of the 2 primers was:

```
                                   (SEQ ID NO: 4, FIG. 21)
BsyhfLBspHIF:  5'-CATCATGAATCTTGTTTC-3'

(SEQ ID NO: 5, FIG. 22)
BsyhfLEcoR:    5'-CGGAATTCTTATTGGGGCAAAATATC-3'
```

These two primers introduced a BspHI recognition site at the 5'-end and an EcoRI recognition site at the 3'-end. The PCR product was cloned directly into pCR-Blunt II-TOPO vector using the Zero Blunt TOPO PCR cloning kit (Invitrogen, Carlsbad, Calif.). A plasmid carrying the yhfL gene was named pDS1. To subclone yhfL, plasmid pDS1 was digested with BspHI and EcoRI. The resulting DNA sequence fragment (SEQ ID NO: 6, FIG. 23) was gel-purified and cloned into pOP-80, which was previously digested with NcoI and EcoRI. The plasmid carrying the *B. subtilis* yhfL gene cloned into pOP-80 was named pDS4

5) Cloning of faa3p from *Saccharomyces cerevisiae* (NP_012257)

The faa3p gene was amplified by PCR using commercial *Saccharomyces cerevisiae* chromosomal DNA sequence ATCC 204508D (American Type Culture Collection, Manassas, Va.) as a template, and two primers that were designed based on the DNA sequence deposited at NCBI with the accession code NC_001141. The sequence of the two primers was:

```
                                   (SEQ ID NO: 7, FIG. 24)
Scfaa3pPciF:   5'-CGACATGTCCGAACAACAC-3'

(SEQ ID NO: 8, FIG. 25)
Scfaa3pPciI:   5'-GCAAGCTTCTAAGAATTTTCTTTG-3'
```

These two primers introduced a PciI recognition site at the 5'-end and an HindIII recognition site at the 3'-end.

The PCR product was cloned directly into pCR-Blunt II-TOPO vector using the Zero Blunt TOPO PCR cloning kit (Invitrogen, Carlsbad, Calif.). A plasmid carrying the faa3p gene was named pDS2. To subclone faa3p, plasmid pDS2 was digested with PciI and HindIII. The DNA sequence fragment (SEQ ID NO: 9, FIG. 26) was gel-purified and cloned into pOP-80, which was previously digested with NcoI and HindIII. The plasmid carrying the *S. cerevisiae* faa3p gene cloned into pOP-80 was named pDS5.

6) Cloning of ZP_01644857 from *Stenotrophomonas maltophilia* R551-3

The structural gene sequence for the protein ZP_01644857 is available at NCBI as part of the locus NZ_AAVZ01000044. The gene was amplified by PCR using *Stenotrophomonas maltophilia* R551-3 chromosomal DNA sequence as template, and two primers designed based on the deposited DNA sequence. The sequence of the two primers was:

```
                                   (SEQ ID NO: 10, FIG. 27)
Smprk59BspF:   5'-AGTCATGAGTCTGGATCG-3'

(SEQ ID NO: 11, FIG. 28)
Smprk59HindR:  5'-GGAAGCTTACGGGGCGGGCG-3'
```

These two primers introduced a BspHI recognition site at the 5'-end and an HindIII recognition site at the 3'-end.

The PCR product was cloned directly into pCR-Blunt II-TOPO vector using the Zero Blunt TOPO PCR cloning kit (Invitrogen, Carlsbad, Calif.). A plasmid carrying the gene encoding the protein ZP_01644857 was named pDS3. To facilitate further subcloning of the gene, an internal BspHI site was removed by site directed mutagenesis using the primer Prldisp-(5'-GCGAACGGCCTGGTCTTTAT-GAAGTTCGGTGG-3') (SEQ ID NO: 12, FIG. 29) and the QuikChange Multi Site-Directed mutagenesis kit (Stratagene, La Jolla, Calif.). After the proper mutation was corroborated by DNA sequencing, the resulting plasmid was digested with BspHI and HindIII, and was named pDS6. The DNA sequence fragment (SEQ ID NO: 13, FIG. 30) was gel-purified and cloned into pOP-80 previously digested with NcoI and HindIII. The plasmid carrying the gene encoding the protein ZP_01644857 cloned into pOP-80 was named pDS7. The protein sequence of ZP_01644857 is disclosed in SEQ ID NO: 14 (FIG. 31).

7) Construction of Strains to Produce Fatty Esters. An *E. coli* BL21(DE3) strain was first transformed with plasmid pETDuet-1-tesA (described in Example 2) carrying the *E. coli* tesA gene, and plasmid pHZ1.97 (described in Example 12) carrying the atfA2 ester synthetase gene, respectively. Both genes were under the T7 promoter inducible by IPTG. Two independent transformants carrying both plasmids were transformed with each of the recombinant plasmids carrying the heterologous fadD genes, and selected on Luria agar plates containing 100 μg/mL carbenicillin, 50 μg/mL kanamycin, and 100 μg/mL spectinomycin. Three independent colonies carrying the three plasmids were tested for fatty-ester production.

8) Analysis of Fatty Esters Produced Using ZP_01644857 from *Stenotrophomonas maltophilia* R551-3

To evaluate the use of the protein ZP_01644857 from *Stenotrophomonas maltophilia* R551-3 in a production host to produce fatty esters, an *E. coli* BL21(DE3) strain was transformed with plasmid pETDuet-1-tesA (described in Example 2) carrying the *E. coli* tesA gene, plasmid pHZ1.97 (described in Example 12) carrying the atfA2 ester synthetase gene, and plasmid pDS7 carrying the gene encoding the protein ZP_01644857 (described above in this example). This production host was fermented to produce fatty esters as described in Example 13. As a control, a second *E. coli* strain BL21(DE3)ΔfadE, containing plasmids pETDuet-1-tesA, pHZ1.97, and pCL1920 was used as a production host to produce fatty esters.

Table 20 below shows the fatty ester yields from these production hosts.

TABLE 20

Fatty ester yields from a production host that produced ZP_01644857

| Ester type: | $C_2C_{12:1}$ mg/L | $C_2C_{12:0}$ mg/L | $C_2C_{14:1}$ mg/L | $C_2C_{14:0}$ mg/L | $C_2C_{16:1}$ mg/L | $C_2C_{16:0}$ mg/L | $C_2C_{18:1}$ mg/L | $C_2C_{18:0}$ mg/L | Total mg/L[c] |
|---|---|---|---|---|---|---|---|---|---|
| Control[a] | 0.0 | 0.0 | 0.0 | 1.78 | 9.80 | 5.65 | 33.7 | 0.00 | 50.93 |
| fadD ZP_01644857[b] | 1.49 | 3.57 | 3.68 | 33.22 | 52.77 | 43.09 | 91.11 | 10.08 | 239.01 |

[a]Control: strain BL21(DE3) D fadE, containing plasmids pETDuet-1-tesA, pHZ1.97 and pCL1920.
[b]Strain BL21(DE3) D fadE, containing plasmids pETDuet-1-tesA, pHZ1.97 and pDS7.
[c]These values represent the average of 3 cultures.

Example 19

Down-Regulation of Beta-Oxidation

This example describes the creation of an *E. coli* strain MG1655 ΔfadE ΔydiO.

Fatty acid degradation can be eliminated or attenuated by attenuating any of the β-oxidation enzymatic reactions described above (see FIG. 3). For example, the *E. coli* strain MG1655 ΔfadE can be further engineered by using primers to amplify up-stream of ydiO and additional primers to amplify downstream of ydiO. Overlap PCR can then be used to create a construct for in-frame deletion of the complete ydiO gene.

way. For example, several species of *Streptococcus* have been sequenced and none of the genes involved in beta-oxidation have been found.

Example 20

Identification of Additional Ester Synthases

This example provides additional ester synthases and methods of using such synthases for the production of fatty esters.

Using bioinformatics, additional ester synthases were identified. These ester synthases contain motifs that differ from other known motifs, such as the motifs found in ADP1. The differences in the motifs are noted in Table 21, below.

TABLE 21

Comparison of ester synthases motifs

| ADP1-motifs | HHAXVDGV | NDVVLA | GALRXYL | PLXAMVP | ISNVPGP | REPLYXNGA |
|---|---|---|---|---|---|---|
| Hypothetical protein BCG_3544c [*Mycobacterium bovis* BCG str. Pasteur 1173P2] gi/121639399 | HHSLIDGY (SEQ ID NO: 31) | NDVALA (SEQ ID NO: 32) | GGLRRFL (SEQ ID NO: 33) | SLIVVLP (SEQ ID NO: 34) | VSNVPGP (SEQ ID NO: 35) | EDVLYLRGS (SEQ ID NO: 36) |
| Protein of unknown function UPF0089 [*Mycobacterium gilvum* PYR-GCK] gi/145221651 | HHALVDGY (SEQ ID NO: 37) | NDVALA (SEQ ID NO: 38) | GGLRKFL (SEQ ID NO: 39) | SLIAFLP (SEQ ID NO: 40) | VSNVPGP (SEQ ID NO: 41) | REPLYFNGS (SEQ ID NO: 42) |
| Protein of unknown function UPF0089 [*Mycobacterium vanbaalenii* PYR-1] gi/120406715 | HHALVDGY (SEQ ID NO: 43) | NDVALA (SEQ ID NO: 44) | GGLRKFL (SEQ ID NO: 45) | SLIAFLP (SEQ ID NO: 46) | VSNVPGP (SEQ ID NO: 47) | REPLYFNGS (SEQ ID NO: 48) |

The ydiO deletion construct is then cloned into the temperature sensitive plasmid pKOV3, which contains a sacB gene for counter-selection, and a chromosomal deletion of ydiO is made according to the method of Link et al., *J. Bact.* 179: 6228-6237, 1997. The resulting strain will not be capable of degrading fatty acids and fatty acyl-CoAs. Additional methods of generating a double knockout of fadE and ydiO are described in Campbell et al., *Mol. Microbiol.* 47:793-805, 2003.

It is also possible to avoid fatty acid degradation by using a production host that does not contain the beta-oxidation path- The identified sequences can be cloned using standard molecular biology techniques. These sequences can be expressed using the vectors described herein and used to make various fatty esters. The motifs can also be used to identify other ester synthases.

Example 21

Product Characterization

To characterize and quantify the fatty alcohols and fatty esters, gas chromatography (GC) coupled with electron impact mass spectra (MS) detection was used. Fatty alcohol samples were first derivatized with an excess of N-trimethylsilyl (TMS) imidazole to increase detection sensitivity. Fatty esters did not required derivatization. Both fatty alcohol-TMS derivatives and fatty esters were dissolved in an appropriate volatile solvent, such as ethyl acetate.

The samples were analyzed on a 30 m DP-5 capillary column using the following method. After a 1 µL splitless injection onto the GC/MS column, the oven was held at 100° C. for 3 minutes. The temperature was ramped up to 320° C. at a rate of 20° C./minute. The oven was held at 320° C. for an additional 5 minutes. The flow rate of the carrier gas helium was 1.3 mL/minute. The MS quadrapole scanned from 50 to 550 m/z. Retention times and fragmentation patterns of product peaks were compared with authentic references to confirm peak identity.

For example, hexadeconic acid ethyl ester eluted at 10.18 minutes (FIG. 16A and FIG. 16B). The parent ion of 284 mass units was readily observed. More abundant were the daughter ions produced during mass fragmentation. This included the most prevalent daughter ion of 80 mass units. The derivatized fatty alcohol hexadecanol-TMS eluted at 10.29 minutes and the parent ion of 313 could be observed. The most prevalent ion was the M-14 ion of 299 mass units.

Quantification was carried out by injecting various concentrations of the appropriate authentic references using the GC/MS method described above. This information was used to generate a standard curve with response (total integrated ion count) versus concentration.

EQUIVALENTS

While specific examples of the subject inventions are explicitly disclosed herein, the above specification and examples herein are illustrative and not restrictive. Many variations of the inventions will become apparent to those skilled in the art upon review of this specification including the examples. The full scope of the inventions should be determined by reference to the examples, along with their full scope of equivalents, and the specification, along with such variations.

All publications, patents, patent applications, and other references cited in this application are herein incorporated by reference in their entirety as if each publication, patent, patent application or other reference were specifically and individually indicated to be incorporated by reference.

The invention claimed is:

1. A recombinant microbial cell that is modified to express at least one exogenous nucleic acid sequence encoding a fatty acid derivative enzyme comprising an acyl-CoA reductase, wherein the recombinant microbial cell converts a carbohydrate carbon source into a fatty alcohol composition that is released into a fermentation media.

2. The recombinant microbial cell of claim 1, wherein the microbial cell is a bacterial cell that is further modified to express an exogenous nucleic acid sequence encoding an acyl-CoA synthase (FadD).

3. The recombinant microbial cell of claim 1, wherein the fatty alcohol composition that is released into the fermentation media is collected in an organic phase extracellularly.

4. The recombinant microbial cell of claim 1, wherein the fatty alcohol composition is produced at a level of at least 1 mg/L.

5. The recombinant microbial cell of claim 1, wherein a greater amount of fatty alcohol is produced at 37° C. than at 25° C.

6. The recombinant microbial cell of claim 1, wherein the microbial cell is a bacterial cell, a yeast cell, an algal cell, or a filamentous fungal cell.

7. The recombinant microbial cell of claim 1, wherein the fermentation media comprises one or more of C10, C12, C14, C16 and C18 fatty alcohols.

8. The genetically engineered recombinant microbial cell of claim 7, wherein the fermentation media comprises C12 and C14 fatty alcohols.

9. The recombinant microbial cell of claim 1, wherein the fermentation media comprises unsaturated fatty alcohols.

10. The recombinant microbial cell of claim 1, wherein the fermentation media comprises saturated fatty alcohols.

11. The recombinant microbial cell of claim 1, wherein the fermentation media comprises straight chain or branched chain fatty alcohols.

12. A recombinant microbial cell that is modified to express at least one exogenous nucleic acid sequence encoding a fatty acid derivative enzyme comprising an acyl-CoA reductase, wherein the recombinant microbial cell converts a fatty acid carbon source into a fatty alcohol composition that is released into a fermentation media.

13. The recombinant microbial cell of claim 12, wherein an acyl-CoA synthase (fadD; EC 2.3.1.86, 6.2.1.3) is overexpressed.

14. The recombinant microbial cell of claim 12, wherein an acyl-CoA dehydrogenase (fadE; EC 1.3.99.3, 1.3.99.-) is attenuated.

15. The recombinant microbial cell of claim 12, wherein a fatty acid transport protein (fadL) is overexpressed.

16. The recombinant microbial cell of claim 12, wherein said fatty acid carbon source is converted to acyl-CoA esters, which bind to transcription factor FadR.

17. The recombinant microbial cell of claim 12, wherein a 3-ketoacyl-CoA thiolase (fadA; EC 2.3.1.16) is deleted or reduced.

18. The recombinant microbial cell of claim 12, wherein a β-oxidation protein (fadB; EC 4.2.1.17, 5.1.2.3, 5.3.3.8, 1.1.1.35) is deleted or reduced.

19. The recombinant microbial cell of claim 12, wherein an acyl-CoA dehydrogenase (YdiO; EC 1.3.99.-) is deleted or reduced.

20. The recombinant microbial cell of claim 12, wherein a beta-ketoacyl-CoA thiolase (fadI; EC 2.3.1.16) is deleted or reduced.

21. The recombinant microbial cell of claim 12, wherein an epimerase (fadJ; EC 5.1.2.3, 4.2.1.17, 1.1.1.35) is deleted or reduced.

22. The recombinant microbial cell of claim 12, wherein said fatty acid carbon source is converted to acyl-CoA esters, which bind to transcription factor FadR.

* * * * *